US011504391B1

(12) United States Patent
Schlegel et al.

(10) Patent No.: US 11,504,391 B1
(45) Date of Patent: Nov. 22, 2022

(54) MODIFIED RNA AGENTS WITH REDUCED OFF-TARGET EFFECT

(71) Applicant: Alnylam Pharmaceuticals, Inc., Cambridge, MA (US)

(72) Inventors: Mark K. Schlegel, Cambridge, MA (US); Maja Janas, Cambridge, MA (US); Vasant R. Jadhav, Cambridge, MA (US); Donald Foster, Cambridge, MA (US); Muthiah Manoharan, Cambridge, MA (US); Kallanthottathil G. Rajeev, Cambridge, MA (US); Muthusamy Jayaraman, Cambridge, MA (US); Alexander V. Kel'in, Cambridge, MA (US); Shigeo Matsuda, Cambridge, MA (US); Klaus Charisse, Cambridge, MA (US); Jayaprakash K. Nair, Cambridge, MA (US); Martin A. Maier, Cambridge, MA (US); Alfica Sehgal, Cambridge, MA (US); Christopher Brown, Cambridge, MA (US); Christopher Theile, Cambridge, MA (US); Stuart Milstein, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 66 days.

(21) Appl. No.: 16/461,523

(22) PCT Filed: Nov. 22, 2017

(86) PCT No.: PCT/US2017/063078
§ 371 (c)(1),
(2) Date: May 16, 2019

(87) PCT Pub. No.: WO2018/098328
PCT Pub. Date: May 31, 2018

Related U.S. Application Data

(60) Provisional application No. 62/425,907, filed on Nov. 23, 2016, provisional application No. 62/548,589, filed on Aug. 22, 2017, provisional application No. 62/561,514, filed on Sep. 21, 2017.

(51) Int. Cl.
*A61K 31/713* (2006.01)
*C12N 15/113* (2010.01)

(52) U.S. Cl.
CPC .......... *A61K 31/713* (2013.01); *C12N 15/113* (2013.01); *C12N 2310/14* (2013.01); *C12N 2310/31* (2013.01); *C12N 2310/351* (2013.01)

(58) Field of Classification Search
None
See application file for complete search history.

(56) References Cited

U.S. PATENT DOCUMENTS

| 2011/0059187 | A1  | 3/2011  | Basu |
| 2013/0130378 | A1* | 5/2013  | Manoharan ......... C07F 9/65583 435/375 |
| 2014/0170191 | A1  | 6/2014  | Carter et al. |
| 2015/0247147 | A1  | 9/2015  | Rusconi |
| 2015/0315594 | A1* | 11/2015 | Prakash ............. C12N 15/1136 536/24.5 |
| 2017/0275626 | A1  | 9/2017  | Maier et al. |

FOREIGN PATENT DOCUMENTS

| EP | 1681347 A1    | 7/2006 |
| WO | 2016028649 A1 | 2/2016 |
| WO | 2016100716 A1 | 6/2016 |
| WO | 2018098328 A1 | 5/2018 |
| WO | 202172395 A1  | 4/2021 |

OTHER PUBLICATIONS

OligoCalc: Oligonucleotide Properties calculator accessed Dec. 8, 2020 at <http://biotools.nubic.northwestern.edu/OligoCalc.html>, 5 pages.*
Elkayam et al. "siRNA carrying an (E)-vinylphosphonate moiety at th 5' end of the guide strand augments gene silencing by enhanced binding to human Argonaute-2." Nucleic Acids Research 45(6): 3528-3536 (2017).
Clark et al., "Knockdown of TNFR1 by the sense strand of an ICAM-1 siRNA: dissection of an off-target effect." Nucleic acids research 36.4 (2008): 1081-1097.
Kumar et al., "5'-Morpholino modification of the sense strand of an siRNA makes it a more effective passenger." Chemical Communications 55.35 (2019): 5139-5142.
Janas et al. "Selection of GalNAc-conjugated siRNAs with limited off-target-driven rat hepatotoxicity." Nature communications 9.1 (2018): 1-10.
Haraszti et al., "5'-Vinylphosphonate improves tissue accumulation and efficacy of conjugated siRNAs in vivo." Nucleic acids research 45.13 (2017): 7581-7592.

(Continued)

Primary Examiner — Tracy Vivlemore
(74) Attorney, Agent, or Firm — Nixon Peabody LLP; David S. Resnick; Ravinderjit Braich

(57) ABSTRACT

One aspect of the present invention relates to double-stranded RNA (dsRNA) agent capable of inhibiting the expression of a target gene. The antisense strand of the dsRNA molecule comprises at least one thermally destabilizing nucleotide occurring at a seed region; the dsRNA comprises at least four 2'-fluoro modifications, and the sense strand of the dsRNA molecule comprises ligand, wherein the ligand is an ASGPR ligand. Other aspects of the invention relates to pharmaceutical compositions comprising these dsRNA molecules suitable for therapeutic use, and methods of inhibiting the expression of a target gene by administering these dsRNA molecules, e.g., for the treatment of various disease conditions.

42 Claims, 61 Drawing Sheets

Specification includes a Sequence Listing.

(56) References Cited

OTHER PUBLICATIONS

Parmar et al.,"5'-(E)-Vinylphosphonate: A Stable Phosphate Mimic Can Improve the RNAi Activity of siRNA-GalNAc Conjugates." ChemBioChem 17.11 (2016): 985-989.
Supporting information for Parmar et al.,"5'-(E)-Vinylphosphonate: A Stable Phosphate Mimic Can Improve the RNAi Activity of siRNA-GalNAc Conjugates." ChemBioChem 17.11 (2016): 985-989.
Supplementary Information for Janas et al. "Selection of GalNAc-conjugated siRNAs with limited off-target-driven rat hepatotoxicity." Nature communications 9.1 (2018): 1-10.
Schlegel et al. "Chirality Dependent Potency Enhancement and Structural Impact of Glycol Nucleic Acid Modification on siRNA", JACS (2017), vol. 139, pp. 8537-8546.
Supporting Information for Schlegel et al. "Chirality Dependent Potency Enhancement and Structural Impact of Glycol Nucleic Acid Modification on siRNA", JACS (2017), vol. 139, pp. 8537-8546.
Alagia et al., "Modulation of the RNA Interference Activity Using Central Mismatched siRNAs and Acyclic Threoninol Nucleic Acids (aTNA) Units." Molecules, 20, 7602-7619 (2015).
Bramsen et al. A screen of chemical modifications identifies position-specific modification by UNA to most potently reduce siRNA off-target effects. Nucleic Acids Res, 38, 5761-5773 (2010).
Egli et al. Conformational influence of the ribose 2'-hydroxyl group: Crystal structures of DNA-RNA chimeric duplexes. Biochemistry, 32, 3221-3237 (1993).
Kenski et al., "Analysis of acyclic nucleoside modifications in siRNAs finds sensitivity at position 1 that is restored by 5'-terminal phosphorylation both in vitro and in vivo." Nucleic Acids Research, 38, 660-671 (2010).
Laursen et al. "Utilization of unlocked nucleic acid (UNA) to enhance siRNA performance in vitro and in vivo." Molecular BioSystems, 6, 862-870 (2010).

Lee et al. "Abasic pivot substitution harnesses target specificity of RNA interference." Nat. Commun., 6, 10154 (2015).
Mook et al. "In vivo efficacy and off-target effects of locked nucleic acid (LNA) and unlocked nucleic acid (UNA) modified siRNA and small internally segmented interfering RNA (sisiRNA) in mice bearing human tumor xenografts." Artif DNA PNA XNA, 1, 36-14 (2010).
Schirle et al. "Structural Analysis of Human Argonaute-2 Bound to a Modified siRNA Guide." J. Am. Chem. Soc., 138, 8694-8697(2016).
Schlegel et al. "Improved Phosphoramidite Building Blocks for the Synthesis of the Simplified Nucleic Acid GNA." J. Org. Chem., 74, 4615-1618 (2009).
Seok et al. "Rationally designed siRNAs without miRNA-like off-target repression." BMB Rep, 49, 135-136 (2016).
Sheng et al. "Structural insights into the effects of 2'-5' linkages on the RNA duplex." Proc. Natl. Acad. Sci., 111, 3050-3055 (2014).
Ui-Tei et al. "Functional dissection of siRNA sequence by systematic DNA substitution: modified siRNA with a DNA seed arm is a powerful tool for mammalian gene silencing with significantly reduced off-target effect." Nucleic Acids Res., 36, 2136-2151 (2008).
Vaish et al. Improved specificity of gene silencing by siRNAs containing unlocked nucleobase analogs. Nucleic Acids Res., 39, 1823-1832 (2010).
Wahl et al. "B-form to A-form conversion by a 3'-terminal ribose: crystal structure of the chimera d(CCACTAGTG)r (G)." Nucleic Acids Res., 28, 4356-4363 (2000).
Wasner et al. "Physicochemical and Biochemical Properties of 2',5'-Linked RNA and 2',5'-RNA:3',5'-RNA "Hybrid" Duplexes." Biochemistry, 37, 7478-7486 (1998).
Zhang et al. "A Simple Glycol Nucleic Acid." J. Am. Chem. Soc., 127, 4174-4175 (2005).
Zhang et al. "Synthesis of Glycol Nucleic Acids." Synthesis, 2006, 645-653 (2006).

* cited by examiner

MODIFIED RNA AGENTS WITH REDUCED OFF-TARGET EFFECT

RELATED APPLICATIONS

This application is a 35 U.S.C. § 371 National Phase Entry Application of International Application No. PCT/US2017/063078, filed Nov. 22, 2017, which designates the U.S. and claims benefit under 35 U.S.C. § 119(e) of the U.S. Provisional Application No. 62/425,907, filed Nov. 23, 2016, U.S. Provisional Application No. 62/548,589, filed Aug. 22, 2017, and U.S. Provisional Application No. 62/561,514, filed Sep. 21, 2017, and the contents of all which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 18, 2017, is named 051058-088343-PCT_SL.txt and is 19,559 bytes in size.

FIELD OF THE INVENTION

The invention relates to RNAi duplex agents having particular motifs that are advantageous for inhibition of target gene expression by reducing the undesired off-target effects, as well as RNAi compositions suitable for therapeutic use. Additionally, the invention provides methods of inhibiting the expression of a target gene by administering these RNAi duplex agents, e.g., for the treatment of various diseases.

BACKGROUND

RNA interference or "RNAi" is a term initially coined by Fire and co-workers to describe the observation that double-stranded RNAi (dsRNA) can block gene expression (Fire et al. (1998) Nature 391, 806-811; Elbashir et al. (2001) Genes Dev. 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

One of the off-target effects of siRNA is the miRNA-like effect—the argonaute protein, the core effector in RNA interference, treats siRNA, which is artificially introduced in order to induce RNA interference, as a miRNA (microRNA). (Lam et al. (2015) Molecular Therapy Nucleic Acids (2015) 4, e252). The miRNA recognizes a target gene majorly through base-pairing between the seed region (positions 2-9 from the 5' end) and the target mRNA for gene suppression. The off-targets caused by siRNAs originate from base-complementarity of the seed regions of the RISC-loaded antisense strand of siRNA with one or more mRNA. The miRNA-like off-target effects in siRNAs have been reported in several studies, and affect expression of multitude of genes depending on sequences of the seed regions and are serious enough to cause up to 30% of the positive hits in siRNA based phenotype screening. Additionally, in the case of miRNAs, they are also reported to silence target genes through compensatory pairings within their 3' end regions (3'-compensatory pairing) when the interactions between seed region and targets become weak, implicating that the miRNA-like off-target effects are likely to be mediated by such mechanism.

There is thus an ongoing effort to eliminate or reduce miRNA-like off-target effects of siRNAs by modulating siRNA design by judicious application of chemical modifications without compromising the gene silencing efficacy of siRNA gene therapeutics. This invention is directed to that effort.

SUMMARY

This invention provides effective nucleotide or chemical motifs for dsRNA molecules, which are advantageous for inhibition of target gene expression, while having reduced off-target gene silencing effects, as well as RNAi compositions suitable for therapeutic use.

The inventors have discovered inter alia that dsRNA molecules where the antisense strand comprises at least one thermally destabilizing modification of the duplex within the seed region (i.e., at position 2-9 of the 5'-end of the antisense strand, counting from the 5'-end) and the dsRNA molecule has a melting temperature in the range of from about 40° C. to about 80° C. can be more effective in mediating RNA interference than the parent dsRNA molecule lacking the destabilizing modification.

Thus, in one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight or all nine) of the following characteristics: (i) a melting temperature ($T_m$) of from about 40° C. to about 80° C.; (ii) the antisense comprises 2, 3, 4, 5 or 6 2'-fluoro modifications; (iii) the antisense comprises 1, 2, 3 or 4 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3 or 4 phosphorothioate internucleotide linkages; (vii) the dsRNA comprises at least four 2'-fluoro modifications; (viii) the dsRNA comprises a duplex region of 12-40 nucleotide pairs in length; and (ix) a blunt end at 5'end of the antisense strand.

In some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9, preferably 3-8, of the 5'-end of the antisense strand, counting from the 5'-end), and the dsRNA further has at least one (e.g., one, two, three, four, five, six seven, eight or all nine) of the following characteristics: (i) a melting temperature ($T_m$) of from about 40° C. to about 80° C.; (ii) the antisense comprises 6, 7, 8, 9, 10, 11 or 12 2'-OMe modifications; (iii) the antisense comprises 1, 2, 3 or 4 phosphorothioate internucleotide linkages; (iv) the sense strand is conjugated with a ligand; (v) the sense strand comprises 6, 7, 8, 9, 10, 11 or 12 2'-OMe modifications; (vi) the sense strand comprises 1, 2, 3 or 4 phosphorothioate internucleotide linkages; (vii) the dsRNA comprises at least 1, 2, 3, 4 or 5 2'-deoxy modification(s); (viii) the dsRNA comprises a duplex region of 12-40 nucleotide pairs in length; and (ix) a blunt end at 5'end of the antisense strand.

In some embodiments, the dsRNA has a melting temperature with a lower end of the range from about 40° C., 45° C., 50° C., 55° C., 60° C. or 65° C., and upper end of the range from about 70° C., 75° C. or 80° C. In some embodiments, the dsRNA has a melting temperature in the range from about 55° C. to about 70° C. In some embodiments, the dsRNA has a melting temperature in the range from about 57° C. to about 67° C. In some particular embodiments, the dsRNA has a melting temperature in the range from about 60° C. to about 67° C. In some additional embodiments, the dsRNA has a melting temperature in the range from about 62° C. to about 66° C.

The inventors have also discovered that dsRNA molecules having a melting temperature of at least 60° C. are more effective in vivo and in vitro. Thus, in some embodiments, the dsRNA has a melting temperature of at least 60° C.

The inventors also discovered that for the dsRNA molecules to be more effective in vivo, there must be at least 40-50% of the antisense strand present at day 7 in vivo, for example in the mouse liver, after administration.

In another aspect, the invention further provides a method for delivering the dsRNA molecule of the invention to a specific target in a subject by subcutaneous or intravenous administration. The invention further provides the dsRNA molecules of the invention for use in a method for delivering said agents to a specific target in a subject by subcutaneous or intravenous administration.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 37A shows TTR mRNA levels measured in the liver. FIG. 37B shows TTR protein levels measured in the serum. Error bars represent the SD from each cohort (n=3). Only those comparisons which are statistically significant are shown in the graph; all others are nonsignificant with the exception of all comparisons to PBS which were all significant. G=guide strand, P=Passenger strand.

FIG. 38A depicts structures of nucleotide analogs used at 5'-ends of siRNAs to prevent 5'-phosphorylation thus reducing RISC loading. FIG. 38B are bar graphs showing liver exposures for parent (RNAi-active) and capped (RNAi-inactive) GalNAc-siRNAs in rat and mouse toxicity studies as assessed by stem-loop RT-qPCR for the antisense strand (AS) at necropsy (nx). Dashed vertical lines demarcate studies conducted separately. FIG. 38C shows serum alanine aminotransferase (ALT) levels measured at necropsy. Differences between group means were evaluated for statistical significance using one-way ANOVA in GraphPad Prism 7. ns, not significant; *, p<0.05; , p<0.01; *, p<0.001; ****, p<0.0001. FIG. 38D are images showing H&E staining of liver sections collected at necropsy. In the rat, hepatotoxic siRNAs (siRNA-1 shown here) had hepatocellular degeneration (bracketed area), increased sinusoidal cells due to Kupffer cell hyperplasia and/or leukocyte infiltration (#), single cell necrosis (*), increased mitoses (^), and hepatocellular vacuolation (arrow). In the mouse, hepatotoxic siRNAs (siRNA-7 shown here) were associated with single cell necrosis and lower incidence and severity of the other findings commonly seen in the rat. Capped RNAi-inactive siRNAs had minimal vacuolation or no histologic findings in both species. Cytoplasmic clearing present in the mice was consistent with glycogen due to incomplete fasting and was not considered test article-related.

FIGS. 39A-39-C show effects of antisense strand 5'-modifications on RNAi activity and liver enzyme elevations of toxic GalNAc-siRNAs in rat toxicity studies. FIG. 39A is a bar graph showing liver RISC loading of GalNAc-siRNAs with or without 5'-caps as assessed at necropsy (nx) by stem-loop RT-qPCR for the antisense strand (AS). FIG. 39B is a bar graph showing Liver mRNA knockdown with or without 5'-caps as assessed at necropsy by RT-qPCR for target mRNA and normalized to a housekeeping mRNA (18S rRNA), relative to the saline control group.

FIG. 40A is a bar graph showing liver exposures for a toxic GalNAc-siRNA with or without modifications on the 5'-end of the sense strand (SS) in rat toxicity studies as assessed at necropsy (nx) by stem-loop RT-qPCR for the antisense strand (AS). FIG. 40B shows serum alanine aminotransferase (ALT) levels measured at necropsy. FIG. 40C are images showing H&E staining of liver sections collected at necropsy. The toxic siRNA had microscopic findings consisting of hepatocellular degeneration (bracket), single cell necrosis (*), increased sinusoidal cells consistent with Kupffer cell hyperplasia and/or infiltrating leukocytes (#), and hepatocellular vacuolation (arrow). The addition of sense strand caps had no effect on the incidence or severity of findings. Q2d, every other day dosing; iB, inverted abasic; Mo, morpholino.

FIG. 41A is a bar graph showing liver exposures for a non-toxic GalNAc-siRNA with or without modifications on the 5'-end of both sense strand and the antisense strands in rat toxicity studies as assessed at necropsy (nx) by stem-loop RT-qPCR for the antisense strand (AS). FIG. 41B shows serum alanine aminotransferase (ALT) levels measured at necropsy. FIG. 41C are images showing H&E staining of liver sections collected at necropsy. Administration of the known non-toxic siRNA with or without 5'-caps led to minimal hepatocellular vacuolation (arrow) in both cases. Q2d, every other day dosing; iB, inverted abasic; Mo, morpholino.

FIG. 442A shows chemical modification patterns of the high 2'F and low 2'F GalNAc-siRNAs with the same PS content and sequence. FIG. 42B are bar graphs showing liver exposures in rat and mouse toxicity studies as assessed by stem-loop RT-qPCR for the antisense strand (AS) at necropsy (nx). FIG. 42C is a bar graph showing liver RISC loading as assessed by stem-loop RT-qPCR for the antisense at necropsy. FIG. 42D shows serum alanine aminotransferase (ALT) levels measured at necropsy. Differences between group means were evaluated for statistical significance using one-way ANOVA in GraphPad Prism 7. ns, not significant; *, p<0.05; , p<0.01; *, p<0.001; ****, p<0.0001. FIG. 42E are images showing H&E staining of liver sections collected at necropsy. In the rat, both high 2'F and low 2'F siRNA-6 compounds were associated with hepatocellular degeneration (bracket), single cell necrosis (*), increased sinusoidal cells consistent with Kupffer cell hyperplasia and/or infiltrating leukocytes (#), and hepatocellular vacuolation (arrow). In the mouse, findings consisted of single cell necrosis for both chemical modification patterns.

FIG. 44A is a study design depicting prevention and treatment of rat toxicity by GalNAc-siRNAs using REVERSIR™. FIG. 44B is a bar graph showing liver exposures for GalNAc-siRNAs in rat prevention (siRNA-1 and siRNA-4) or treatment (siRNA-5) toxicity studies as assessed by stem-loop RT-qPCR for the antisense strand (AS) at necropsy (nx). FIG. 44C is a bar graph showing liver RISC loading with or without REVERSIR™ treatment as assessed by stem-loop RT-qPCR for the antisense strand at necropsy. FIG. 44D shows serum glutamate dehydrogenase (GLDH) levels measured at necropsy. Differences between group means were evaluated for statistical significance using one-way ANOVA in GraphPad Prism 7. ns, not significant; *, $p<0.05$; , $p<0.01$; *, $p<0.001$; ****, $p<0.0001$. FIG. 44E are images showing H&E staining of liver sections collected at necropsy. Known toxic siRNAs administered alone or with a scrambled, control (Ctr) REVERSIR™ were associated with hepatocellular degeneration (bracket), single cell necrosis (*), increased sinusoidal cells consistent with Kupffer cell hyperplasia and/or infiltrating leukocytes (#), increased mitoses (^), bile duct hyperplasia with fibrosis (+), and hepatocellular vacuolation (arrow). Co-administration of a complementary REVERSIR™ decreased the severity of these findings and often limited their distribution.

FIG. 46A shows chemical structures of seed swapping between a hepatotoxic and a non-hepatotoxic GalNAc-siRNA. FIG. 46B is a bar graph showing liver exposures for parent and seed-swapped GalNAc-siRNAs in rat toxicity study as assessed by stem-loop RT-qPCR for the antisense strand (AS) at necropsy (nx). FIG. 46C is a bar graph showing Liver RISC loading as assessed by stem-loop RT-qPCR for the antisense strand at necropsy. FIG. 46D shows serum alanine aminotransferase (ALT) levels measured at necropsy. Differences between group means were evaluated for statistical significance using one-way ANOVA in GraphPad Prism 7. ns, not significant; *, $p<0.05$; , $p<0.01$; *, $p<0.001$; ****, $p<0.0001$. FIG. 46E are images showing H&E staining of liver sections collected at necropsy. The toxic siRNA had hepatocellular degeneration (bracket), single cell necrosis (*), increased sinusoidal cells consistent with Kupffer cell hyperplasia and/or infiltrating leukocytes (#), and hepatocellular vacuolation (arrow), while the non-toxic siRNA had only minimal vacuolation. The non-toxic seed in the toxic backbone was comparable to the full non-toxic siRNA, and the toxic seed in the non-toxic backbone had single cell necrosis, increased sinusoidal cells and vacuolation but at a lower severity grade than the full-length toxic compound.

FIG. 47A are volcano plots depicting global gene expression changes in rat hepatocytes at 24 h after transfection with 10 nM of GalNAc-siRNAs of four different sequences. FIG. 47B are volcano plots depicting global gene expression changes in rat liver at 24 h after subcutaneous administration of GalNAc-siRNAs at 50 mg/kg. Two parent GalNAc-siRNAs and their RNAi-inactive versions blocked with inverted abasic (iB) caps are shown. Light points, adjusted p-value<0.05; dark points, adjusted p-value>0.05; N=3 animals/group. The adjusted p-value for fold change was calculate in DESeq2 using the Wald test with multiple test correction. Seed enrichment p-value was calculated using the Fisher's exact test. The variance was similar between groups that were statistically compared.

FIG. 48A shows thermally-destabilizing glycol nucleic acid (GNA) modification at position seven of the antisense strand of exemplary toxic siRNA-5. FIG. 48B are volcano plots depicting global gene expression changes in rat hepatocytes at 24 h after transfection with 10 nM of parent or GNA-modified GalNAc-siRNAs. N=3 technical replicates. FIG. 48C is a bar graph showing liver exposures for parent and seed-modified siRNA-5 in rat toxicity study as assessed by stem-loop reverse transcription-quantitative PCR (RT-qPCR) for the antisense strand (AS) at necropsy (nx). FIG. 48D is a bar graph showing liver RISC loading as assessed by stem-loop RT-qPCR for the antisense strand at necropsy. FIG. 48E shows serum glutamate dehydrogenase (GLDH) levels measured at necropsy. Differences between group means were evaluated for statistical significance using one-way ANOVA in GraphPad Prism 7. ns, not significant; *, $p<0.05$; , $p<0.01$; *, $p<0.001$; ****, $p<0.0001$. FIG. 48F are images showing H&E staining of liver sections collected at necropsy. The toxic parent siRNA-5 had fibrosis (circle), hepatocellular degeneration (bracket), single cell necrosis (*), increased mitoses (^), increased sinusoidal cells consistent with Kupffer cell hyperplasia and/or infiltrating leukocytes (#), and hepatocellular vacuolation (arrow), while the non-toxic siRNA had only minimal vacuolation. The seed GNA-modified siRNA-5 had degeneration, single cell necrosis, increased mitoses and vacuolation but at a lower incidence and severity grade than the parent siRNA-5 N=4 animals/group; qw, weekly dosing; GNA, glycol nucleic acid.

FIG. 49A is a bar graph showing rat hepatocyte mRNA knockdown which was assessed at 24 hrs post-10 nM transfection by reverse transcription-quantitative PCR (RT-qPCR) for target mRNA and normalized to a housekeeping mRNA (18S rRNA), relative to the mock transfection. FIG. 49B is a bar graph showing liver mRNA knockdown which was assessed at necropsy by RT-qPCR for target mRNA and normalized to a housekeeping mRNA (18S rRNA), relative to the saline control group. Qw, weekly dosing; GNA, glycol nucleic acid.

FIG. 52 shows a position specific reduction in off-target effects in TTR-targeting dsRNAs in vitro. FIG. 53 shows a position specific reduction in off-target effects in F9-targeting dsRNAs in vitro. As seen, dsRNAs significantly reduced the number of genes that were down- or up-regulated by their respective parent dsRNAs.

DETAILED DESCRIPTION

Figure 1:
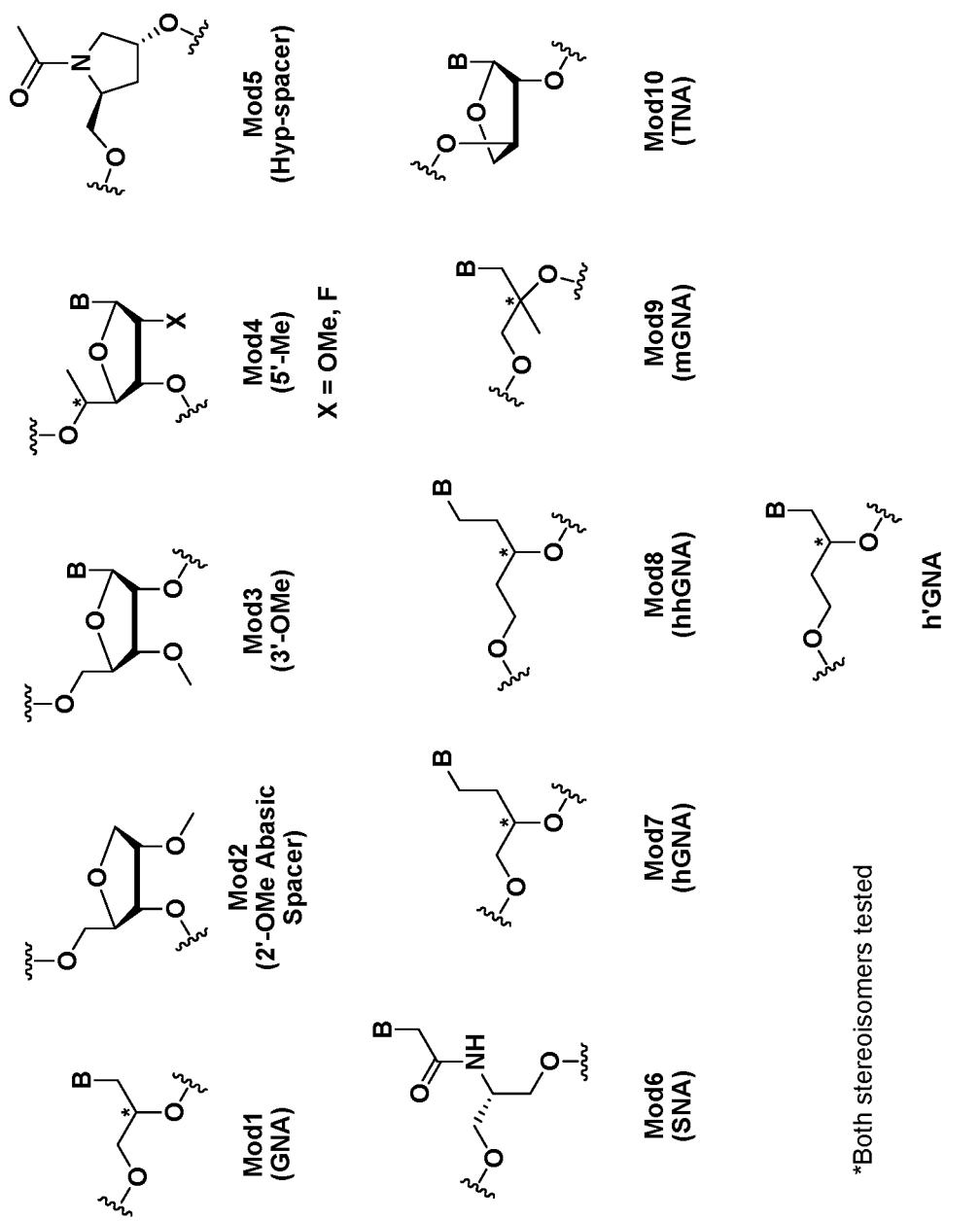
FIG. 1 shows some exemplary destabilizing modifications of the invention.
Figure 2:
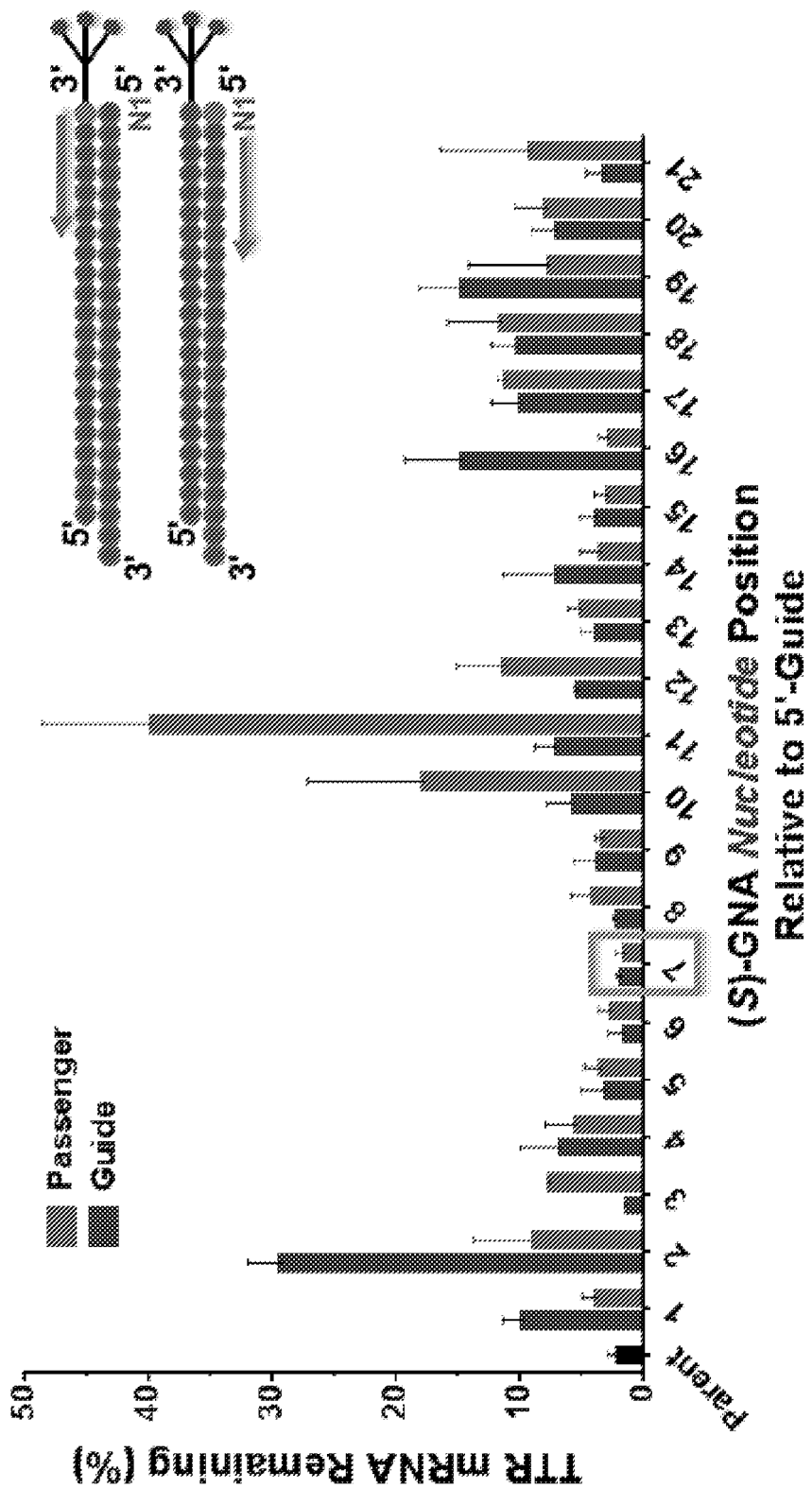
FIG. 2 shows positional effect of a single (5)-glycol nucleic acid (GNA) modification in the antisense strand on in vitro conjugate activity. Single substitution with the (S)-GNA is well tolerated at or opposite antisense seed region (positions 5-8 of antisense strand) but not tolerated in sensitive positions (positions 1 and 2 of antisense strand, and positions 11 and 12 of sense strand)
Figure 3:
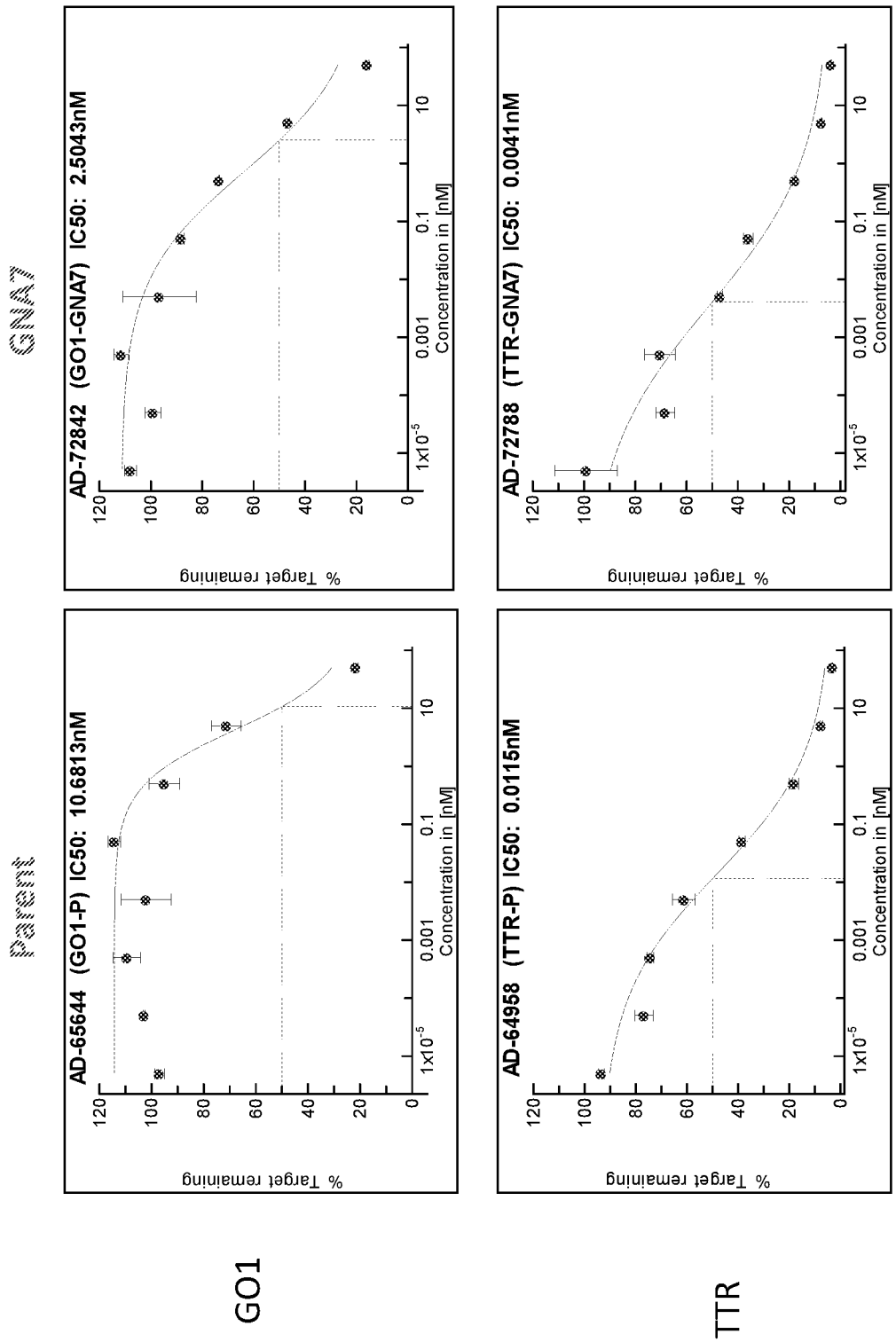
FIG. 3 shows that an exemplary dsRNA according to the invention had equivalent on target activity relative to the parent dsRNA.
Figure 4:
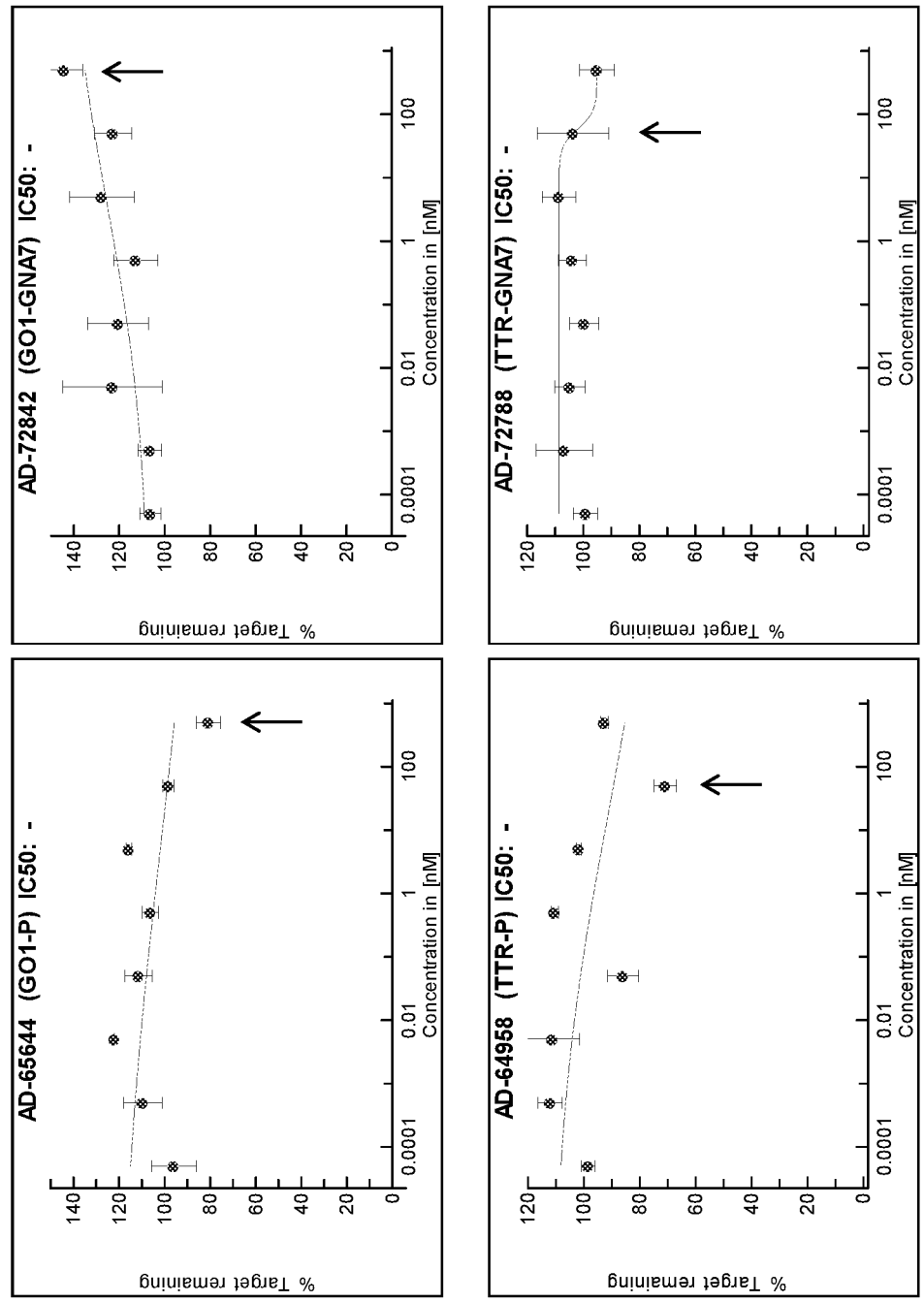
FIG. 4 shows that an exemplary dsRNA of the invention had no off-target activity at high doses.
Figure 5:
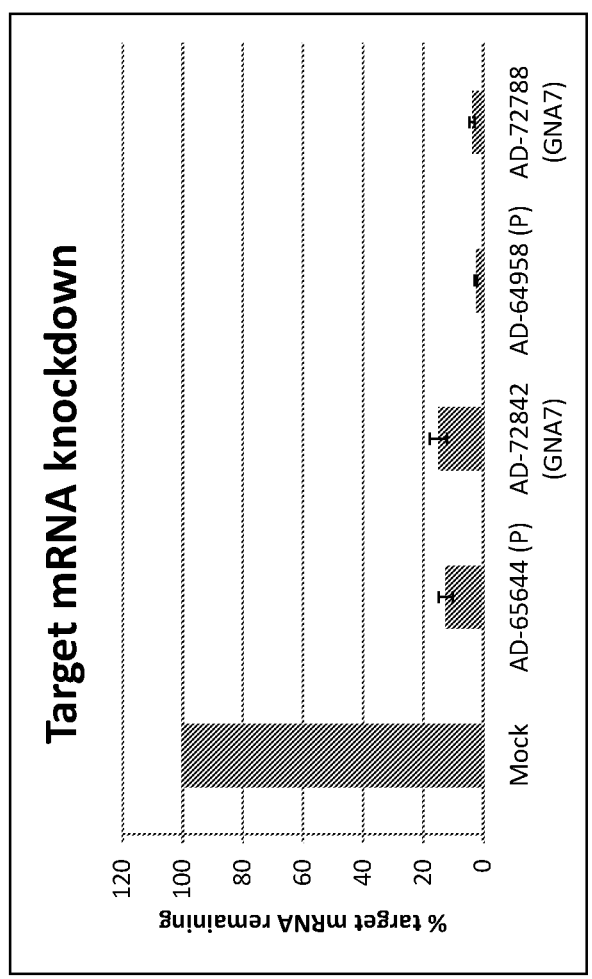
FIG. 5 shows that exemplary dsRNAs of the invention have comparable gene (GO1 and TTR) knockdown in rat hepatocytes.
Figure 6:
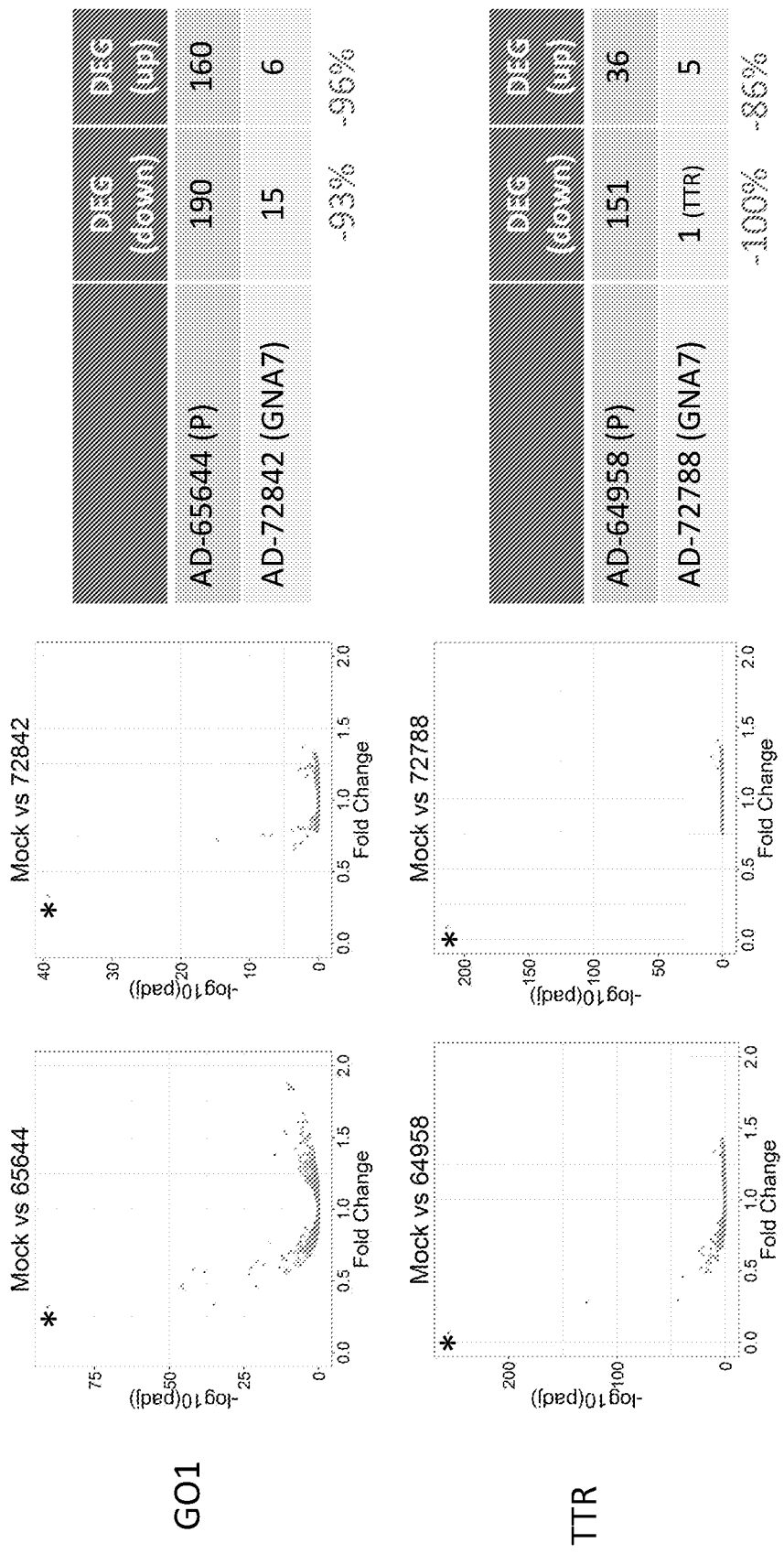
FIG. 6 shows that exemplary dsRNAs of the invention mitigate endogenous off-target effects. As seen, both dsR-NAs significantly reduced the number of genes that were down- or up-regulated by their respective parent dsRNAs.
Figure 7:
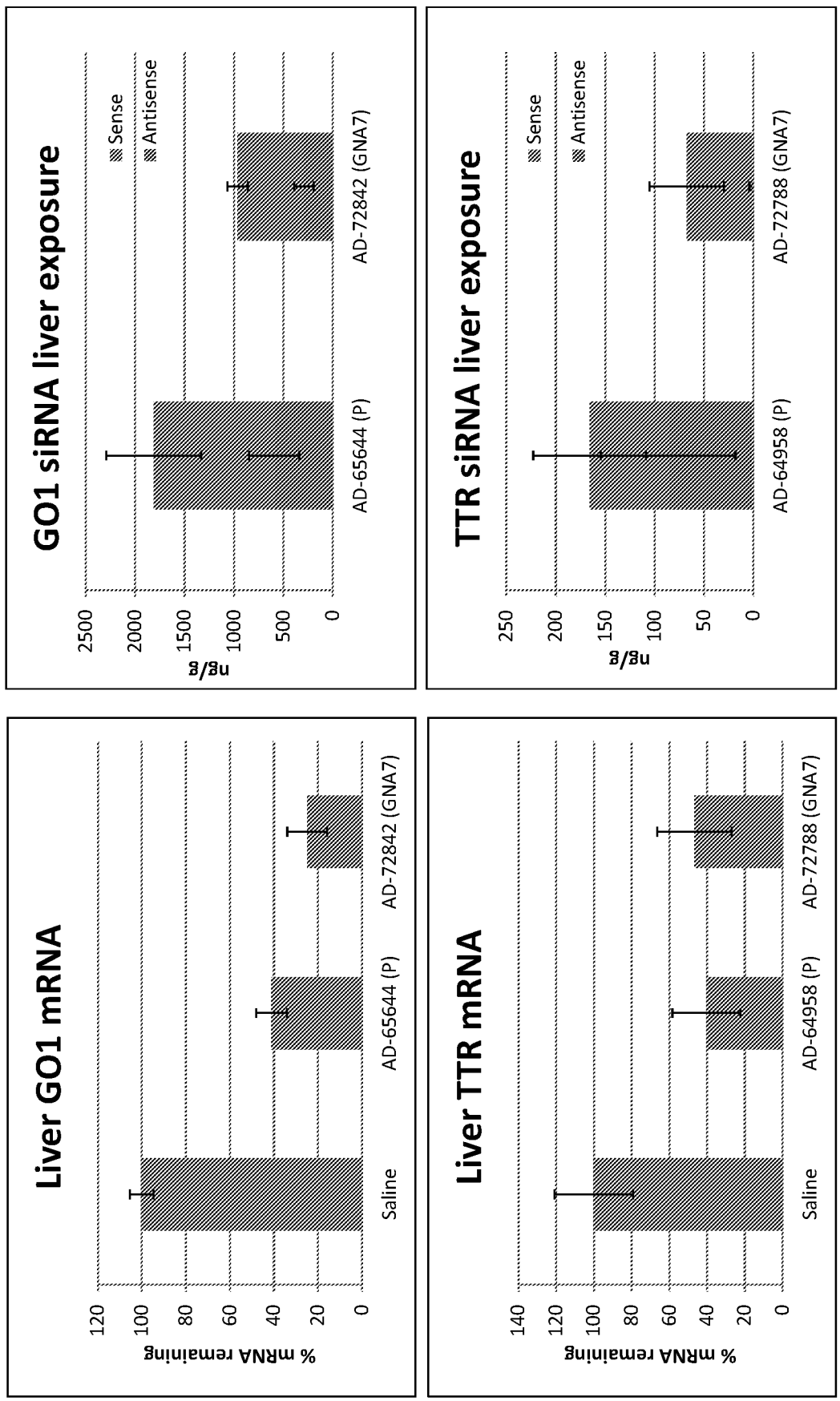
FIG. 7 shows that exemplary dsRNAs according to the invention have comparable potency as the parent dsRNA.
Figure 8:
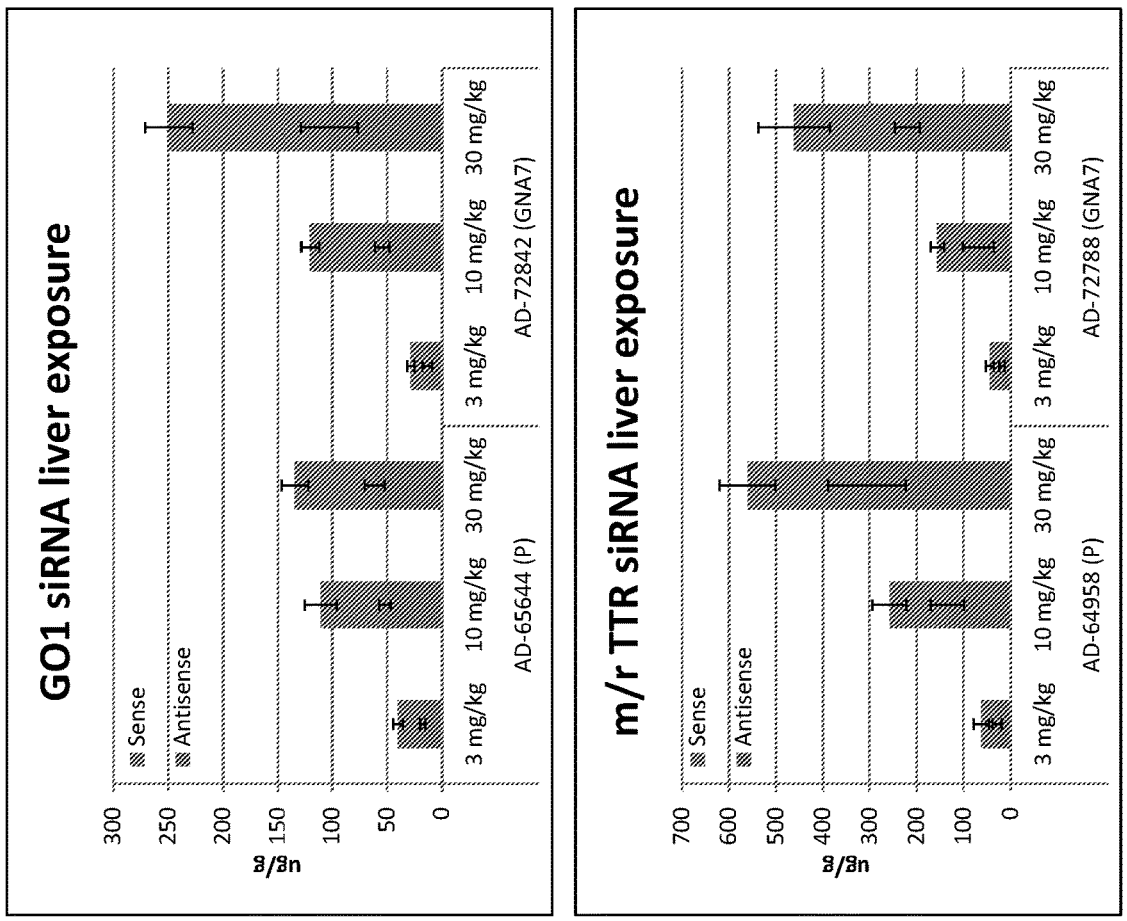
FIG. 8 shows that exemplary dsRNAs according to the invention have comparable liver accumulation as the parent dsRNA.
Figure 9:
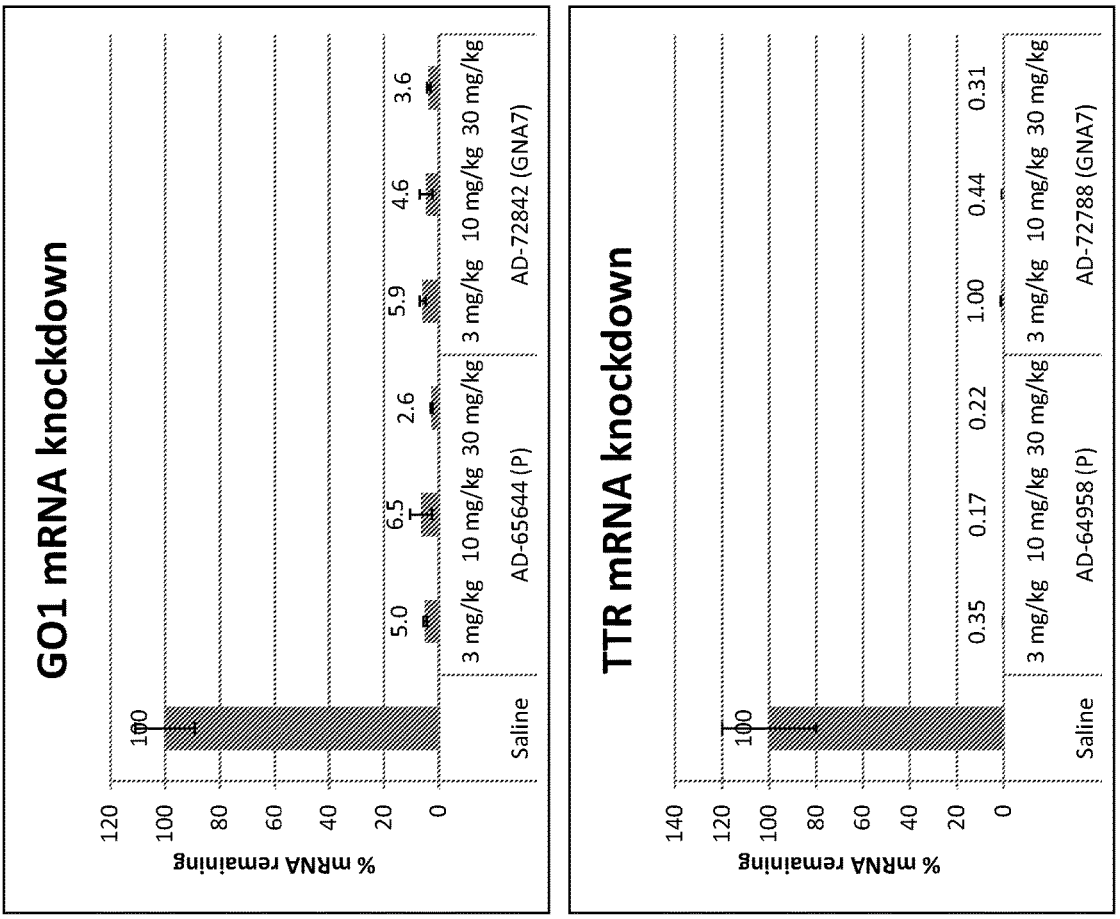
FIG. 9 shows that exemplary dsRNAs according to the invention have comparable on-target activity as the parent dsRNA.
Figure 10:
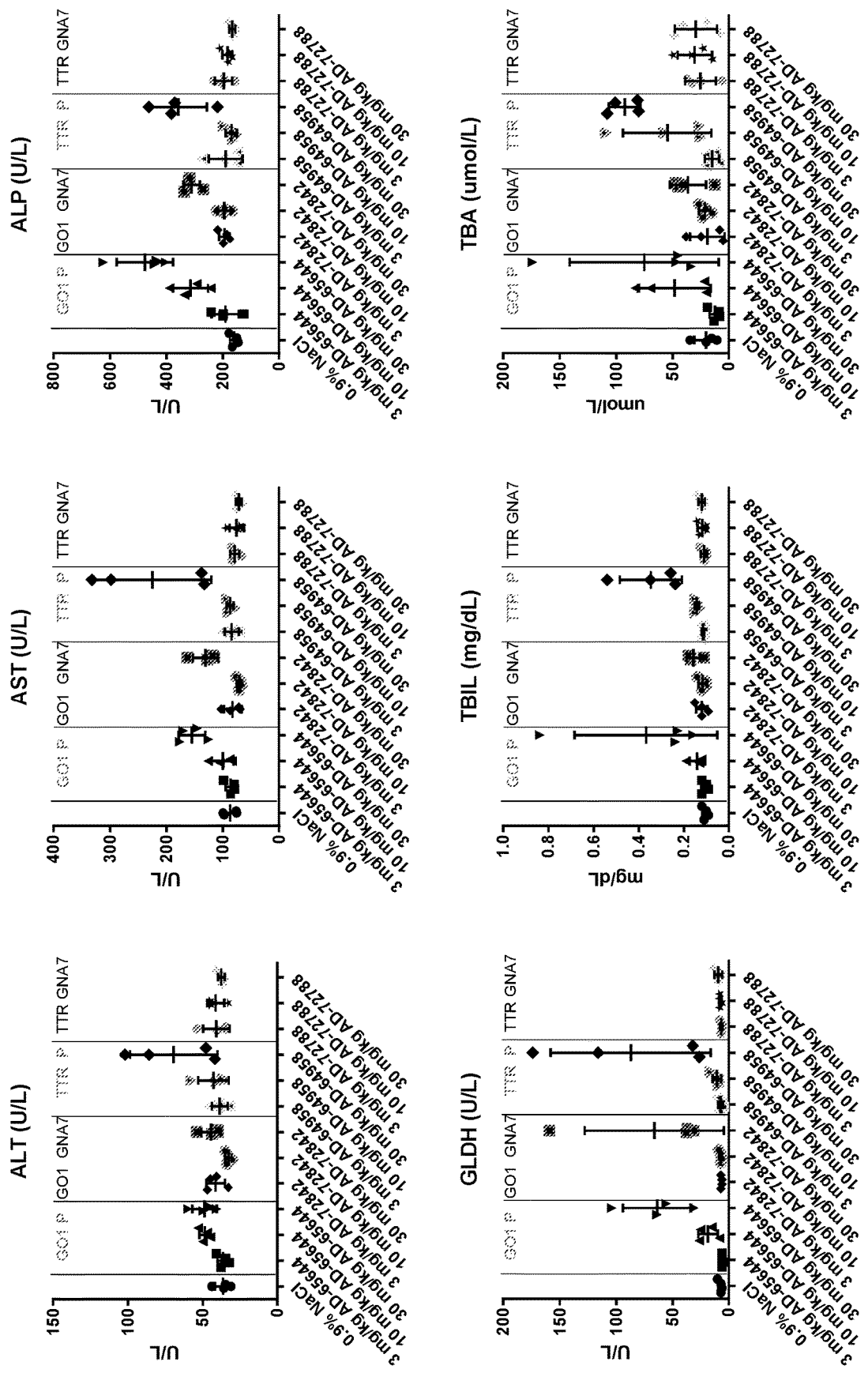
FIG. 10 shows clinical pathology parameters of exemplary dsRNAs administered at various concentrations.
Figure 11:
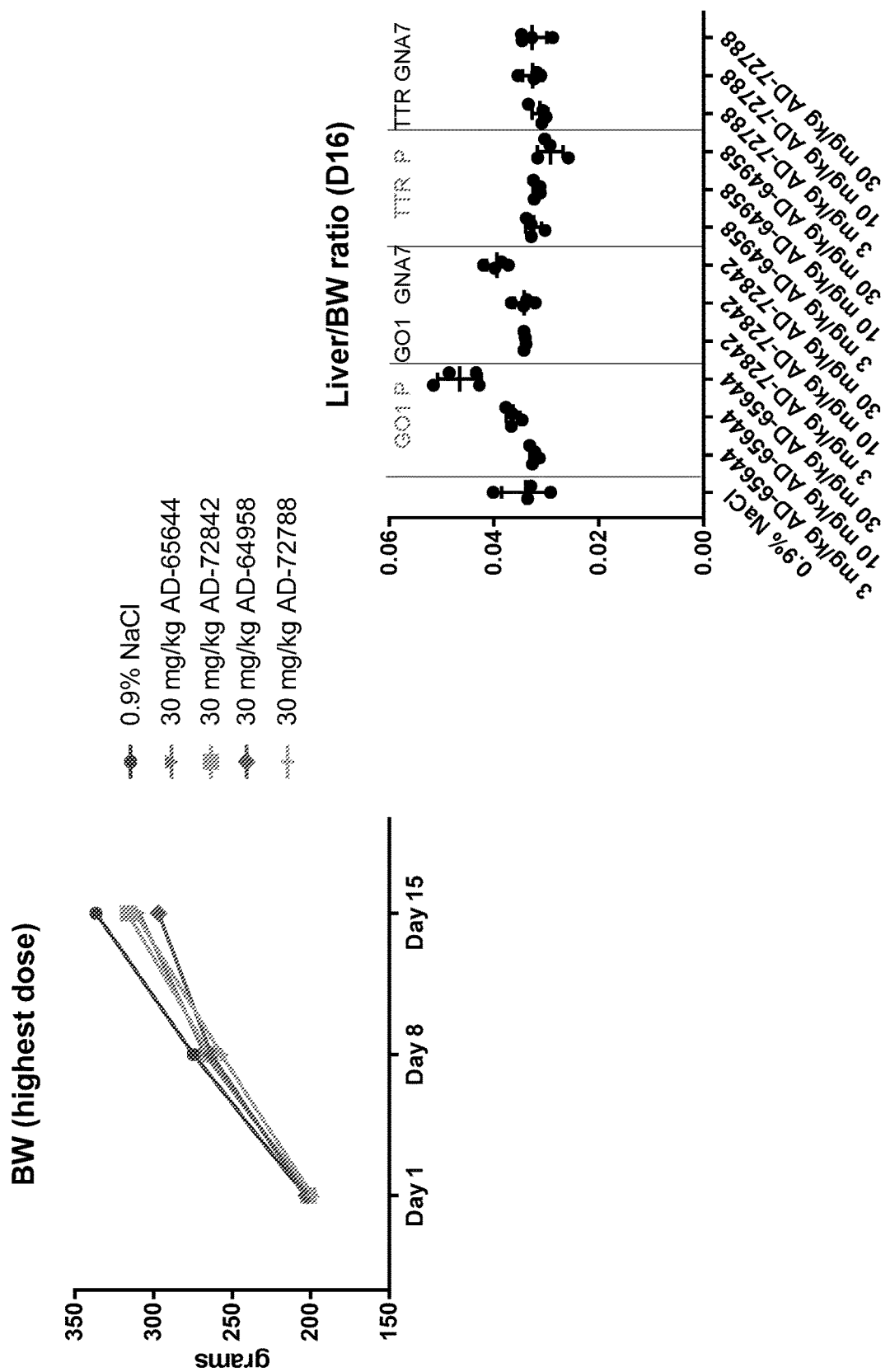
FIG. 11 shows normalized body weight gain and liver/body weight ratio on administering an exemplary dsRNA of the invention.
Figure 12:
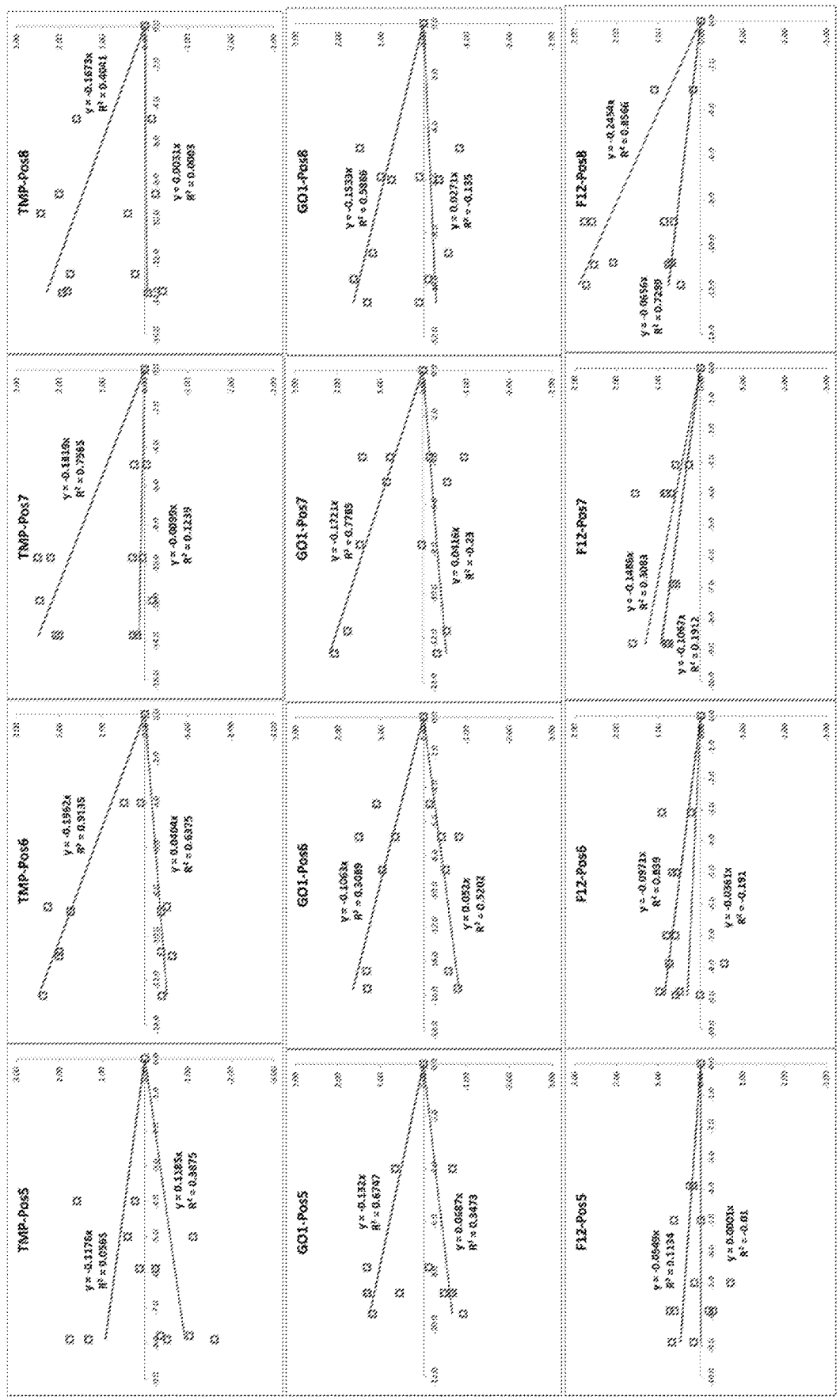
FIG. 12 shows the correlation between $\Delta T_m$ and On- and Off-target activity across specified positions of different sequences. Light data points=on-target activity; Dark data points=off-target activity.
Figure 13:
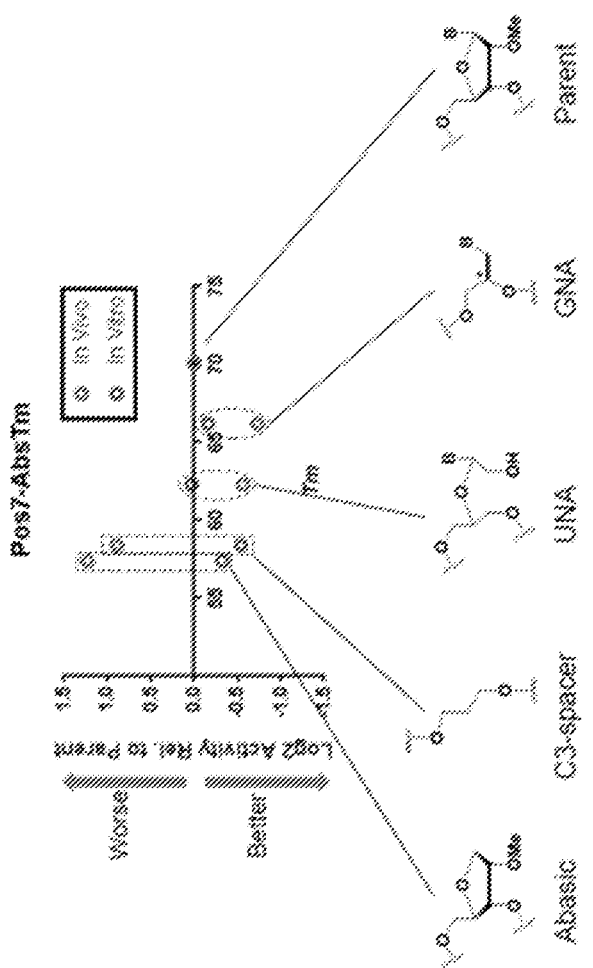
FIG. 13 shows the effect of dsRNA duplex melting temperature on in vitro and in vivo activity.
Figure 14:
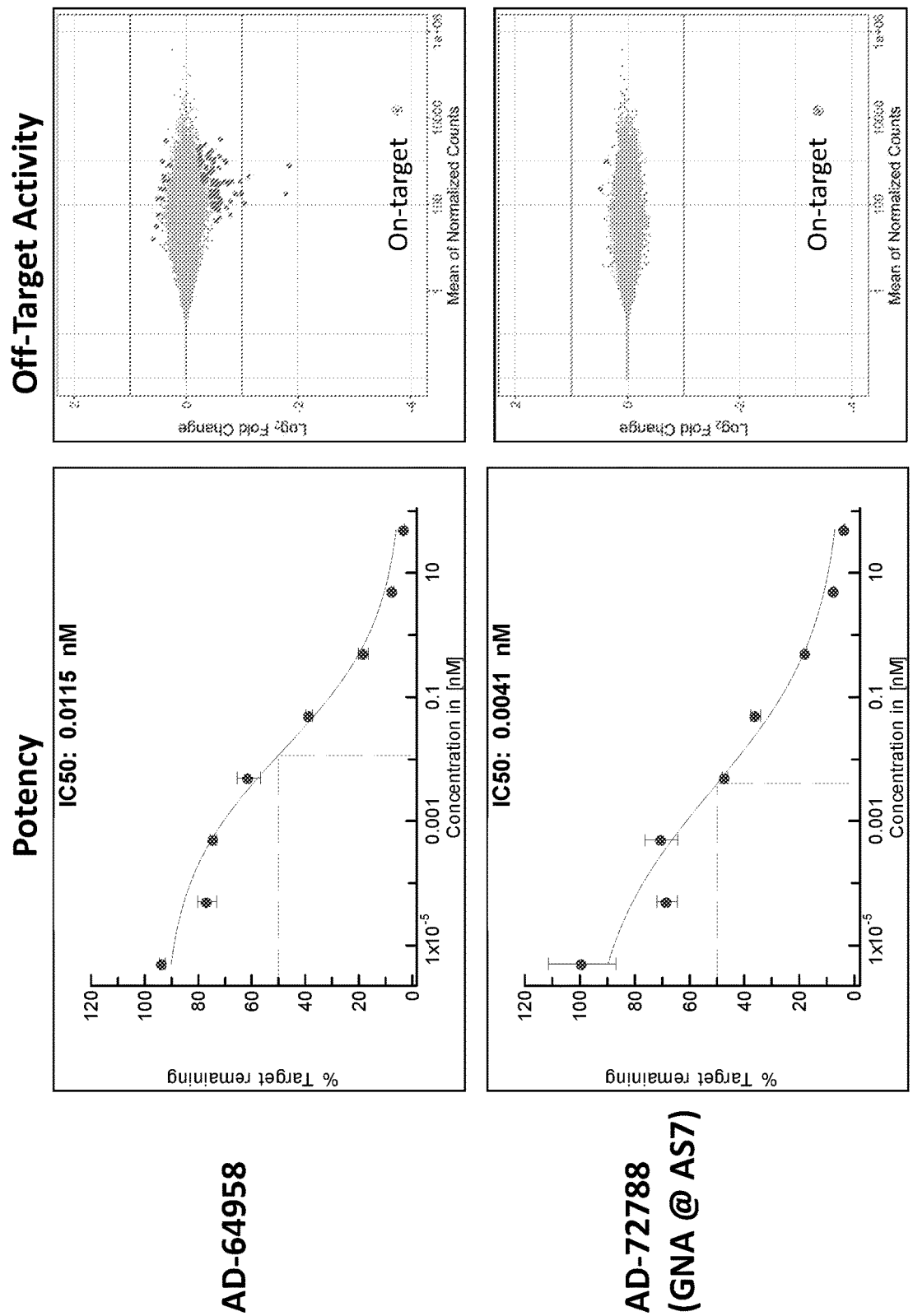
FIG. 14 shows that an exemplary dsRNA according to the invention had comparable potency but reduced off-target activity in vitro (PMH) relative to the parent dsRNA.
Figure 15:
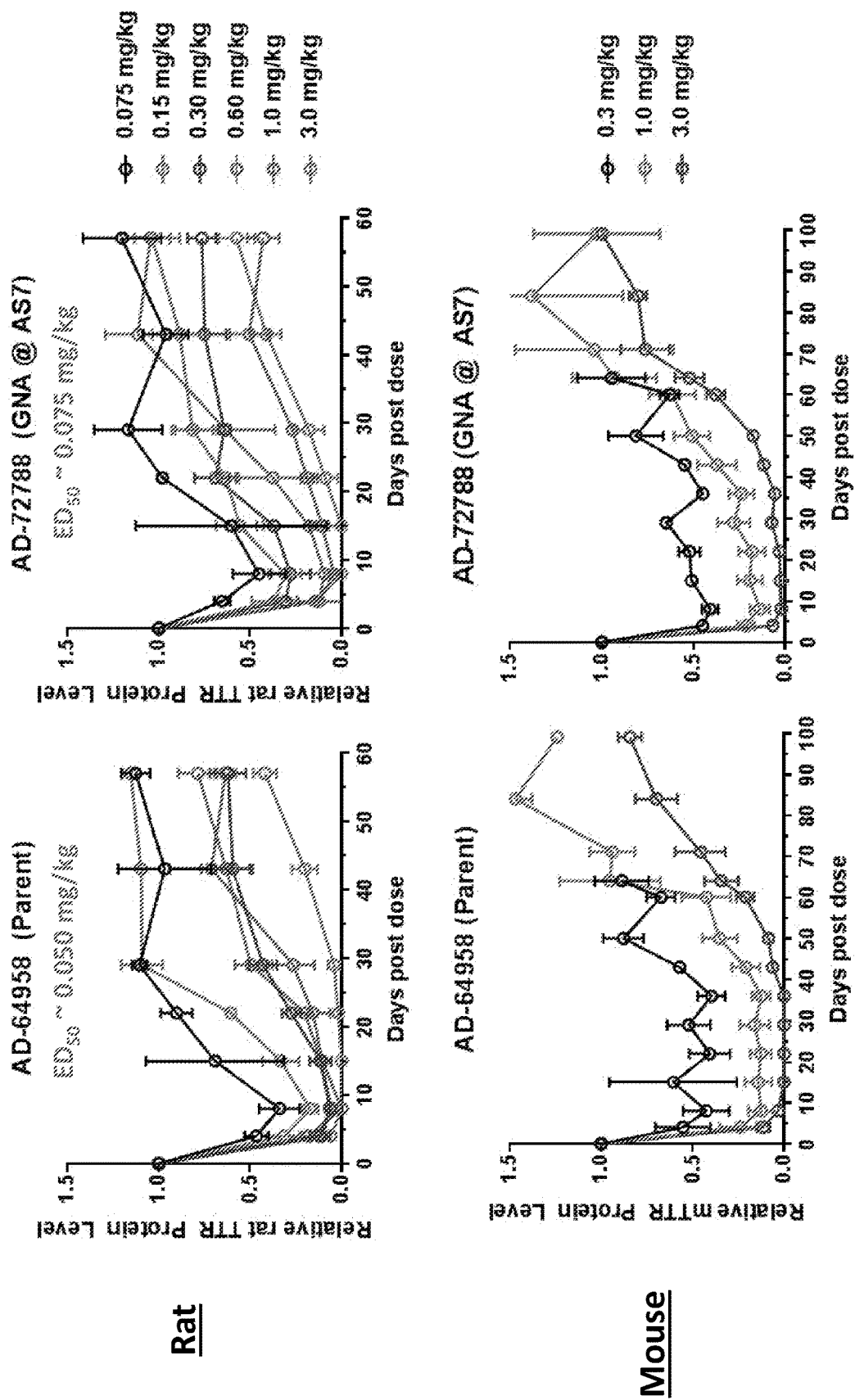
FIG. 15 shows that an exemplary dsRNA had comparable potency in vivo (rodents) relative to the parent dsRNA.
Figure 16:
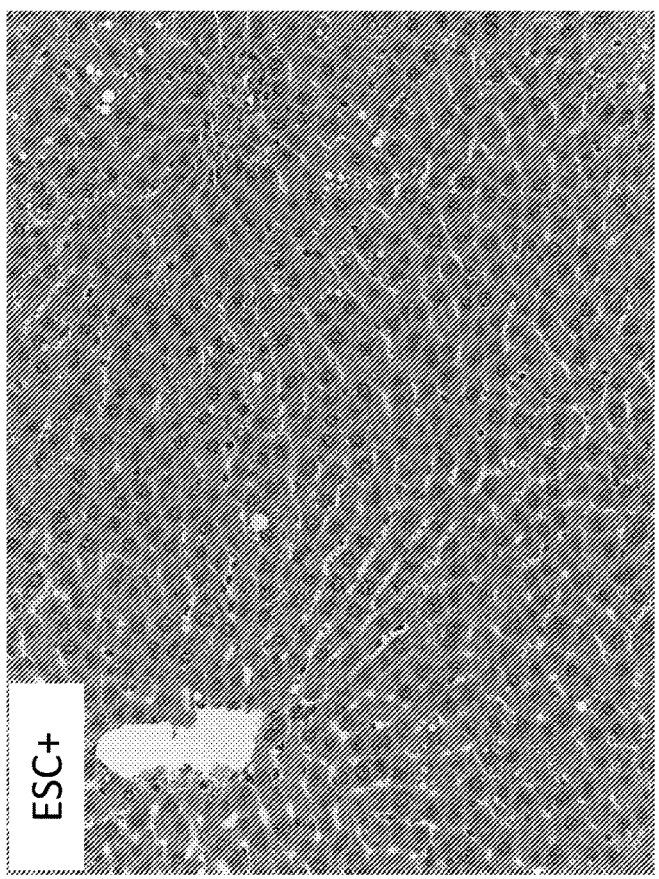
FIG. 16 shows that hepatotoxicity is mitigated in rats with an exemplary dsRNA of the invention (ESC+) relative to the parent dsRNA (ESC).
Figure 16:
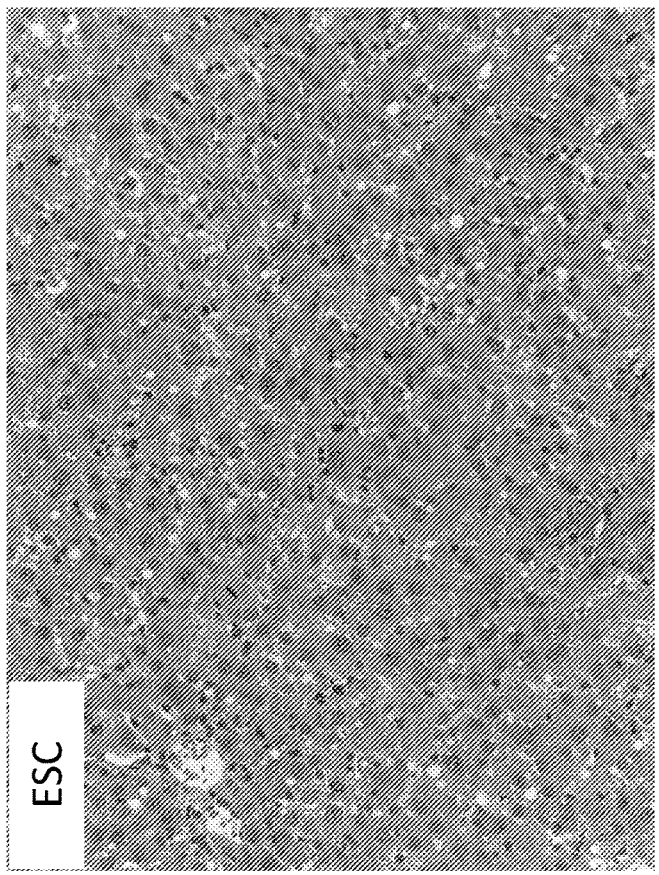
Figure 17:
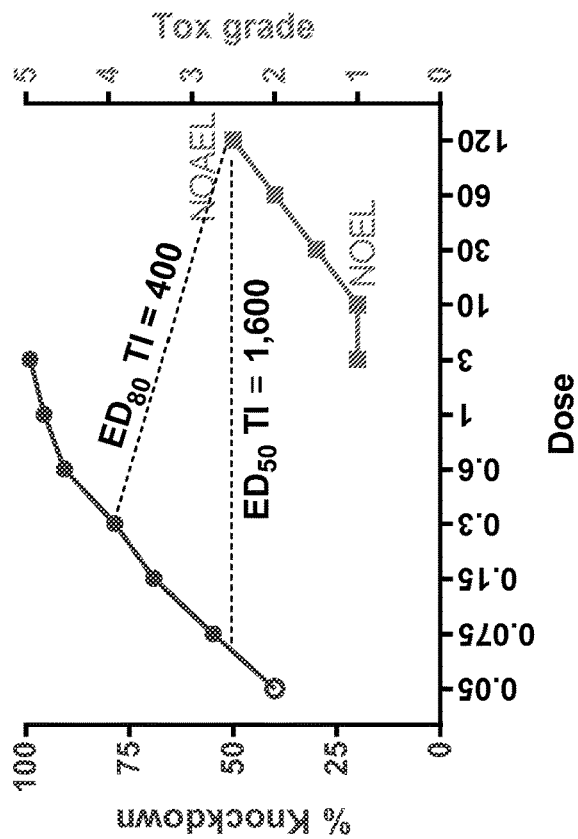
FIG. 17 shows that an exemplary dsRNA according to the invention had a 6 to 8-fold improvement in therapeutic index in vivo (rats) relative to the parent dsRNA.
Figure 17:
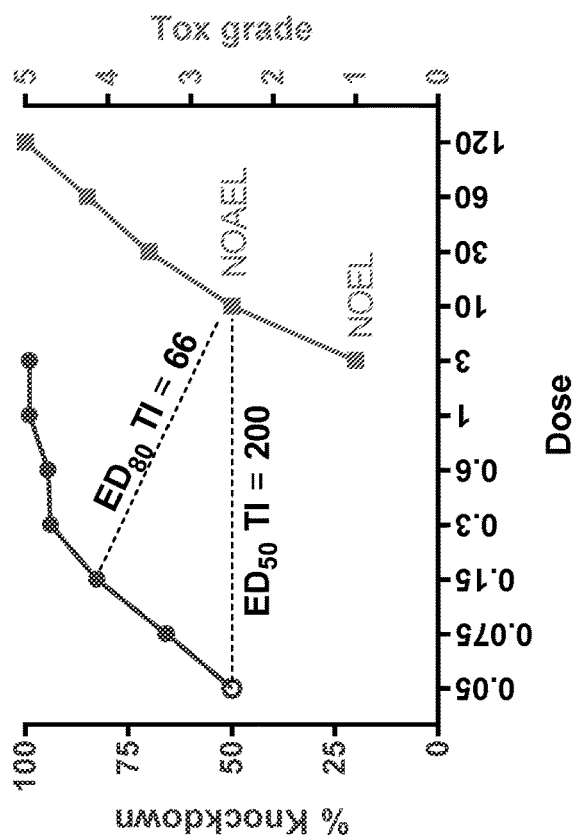
Figure 18:
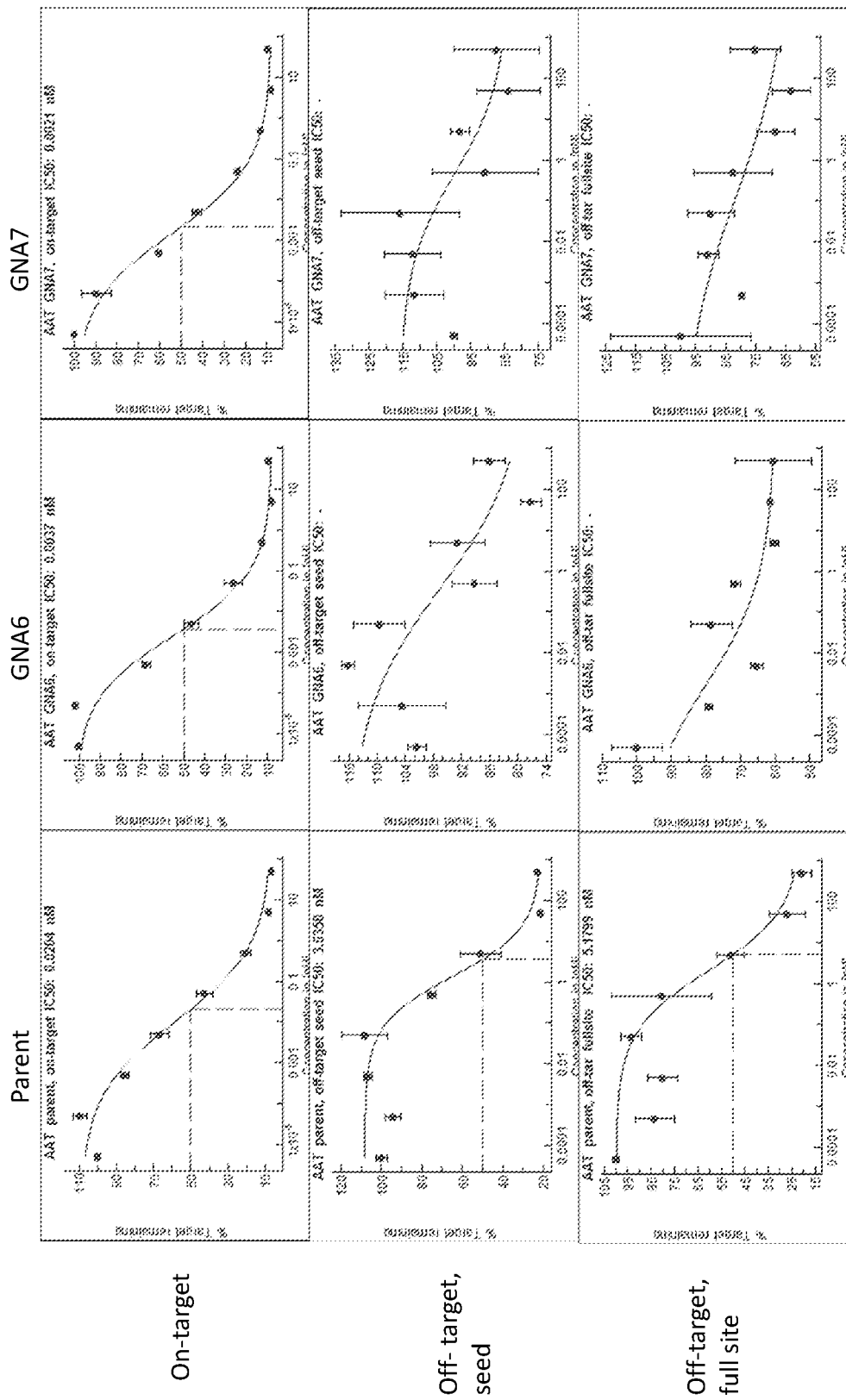
FIGS. 18 and 19 show that exemplary dsRNAs according to the invention had comparable IC50 for on-target activity but much lower off-target activity at comparable concentrations relative to the parent dsRNA, AD-61444 (FIG. 18) and AD-77407 (FIG. 19), in COS luciferase system.
Figure 19:
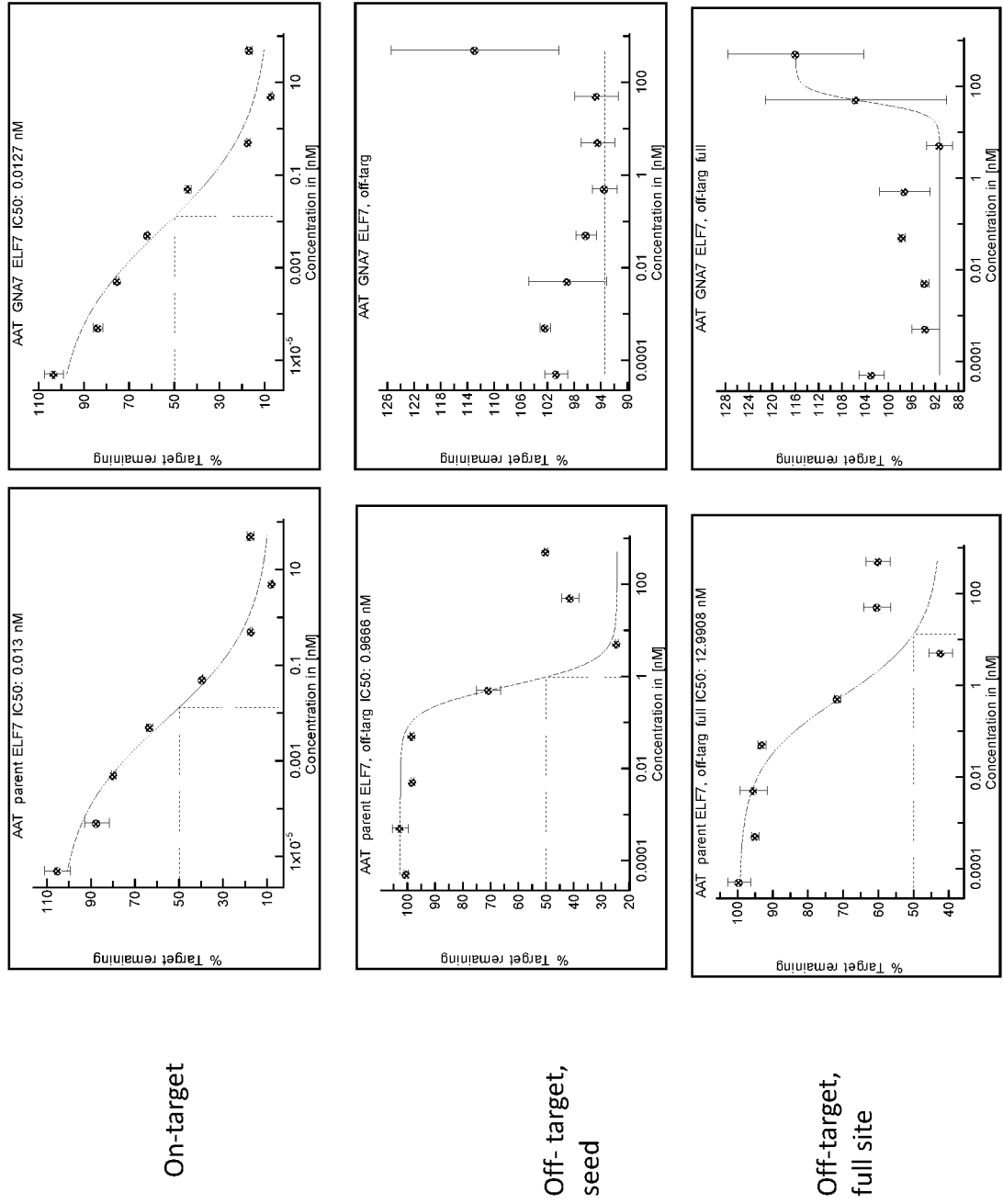
Figure 20:
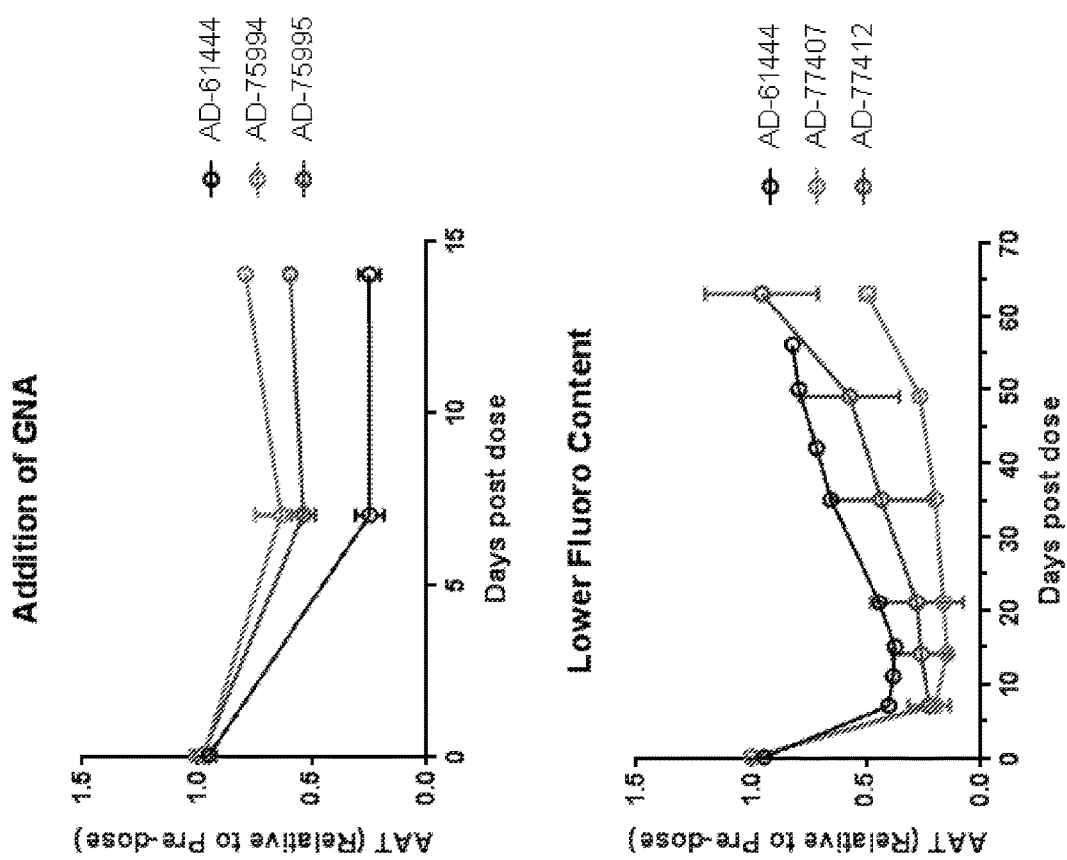
FIG. 20 shows that substitutions with GNA and 2'-F at exemplary positions according to the invention do not adversely effect in vivo activity relative the parent dsRNA. Sequences of dsRNA are listed in Table 9.
Figure 21:
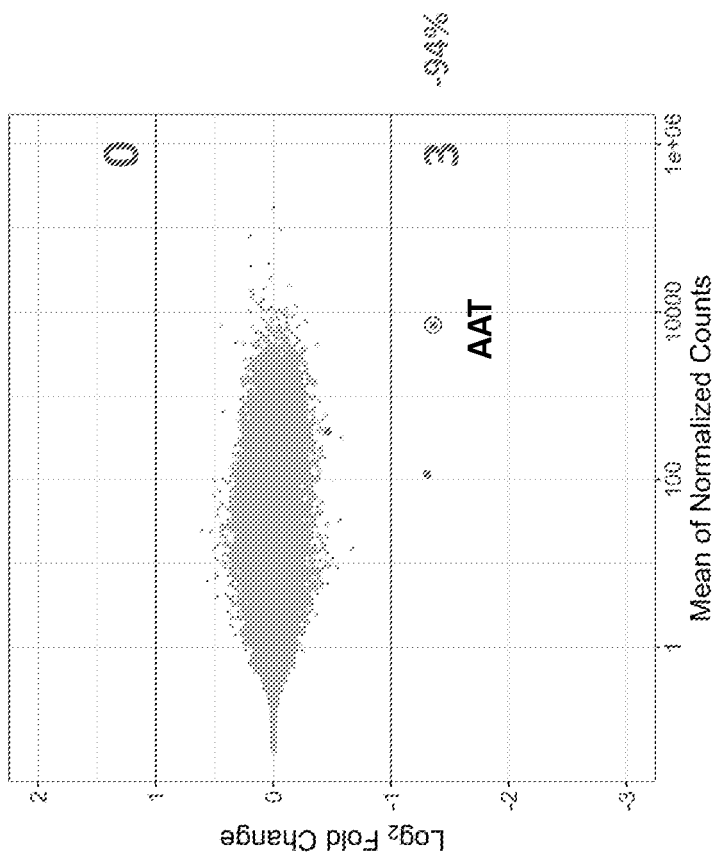
FIG. 21 shows that an exemplary dsRNA according to the invention reduced off-target effects. RNAseq from Hep3B cells transfected with 10 nm siRNA, 16 hrs. treatment.
Figure 21:
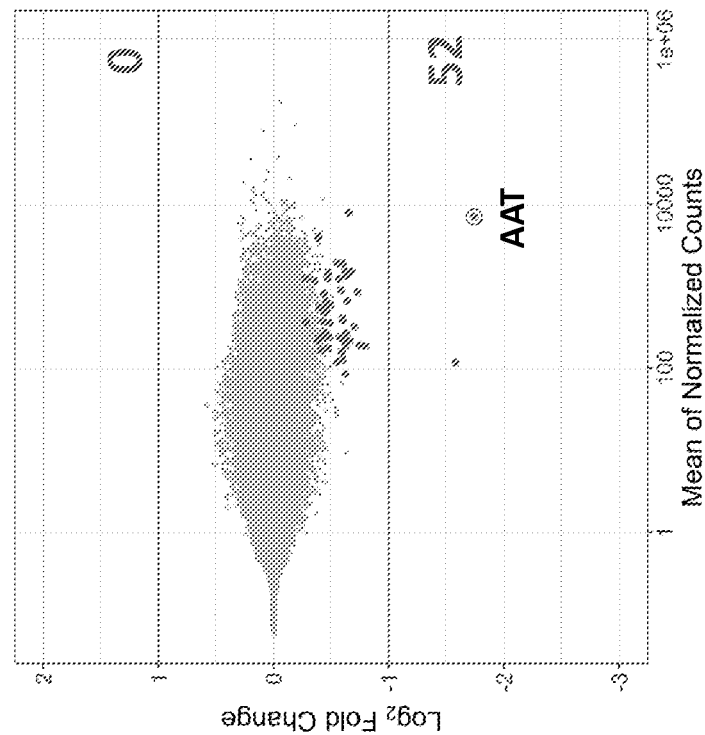
Figure 22:
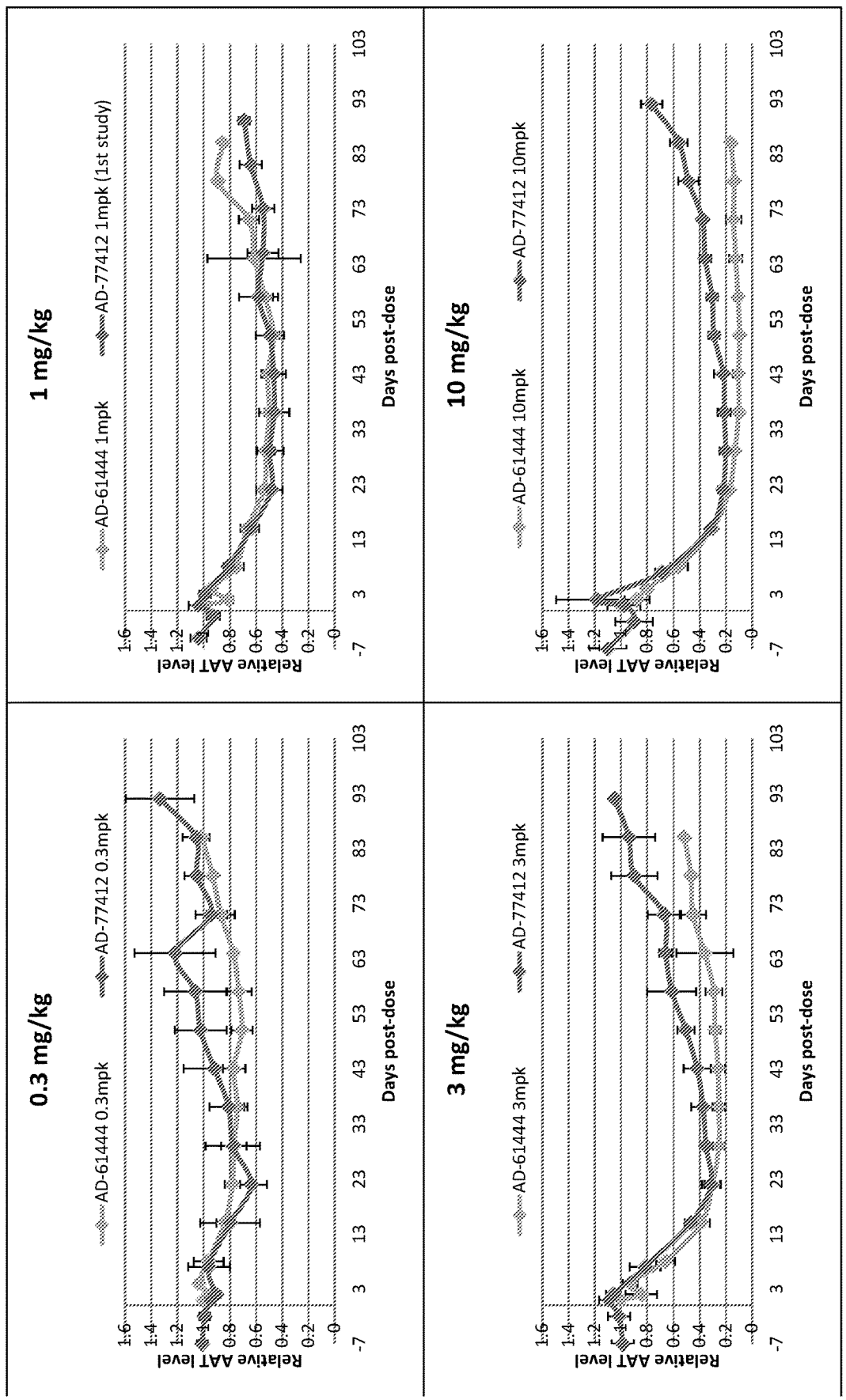
FIG. 22 shows that an exemplary dsRNA according to the invention had comparable single dose activity in non-human primates relative to the parent dsRNA at various dosages.
Figure 23:
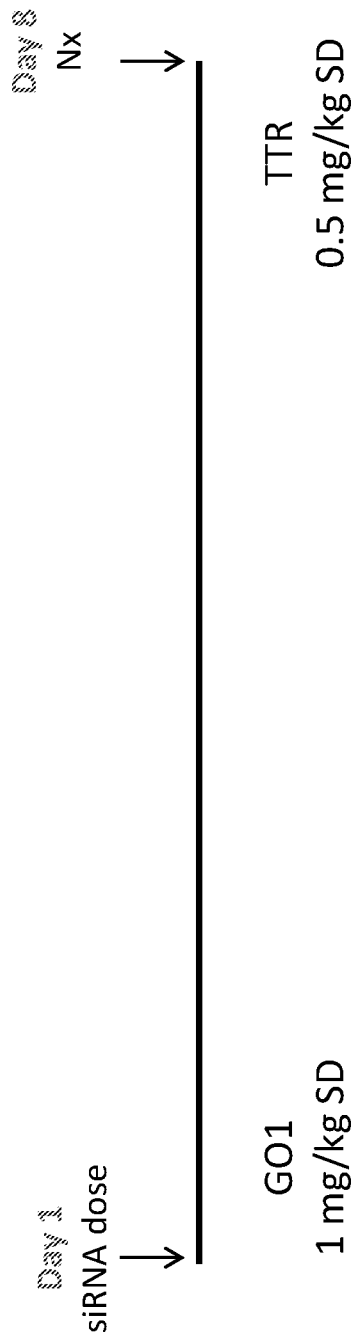
FIG. 23 shows a study design for in vivo mouse studies and exemplary dsRNAs for the study. Sequences of dsRNA sequences are listed in Table 9.
Figure 24:
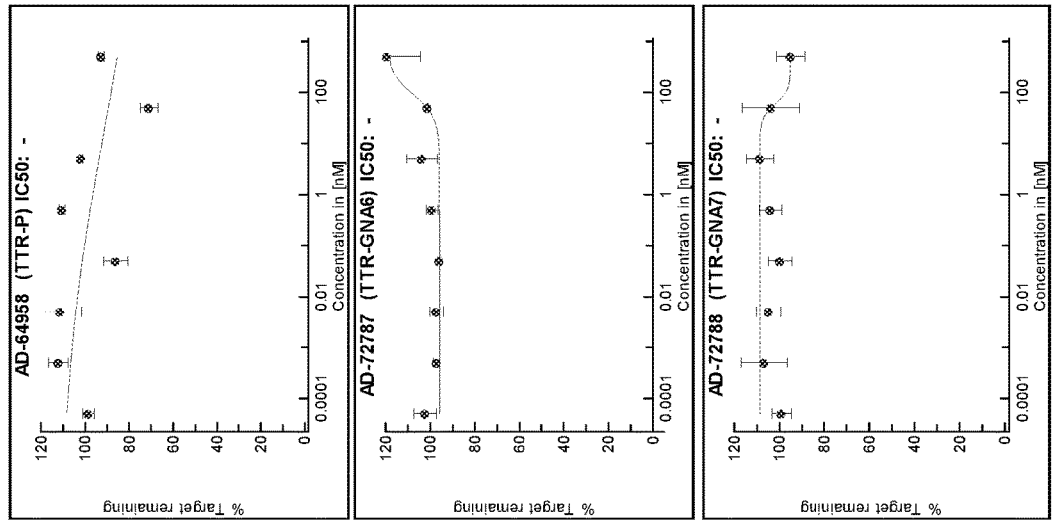
FIGS. 24 and 25 show that exemplary dsRNAs according to the invention had comparable IC50 for on-target activity but little or no off-target activity at comparable concentrations relative to the parent dsRNA in a COS luciferase system.
Figure 24:
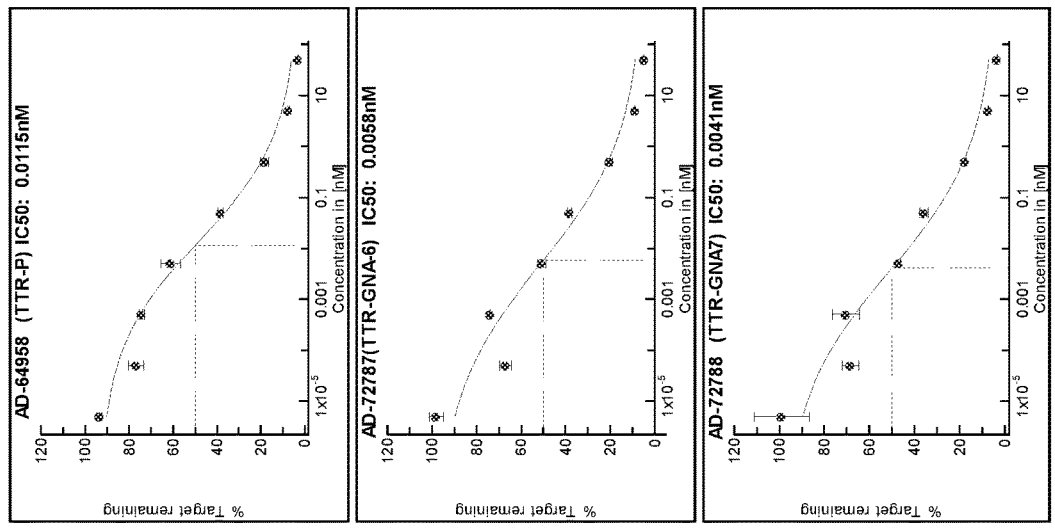
Figure 25:
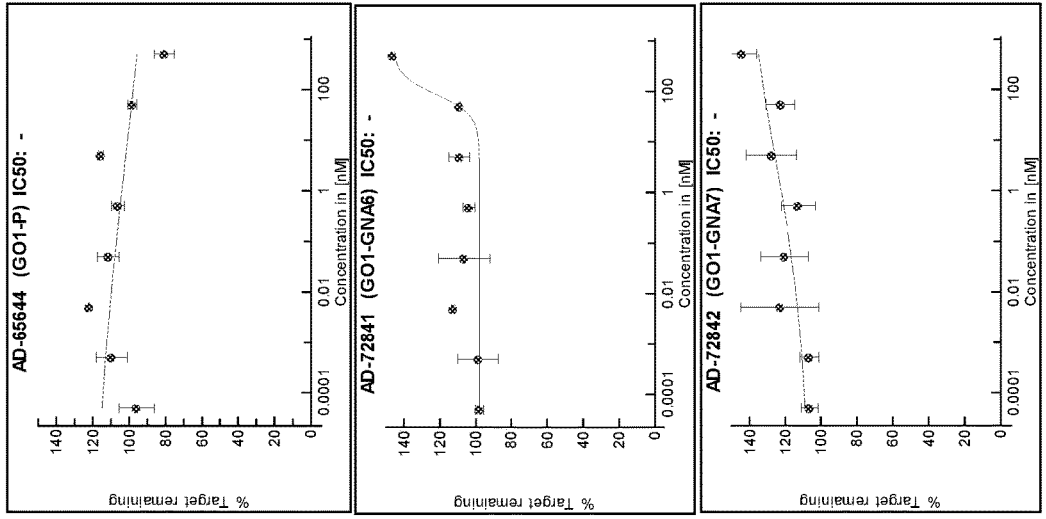
Figure 25:
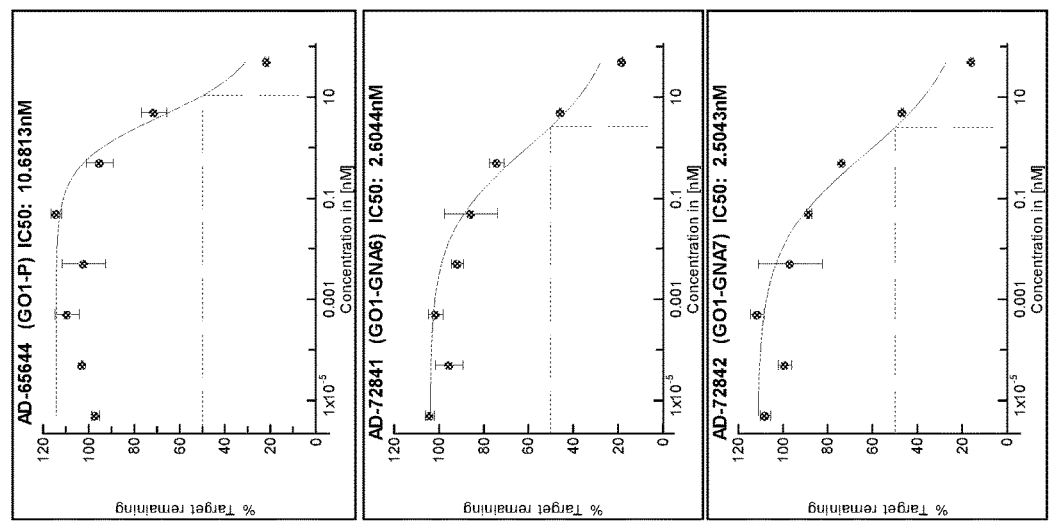
Figure 26:
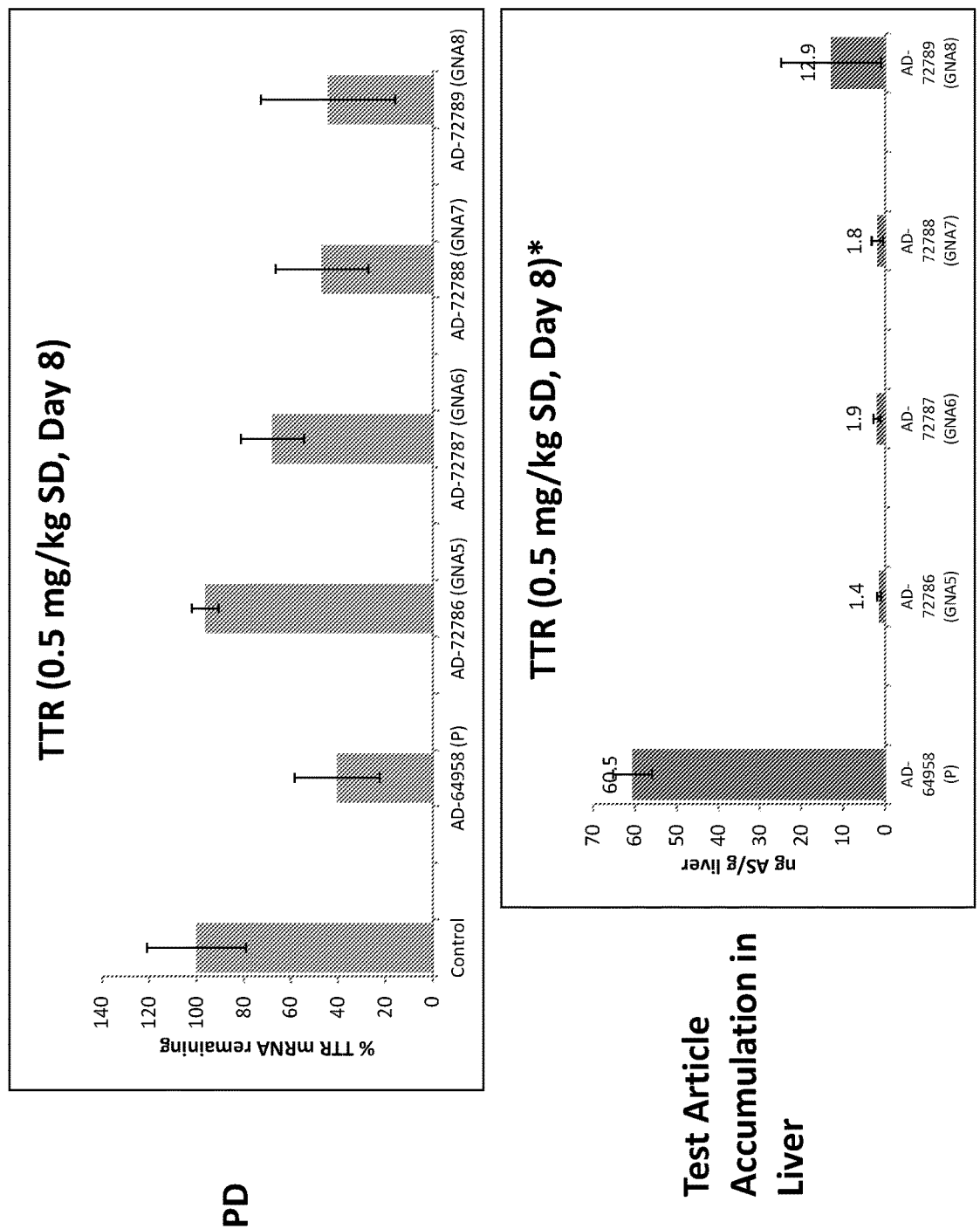
FIGS. 26 and 27 show that exemplary dsRNAs according to the invention have comparable gene knockdown in liver as the parent dsRNA despite reduced accumulation in liver.
Figure 27:
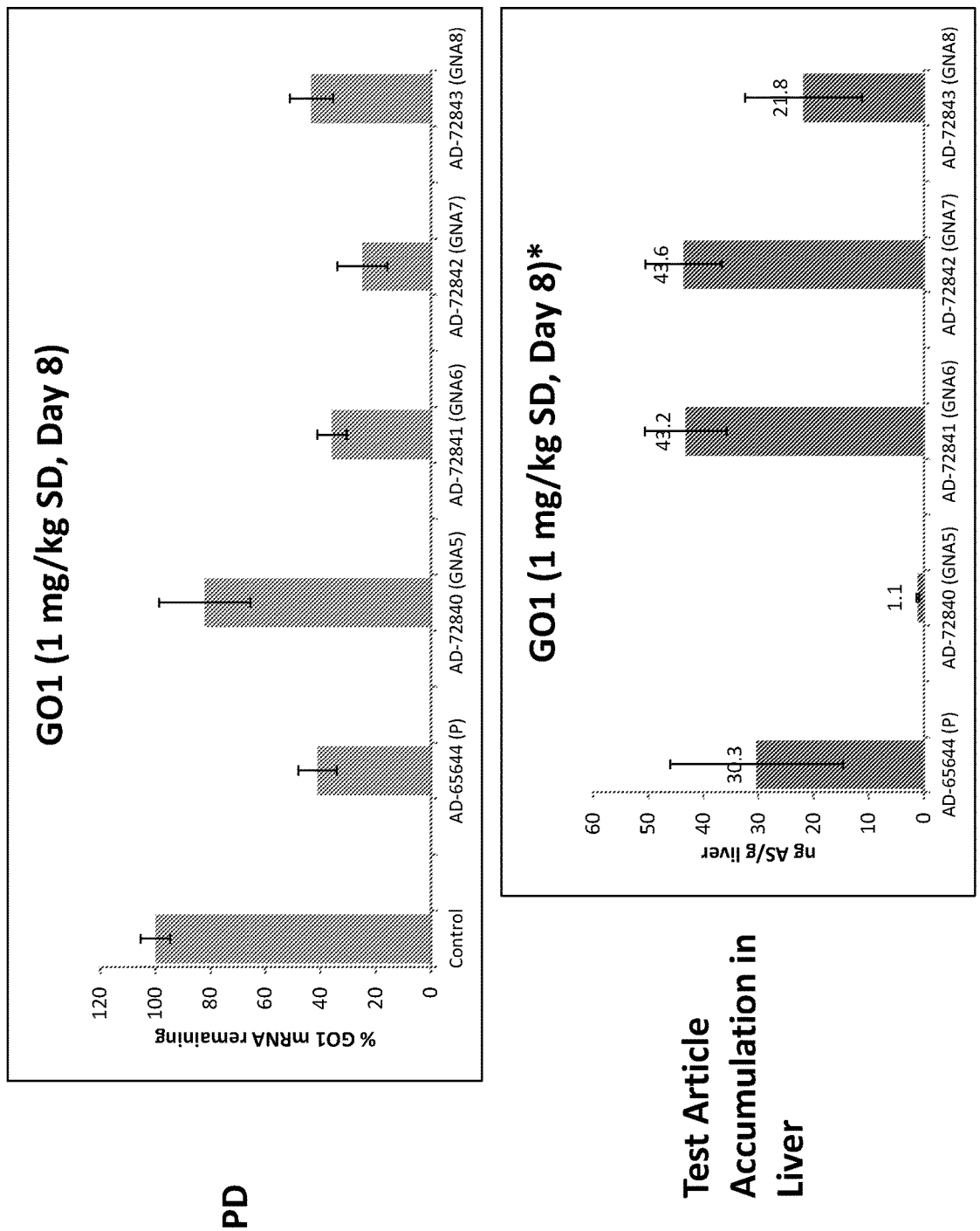
Figure 29:
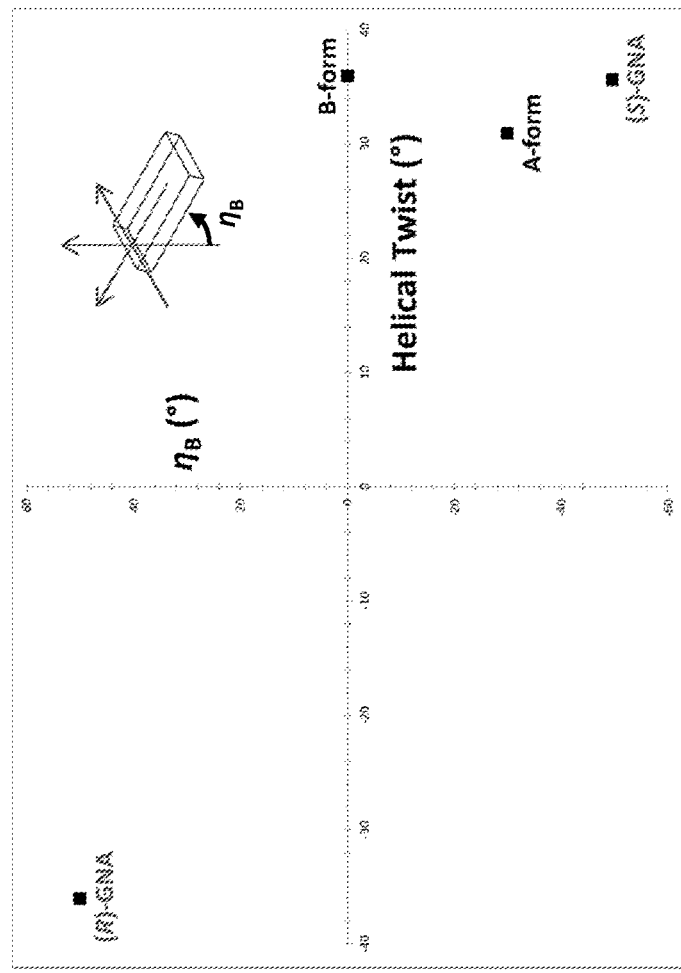
FIG. 29 shows backbone-base inclination ($\eta_B$) and helical twist values for A-form and B-form RNA/DNA, as well as for (S)-GNA. Values for (R)-GNA are extrapolated from the (S)-GNA values by using simple inversion.
Figure 28:
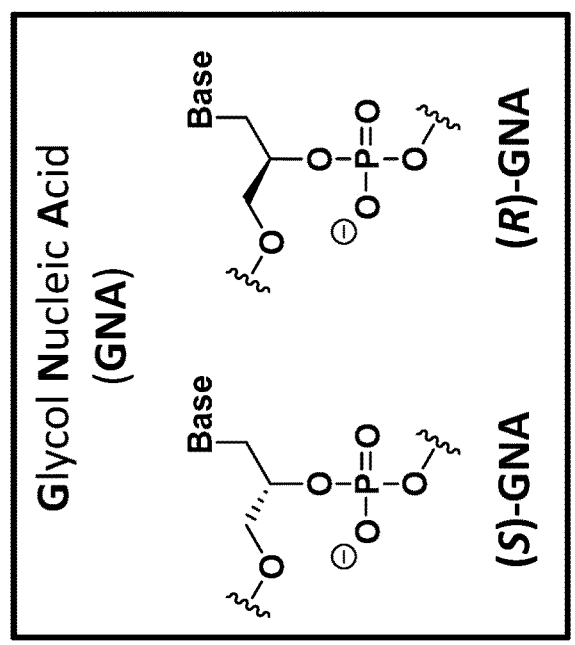
FIG. 28 is a schematic representation of structures of (S)-GNA and (R)-GNA.
Figure 30:
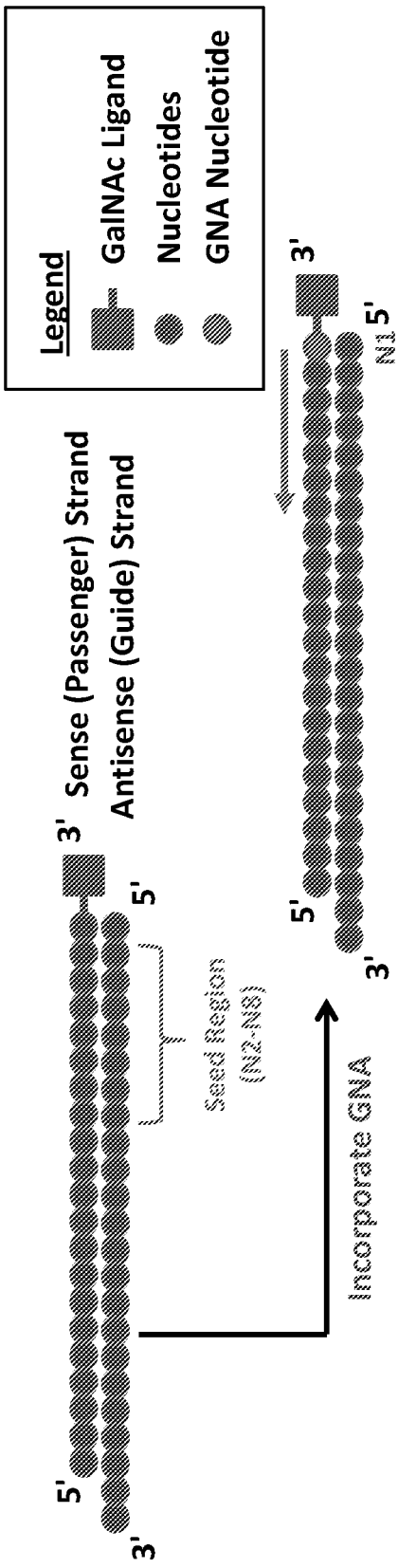
FIG. 30 is a schematic representation of thermal modulation of siRNA conjugate duplexes using GNA.
Figure 31:
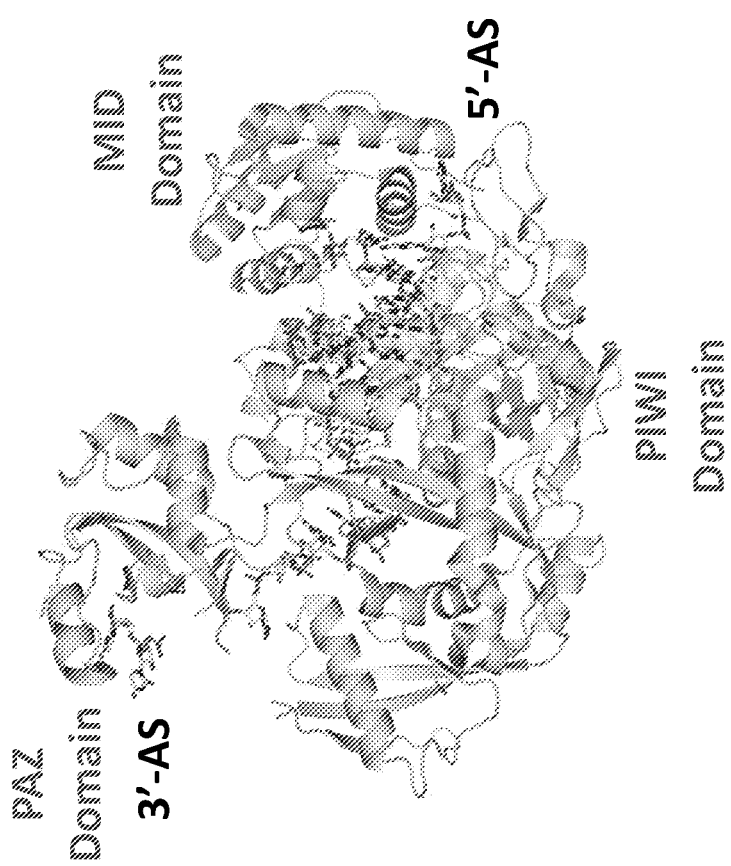
FIG. 31 is a schematic representation of structure of hAgo2, adapted from PDB file 4W5O and generated using PyMOL.

Inventors have discovered inter alia that off-target effects of dsRNA molecules can be reduced or inhibited by incorporating thermally destabilizing nucleotides at certain positions in the antisense strand of the dsRNA. With these thermally destabilizing modifications at certain positions in antisense strand, the dsRNA molecules were able to retain gene silencing activity similar to the parent dsRNA while having reduced off-target gene silencing. Further, the number of off-target genes that are down-regulated or up-regulated is also reduced by dsRNA molecules comprising these thermally destabilizing modifications when compared to the parent dsRNA.

As such, in one aspect, the invention provides a double-stranded RNAi (dsRNA) agent capable of inhibiting expression of a target gene. Generally, the dsRNA molecules of the invention show high on-target gene silencing while reducing or minimizing off-target gene silencing and/or toxicity. Without limitations, the dsRNA molecules of the invention can be substituted for the dsRNA molecules and can be used for in RNA interference based gene silencing techniques, including, but not limited to, in vitro or in vivo applications.

Generally, the dsRNA molecule comprises a sense strand (also referred to as passenger strand) and an antisense strand (also referred to as guide strand). Each strand of the dsRNA molecule can range from 12-40 nucleotides in length. For example, each strand can be between 14-40 nucleotides in length, 17-37 nucleotides in length, 25-37 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. Without limitations, the sense and antisense strands can be equal length or unequal length.

In some embodiments, the antisense strand is of length 18 to 35 nucleotides. In some embodiments, the antisense strand is 21-25, 19-25, 19-21 or 21-23 nucleotides in length. In some particular embodiments, the antisense strand is 23 nucleotides in length. Similar to the antisense strand, the sense strand can be, in some embodiments, 18-35 nucleotides in length. In some embodiments, the sense strand is 21-25, 19-25, 19-21 or 21-23 nucleotides in length. In some particular embodiments, the antisense strand is 21 nucleotides in length.

The inventors also discovered that for the dsRNA molecules to be more effective in vivo, the antisense strand must have some metabolic stability. In other words, for the dsRNA molecules to be more effective in vivo, some amount of the antisense stand may need to be present in vivo after a period time after administration. Accordingly, in some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 5 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 6 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 7 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 8 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 9 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 10 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 11 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 12 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 13 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 14 after in vivo administration. In some embodiments, at least 40%, for example at least 45%, at least 50%, at least 55%, at least 60%, at least 65%, at least 70%, at least 75%, or at least 80% of the antisense strand of the dsRNA is present in vivo, for example in mouse liver, at day 15 after in vivo administration.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), the dsRNA has a melting temperature ($T_m$) of from about 40° C. to about 80° C., and the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2% fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 12-40 nucleotide pairs in length; and (viii) a blunt end at 5'end of the antisense strand. In some embodiments, $T_m$ of from about 40° C. to about 80° C. is optional.

In some embodiments, the dsRNA molecule has a duplex region of 12-40 nucleotide pairs in length, wherein the antisense strand comprises at least one thermally destabilizing modification of the duplex within the seed region (i.e., at position 2-9 of the 5'-end of the antisense strand, counting from the 5'-end), and the dsRNA has a $T_m$ of from about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; and vii) a blunt end at 5'end of the antisense strand. In some embodiments, the $T_m$ of from about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), and wherein the dsRNA has a melting temperature of about 40° C. to about 80° C. In some embodiments, the $T_m$ of from about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), and wherein the dsRNA has a melting temperature of about 40° C. to about 80° C. (e.g., 40° C., 50° C., 60° C., 70° C. or 80° C.). In some embodiments, the $T_m$ of from about 40° C. to about 80° C. is optional.

In some particular embodiments, the thermally destabilizing modification of the duplex is at position 5, 6, 7, or 8 of the antisense strand, counting from 5'-end of the antisense strand.

In some particular embodiments, the thermally destabilizing modification of the duplex is at position 5 of the antisense strand, counting from 5'-end of the antisense strand.

In some particular embodiments, the thermally destabilizing modification of the duplex is at position 6 of the antisense strand, counting from 5'-end of the antisense strand.

In some particular embodiments, the thermally destabilizing modification of the duplex is at position 7 of the antisense strand, counting from 5'-end of the antisense strand.

In some particular embodiments, the thermally destabilizing modification of the duplex is at position 8 of the antisense strand, counting from 5'-end of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises one or both of the following characteristics:

(i) 2, 3, 4, 5 or 6 2'-fluoro modifications; and
(ii) 1, 2, 3 or 4 phosphorothioate internucleotide linkages; and the sense strand comprises one, two or three of the following characteristics:

(i) a ligand conjugated with the sense strand;
(ii) 2, 3, 4 or 5 2'-fluoro modifications; and
(iii) 1, 2, 3 or 4 phosphorothioate internucleotide linkages.

In some embodiments of this, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, and a ligand is conjugated with the sense strand, and wherein the dsRNA has a melting temperature of about 40° C. to about 80° C.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, said sense strand comprises a ligand, and wherein the dsRNA has a melting temperature of about 40° C. to about 80° C. In some further embodiments of this, the ligand is an ASGPR ligand. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, wherein each of the sense and antisense strands comprise at least two 2'-fluoro modifications, and wherein the dsRNA has a melting temperature of about 40° C. to about 80° C. In some further embodiments of this, the ligand is an ASGPR ligand. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the antisense further comprises at least two of the following characteristics: (i) the thermally destabilizing modification of the duplex is located in position 4 to 8 of the antisense strand; (ii) at least two 2% fluoro modifications; (iii) phosphorothioate internucleotide linkages between nucleotide positions 1 and 2 (counting from the 5' end); and antisense strand has a length of 18 to 35 nucleotides. In some further embodiments the ligand is an ASGPR ligand. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and the sense strand has at least one of the following characteristics: (i) the ligand is attached to either end of the sense strand; (ii) sense strand comprises at least two 2'-fluoro modifications; and (iii) the sense strand and the antisense strand show sufficient complementarity to form a double stranded region spanning at least 19 nucleotide positions and wherein the thermally destabilizing modification of the duplex is located within said double-stranded region. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the thermally destabilizing modification of the duplex is selected from the group consisting of:

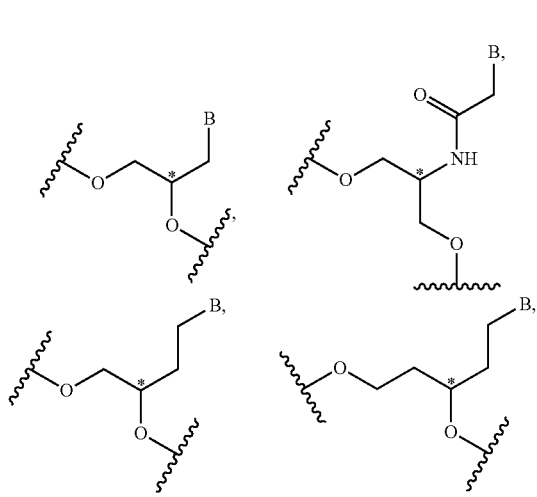

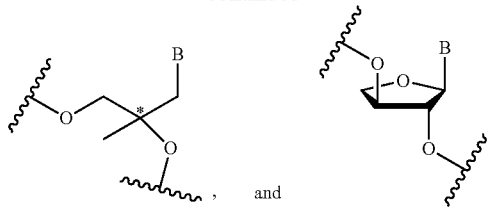

wherein B is a modified or unmodified nucleobase and the asterisk on each structure represents either R, S or racemic. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, wherein the dsRNA has a melting temperature of about 40° C. to about 80° C., and wherein the thermally destabilizing modification of the duplex is selected from the group consisting of:

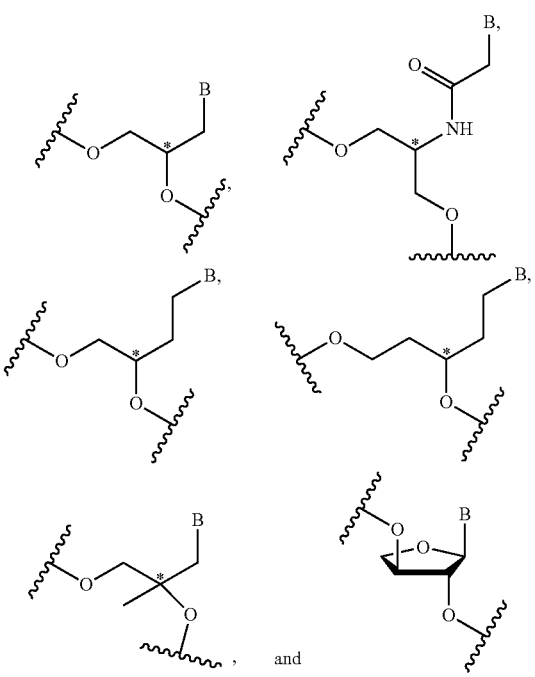

wherein B is a modified or unmodified nucleobase and the asterisk on each structure represents either R, S or racemic. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 7, counting from the 5'-end of the antisense strand, wherein said sense strand comprises a ligand, and wherein the dsRNA has a melting temperature of about 40° C. to about 80° C. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 7, counting from the 5'-end, wherein said sense strand comprises a ligand, and wherein each of the sense and antisense strands comprise at least two 2'-fluoro modifications, wherein the dsRNA has a melting temperature of about 40° C. to about 80° C., and wherein the thermally destabilizing modification of the duplex is selected from the group consisting of:

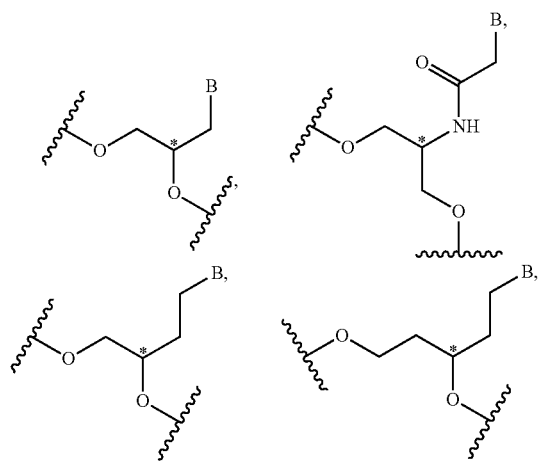

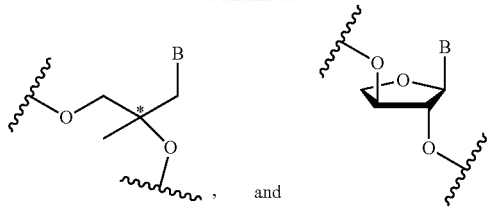

wherein B is a modified or unmodified nucleobase and the asterisk on each structure represents either R, S or racemic. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, wherein said sense strand comprises a ligand, wherein the dsRNA has a melting temperature of about 40° C. to about 80° C., and wherein the ligand comprises one or more GalNAc derivatives attached through a bivalent or trivalent branched linker. In some embodiments, the $T_m$ of from about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA optionally has a melting temperature of about 40° C. to about 80° C., and wherein the ligand is an ASGPR ligand of structure:

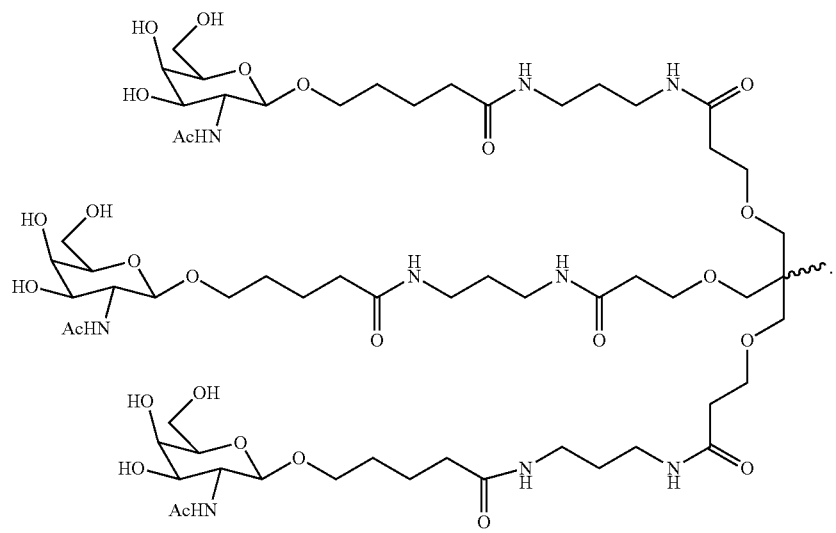 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, and comprises 2, 3, 4 or 5 phosphorothioate internucleotide linkages; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 3, 4, 5 or 6 2'-fluoro modifications, comprises 2, 3, 4 or 5 phosphorothioate internucleotide linkages; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the $T_m$ of from about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6

2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; and (viii) the dsRNA comprises a blunt end at 5'-end of the sense strand. In some particular embodiments, sense strand is 19, 20 or 21 or 22 nucleotides in length and the antisense strand is 20, 21 or 22 nucleotides in length. In some embodiments, the $T_m$ of from about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the $T_m$ of from about 40° C. to about 80° C. is optional.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) and the dsRNA comprises a duplex region of 12-40 nucleotide pairs in length. In some embodiments, the overhang is on the 3'-end of the antisense strand and the blunt end is at the 5'-end of the antisense strand. In some particular embodiments, the overhang is 2, 3 or 4-nucleotides in length. In some embodiments, the $T_m$ of from about 40° C. to about 80° C. is optional.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five or all six) of the following characteristics: (i) the antisense comprises 2, 3, 4, 5 or 6 2% fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications, and optionally the 2 nucleotide overhang is on the 3'-end of the antisense strand and the blunt end is at the 5'-end of the antisense strand. In some embodiments, the overhang is on the 3'-end of the antisense strand and the blunt end is at the 5'-end of the antisense strand. In some embodiments, the $T_m$ of from about 40° C. to about 80° C. is optional.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a duplex region of 12-40 nucleotide pairs in length. In some embodiments, the $T_m$ of from about 40° C. to about 80° C. is optional.

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications. In some embodiments, the $T_m$ of from about 40° C. to about 80° C. is optional.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2% fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense. In some embodiments, the $T_m$ of from about 40° C. to about 80° C. is optional.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 ' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), and wherein the dsRNA has a melting temperature of about 40° C. to about 80° C. For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a duplex region of 12-30 nucleotide pairs in length. In some embodiments, the $T_m$ of from about 40° C. to about 80° C. is optional.

In some embodiments, the dsRNA molecule of the invention comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA has a duplex region of 12-29 nucleotide pairs in length. In some embodiments, the $T_m$ of from about 40° C. to about 80° C. is optional.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2% fluoro modifications; (vii) the dsRNA comprises a duplex region of 12-40 nucleotide pairs in length; and (viii) the dsRNA has a blunt end at 5'-end of the antisense strand. In some embodiments, the $T_m$ of from about 40° C. to about 80° C. is optional.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand. In some embodiments, the $T_m$ of from about 40° C. to about 80° C. is optional.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2% fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand. In some embodiments, the $T_m$ of from about 40° C. to about 80° C. is optional.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand. In some embodiments, the $T_m$ of from about 40° C. to about 80° C. is optional.

In one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven or all eight) of the following characteristics:

(i) the antisense comprises 2, 3, 4, 5 or 6 2'-fluoro modifications;

(ii) the antisense comprises 1, 2, 3, 4 or 5 phosphorothioate internucleotide linkages;

(iii) the sense strand is conjugated with a ligand;

(iv) the sense strand comprises 2, 3, 4 or 5 2'-fluoro modifications;

(v) the sense strand comprises 1, 2, 3, 4 or 5 phosphorothioate internucleotide linkages;

(vi) the dsRNA comprises at least four 2'-fluoro modifications;

(vii) the dsRNA comprises a duplex region of 12-40 nucleotide pairs in length; and (viii) a blunt end at 5'end of the antisense strand.

In some particular embodiments, the thermally destabilizing modification of the duplex is at position 7 of the antisense strand, counting from 5'-end of the antisense strand.

In some embodiments, the thermally destabilizing modification of the duplex is at position 2, 3, 4, 5, 6, 8 or 9 of the antisense strand, counting from 5'-end of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the antisense strand further comprises one or both of the following characteristics:

(i) 2, 3, 4, 5 or 6 2'-fluoro modifications; and (ii) 1, 2, 3, 4 or 5 phosphorothioate internucleotide linkages; and the sense strand comprises one, two or three of the following characteristics:

(i) a ligand conjugated with the sense strand;

(ii) 2, 3, 4 or 5 2'-fluoro modifications; and (iii) 1, 2, 3, 4 or 5 phosphorothioate internucleotide linkages.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, and a ligand is conjugated with the sense strand.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand. In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications. In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and antisense strand has a length of 18 to 35 nucleotides. In some further embodiments the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and the sense strand has at least one of the following characteristics: (i) the ligand is attached to either end of the sense strand; (ii) sense strand comprises at least two 2'-fluoro modifications; and (iii) the sense strand and the antisense strand show sufficient complementarity to form a double stranded region spanning at least 19 nucleotide positions and wherein the thermally destabilizing modification of the duplex is located within said double-stranded region.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the thermally destabilizing modification of the duplex is selected from the group consisting of:

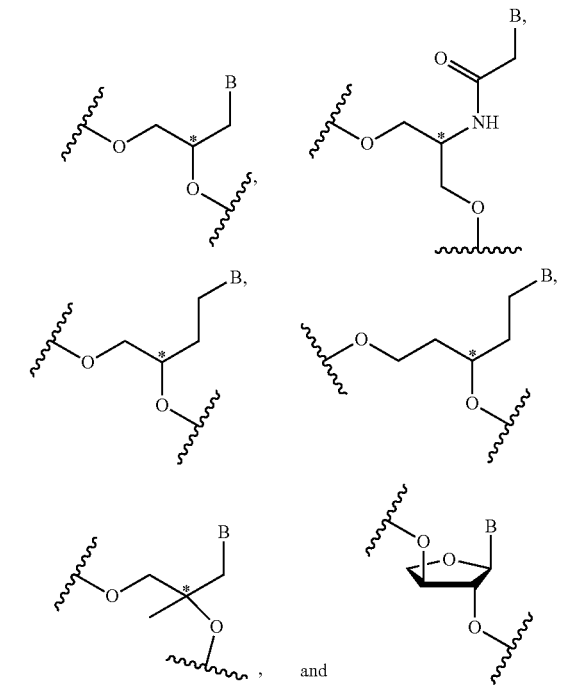

wherein B is a modified or unmodified nucleobase and the asterisk on each structure represents either R, S or racemic.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, and wherein the thermally destabilizing modification of the duplex is selected from the group consisting of:

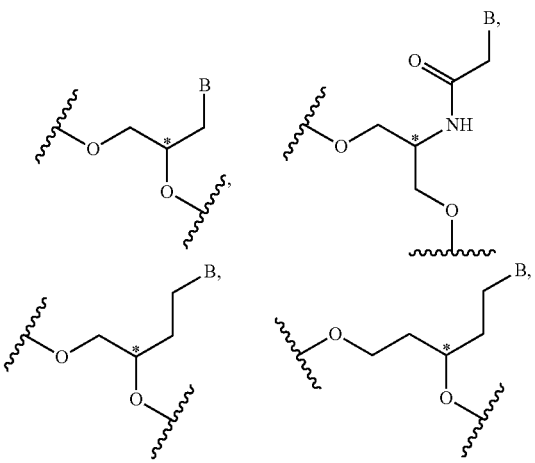

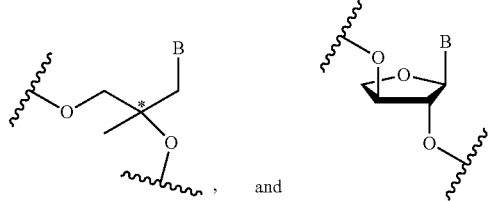

and wherein B is a modified or unmodified nucleobase and the asterisk on each structure represents either R, S or racemic.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 7, counting from the 5'-end of the antisense strand, and wherein said sense strand comprises a ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 7, counting from the 5'-end, wherein said sense strand comprises a ligand, and wherein each of the sense and antisense strands comprise at least two 2'-fluoro modifications, and wherein the thermally destabilizing modification of the duplex is selected from the group consisting of:

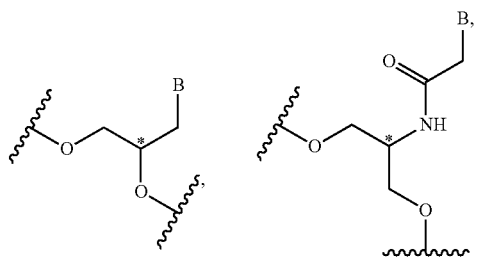

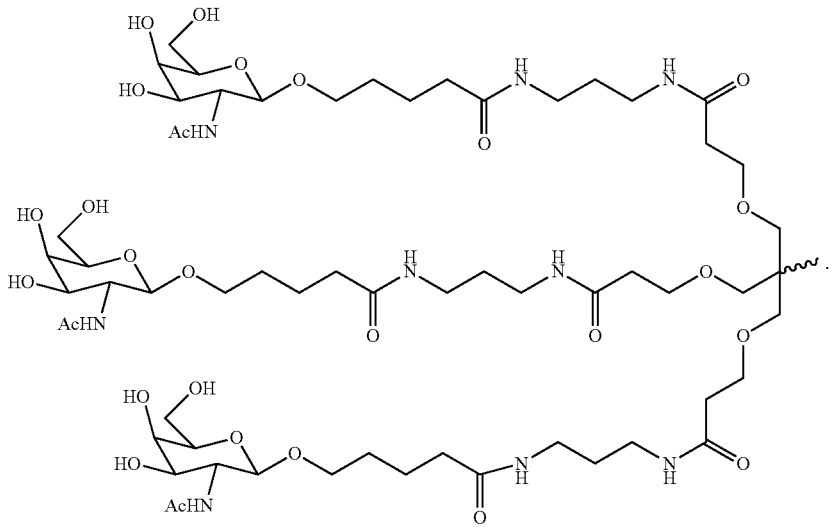 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

and wherein B is a modified or unmodified nucleobase and the asterisk on each structure represents either R, S or racemic.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the ligand comprises one or more GalNAc derivatives attached through a bivalent or trivalent branched linker.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the ligand is an ASGPR ligand of structure:

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, comprises 2, 3, 4 or 5 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 3, 4, 5 or 6 2% fluoro modifications, comprises 2, 3, 4 or 5 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In a particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker; and
  (iii) 2'-F modifications at positions 7, 10, and 11 (counting from the 5' end); and
(b) an antisense strand having:
  (i) a length of 23 nucleotides;
  (ii) 2'-F modifications at positions 2, 6 to 8, 9, 14, and 16 (counting from the 5' end);
  (iii) phosphorothioate internucleotide linkages between nucleotide positions 21 and 22, and between nucleotide positions 22 and 23 (counting from the 5' end); and
  (iv) a thermally destabilizing modification of the duplex at position 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-F modifications at positions 2, 6, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 6 or 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 7, 9, 10, and 11 (counting from the 5' end); and (iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-F modifications at positions 2, 6, 8, 9, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
(iv) a thermally destabilizing modification of the duplex at position 7 (counting from the 5' end); wherein the dsRNA molecules have a two nucleotide overhang at the 3'-end of the antisense strand, and a blunt end at the 5'-end of the antisense strand.

In another particular embodiment, the dsRNA molecules of the present invention comprising an antisense strand having:
  (i) 2'-F modifications at positions 2, 14, and 16 (counting from the 5' end); and
  (2) a thermally destabilizing modification of the duplex at position 6 or 7 (counting from the 5' end).

In another particular embodiment, the dsRNA molecules of the present invention comprise:
(a) a sense strand having:
  (i) an ASGPR ligand, wherein said ASGPR ligand comprises three GalNAc derivatives attached through a trivalent branched linker;
  (ii) phosphorothioate internucleotide linkages between nucleotide positions 1 and 2, and between nucleotide positions 2 and 3 (counting from the 5' end);
  and
(b) an antisense strand having:
  (i) 2'-F modifications at positions 2, 14, and 16 (counting from the 5' end);
  (ii) a thermally destabilizing modification of the duplex at position 6 or 7 (counting from the 5' end);

In another particular embodiment, the dsRNA molecules of the present invention comprise:
(a) a sense strand having:
  (i) an ASGPR ligand attached to the 3'-end, wherein said ASGPR ligand comprises three GalNAc derivatives attached through a trivalent branched linker;
  (ii) phosphorothioate internucleotide linkages between nucleotide positions 1 and 2, and between nucleotide positions 2 and 3 (counting from the 5' end);

and
(b) an antisense strand having:
- (ii) 2'-F modifications at positions 2, 14, and 16 (counting from the 5' end);
- (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
- (iv) a thermally destabilizing modification of the duplex at position 6 or 7 (counting from the 5' end);

wherein the dsRNA molecules have a two nucleotide overhang at the 3'-end of the antisense strand, and a blunt end at the 5'-end of the antisense strand.

In some embodiments, the dsRNA molecule further comprises at least one ASGPR ligand. For example, the ASGPR ligand is one or more GalNAc derivatives attached through a bivalent or trivalent branched linker, such as:

the antisense comprises 2, 3, 4, 5, 6, 7, 8, 9, or 10 2'-fluoro modifications; (iii) the antisense comprises 1, 2, 3, 4 or 5 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3, 4 or 5 phosphorothioate internucleotide linkages; (vii) the dsRNA comprises at least four 2'-fluoro modifications; (viii) the dsRNA comprises a duplex region of 12-40 nucleotide pairs in length; (ix) a blunt end at 5'end of the antisense strand; (x) the sense strand comprises 1, 2, 3, 4, 5, 6, 7, 8, 9 or 10 LNA modifications.

In some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabiliz-

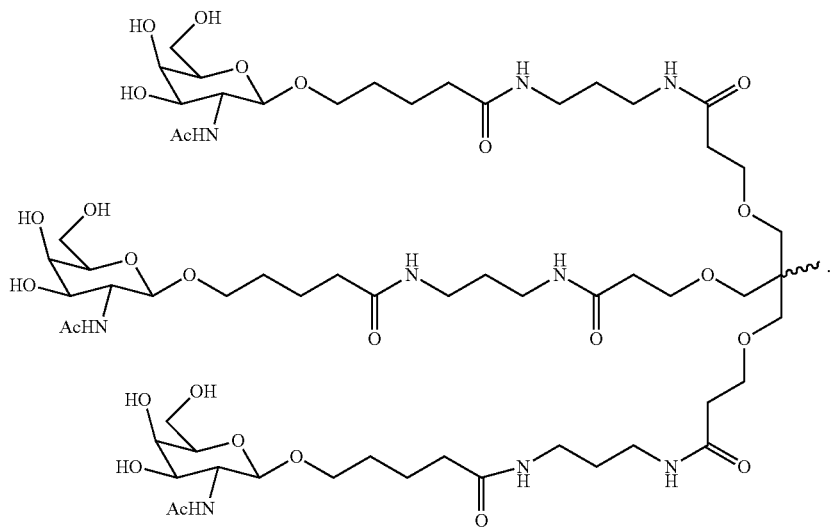 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one example, the ASGPR ligand is attached to the 3' end of the sense strand.

In some cases 2'-fluoro modifications in the seed region of the antisense strand, e.g., positions 2-9, particularly positions 3-9, can adversely affect the in vivo activity of the dsRNA while having minimal effect on in vitro potency of the dsRNA. Inventors have discovered inter alia that in vivo activity of such dsRNAs can be restored to comparable levels relative to the parent dsRNA by removing—some or all of 2'-fluoro modifications from the seed region of the antisense strand, i.e., position 2-9, particularly position 3-9 counting from the 5'-end.

Accordingly, in some embodiments, the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight, nine or all ten) of the following characteristics: (i) a melting temperature (Tm) of from about 40° C. to about 80° C.; (ii)

ing modification of the duplex within the seed region (i.e., at position 2-9 of the 5'-end of the antisense strand, counting from the 5'-end), and the dsRNA further has at least one (e.g., one, two, three, four, five, six seven, eight, nine or all ten) of the following characteristics: (i) a melting temperature ($T_m$) of from about 40° C. to about 80° C.; (ii) the antisense comprises 2, 3, 4, 5, 6, 7, 8, 9, or 10 2'-fluoro modifications; (iii) the antisense comprises 1, 2, 3, 4 or 5 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3, 4 or 5 phosphorothioate internucleotide linkages; (vii) the dsRNA comprises at least four 2'-fluoro modifications; (viii) the dsRNA comprises a duplex region of 12-40 nucleotide pairs in length; (ix) a blunt end at 5'end of the antisense strand; and (x) the sense strand comprises 1, 2, 3, 4, 5, 6, 7, 8, 9 or 10 LNA modifications, and wherein no 2'-fluoro modification is present at positions 3-9 (counting from 5'-end) of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises one or both of the following characteristics: (i) 2, 3, 4, 5, 6, 7, 8, 9 or 10 2'-fluoro modifications, wherein the antisense does not have a 2'-fluoro modification at positions 3-9 (counting from 5'-end); and (ii) 1, 2, 3, 4 or 5 phosphorothioate internucleotide linkages; and the sense strand comprises one, two, three of four of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises: (i) 2, 3, 4, 5, 6, 7, 8, 9 or 10 2'-fluoro modifications; and (ii) 1, 2, 3, 4 or 5 phosphorothioate internucleotide linkages; and the sense strand comprises: 1, 2, 3, 4, 5, 6, 7, 8, 9 or 10 LNA modifications, and wherein the sense strand optionally comprises one, two or three of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises 1, 2, 3 or 4 phosphorothioate internucleotide linkages, wherein the antisense strand optionally comprises 2, 3, 4, 5, 6, 7, 8, 9 or 10 2'-fluoro modifications; and the sense strand comprises 1, 2, 3, 4, 5, 6, 7, 8, 9 or 10 LNA modifications, and wherein the sense strand optionally comprises a ligand conjugated with the sense strand, 2, 3, 4 or 5 2'-fluoro modifications; and/or 1, 2, 3, 4 or 5 phosphorothioate internucleotide linkages. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises 1, 2, 3 or 4 phosphorothioate internucleotide linkages, wherein the antisense strand optionally comprises 2, 3, 4, 5, 6, 7, 8, 9 or 10 2'-fluoro modifications, provided that no 2'-fluoro modification is present at positions 3-9 (counting from 5'-end); and the sense strand comprises 1, 2, 3, 4, 5, 6, 7, 8, 9 or 10 LNA modifications, and wherein the sense strand optionally comprises a ligand conjugated with the sense strand, 2, 3, 4 or 5 2'-fluoro modifications; and/or 1, 2, 3, 4 or 5 phosphorothioate internucleotide linkages. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications, and wherein no 2'-fluoro modification is present at positions 3-9 of the antisense strand (counting from 5'-end).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, said sense strand comprises a ligand, wherein the dsRNA has a melting temperature of about 40° C. to about 80° C., and wherein no 2'-fluoro modification is present at positions 3-9 of the antisense strand (counting from 5'-end). In some further embodiments of this, the ligand is an ASGPR ligand. In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, wherein each of the sense and antisense strands comprise at least two 2'-fluoro modifications, wherein the dsRNA has a melting temperature of about 40° C. to about 80° C., and wherein no 2'-fluoro modification is present at positions 3-9 of the antisense strand (counting from 5'-end). In some further embodiments of this, the ligand is an ASGPR ligand. In some embodiments, the melting temperature of about 40° C. to about 80° C. is optional.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and (iv) antisense strand has a length of 18 to 35 nucleotides, and wherein no 2'-fluoro modification is present at positions 3-9 of the antisense strand (counting from 5'-end). In some further embodiments the ligand is an ASGPR ligand. In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and the sense strand has at least one of the following characteristics: (i) the ligand is attached to either end of the sense strand; (ii) sense strand comprises at least two 2'-fluoro modifications; (iii) sense strand comprises 1, 2, 3, 4, 5, 6, 78, 9 or 10 LNA modifications; and (iv) the sense strand and the antisense strand show sufficient complementarity to form a double stranded region spanning at least 19 nucleotide positions, wherein the thermally destabilizing modification of the duplex is located within said double-stranded region, and wherein no 2'-fluoro modification is present at positions 3-9 of the antisense strand (counting from 5'-end). In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand and optionally at least one LNA modification, and wherein each of the sense and antisense strands comprise at least two 2'-fluoro modifications, wherein no 2'-fluoro modification is present at positions 3-9 of the antisense strand (counting from 5'-end), wherein the dsRNA has a melting temperature of about 40° C. to about 80° C., and wherein the thermally destabilizing modification of the duplex is selected from the group consisting of:

In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex located at position 5, 6 or 7, counting from the 5'-end of the antisense strand, wherein no 2'-fluoro modification is present at positions 3-9 of the antisense strand (counting from 5'-end), wherein said sense strand comprises a ligand and optionally at least one LNA modification, and wherein the dsRNA has a melting temperature of about 40° C. to about 80° C.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 5, 6 or 7, counting from the 5'-end, wherein said sense strand comprises a ligand and optionally at least one LNA modification, and wherein each of the sense and antisense strands comprise at least two 2'-fluoro modifications, wherein no 2'-fluoro modification is present at positions 3-9 of the antisense strand (counting from 5'-end), wherein the dsRNA has a melting temperature of about 40° C. to about 80° C., and wherein the thermally destabilizing modification of the duplex is selected from the group consisting of:

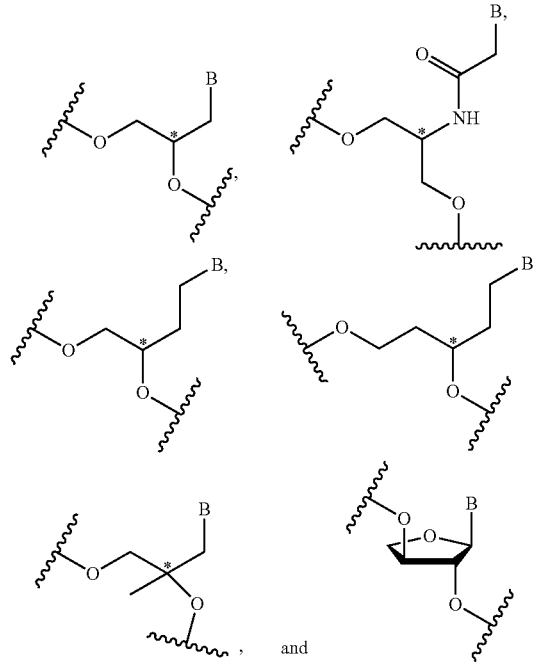

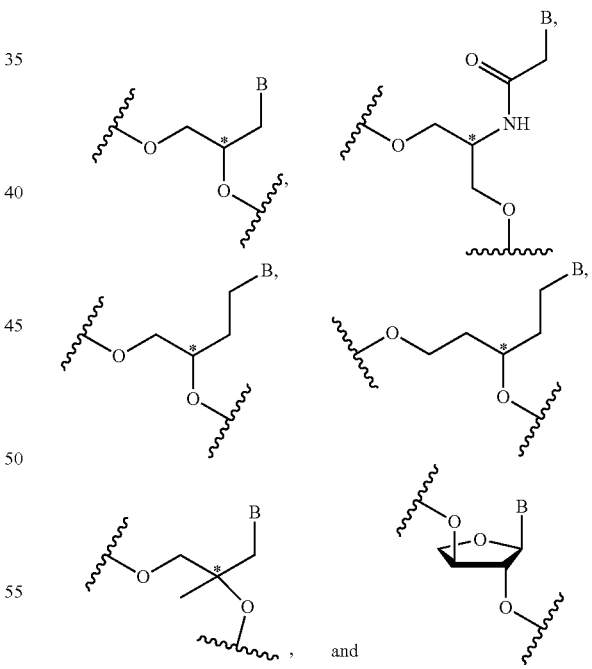

wherein B is a modified or unmodified nucleobase and the asterisk on each structure represents either R, S or racemic.

wherein B is a modified or unmodified nucleobase and the asterisk on each structure represents either R, S or racemic. In some embodiments, the melting temperature of about 40° C. to about 80° C. is optional In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, wherein said sense strand comprises a ligand and optionally at least one LNA modification, wherein no 2'-fluoro modification is present at positions 3-9 of the antisense strand (counting from 5'-end), wherein the dsRNA has a melting temperature of about 40° C. to about 80° C., and wherein the ligand comprises one or more GalNAc derivatives attached through a bivalent or trivalent branched linker.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand and optionally at least one LNA modification, wherein no 2'-fluoro modification is present at positions 3-9 of the antisense strand (counting from 5'-end), wherein the dsRNA has a melting temperature of about 40° C. to about 80° C., and wherein the ligand is an ASGPR ligand of structure:

of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3, and optionally comprises at least one LNA modification; wherein the antisense strand comprises 3, 4, 5 or 6 2'-fluoro modifications, provided that no 2'-modification is present at positions 3-9 of the antisense strand (counting from 5'-end), comprises 2, 3, 4 or 5 phosphorothioate internucleotide linkages; wherein the dsRNA has a melting temperature of about 40° C. to about 80° C.; and wherein the dsRNA optionally

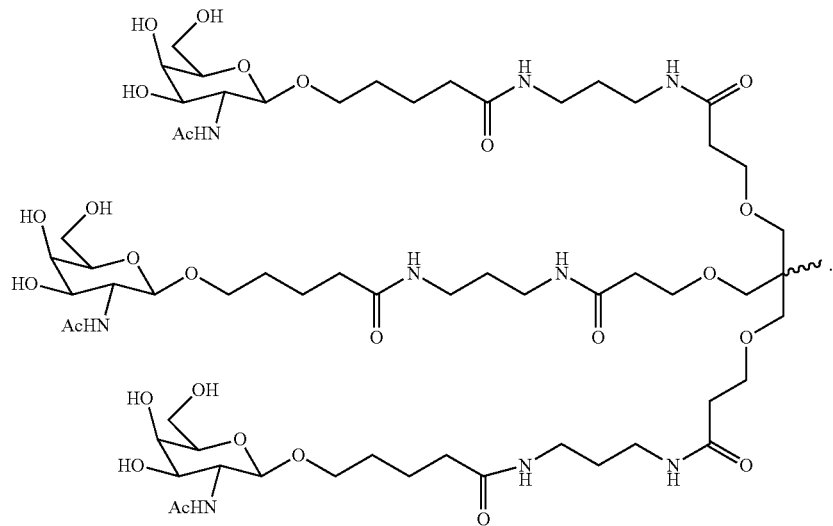 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand and optionally comprises at least one LNA modification, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, provided that no 2'-modification is present at positions 3-9 of the antisense strand (counting from 5'-end), comprises 2, 3, 4 or 5 phosphorothioate internucleotide linkages; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2 or 3 phosphorothioate internucleotide linkages, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises at least one LNA modification, and optionally comprises 0, 1, 2 or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2, or 3 phosphorothioate internucleotide linkages, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2, or 3 phosphorothioate internucleotide linkages, and comprises at least one LNA modification; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises at least one LNA modification; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises at least one LNA modification, and optionally comprises phosphorothioate internucleotide linkages between nucleotide positions 1 and 2, and between nucleotide positions 2 and 3; wherein the antisense strand comprises 2'-fluoro modifications at positions 2, 14 or 16; and the antisense comprises phosphorothioate internucleotide linkages between nucleotide positions 21 and 22, and between nucleotide positions 22 and 23; wherein the dsRNA has a melting temperature of about 40° C. to about 80° C.;

and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, provided that no 2'-modification is present at positions 3-9 of the antisense strand (counting from 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; (viii) the dsRNA comprises a blunt end at 5'-end of the sense strand; and (ix) the sense strand comprises 1, 2, 3, 4, 5, 6, 7, 8, 9 for 10 LNA modifications. In some particular embodiments, sense strand is 19, 20 or 21 or 22 nucleotides in length and the antisense strand is 20, 21 or 22 nucleotides in length. In some embodiments, the melting temperature of about 40° C. to about 80° C. is optional.

In some embodiments, the sense and antisense strands are independently 19, 20, 21, 22, 23, 24 or 25 nucleotides in length, wherein the antisense strand contains at least one thermally destabilizing nucleotide and 1, 2, 3 or 4 phosphorothioate internucleotide linkages, and where the at least one thermally destabilizing nucleotide is in the seed region of the antisense strand (i.e., at position 2-9 of the 5'-end of the antisense strand), the sense strand comprises 1, 2, 3, 4, 5, 6, 7, 8, 9 or 10 LNA modifications, wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications, provided that no 2'-modification is present at positions 3-9 of the antisense strand (counting from 5'-end); (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 18, 19, 20, 21, 22, 23, 24 or 24 nucleotide pairs in length; and (vii) the dsRNA comprises a blunt end at 5'-end of the sense strand. In some particular embodiments, sense strand is 19, 20 or 21 or 22 nucleotides in length and the antisense strand is 20, 21 or 22 nucleotides in length. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises 1, 2, 3, 4, 5, 6, 7, 8, 9 or 10 LNA modifications, and optionally comprises phosphorothioate internucleotide linkages between nucleotide positions 1 and 2, and between nucleotide positions 2 and 3; wherein the antisense strand comprises 2'-fluoro modifications at positions 2, 9, 14 or 16, or at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LAN modifications, and optionally comprises phosphorothioate internucleotide linkages between nucleotide positions 1 and 2, and between nucleotide positions 2 and 3; wherein the antisense strand comprises 2'-fluoro modifications at positions 2, 9, 14 or 16, or at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand. In some embodiments, the melting temperature of about 40° C. to about 80° C. is optional.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present in positions 3-9 (counting from the 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (vii) the sense strand comprises 1, 2, 3, 4, 5, 6, 7, 8, 9 or 10 LNA modifications. In some embodiments, the overhang is on the 3'-end of the antisense strand and the blunt end is at the 5'-end of the antisense strand. In some particular embodiments, the overhang is 2, 3 or 4-nucleotides in length. In some embodiments, the melting temperature of about 40° C. to about 80° C. is optional.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five, six or all seven) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the sense strand comprises 1, 2, 3, 4, 5, 6, 7, 8, 9 or 10 LNA modifications, and optionally the 2 nucleotide overhang is on the 3'-end of the antisense strand and the blunt end is at the 5'-end of the antisense strand. In some embodiments, the overhang is on the 3'-end of the antisense strand and the blunt end is at the 5'-end of the antisense strand. In some embodiments, the melting temperature of about 40° C. to about 80° C. is optional.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the sense strand comprises at least 1, 2, 3, 4, 5, 6, 7, 8, 9 or 10 LNA modifications. In some embodiments, the melting temperature of about 40° C. to about 80° C. is optional.

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five, six or all seven) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the sense strand comprises at least 1, 2, 3, 4, 5, 6, 7, 8, 9 or 10 LNA modifications. In some embodiments, the melting temperature of about 40° C. to about 80° C. is optional.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from the 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a blunt end at 5'-end of the antisense strand. Preferably, the 2 nt overhang is at the 3'-end of the antisense; and (viii) the sense strand comprises at least 1, 2, 3, 4, 5, 6, 7, 8, 9 or 10 LNA modifications. In some embodiments, the melting temperature of about 40° C. to about 80° C. is optional.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3 ' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), and wherein the dsRNA has a melting temperature of about 40° C. to about 80° C. For example, the thermally destabilizing nucleotide occurs between positions opposite or complimentary to positions 14-17 of the 5'-end of the sense strand, and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; (vii) the dsRNA comprises a duplex region of 12-30 nucleotide pairs in length; and the sense strand comprises 1, 2, 3, 4, 5, 6, 7, 8, 9 or 10 LNA modifications. In some embodiments, the melting temperature of about 40° C. to about 80° C. is optional.

In some embodiments, the dsRNA molecule of the invention comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications, wherein no 2'-fluoro modification is present at positions 3-9 (counting from 5'-end of antisense strand); (ii) the antisense comprises 1, 2, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; (vii) the dsRNA has a duplex region of 12-29 nucleotide pairs in length; (viii) and the sense strand comprises 1, 2, 3, 4, 5, 7, 8, 9 or 10 LNA modifications. In some embodiments, the melting temperature of about 40° C. to about 80° C. is optional.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of antisense strand); (ii) the antisense comprises 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) the dsRNA has a blunt end at 5'-end of the antisense strand; (ix) and the sense strand comprises 1, 2, 3, 4, 5, 6, 7, 8, 9 or 10 LNA modifications. In some embodiments, the melting temperature of about 40° C. to about 80° C. is optional.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; (viii) the dsRNA has a blunt end at 5'-end of the antisense strand; and (ix) and the sense strand comprises 1, 2, 3, 4, 5, 6, 7, 8, 9 or 10 LNA modifications. In some embodiments, the melting temperature of about 40° C. to about 80° C. is optional.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end of the antisense strand); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) the dsRNA has a blunt end at 5'-end of the antisense strand; and (ix) the sense strand comprises 1, 2, 3, 4, 5, 6, 7, 8, 9 or 10 LNA modifications. In some embodiments, the melting temperature of about 40° C. to about 80° C. is optional.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications, wherein no 2'-fluoro modification is present at positions 3-9 (counting from 5'-end of the antisense strand); (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA has a blunt end at 5'-end of the antisense strand; and (viii) the sense strand comprises 1, 2, 3, 4, 5, 6, 7, 8, 9 or 10 LNA modifications. In some embodiments, the melting temperature of about 40° C. to about 80° C. is optional.

In one aspect the invention provides a dsRNA molecule capable of inhibiting the expression of a target gene, comprising a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five six, seven, eight or all nine) of the following characteristics: (i) the antisense comprises 2, 3, 4, 5 or 6 2'-fluoro modifications, wherein no 2'-fluoro modification is present at positions 3-9 (counting from 5'-end); (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) a blunt end at 5'end of the antisense strand; and (ix) the sense strand comprises 1, 2, 3, 4, 5, 6, 7, 8, 9 or 10 LNA modifications. In some embodiments, the melting temperature of about 40° C. to about 80° C. is optional.

In some particular embodiments, the thermally destabilizing modification of the duplex is at position 5, 6 or 7 of the antisense strand, counting from 5'-end of the antisense strand. In some embodiments, the thermally destabilizing modification of the duplex is at position 2, 3, 4, 8 or 9 of the antisense strand, counting from 5'-end of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the antisense strand further comprises one or both of the following characteristics: (i) 2, 3, 4, 5 or 6 2'-fluoro modifications, wherein no 2'-modification is present at positions 3-9 (counting from 5'-end of the antisense strand); and (ii) 1, 2, 3, 4 or 5 phosphorothioate internucleotide linkages; and the sense strand comprises one, two, three or four of the following characteristics: (i) a ligand conjugated with the sense strand; (ii) 2, 3, 4 or 5 2'-fluoro modifications; (iii) 1, 2, 3, 4 or 5 phosphorothioate internucleotide linkages; and (iv) 1, 2, 3, 4, 5, 6, 7, 8, 9 or 10 LNA modifications.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications, and wherein no 2'-modification is present at positions 3-9 of the antisense strand (counting from 5'-end of the antisense strand).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein no 2'-modification is present at positions 3-9 of the antisense strand (counting from 5'-end of the antisense strand). In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, and wherein no 2'-modification is present at positions 3-9 of the antisense strand (counting from 5'-end of the antisense strand). In some further embodiments of this, the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the antisense further comprises at least two of the following characteristics: (i) the thermally destabilizing modification of the duplex is located in position 4 to 8 of the antisense strand; (ii) at least two 2'-fluoro modifications, and wherein no 2'-modification is present at positions 3-9 of the antisense strand (counting from 5'-end of the antisense strand); (iii) phosphorothioate internucleotide linkages between nucleotide positions 1 and 2 (counting from the 5' end); and antisense strand has a length of 18 to 35 nucleotides. In some further embodiments the ligand is an ASGPR ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and the sense strand has at least one of the following characteristics: (i) the ligand is attached to either end of the sense strand; (ii) sense strand comprises at least two 2'-fluoro modifications; (iii) the sense strand and the antisense strand show sufficient complementarity to form a double stranded region spanning at least 19 nucleotide positions; (iv) the sense strand comprises at least 1, 2, 3, 4, 5, 6, 7, 8, 9 or 10 LNA modifications, and wherein the thermally destabilizing modification of the duplex is located within said double-stranded region, and wherein no 2'-modification is present at positions 3-9 of the antisense strand (counting from 5'-end of the antisense strand).

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, where no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, and wherein the thermally destabilizing modification of the duplex is selected from the group consisting of:

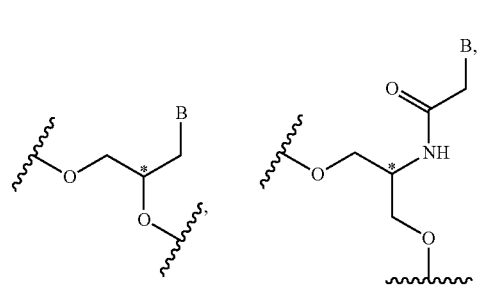

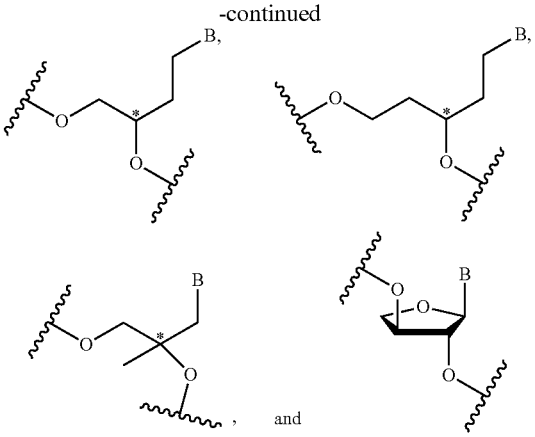

wherein B is a modified or unmodified nucleobase and the asterisk on each structure represents either R, S or racemic In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, wherein no 2'-modification is present at positions 3-9 of the antisense strand (counting from 5'-end of the antisense strand), and wherein the thermally destabilizing modification of the duplex is selected from the group consisting of:

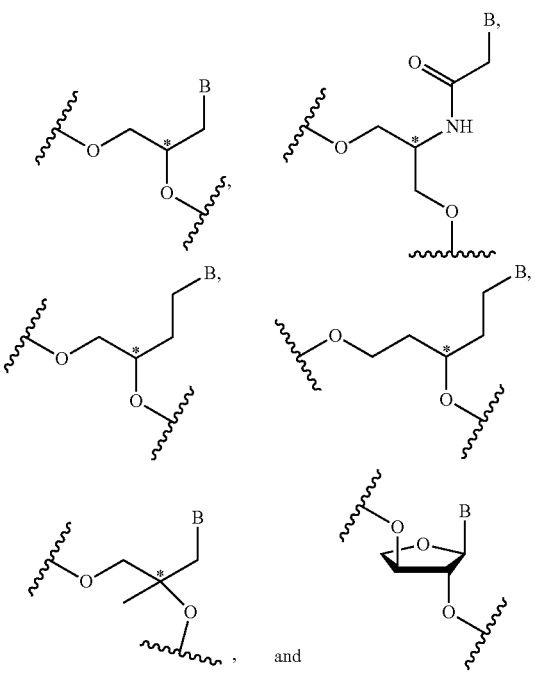

wherein B is a modified or unmodified nucleobase and the asterisk on each structure represents either R, S or racemic.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex located at position 5, 6 or 7, counting from the 5'-end of the antisense strand, and wherein said sense strand comprises a ligand.

In some embodiments, the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex located at position 5, 6 or 7, counting from the 5'-end, wherein said sense strand comprises a ligand, and wherein each of the sense and antisense strands comprise at least two 2'-fluoro modifications, wherein no 2'-modification is present at positions 3-9 of the antisense strand (counting from 5'-end of the antisense strand) and wherein the thermally destabilizing modification of the duplex is selected from the group consisting of:

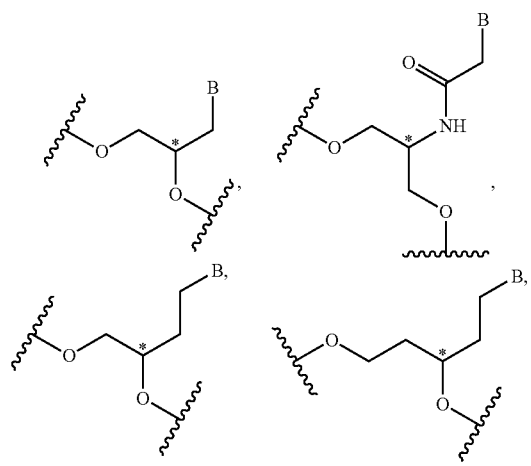

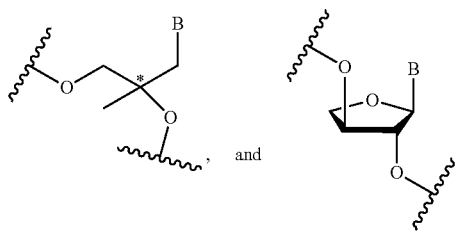

wherein B is a modified or unmodified nucleobase and the asterisk on each structure represents either R, S or racemic.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, wherein the ligand comprises one or more GalNAc derivatives attached through a bivalent or trivalent branched linker.

In some embodiments, the dsRNA molecule comprises a sense strand and an antisense strand, each strand having 14 to 40 nucleotides, wherein the antisense strand has sufficient complementarity to the target sequence to mediate RNA interference, wherein the dsRNA comprises at least four 2'-fluoro, wherein no 2'-modification is present at positions 3-9 of the antisense strand (counting from 5'-end of the antisense strand), wherein said antisense strand comprises at least one thermally destabilizing modification of the duplex within the first 9 nucleotide positions, counting from the 5'-end, and wherein said sense strand comprises a ligand, wherein the ligand is an ASGPR ligand of structure:

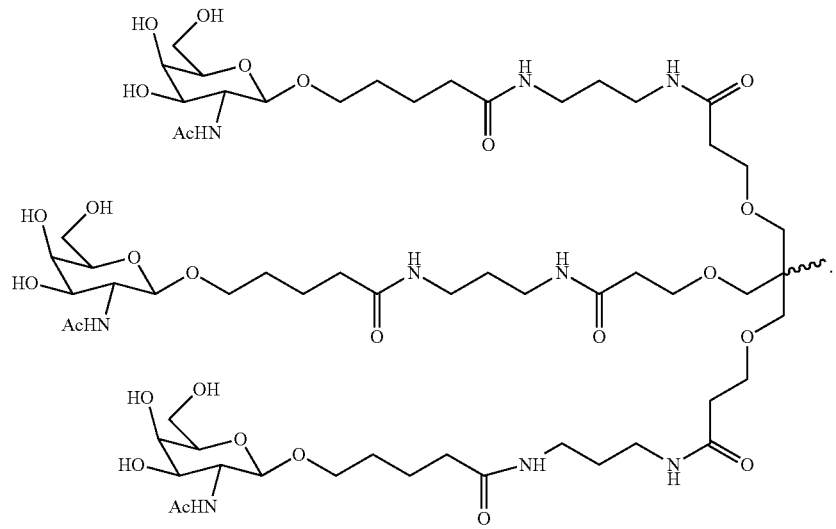 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1, 2 or 3 phosphorothioate internucleotide linkages; wherein the antisense strand comprises 3, 4, 5 or 6 2'-fluoro modifications, comprises 2, 3, 4 or 5 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 3, 4, 5 or 6 2'-fluoro modifications, where no 2'-fluoro modification is present at positions 3-9 of the antisense strand, comprises 2, 3 or 4 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0 or 2 phosphorothioate internucleotide linkages, and optionally comprises 1, 2, 3, 4, 5, 6, 7, 8, 9 or 10 LNA modifications; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and optionally comprises 0 or 2 phosphorothioate internucleotide linkages; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and comprises 0, 1, 2 or 3 phosphorothioate internucleotide linkages; wherein the antisense strand comprises 2'-fluoro modifications at positions 2, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 0, 1, 2 or 3 phosphorothioate internucleotide linkages, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and optionally comprises 0, 1, 2 or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, comprises 1, 2, 3, 4, 5, 6, 7, 8, 9 or 10 LNA modifications, and comprises 0, 1, 2, or 3 phosphorothioate internucleotide linkages; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LNA modifications and optionally comprises phosphorothioate internucleotide linkages between nucleotide positions 1 and 2, and between nucleotide positions 2 and 3; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises 1, 2, 3, 4, 5, 6, 7, 8, 9 or 10 LNA modifications, and comprises phosphorothioate internucleotide linkages between nucleotide positions 1 and 2, and between nucleotide positions 2 and 3; wherein the antisense strand comprises 2'-fluoro modifications at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), comprises phosphorothioate internucleotide linkages between nucleotide positions 1 and 2, and between nucleotide positions 2 and 3, and optionally comprises 1, 2, 3, 4, 5, 6, 7, 8, 9 or 10 LNA modifications; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), optionally comprises 1, 2, 3, 4, 5, 6, 7, 8, 9 or 10 LNA modifications, and optionally comprises phosphorothioate internucleotide linkages between nucleotide positions 1 and 2, and between nucleotide positions 2 and 3; wherein the antisense strand comprises 2'-fluoro modifications at positions 2, 14 or 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the dsRNA molecule comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), the dsRNA has a melting temperature (Tm) of from about 40° C. to about 80° C., and the dsRNA optionally further has at least one (e.g., one, two, three, four, five, six, seven, eight or all nine) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; (viii) a blunt end at 5'end of the antisense strand; (ix) provided that no 2'-fluoro modification is present at positions 3-9 (counting from 5'-end) of the antisense strand. In some embodiments, the melting temperature of about 40° C. to about 80° C. is optional.

In some embodiments, the dsRNA molecule has a duplex region of 12-40 nucleotide pairs in length, wherein the antisense strand comprises at least one thermally destabilizing modification of the duplex within the seed region (i.e., at position 2-9 of the 5'-end of the antisense strand, counting from the 5'-end), and the dsRNA has a $T_m$ of from about 40° C. to about 80° C., and wherein the dsRNA optionally further has at least one (e.g., one, two, three, four, five, six or all seven) of the following characteristics: (i) the antisense comprises 2, 3, 4, 5 or 6 2% fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and vii) a blunt end at 5'end of the antisense strand, provided that no 2'-fluoro modification is present at positions 3-9 (counting from 5'-end) of the antisense strand. In some embodiments, the melting temperature of about 40° C. to about 80° C. is optional.

In some embodiments, the dsRNA molecule has a duplex region of 19, 20, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), and wherein the dsRNA has a melting temperature of about 40° C. to about 80° C., provided that no 2'-fluoro modification is present at positions 3-9 (counting from 5'-end) of the antisense strand. In some embodiments, the melting temperature of about 40° C. to about 80° C. is optional.

In a particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker; and
  (iii) 2'-F modifications at positions 7, 10, and 11 (counting from the 5' end);
  and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 21 and 22, and between nucleotide positions 22 and 23 (counting from the 5' end); and
  (iv) a thermally destabilizing modification of the duplex at position 5, 6 or 7 (counting from the 5' end);
  wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
  and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 7, 9, 10, and 11 (counting from the 5' end); and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-F modifications at positions 2, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
(iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) at least one (e.g., one, two, three, four, five, six, seven, eight, nine, ten or more) LNA modification;
  and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) at least one (e.g., one, two or three) LNA modifications at positions 1, 2 and 3 (counting from the 5' end);
  and
(b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:

(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 7, 9, 10, and 11 (counting from the 5' end);
(iv) at least one (e.g., one, two, three, four, five, six, seven, eight, nine, ten or more) LNA modification; and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-F modifications at positions 2, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
and
(iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
 (i) a length of 21 nucleotides;
 (ii) an ASGPR ligand attached to the 3'-end, wherein said ASGPR ligand comprises three GalNAc derivatives attached through a trivalent branched linker;
 (iii) 2'-F modifications at positions 7, 9, 10, and 11 (counting from the 5' end); and
 (iv) at least one (e.g., one, two or three) LNA modifications at positions 1, 2 and 3 (counting from the 5' end);
and
(b) an antisense strand having:
 (i) a length of 23 nucleotides;
 (ii) 2'-F modifications at positions 2, 14, and 16 (counting from the 5' end);
 (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
 (iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand.

In another particular embodiment, the dsRNA molecules of the present invention comprise:
(a) a sense strand having:
(i) a length of 21 nucleotides;
(ii) an ASGPR ligand attached to the 3'-end, wherein said ASGPR ligand comprises three GalNAc derivatives attached through a trivalent branched linker;
(iii) 2'-F modifications at positions 7, 9, 10, and 11 (counting from the 5' end);
(iv) at least one (e.g., one, two or three) LNA modifications at positions 1, 2 and 3 (counting from the 5' end); and
(iv) phosphorothioate internucleotide linkages between nucleotide positions 1 and 2, and between nucleotide positions 2 and 3 (counting from the 5' end);
and
(b) an antisense strand having:
(i) a length of 23 nucleotides;
(ii) 2'-F modifications at positions 2, 14, and 16 (counting from the 5' end);
(iii) phosphorothioate internucleotide linkages between nucleotide positions 1 and 2, between nucleotide positions 2 and 3, between nucleotide positions 21 and 22, and between nucleotide positions 22 and 23 (counting from the 5' end);
and
(iv) a thermally destabilizing modification of the duplex at position 5, 6 or 7 (counting from the 5' end);
wherein the dsRNA molecules have a two nucleotide overhang at the 3'-end of the antisense strand, and a blunt end at the 5'-end of the antisense strand.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 18, 19, 20, 21, 22, 23, 24 or 24 nucleotide pairs in length; and (viii) the dsRNA comprises a blunt end at 5'-end of the sense strand. In some particular embodiments, sense strand is 19, 20 or 21 or 22 nucleotides in length and the antisense strand is 20, 21 or 22 nucleotides in length.

The sense strand and antisense strand typically form a duplex dsRNA. The duplex region of a dsRNA molecule may be 12-40 nucleotide pairs in length. For example, the duplex region can be between 14-40 nucleotide pairs in length, 17-30 nucleotide pairs in length, 25-35 nucleotides in length, 27-35 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotide pairs in length.

In some embodiments, the dsRNA molecule of the invention has a duplex region of 12-40 nucleotides pairs in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a blunt end at 5'-end of the antisense strand. In some particular embodiments, the duplex region is 18, 19, 20, 21, 22 or 23 nucleotides pairs in length. In a particular embodiment, the duplex region is 21 nucleotide pairs in length.

In some embodiments, the dsRNA molecule of the invention comprises one or more overhang regions and/or capping groups of dsRNA molecule at the 3'-end, or 5'-end or both ends of a strand. The overhang can be 1-10 nucleotides in length, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In some embodiments, the nucleotides in the overhang region of the dsRNA molecule of the invention can each independently be a modified or unmodified nucleotide including, but not limited to 2'-sugar modified, such as, 2'-Fluoro 2'-O-methyl, thymidine (T), 2'-O-methoxyethyl-5-methyluridine, 2'-O-methoxyethyladenosine, 2'-O-methoxyethyl-5-methylcytidine, GNA, SNA, hGNA, hhGNA, mGNA, TNA, h'GNA, and any combinations thereof. For example, TT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the dsRNA molecule of the invention may be phosphorylated. In some embodiments, the overhang region contains two nucleotides having a phosphorothioate between the two nucleotides, where the two nucleotides can be the same or different. In some embodiments, the overhang is present at the 3'-end of the sense strand, antisense strand or both strands. In some embodiments, this 3'-overhang is present in the antisense strand. In some embodiments, this 3'-overhang is present in the sense strand.

The dsRNA molecule of the invention may comprise only a single overhang, which can strengthen the interference activity of the dsRNA, without affecting its overall stability. For example, the single-stranded overhang is located at the 3'-terminal end of the sense strand or, alternatively, at the 3'-terminal end of the antisense strand. The dsRNA may also have a blunt end, located at the 5'-end of the antisense strand (or the 3'-end of the sense strand) or vice versa. Generally, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process. For example the single overhang comprises at least two, three, four, five, six, seven, eight, nine, or ten nucleotides in length. In some embodiments, the dsRNA has a 2 nucleotide overhang on the 3'-end of the antisense strand and a blunt end at the 5'-end of the antisense strand.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) and the dsRNA comprises a duplex region of 12-40 nucleotide pairs in length. In some embodiments, the overhang is on the 3'-end of the antisense strand and the blunt end is at the 5'-end of the antisense strand. In some particular embodiments, the overhang is 2, 3 or 4-nucleotides in length.

In some embodiments, the dsRNA molecule has a duplex region of 19, 20, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications, and optionally the 2 nucleotide overhang is on the 3'-end of the antisense strand and the blunt end is at the 5'-end of the antisense strand. In some embodiments, the overhang is on the 3'-end of the antisense strand and the blunt end is at the 5'-end of the antisense strand.

In some embodiments, the dsRNA molecule of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a duplex region of 12-40 nucleotide pairs in length.

In some embodiments, the dsRNA molecule has a duplex region of 19, 20, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications.

Thermally Destabilizing Modifications.

As noted above, dsRNA molecule can be optimized for RNA interference by incorporating thermally destabilizing modifications in the seed region of the antisense strand (i.e., at positions 2-9 of the 5'-end of the antisense strand) to reduce or inhibit off-target gene silencing. Inventors have discovered that dsRNAs with an antisense strand comprising at least one thermally destabilizing modification of the duplex within the first 9 nucleotide positions, counting from the 5' end, of the antisense strand have reduced off-target gene silencing activity. Accordingly, in some embodiments, the antisense strand comprises at least one (e.g., one, two, three, four, five or more) thermally destabilizing modification of the duplex within the first 9 nucleotide positions of the 5' region of the antisense strand. In some embodiments, thermally destabilizing modification of the duplex is located in positions 2-9, or preferably positions 4-8, from the 5'-end of the antisense strand. In some further embodiments, the thermally destabilizing modification of the duplex is located at position 6, 7 or 8 from the 5'-end of the antisense strand. In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a $T_m$ with one, two, three or four degrees lower than the $T_m$ of the dsRNA without having such modification(s). In some embodiments, the thermally destabilizing modification of the duplex is located at position 2, 3, 4, 5 or 9 from the 5'-end of the antisense strand.

The thermally destabilizing modifications can include, but are not limited to, abasic modification; mismatch with the opposing nucleotide in the opposing strand; and sugar modification such as 2'-deoxy modification or acyclic nucleotide, e.g., unlocked nucleic acids (UNA) or glycol nucleic acid (GNA).

Exemplified abasic modifications include, but are not limited to the following:

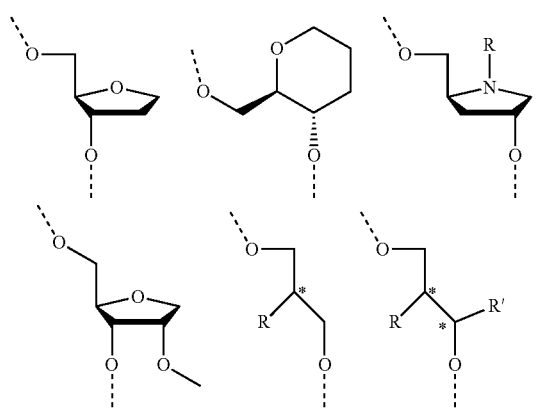

-continued

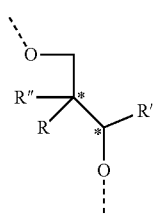

Wherein R=H, Me, Et or OMe; R'=H, Me, Et or OMe; R"=H, Me, Et or OMe

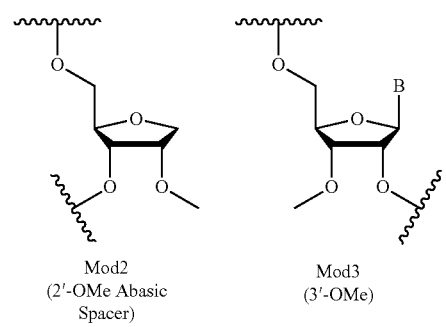

Mod2
(2'-OMe Abasic Spacer)

Mod3
(3'-OMe)

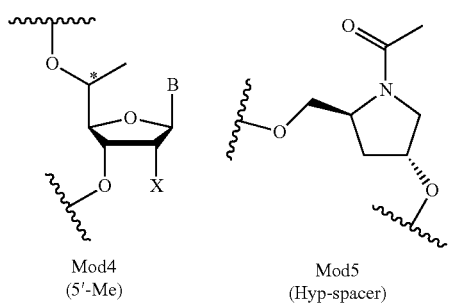

Mod4
(5'-Me)

Mod5
(Hyp-spacer)

X = OMe, F wherein B is a modified or unmodified nucleobase.

Exemplified sugar modifications include, but are not limited to the following:

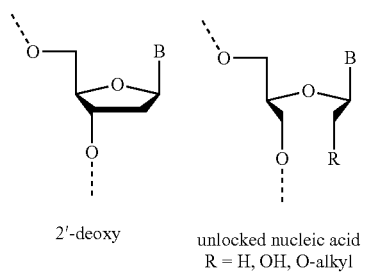

2'-deoxy unlocked nucleic acid
R = H, OH, O-alkyl

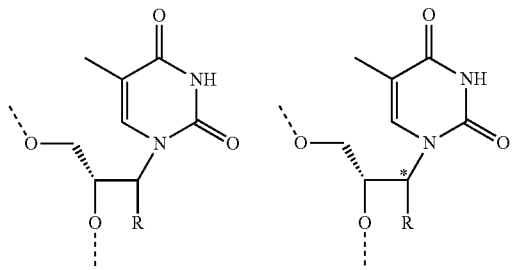

glycol nucleic acid
R = H, OH, O-alkyl glycol nucleic acid
R = H, OH, O-alkyl

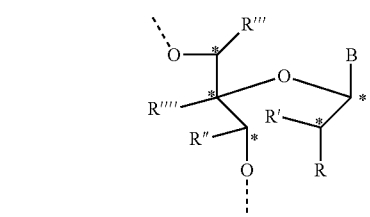

unlocked nucleic acid
R = H, OH, CH$_3$, CH$_2$CH$_3$, O-alkyl, NH$_2$, NHMe, NMe$_2$
R' = H, OH, CH$_3$, CH$_2$CH$_3$, O-alkyl, NH$_2$, NHMe, NMe$_2$
R'' = H, OH, CH$_3$, CH$_2$CH$_3$, O-alkyl, NH$_2$, NHMe, NMe$_2$
R''' = H, OH, CH$_3$, CH$_2$CH$_3$, O-alkyl, NH$_2$, NHMe, NMe$_2$
R'''' = H, OH, CH$_3$, CH$_2$CH$_3$, O-alkyl, NH$_2$, NHMe, NMe$_2$

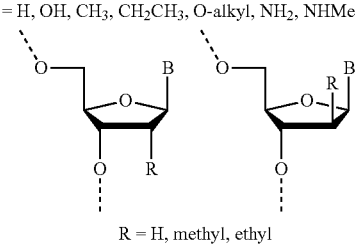

R = H, methyl, ethyl wherein B is a modified or unmodified nucleobase.

In some embodiments the thermally destabilizing modification of the duplex is selected from the group consisting of:

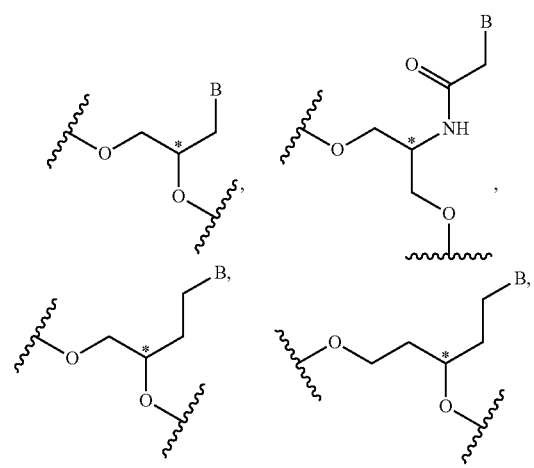

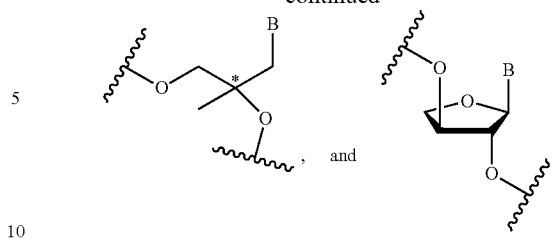

and wherein B is a modified or unmodified nucleobase and the asterisk on each structure represents either R, S or racemic.

The term "acyclic nucleotide" refers to any nucleotide having an acyclic ribose sugar, for example, where any of bonds between the ribose carbons (e.g., C1'-C2', C2'-C3', C3'-C4', C4'-O4', or C1-C4') is absent and/or at least one of ribose carbons or oxygen (e.g., C1', C2', C3', C4' or O4') are independently or in combination absent from the nucleotide. In some embodiments, acyclic nucleotide is

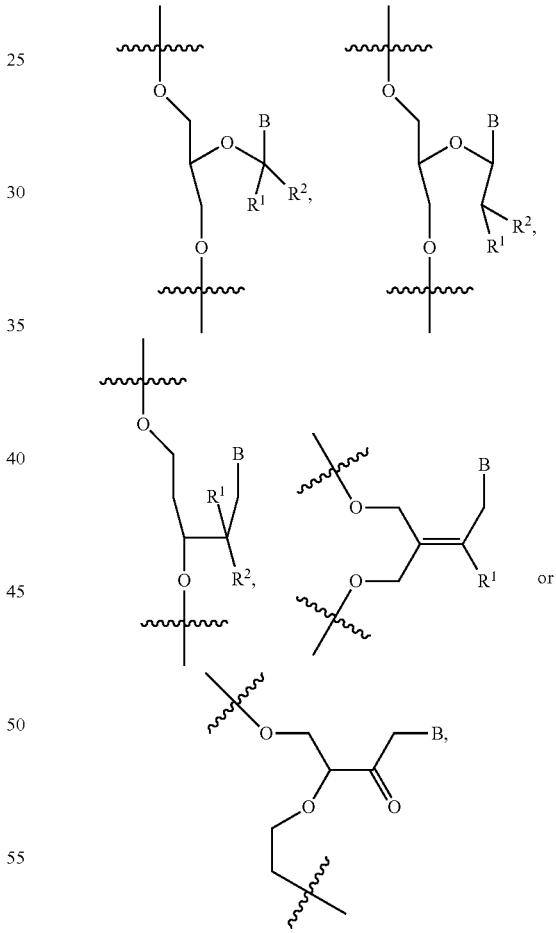

wherein B is a modified or unmodified nucleobase, R$^1$ and R$^2$ independently are H, halogen, OR$_3$, or alkyl; and R$_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., Tetrahedron Letters, 26 (17): 2059 (1985); and Fluiter et al., Mol. Biosyst., 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

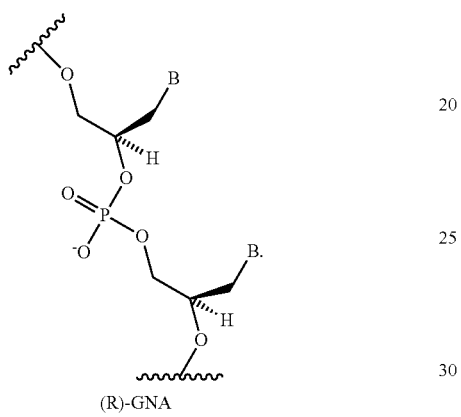

(R)-GNA

The thermally destabilizing modification of the duplex can be mismatches (i.e., noncomplementary base pairs) between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA molecule contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired W-C H-bonding to complementary base on the target mRNA, such as:

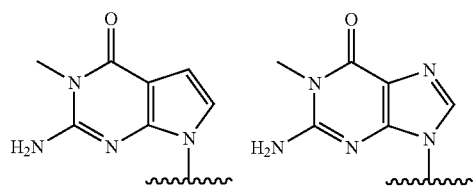

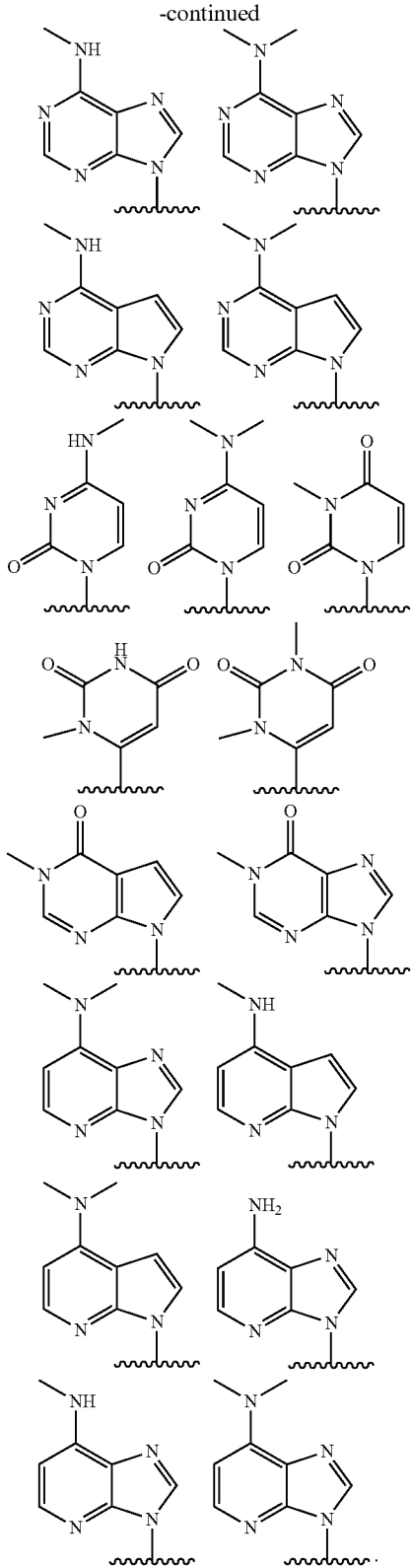

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

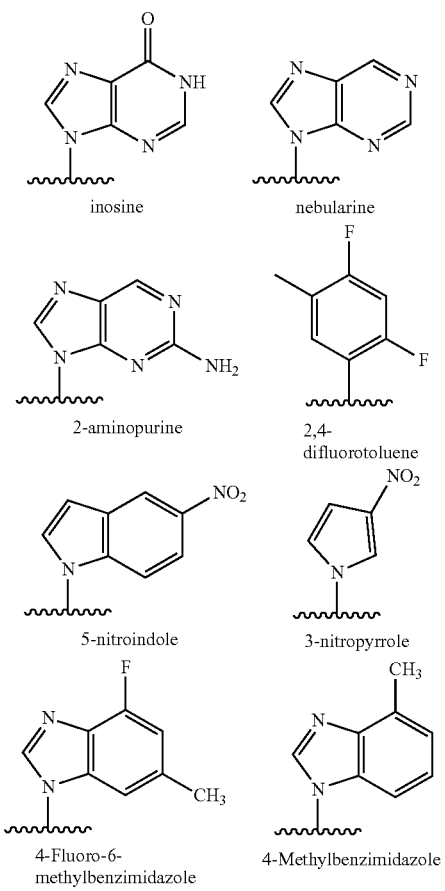

In some embodiments, the thermally destabilizing modification of the duplex in the seed region of the antisense strand includes one or more α-nucleotide complementary to the base on the target mRNA, such as:

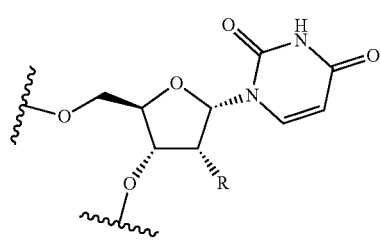

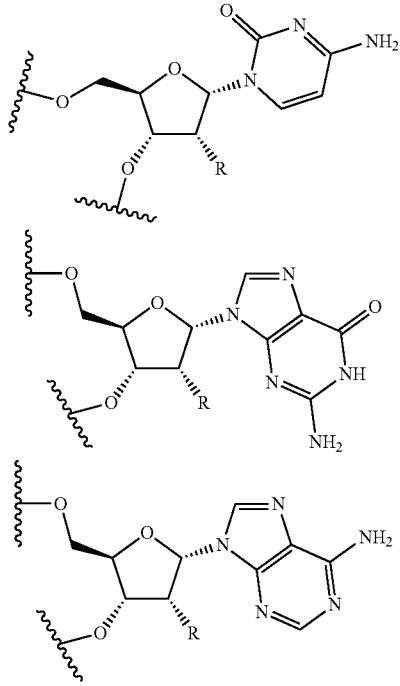

Wherein R is H, OH, OCH₃, F, NH₂, NHMe, NMe₂ or O-alkyl

Exemplary phosphate modifications known to decrease the thermal stability of dsRNA duplexes compared to natural phosphodiester linkages are:

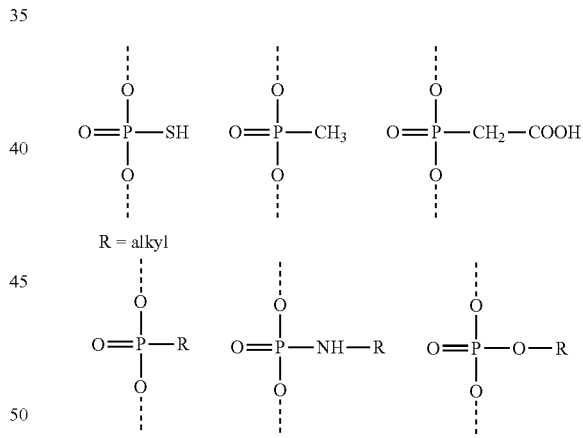

The alkyl for the R group can be a $C_1$-$C_6$ alkyl. Specific alkyls for the R group include, but are not limited to methyl, ethyl, propyl, isopropyl, butyl, pentyl and hexyl.

In some embodiments, exemplary destabilizing modifications shown in FIG. 1.

In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand and/or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14 and 16 from the 5'-end. In some other embodiments, the antisense comprises stabilizing modifications at positions 2, 6, 14 and 16 from the 5'-end. In still some other embodiments, the antisense comprises stabilizing modifications at positions 2, 14 and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions −1 and +1 from the position of the destabilizing modification.

In some embodiments, the antisense strand comprises at least two stabilizing modifications at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10 and 11 from the 5'-end. In some other embodiments, the sense strand comprises stabilizing modifications at positions 7, 9, 10 and 11 from the 5'-end. In some embodiments, the sense strand comprises stabilizing modifications at positions opposite or complimentary to positions 11, 12 and 15 of the antisense strand, counting from the 5'-end of the antisense strand. In some other embodiments, the sense strand comprises stabilizing modifications at positions opposite or complimentary to positions 11, 12, 13 and 15 of the antisense strand, counting from the 5'-end of the antisense strand. In some embodiments, the sense strand comprises a block of two, three or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to 2'-fluoro modifications. Other thermally stabilizing modifications include, but are not limited to LNA.

In some embodiments, the dsRNA of the invention comprises at least four (e.g., four, five, six, seven, eight, nine, ten or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand and/or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14 and 16 from the 5'-end. In some other embodiments, the antisense comprises 2'-fluoro nucleotides at positions 2, 6, 14 and 16 from the 5'-end. In still some other embodiments, the antisense comprises 2'-fluoro nucleotides at positions 2, 14 and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position −1 or +1 from the position of the destabilizing modification. In some embodiments, the antisense strand comprises a 2'-fluoro nucleotide at each of the 5'-end and the 3'-end of the destabilizing modification, i.e., positions −1 and +1 from the position of the destabilizing modification.

In some embodiments, the antisense strand comprises at least two 2'-fluoro nucleotides at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) 2'-fluoro nucleotides. Without limitations, a 2'-fluoro modification in the sense strand can be present at any positions. In some embodiments, the antisense comprises 2'-fluoro nucleotides at positions 7, 10 and 11 from the 5'-end. In some other embodiments, the sense strand comprises 2'-fluoro nucleotides at positions 7, 9, 10 and 11 from the 5'-end. In some embodiments, the sense strand comprises 2'-fluoro nucleotides at positions opposite or complimentary to positions 11, 12 and 15 of the antisense strand, counting from the 5'-end of the antisense strand. In some other embodiments, the sense strand comprises 2'-fluoro nucleotides at positions opposite or complimentary to positions 11, 12, 13 and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

In some embodiments, the dsRNA molecule of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense.

In some embodiments, the dsRNA molecule of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA molecule of the invention comprises a sense and antisense strands, wherein said dsRNA molecule comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA molecule is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; and (vi) the dsRNA comprises at least four 2'-fluoro modifications; and (vii) the dsRNA has a duplex region of 12-29 nucleotide pairs in length.

In some embodiments, every nucleotide in the sense strand and antisense strand of the dsRNA molecule may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. E.g., a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In some embodiments, each residue of the sense strand and antisense strand is independently modified with 2'-O-methyl or 2'-fluoro. It is to be understood that these modifications are in addition to the at least one thermally destabilizing modification of the duplex present in the antisense strand.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxy-2'-fluoro nucleotide, 2'-O—N-methylacetamido (2'-O—NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide. Again, it is to be understood that these modifications are in addition to the at least one thermally destabilizing modification of the duplex present in the antisense strand.

In some embodiments, the dsRNA molecule of the invention comprises modifications of an alternating pattern, particular in the B1, B2, B3, B1', B2', B3', B4' regions. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAAB-BAABB . . . ," "AABAABAABAAB . . . ," "AAABAAA-BAAAB . . . ," "AAABBBAAABBB . . . ," or "ABCAB-CABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABA-BAB . . . ", "ACACAC . . . " "BDBDBD . . . " or "CDCDCD . . . ," etc.

In some embodiments, the dsRNA molecule of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

The dsRNA molecule of the invention may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA molecule comprises the phosphorothioate or methylphosphonate internucleotide linkage modification in the overhang region. For example, the overhang region comprises two nucleotides having a phosphorothioate or methylphosphonate internucleotide linkage between the two nucleotides. internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA molecule comprises 1-10 blocks of two to ten phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of three phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of four phosphorothioate or methylphosphonate internucleotide linkages separated by 1, 2, 3, 4, 5, 6, 7, 8, 9, 10, 11, 12, 13 or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of five phosphorothioate or methylphosphonate internucleotide linkages separated by 1, 2, 3, 4, 5, 6, 7, 8, 9, 10, 11 or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of six phosphorothioate or methylphosphonate internucleotide linkages separated by 1, 2, 3, 4, 5, 6, 7, 8, 9 or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of seven phosphorothioate or methylphosphonate internucleotide linkages separated by 1, 2, 3, 4, 5, 6, 7 or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of eight phosphorothioate or methylphosphonate internucleotide linkages separated by 1, 2, 3, 4, 5 or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA molecule comprises two blocks of nine phosphorothioate or methylphosphonate internucleotide linkages separated by 1, 2, 3 or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA molecule of the invention further comprises one or more phosphorothioate or methylphosphonate internucleotide linkage modification within 1-10 of the termini position(s) of the sense and/or antisense strand. For example, at least 2, 3, 4, 5, 6, 7, 8, 9 or 10 nucleotides may be linked through phosphorothioate or methylphosphonate internucleotide linkage at one end or both ends of the sense and/or antisense strand.

In some embodiments, the dsRNA molecule of the invention further comprises one or more phosphorothioate or methylphosphonate internucleotide linkage modification within 1-10 of the internal region of the duplex of each of the sense and/or antisense strand. For example, at least 2, 3, 4, 5, 6, 7, 8, 9 or 10 nucleotides may be linked through phosphorothioate methylphosphonate internucleotide linkage at position 8-16 of the duplex region counting from the 5'-end of the sense strand; the dsRNA molecule can optionally further comprise one or more phosphorothioate or methylphosphonate internucleotide linkage modification within 1-10 of the termini position(s).

In some embodiments, the dsRNA molecule of the invention further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA molecule of the invention further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the invention further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the invention further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA molecule of the invention further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the invention further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA molecule of the invention further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA molecule of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, compound of the invention comprises a pattern of backbone chiral centers. In some embodiments, a common pattern of backbone chiral centers comprises at least 5 internucleotidic linkages in the Sp configuration. In some embodiments, a common pattern of backbone chiral centers comprises at least 6 internucleotidic linkages in the Sp configuration. In some embodiments, a common pattern of backbone chiral centers comprises at least 7 internucleotidic linkages in the Sp configuration. In some embodiments, a common pattern of backbone chiral centers comprises at least 8 internucleotidic linkages in the Sp configuration. In some embodiments, a common pattern of backbone chiral centers comprises at least 9 internucleotidic linkages in the Sp configuration. In some embodiments, a common pattern of backbone chiral centers comprises at least 10 internucleotidic linkages in the Sp configuration. In some embodiments, a common pattern of backbone chiral centers comprises at least 11 internucleotidic linkages in the Sp configuration. In some embodiments, a common pattern of backbone chiral centers comprises at least 12 internucleotidic linkages in the Sp configuration. In some embodiments, a common pattern of backbone chiral centers comprises at least 13 internucleotidic linkages in the Sp configuration. In some embodiments, a common pattern of backbone chiral centers comprises at least 14 internucleotidic linkages in the Sp configuration. In some embodiments, a common pattern of backbone chiral centers comprises at least 15 internucleotidic linkages in the Sp configuration. In some embodiments, a common pattern of backbone chiral centers comprises at least 16 internucleotidic linkages in the Sp configuration. In some embodiments, a common pattern of backbone chiral centers comprises at least 17 internucleotidic linkages in the Sp configuration. In some embodiments, a common pattern of backbone chiral centers comprises at least 18 internucleotidic linkages in the Sp configuration. In some embodiments, a common pattern of backbone chiral centers comprises at least 19 internucleotidic linkages in the Sp configuration. In some embodiments, a common pattern of backbone chiral centers comprises no more than 8 internucleotidic linkages in the Rp configuration. In some embodiments, a common pattern of backbone chiral centers comprises no more than 7 internucleotidic linkages in the Rp configuration. In some embodiments, a common pattern of backbone chiral centers comprises no more than 6 internucleotidic linkages in the Rp configuration. In some embodiments, a common pattern of backbone chiral centers comprises no more than 5 internucleotidic linkages in the Rp configuration. In some embodiments, a common pattern of backbone chiral centers comprises no more than 4 internucleotidic linkages in the Rp configuration. In some embodiments, a common pattern of backbone chiral centers comprises no more than 3 internucleotidic linkages in the Rp configuration. In some embodiments, a common pattern of backbone chiral centers comprises no more than 2 internucleotidic linkages in the Rp configuration. In some embodiments, a common pattern of backbone chiral centers comprises no more than 1 internucleotidic linkages in the Rp configuration. In some embodiments, a common pattern of backbone chiral centers comprises no more than 8 internucleotidic linkages which are not chiral (as a non-limiting example, a phosphodiester). In some embodiments, a common pattern of backbone chiral centers comprises no more than 7 internucleotidic linkages which are not chiral. In some embodiments, a common pattern of backbone chiral centers comprises no more than 6 internucleotidic linkages which are not chiral. In some embodiments, a common pattern of backbone chiral centers comprises no more than 5 internucleotidic linkages which are not chiral. In some embodiments, a common pattern of backbone chiral centers comprises no more than 4 internucleotidic linkages which are not chiral. In some embodiments, a common pattern of backbone chiral centers comprises no more than 3 internucleotidic linkages which are not chiral. In some embodiments, a common pattern of backbone chiral centers comprises no more than 2 internucleotidic linkages which are not chiral. In some embodiments, a common pattern of backbone chiral centers comprises no more than 1 internucleotidic linkages which are not chiral. In some embodiments, a common pattern of backbone chiral centers comprises at least 10 internucleotidic linkages in the Sp configuration, and no more than 8 internucleotidic linkages which are not chiral. In some embodiments, a common pattern of backbone chiral centers comprises at least 11 internucleotidic linkages in the Sp configuration, and no more than 7 internucleotidic linkages which are not chiral. In some embodiments, a common pattern of backbone chiral centers comprises at least 12 internucleotidic linkages in the Sp configuration, and no more than 6 internucleotidic linkages which are not chiral. In some embodiments, a common pattern of backbone chiral centers comprises at least 13 internucleotidic linkages in the Sp configuration, and no more than 6 internucleotidic linkages which are not chiral. In some embodiments, a common pattern of backbone chiral centers comprises at least 14 internucleotidic linkages in the Sp configuration, and no more than 5 internucleotidic linkages which are not chiral. In some embodiments, a common pattern of backbone chiral centers comprises at least 15 internucleotidic linkages in the Sp configuration, and no more than 4 internucleotidic linkages which are not chiral. In some embodiments, the internucleotidic linkages in the Sp configuration are optionally contiguous or not contiguous. In some embodiments, the internucleotidic linkages in the Rp configuration are optionally contiguous or not contiguous. In some embodiments, the internucleotidic linkages which are not chiral are optionally contiguous or not contiguous.

In some embodiments, compound of the invention comprises a block is a stereochemistry block. In some embodiments, a block is an Rp block in that each internucleotidic linkage of the block is Rp. In some embodiments, a 5'-block is an Rp block. In some embodiments, a 3'-block is an Rp block. In some embodiments, a block is an Sp block in that each internucleotidic linkage of the block is Sp. In some embodiments, a 5'-block is an Sp block. In some embodiments, a 3'-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage in a natural phosphate linkage.

In some embodiments, compound of the invention comprises a 5'-block is an Sp block wherein each sugar moiety comprises a 2'-F modification. In some embodiments, a 5'-block is an Sp block wherein each of internucleotidic linkage is a modified internucleotidic linkage and each sugar moiety comprises a 2'-F modification. In some embodiments, a 5'-block is an Sp block wherein each of internucleotidic linkage is a phosphorothioate linkage and each sugar moiety comprises a 2'-F modification. In some embodiments, a 5'-block comprises 4 or more nucleoside units. In some embodiments, a 5'-block comprises 5 or more nucleoside units. In some embodiments, a 5'-block comprises 6 or more nucleoside units. In some embodiments, a 5'-block comprises 7 or more nucleoside units. In some embodiments, a 3'-block is an Sp block wherein each sugar moiety comprises a 2'-F modification. In some embodiments, a 3'-block is an Sp block wherein each of internucleotidic linkage is a modified internucleotidic linkage and each sugar moiety comprises a 2'-F modification. In some embodiments, a 3'-block is an Sp block wherein each of internucleotidic linkage is a phosphorothioate linkage and each sugar moiety comprises a 2'-F modification. In some embodiments, a 3'-block comprises 4 or more nucleoside units. In some embodiments, a 3'-block comprises 5 or more nucleoside units. In some embodiments, a 3'-block comprises 6 or more nucleoside units. In some embodiments, a 3'-block comprises 7 or more nucleoside units.

In some embodiments, compound of the invention comprises a type of nucleoside in a region or an oligonucleotide is followed by a specific type of internucleotidic linkage, e.g., natural phosphate linkage, modified internucleotidic linkage, Rp chiral internucleotidic linkage, Sp chiral internucleotidic linkage, etc. In some embodiments, A is followed by Sp. In some embodiments, A is followed by Rp. In some embodiments, A is followed by natural phosphate linkage (PO). In some embodiments, U is followed by Sp. In some embodiments, U is followed by Rp. In some embodiments, U is followed by natural phosphate linkage (PO). In some embodiments, C is followed by Sp. In some embodiments, C is followed by Rp. In some embodiments, C is followed by natural phosphate linkage (PO). In some embodiments, G is followed by Sp. In some embodiments, G is followed by Rp. In some embodiments, G is followed by natural phosphate linkage (PO). In some embodiments, C and U are followed by Sp. In some embodiments, C and U are followed by Rp. In some embodiments, C and U are followed by natural phosphate linkage (PO). In some embodiments, A and G are followed by Sp. In some embodiments, A and G are followed by Rp.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3, 4 or 5 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3, 4 or 5 phosphorothioate internucleotide linkages; (iii) the sense strand is conjugated with a ligand; (iv) the sense strand comprises 2, 3, 4 or 5 2'-fluoro modifications; (v) the sense strand comprises 3, 4 or 5 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3, 4 or 5 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand.

In some embodiments, the dsRNA molecule of the invention comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA molecule of the invention comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

The inventors found that introducing 4'-modified and/or 5'-modified nucleotide to the 3'-end of a phosphodiester (PO), phosphorothioate (PS), and/or phosphorodithioate (PS2) linkage of a dinucleotide at any position of single stranded or double stranded oligonucleotide can exert steric effect to the internucleotide linkage and, hence, protecting or stabilizing it against nucleases.

In some embodiments, 5'-modified nucleoside is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In some embodiments, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-O-alkyl of the ribose sugar can be racemic or chirally pure R or S isomer. An exemplary 4'-O-alkylated nucleoside is 4'-O-methyl nucleoside. The 4'-O-methyl can be either racemic or chirally pure R or S isomer.

In some embodiments, 5'-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In some embodiments, 4'-alkylated nucleoside is introduced at any position on the sense strand or antisense strand of a dsRNA, and such modification maintains or improves potency of the dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In some embodiments, 4'-O-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In some embodiments, the dsRNA molecule of the invention can comprise 2'-5' linkages (with 2'-H, 2'-OH and 2'-OMe and with P=O or P=S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA molecule of the invention can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

Various publications describe multimeric siRNA which can all be used with the dsRNA of the invention. Such publications include WO2007/091269, U.S. Pat. No. 7,858, 769, WO2010/141511, WO2007/117686, WO2009/014887 and WO2011/031520 which are hereby incorporated by their entirely.

The dsRNA molecule that contains conjugations of one or more carbohydrate moieties to a dsRNA molecule can optimize one or more properties of the dsRNA molecule. In many cases, the carbohydrate moiety will be attached to a modified subunit of the dsRNA molecule. E.g., the ribose sugar of one or more ribonucleotide subunits of a dsRNA molecule can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one embodiment the dsRNA molecule of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

The double-stranded RNA (dsRNA) agent of the invention may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

In some embodiments dsRNA molecules of the invention are 5' phosphorylated or include a phosphoryl analog at the 5' prime terminus. 5'-phosphate modifications include those which are compatible with RISC mediated gene silencing. Suitable modifications include: 5'-monophosphate (($HO)_2$(O)P—O-5'); 5'-diphosphate (($HO)_2$(O)P—O—P(HO)(O)—O-5'); 5'-triphosphate (($HO)_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; $(HO)_2$(S)P—O-5'); 5'-monodithiophosphate (phosphorodithioate; (HO)(HS)(S)P—O-5'), 5'-phosphorothiolate (($HO)_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates (($HO)_2$(O)P—NH-5', (HO)($NH_2$)(O)P—O-5'), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), $(OH)_2$(O)P-5'-CH2-), 5'-alkyletherphosphonates (R=alkylether=methoxymethyl (MeOCH2-), ethoxymethyl, etc., e.g. RP(OH)(O)—O-5'-). In one example, the modification can in placed in the antisense strand of a dsRNA molecule.

Ligands

A wide variety of entities can be coupled to the oligonucleotides of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In some embodiments, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972, which is incorporated by reference in its entirety), the EALA peptide (Vogel et al., J. Am. Chem. Soc., 1996, 118: 1581-1586, which is incorporated by reference in its entirety), and their derivatives (Turk et al., Biochem. Biophys. Acta, 2002, 1559: 56-68, which is incorporated by reference in its entirety). In some embodiments, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyamino acids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases or a chelating agent (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptide species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNF-alpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or cross-linked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP. An RFGF analogue (e.g., amino acid sequence AALLPVLLAAP) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) and the Drosophila Antennapedia protein (RQIKIWFQNRRMKWKK) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-94, 1991, which is incorporated by reference in its entirety). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., Cancer Res., 62:5139-43, 2002, which is incorporated by reference in its entirety). An RGD peptide can facilitate targeting of an iRNA agent to tumors of a variety of other tissues, including the lung, kidney, spleen, or liver (Aoki et al., Cancer Gene Therapy 8:783-787, 2001, which is incorporated by reference in its entirety). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001, which is incorporated by reference in its entirety). Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogenesis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003, which is incorporated by reference in its entirety).

In some embodiments, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, H2A peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by $i\pm3$, or $i\pm4$ positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an aptamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycarboxylates, polycations, masked oligo or poly cations or anions, acetals, polyacetals, ketals/polyketals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Exemplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in U.S. patent application U.S. Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP-$(CH_2)_n NH_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithioate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

In some embodiments, the ligand is conjugated to the sense strand. As described herein, the ligand can be conjugated at the 3'-end, 5'-end or at an internal position of the sense strand. In some embodiments, the ligand is conjugated to the 3'-end of the sense strand. Further, the ligand can be conjugated to a nucleobase, sugar moiety or internucleotide linkage of the sense strand.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylgalactosamine) derivatives attached through a monovalent, bivalent or trivalent branched linker.

In some embodiments, the dsRNA of the invention is conjugated to a bivalent and trivalent branched linkers include the structures shown in any of formula (IV)-(VII):

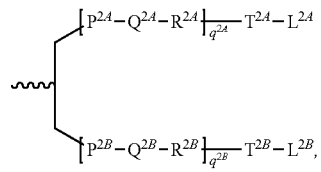

Formula (IV)

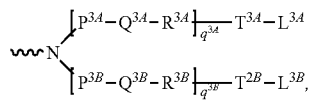

Formula (V)

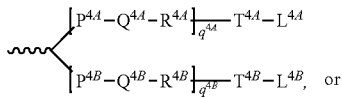

Formula (VI)

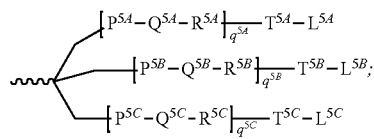

Formula (VII)

wherein:

$q^{2A}$, $q^{2B}$, $q^{3A}$, $q^{3B}$, $q^{4A}$, $q^{4B}$, $q^{5A}$, $q^{5B}$ and $q^{5C}$ represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{5A}$, $T^{5B}$, $T^{5C}$ are each independently for each occurrence absent, CO, NH, O, S, OC(O), NHC(O), CH$_2$, CH$_2$NH or CH$_2$O;

$Q^{2A}$, $Q^{2B}$, $Q^{3A}$, $Q^{3B}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R$^N$), C(R')=C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(Ra)C(O), —C(O)—CH(Ra)—NH—, CO, CH=N—O,

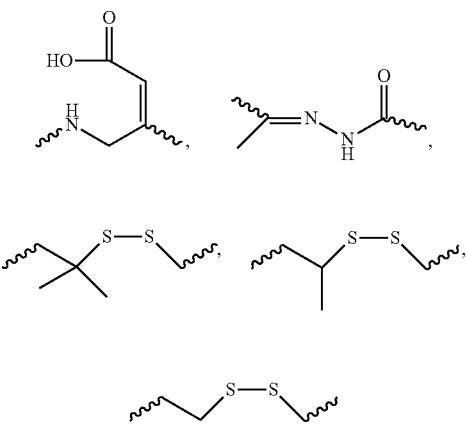

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

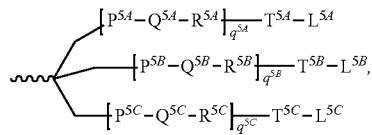

Formula (VII)

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the following compounds:

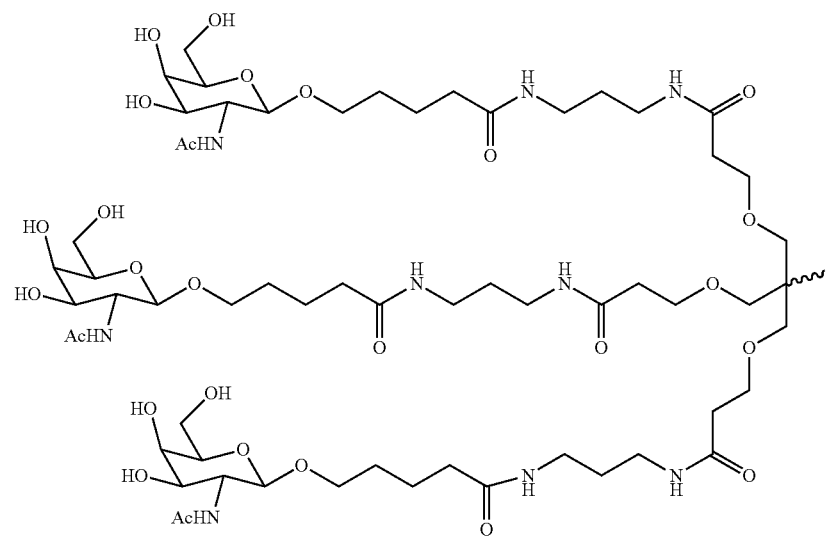
,
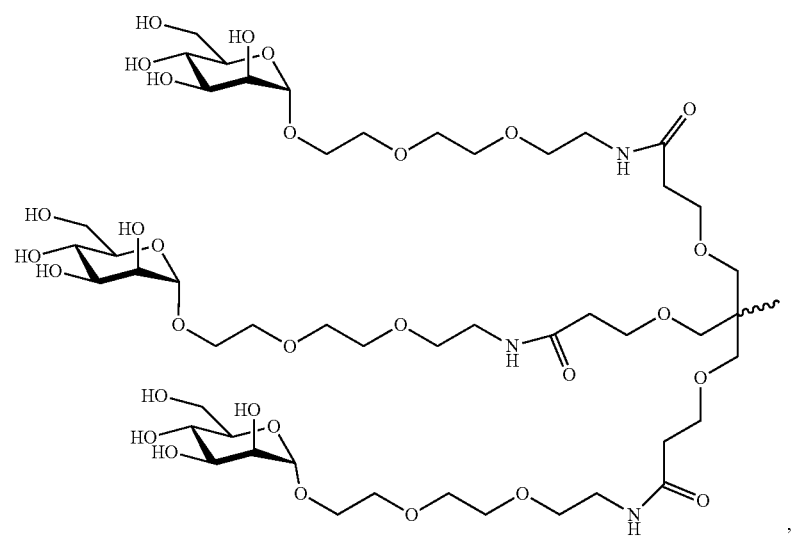
,
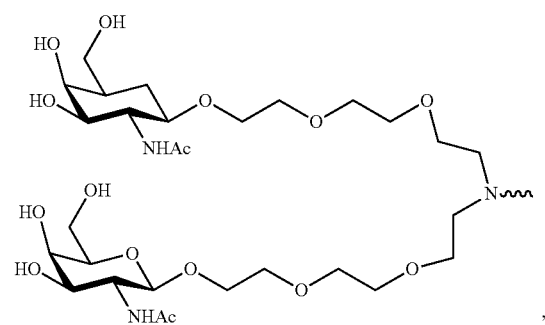
,

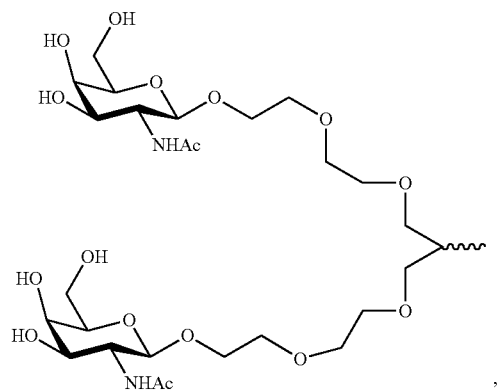
,
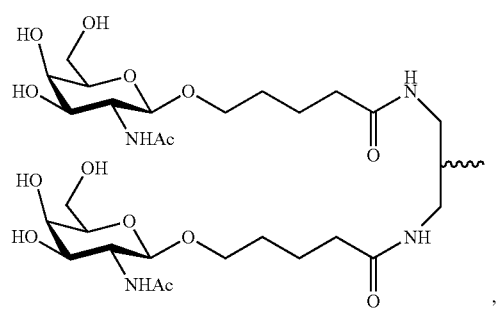
,
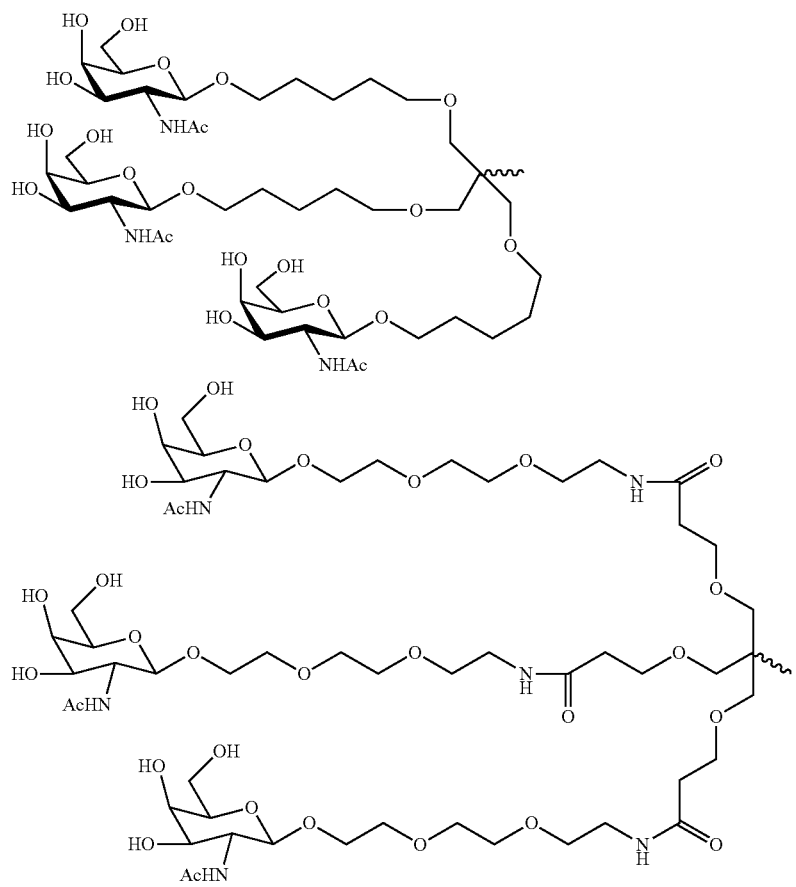
, or

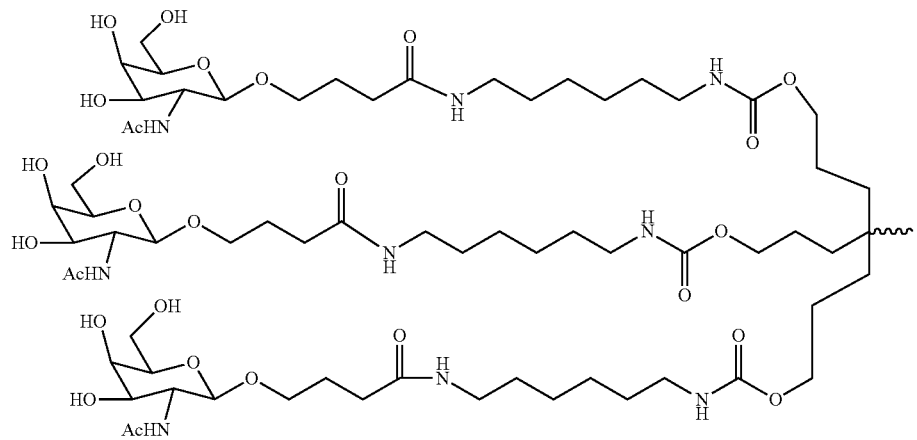

Definitions

As used herein, the terms "dsRNA", "siRNA", and "IRNA agent" are used interchangeably to agents that can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of assays or therapeutic treatment, or in the case of in vitro assays, under conditions in which the assays are performed. The non-target sequences typically differ by at least 5 nucleotides.

In some embodiments, a dsRNA molecule of the invention is "sufficiently complementary" to a target RNA, e.g., a target mRNA, such that the dsRNA molecule silences production of protein encoded by the target mRNA. In another embodiment, the dsRNA molecule of the invention is "exactly complementary" to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA molecule of the invention specifically discriminates a single-nucleotide difference. In this case, the dsRNA molecule only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

The term 'BNA' refers to bridged nucleic acid, and is often referred as constrained or inaccessible RNA. BNA can contain a 5-, 6-membered, or even a 7-membered bridged structure with a "fixed" C3'-endo sugar puckering. The bridge is typically incorporated at the 2'-, 4'-position of the ribose to afford a 2', 4'-BNA nucleotide (e.g., LNA, or ENA). Examples of BNA nucleotides include the following nucleosides:

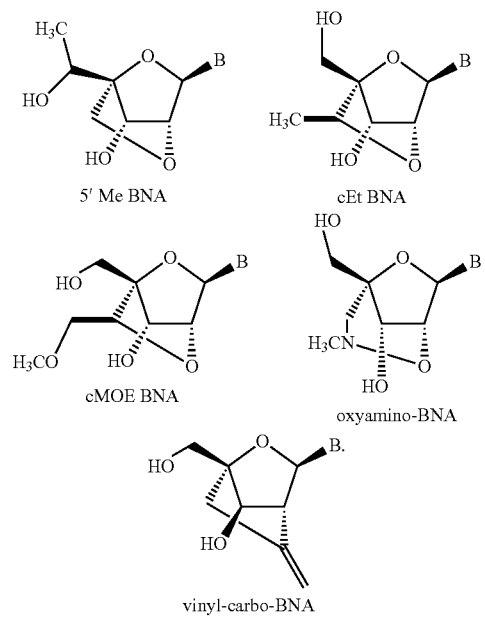

The term 'LNA' refers to locked nucleic acid, and is often referred as constrained or inaccessible RNA. LNA is a modified RNA nucleotide. The ribose moiety of an LNA nucleotide is modified with an extra bridge (e.g., a methylene bridge or an ethylene bridge) connecting the 2' hydroxyl to the 4' carbon of the same ribose sugar. For instance, the bridge can "lock" the ribose in the 3'-endo North) conformation:

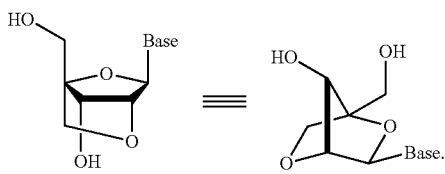

The term 'ENA' refers to ethylene-bridged nucleic acid, and is often referred as constrained or inaccessible RNA.

The "cleavage site" herein means the backbone linkage in the target gene or the sense strand that is cleaved by the RISC mechanism by utilizing the iRNA agent. And the target cleavage site region comprises at least one or at least two nucleotides on both side of the cleavage site. For the sense strand, the cleavage site is the backbone linkage in the sense strand that would get cleaved if the sense strand itself was the target to be cleaved by the RNAi mechanism. The cleavage site can be determined using methods known in the art, for example the 5'-RACE assay as detailed in Soutschek et al., Nature (2004) 432, 173-178, which is incorporated by reference in its entirety. As is well understood in the art, the cleavage site region for a conical double stranded RNAi agent comprising two 21-nucleotides long strands (wherein the strands form a double stranded region of 19 consecutive base pairs having 2-nucleotide single stranded overhangs at the 3'-ends), the cleavage site region corresponds to positions 9-12 from the 5'-end of the sense strand.

Cleavable Linking Groups

A cleavable linking group is one which is sufficiently stable outside the cell, but which upon entry into a target cell is cleaved to release the two parts the linker is holding together. In a preferred embodiment of the dsRNA molecule according to the present invention, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups is redox cleavable linking groups, which may be used in the dsRNA molecule according to the present invention that are cleaved upon reduction or oxidation. An example of reductively cleavable linking group is a disulfide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-based cleavable linking groups

Phosphate-based cleavable linking groups, which may be used in the dsRNA molecule according to the present invention, are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)

(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-S—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups, which may be used in the dsRNA molecule according to the present invention, are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups, which may be used in the dsRNA molecule according to the present invention, are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups, which may be used in the dsRNA molecule according to the present invention, are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynylene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where RA and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

The present invention further relates to a use of a dsRNA molecule as defined herein for inhibiting expression of a target gene. In some embodiments, the present invention further relates to a use of a dsRNA molecule for inhibiting expression of a target gene in vitro.

The present invention further relates to a dsRNA molecule as defined herein for use in inhibiting expression of a target gene in a subject. The subject may be any animal, such as a mammal, e.g., a mouse, a rat, a sheep, a cattle, a dog, a cat, or a human In some embodiments, the dsRNA molecule of the invention is administered in buffer.

In some embodiments, siRNA compounds described herein can be formulated for administration to a subject. A formulated siRNA composition can assume a variety of states. In some examples, the composition is at least partially crystalline, uniformly crystalline, and/or anhydrous (e.g., less than 80, 50, 30, 20, or 10% water). In another example, the siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly.

A siRNA preparation can be formulated in combination with another agent, e.g., another therapeutic agent or an agent that stabilizes a siRNA, e.g., a protein that complexes with siRNA to form an iRNP. Still other agents include chelating agents, e.g., EDTA (e.g., to remove divalent cations such as $Mg^{2+}$), salts, RNAse inhibitors (e.g., a broad specificity RNAse inhibitor such as RNAsin) and so forth.

In some embodiments, the siRNA preparation includes another siRNA compound, e.g., a second siRNA that can mediate RNAi with respect to a second gene, or with respect to the same gene. Still other preparation can include at least 3, 5, ten, twenty, fifty, or a hundred or more different siRNA species. Such siRNAs can mediate RNAi with respect to a similar number of different genes.

In some embodiments, the siRNA preparation includes at least a second therapeutic agent (e.g., an agent other than a RNA or a DNA). For example, a siRNA composition for the treatment of a viral disease, e.g., HIV, might include a known antiviral agent (e.g., a protease inhibitor or reverse transcriptase inhibitor). In another example, a siRNA composition for the treatment of a cancer might further comprise a chemotherapeutic agent.

Exemplary formulations which can be used for administering the dsRNA molecule according to the present invention are discussed below.

Liposomes. For ease of exposition the formulations, compositions and methods in this section are discussed largely with regard to unmodified siRNA compounds. It may be understood, however, that these formulations, compositions and methods can be practiced with other siRNA compounds, e.g., modified siRNAs, and such practice is within the invention. An siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the siRNA composition. The lipophilic material isolates the aqueous interior from an aqueous exterior, which typically does not include the siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the siRNA are delivered into the cell where the siRNA can specifically bind to a target RNA and can mediate RNAi. In some cases the liposomes are also specifically targeted, e.g., to direct the siRNA to particular cell types.

A liposome containing a siRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The siRNA preparation is then added to the micelles that include the lipid component. The cationic groups on the lipid interact with the siRNA and condense around the siRNA to form a liposome. After condensation, the detergent is removed, e.g., by dialysis, to yield a liposomal preparation of siRNA.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Feigner, P. L. et al., *Proc. Natl. Acad. Sci.*, USA 8:7413-7417, 1987; U.S. Pat. Nos. 4,897,355; 5,171,678; Bangham, et al. *M Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984, which are incorporated by reference in their entirety. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986, which is incorporated by reference in its entirety). Microfluidization can be used when consistently small (50 to 200 nm) and relatively uniform aggregates are desired (Mayhew, et al. *Biochim. Biophys. Acta* 775:169, 1984, which is incorporated by reference in its entirety). These methods are readily adapted to packaging siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274, which is incorporated by reference in its entirety).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and include U.S. Pat. Nos. 5,283,185; 5,171, 678; WO 94/00569; WO 93/24640; WO 91/16024; Feigner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

In some embodiments, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated siRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA (see, e.g., Feigner, P. L. et al., Proc. Natl. Acad. Sci., USA 8:7413-7417, 1987 and U.S. Pat. No. 4,897,355 for a description of DOTMA and its use with DNA, which are incorporated by reference in their entirety).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991, which is incorporated by reference in its entirety). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer siRNA, into the skin. In some implementations, liposomes are used for delivering siRNA to epidermal cells and also to enhance the penetration of siRNA into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2,405-410 and du Plessis et al., *Antiviral Research*, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987, which are incorporated by reference in their entirety).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with siRNA are useful for treating a dermatological disorder.

Liposomes that include siRNA can be made highly deformable. Such deformability can enable the liposomes to penetrate through pore that are smaller than the average radius of the liposome. For example, transfersomes are a type of deformable liposomes. Transfersomes can be made by adding surface edge activators, usually surfactants, to a standard liposomal composition. Transfersomes that include siRNA can be delivered, for example, subcutaneously by infection in order to deliver siRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018, 616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Surfactants. For ease of exposition the formulations, compositions and methods in this section are discussed largely with regard to unmodified siRNA compounds. It may be understood, however, that these formulations, compositions and methods can be practiced with other siRNA compounds, e.g., modified siRNA compounds, and such practice is within the scope of the invention. Surfactants find wide application in formulations such as emulsions (including microemulsions) and liposomes (see above). siRNA (or a precursor, e.g., a larger dsiRNA which can be processed into a siRNA, or a DNA which encodes a siRNA or precursor) compositions can include a surfactant. In some embodiments, the siRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, N.Y., 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class.

The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, N.Y., 1988, p. 285).

Micelles and other Membranous Formulations. For ease of exposition the micelles and other formulations, compositions and methods in this section are discussed largely with regard to unmodified siRNA compounds. It may be understood, however, that these micelles and other formulations, compositions and methods can be practiced with other siRNA compounds, e.g., modified siRNA compounds, and such practice is within the invention. The siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles. For ease of exposition the particles, formulations, compositions and methods in this section are discussed largely with regard to modified siRNA compounds. It may be understood, however, that these particles, formulations, compositions and methods can be practiced with other siRNA compounds, e.g., unmodified siRNA compounds, and such practice is within the invention. In another embodiment, an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques.

Pharmaceutical Compositions

The iRNA agents of the invention may be formulated for pharmaceutical use. The present invention further relates to a pharmaceutical composition comprising the dsRNA molecule as defined herein. Pharmaceutically acceptable compositions comprise a therapeutically-effective amount of one or more of the dsRNA molecules in any of the preceding embodiments, taken alone or formulated together with one or more pharmaceutically acceptable carriers (additives), excipient and/or diluents.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Delivery using subcutaneous or intravenous methods can be particularly advantageous.

The phrase "therapeutically-effective amount" as used herein means that amount of a compound, material, or composition comprising a compound of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 0.1 per cent to about ninety-nine percent of active ingredient, preferably from about 5 per cent to about 70 per cent, most preferably from about 10 per cent to about 30 per cent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

iRNA agent preparation can be formulated in combination with another agent, e.g., another therapeutic agent or an agent that stabilizes a IRNA, e.g., a protein that complexes with iRNA to form an iRNP. Still other agents include chelating agents, e.g., EDTA (e.g., to remove divalent cations such as $Mg^{2+}$), salts, RNAse inhibitors (e.g., a broad specificity RNAse inhibitor such as RNAsin) and so forth.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The compounds according to the invention may be formulated for administration in any convenient way for use in human or veterinary medicine, by analogy with other pharmaceuticals.

The term "treatment" is intended to encompass also prophylaxis, therapy and cure. The patient receiving this treatment is any animal in need, including primates, in particular humans, and other mammals such as equines, cattle, swine and sheep; and poultry and pets in general.

Double-stranded RNAi agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470, which is incorporated by reference in its entirety), or by stereotactic injection (see, e.g., Chen et al. (1994) Proc. Natl. Acad. Sci. USA 91:3054-3057, which is incorporated by reference in its entirety). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA molecule and one that produces a transcript that includes the bottom strand of a dsRNA molecule. When the templates are transcribed, the dsRNA molecule is produced, and processed into siRNA agent fragments that mediate gene silencing.

Routes of Delivery

The dsRNA molecule as defined herein or a pharmaceutical composition comprising a dsRNA molecule as defined herein can be administered to a subject using different routes of delivery. A composition that includes an iRNA can be delivered to a subject by a variety of routes. Exemplary routes include: intravenous, subcutaneous, topical, rectal, anal, vaginal, nasal, pulmonary, ocular.

The iRNA molecules and/or the dsRNA molecule of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Dosage

In one aspect, the invention features a method of administering a dsRNA molecule, e.g., a siRNA agent, to a subject (e.g., a human subject). In another aspect, the present invention relates to a dsRNA molecule as defined herein for use in inhibiting expression of a target gene in a subject. The method or the medical use includes administering a unit dose of the dsRNA molecule, e.g., a siRNA agent, e.g., double stranded siRNA agent that (a) the double-stranded part is 14-40 nucleotides (nt) long, for example, 21-23 nt, (b) is complementary to a target RNA (e.g., an endogenous or pathogen target RNA), and, optionally, (c) includes at least one 3' overhang 1-5 nucleotide long. In some embodiments, the unit dose is less than 10 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In some embodiments, the effective dose is administered with other traditional therapeutic modalities. In some embodiments, the subject has a viral infection and the modality is an antiviral agent other than a dsRNA molecule, e.g., other than a siRNA agent. In another embodiment, the subject has atherosclerosis and the effective dose of a dsRNA molecule, e.g., a siRNA agent, is administered in combination with, e.g., after surgical intervention, e.g., angioplasty.

In some embodiments, a subject is administered an initial dose and one or more maintenance doses of a dsRNA molecule, e.g., a siRNA agent, (e.g., a precursor, e.g., a larger dsRNA molecule which can be processed into a siRNA agent, or a DNA which encodes a dsRNA molecule, e.g., a siRNA agent, or precursor thereof). The maintenance dose or doses can be the same or lower than the initial dose, e.g., one-half less of the initial dose. A maintenance regimen can include treating the subject with a dose or doses ranging from 0.01 µg to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, the composition includes a plurality of dsRNA molecule species. In another embodiment, the dsRNA molecule species has sequences that are non-overlapping and non-adjacent to another species with respect to a naturally occurring target sequence. In another embodiment, the plurality of dsRNA molecule species is specific for different naturally occurring target genes. In another embodiment, the dsRNA molecule is allele specific.

The dsRNA molecules of the invention described herein can be administered to mammals, particularly large mammals such as nonhuman primates or humans in a number of ways.

In some embodiments, the administration of the dsRNA molecule, e.g., a siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of dsRNA molecules described herein In particular embodiments, the present invention relates to the dsRNA molecules of the present invention for use in the methods described above.

Methods of Inhibiting Expression of the Target Gene

Embodiments of the invention also relate to methods for inhibiting the expression of a target gene. The method comprises the step of administering the dsRNA molecules in any of the preceding embodiments, in an amount sufficient to inhibit expression of the target gene. The present invention further relates to a use of a dsRNA molecule as defined herein for inhibiting expression of a target gene in a target cell. In a preferred embodiment, the present invention further relates to a use of a dsRNA molecule for inhibiting expression of a target gene in a target cell in vitro.

Another aspect the invention relates to a method of modulating the expression of a target gene in a cell, comprising providing to said cell a dsRNA molecule of this invention. In some embodiments, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF 1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

In particular embodiments, the present invention relates to the dsRNA molecules of the present invention for use in the methods described above.

The invention is further illustrated by the following examples, which should not be construed as further limiting. The contents of all references, pending patent applications and published patents, cited throughout this application are hereby expressly incorporated by reference.

EXAMPLES

Example 1: In Vitro Screening of siRNA Duplexes

Cell Culture and Transfections:

Human Hep3B cells or rat H.II.4.E cells (ATCC, Manassas, Va.) were grown to near confluence at 37° C. in an atmosphere of 5% CO2 in RPMI (ATCC) supplemented with 10% FBS, streptomycin, and glutamine (ATCC) before being released from the plate by trypsinization. Transfection was carried out by adding 14.8 µL of Opti-MEM plus 0.2 µL of Lipofectamine RNAiMax per well (Invitrogen, Carlsbad Calif. cat #13778-150) to 5 µL of siRNA duplexes per well into a 96-well plate and incubated at room temperature for 15 minutes. 80 µL of complete growth media without antibiotic containing ~2×10$^4$ Hep3B cells were then added to the siRNA mixture. Cells were incubated for either 24 or 120 hours prior to RNA purification. Single dose experiments were performed at 10 nM and 0.1 nM final duplex concentration and dose response experiments were done using 8, 4 fold serial dilutions with a maximum dose of 10 nM final duplex concentration.

Total RNA Isolation Using DYNABEADS mRNA Isolation Kit (Invitrogen, Part #: 610-12):

Cells were harvested and lysed in 150 µL of Lysis/Binding Buffer then mixed for 5 minutes at 850 rpm using an Eppendorf Thermomixer (the mixing speed was the same throughout the process). Ten microliters of magnetic beads and 80 µL Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 µL Wash Buffer A and mixed for 1 minute. Beads were captured again and supernatant removed. Beads were then washed with 150 µL Wash Buffer B, captured and supernatant was removed. Beads were next washed with 150 µL Elution Buffer, captured and supernatant removed. Beads were allowed to dry for 2 minutes. After drying, 50 µL of Elution Buffer was added and mixed for 5 minutes at 70° C. Beads were captured on magnet for 5 minutes. 40 µL of supernatant was removed and added to another 96 well plate.

cDNA Synthesis Using ABI High Capacity cDNA Reverse Transcription Kit (Applied Biosystems, Foster City, Calif., Cat #4368813):

A master mix of 1 µL 10× Buffer, 0.4 µL 25× dNTPs, 1 µL Random primers, 0.5 µL Reverse Transcriptase, 0.5 µL RNase inhibitor and 1.6 µL of H$_2$O per reaction were added into 5 µL total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real Time PCR:

2 µL of cDNA were added to a master mix containing 0.5 µL GAPDH TaqMan Probe (Applied Biosystems Cat #4326317E (human) Cat #4308313 (rodent)), 0.5 µL TTR TaqMan probe (Applied Biosystems cat #HS00174914_ml (human) cat #Rn00562124_ml (rat)) and 5 µL Lightcycler 480 probe master mix (Roche Cat #04887301001) per well in a 384 well plate (Roche cat #04887301001). Real time PCR was done in a Roche LC 480 Real Time PCR machine (Roche). Each duplex was tested in at least two independent transfections and each transfection was assayed in duplicate, unless otherwise noted.

To calculate relative fold change, real time data were analyzed using the ΔΔCt method and normalized to assays performed with cells transfected with 10 nM AD-1955 (Luc targeting control), or mock transfected cells. IC$_{50}$ values were calculated using a 4 parameter fit model using XLFit and normalized to cells transfected with AD-1955 or naïve cells over the same dose range, or to its own lowest dose. IC$_{50}$ values were calculated for each individual transfection as well as in combination, where a single IC$_{50}$ was fit to the data from both transfections.

The results of gene silencing of the exemplary siRNA duplex with various motif modifications of the invention are shown in the table below.

Example 2: RNA Synthesis and Duplex Annealing

1. Oligonucleotide Synthesis:

All oligonucleotides were synthesized on an AKTA oligopilot synthesizer or an ABI 394 synthesizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3 '-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N'-diisopropyl-2-cyanoethylphosphoramidite (Pierce Nucleic Acids Technologies) were used for the oligonucleotide synthesis unless otherwise specified. The 2'-F phosphoramidites, 5'-O-dimethoxytrityl-N4-acetyl-2'-fluro-cytidine-3'-O—N,N'-diisopropyl-2-cyanoethyl-phosphoramidite and 5'-O-dimethoxytrityl-2'-fluro-uridine-3'-O—N,N'-di isopropyl-2-cyanoethyl-phosphoramidite were purchased from (Promega). All phosphoramidites were used at a concentration of 0.2 M in acetonitrile ($CH_3CN$) except for guanosine which was used at 0.2 M concentration in 10% THF/ACN (v/v). Coupling/recycling time of 16 minutes was used. The activator was 5-ethyl thiotetrazole (0.75 M, American International Chemicals), for the PO-oxidation Iodine/Water/Pyridine was used and the PS-oxidation PADS (2%) in 2,6-lutidine/ACN (1:1 v/v) was used.

Ligand conjugated strands were synthesized using solid support containing the corresponding ligand. For example, the introduction of carbohydrate moiety/ligand (for e.g., GalNAc) at the 3'-end of a sequence was achieved by starting the synthesis with the corresponding carbohydrate solid support. Similarly a cholesterol moiety at the 3'-end was introduced by starting the synthesis on the cholesterol support. In general, the ligand moiety was tethered to trans-4-hydroxyprolinol via a tether of choice as described in the previous examples to obtain a hydroxyprolinol-ligand moiety. The hydroxyprolinol-ligand moiety was then coupled to a solid support via a succinate linker or was converted to phosphoramidite via standard phosphitylation conditions to obtain the desired carbohydrate conjugate building blocks. Fluorophore labeled siRNAs were synthesized from the corresponding phosphoramidite or solid support, purchased from Biosearch Technologies. The oleyl lithocholic (GalNAc)$_3$ polymer support made in house at a loading of 38.6 μmol/gram. The Mannose (Man)$_3$ polymer support was also made in house at a loading of 42.0 μmol/gram.

Conjugation of the ligand of choice at desired position, for example at the 5'-end of the sequence, was achieved by coupling of the corresponding phosphoramidite to the growing chain under standard phosphoramidite coupling conditions unless otherwise specified. An extended 15 minutes coupling of 0.1 M solution of phosphoramidite in anhydrous $CH_3CN$ in the presence of 5-(ethylthio)-1H-tetrazole activator to a solid bound oligonucleotide. Oxidation of the internucleotide phosphite to the phosphate was carried out using standard iodine-water as reported (1) or by treatment with tert-butyl hydroperoxide/acetonitrile/water (10:87:3) with 10 minutes oxidation wait time conjugated oligonucleotide. Phosphorothioate was introduced by the oxidation of phosphite to phosphorothioate by using a sulfur transfer reagent such as DDTT (purchased from AM Chemicals), PADS and or Beaucage reagent. The cholesterol phosphoramidite was synthesized in house, and used at a concentration of 0.1 M in dichloromethane. Coupling time for the cholesterol phosphoramidite was 16 minutes.

2. Deprotection-I (Nucleobase Deprotection)

After completion of synthesis, the support was transferred to a 100 ml glass bottle (VWR). The oligonucleotide was cleaved from the support with simultaneous deprotection of base and phosphate groups with 80 mL of a mixture of ethanolic ammonia [ammonia:ethanol (3:1)] for 6.5h at 55° C. The bottle was cooled briefly on ice and then the ethanolic ammonia mixture was filtered into a new 250 ml bottle. The CPG was washed with 2×40 mL portions of ethanol/water (1:1 v/v). The volume of the mixture was then reduced to ~30 mL by roto-vap. The mixture was then frozen on dry ice and dried under vacuum on a speed vac.

3. Deprotection-II (Removal of 2' TBDMS Group)

The dried residue was resuspended in 26 mL of triethylamine, triethylamine trihydrofluoride (TEA.3HF) or pyridine-HF and DMSO (3:4:6) and heated at 60° C. for 90 minutes to remove the tert-butyldimethylsilyl (TBDMS) groups at the 2' position. The reaction was then quenched with 50 mL of 20 mM sodium acetate and pH adjusted to 6.5, and stored in freezer until purification.

4. Analysis

The oligonucleotides were analyzed by high-performance liquid chromatography (HPLC) prior to purification and selection of buffer and column depends on nature of the sequence and or conjugated ligand.

5. HPLC Purification

The ligand conjugated oligonucleotides were purified by reverse phase preparative HPLC. The unconjugated oligonucleotides were purified by anion-exchange HPLC on a TSK gel column packed in house. The buffers were 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides were pooled, desalted, and lyophilized. Approximately 0.15 OD of desalted oligonucleotides were diluted in water to 150 μL and then pipetted in special vials for CGE and LC/MS analysis. Compounds were finally analyzed by LC-ESMS and CGE.

6. siRNA Preparation

For the preparation of siRNA, equimolar amounts of sense and antisense strand were heated in 1×PBS at 95° C. for 5 minutes and slowly cooled to room temperature. Integrity of the duplex was confirmed by HPLC analysis.

Example 3: Mitigation of Off-Target Effects and In Vivo Toxicity with Some Exemplary dsRNA 1. Synthesis and Purification All oligonucleotides were prepared on a MerMade 192 synthesizer on a 1 μmole scale using universal or custom supports. All phosphoramidites were used at a concentration 100 mM in 100% Acetonitrile or 9:1 Acetonitrile:DMF with a standard protocol for 2-cyanoethyl phosphoramidites, except that the coupling time was extended to 400 seconds. Oxidation of the newly formed linkages was achieved using a solution of 50 mM 12 in 9:1 Acetonitrile:Water to create phosphate linkages and 100 mM DDTT in 9:1 Pyridine:Acetonitrile to create phosphorothioate linkages. After the trityl-off synthesis, columns were incubated with 150 μL of 40% aqueous Methylamine for 45 minutes and the solution drained via vacuum into a 96-well plate. After repeating the incubation and draining with a fresh portion of aqueous Methylamine, the plate containing crude oligonucleotide solution was sealed and shaken at room temperature for an additional 60 minutes to completely remove all protecting groups. Precipitation of the crude oligonucleotides was accomplished via the addition of 1.2 mL of 9:1 Acetonitrile: EtOH to each well followed by incubation at −20° C. overnight. The plate was then centrifuged at 3000 RPM for 45 minutes, the supernatant removed from each well, and the pellets resuspended in 950 µL of 20 mM aqueous NaOAc. Each crude solution was finally desalted over a GE Hi-Trap Desalting Column (Sephadex G25 Superfine) using water to elute the final oligonucleotide products. All identities and purities were confirmed using ESI-MS and IEX HPLC, respectively.

2. Temperature-Dependent UV Spectroscopy

The melting studies were performed at a duplex concentration of 1 µM (consisting of the modified antisense strand paired with the complementary unmodified RNA sense strand) in 0.33×PBS (3.3 mM Na/K phosphate buffer, pH 7.4, with 46 mM NaCl and 0.9 mM KCl) in I cm path length quartz cells on a Beckman DU800 spectrophotometer equipped with a thermoprogrammer. Each cuvette contained 200 µL of sample solution covered by 125 µL of light mineral oil. Melting curves were monitored at 260 nm with a heating rate of 1° C./min from 15-90° C. Melting temperatures (Tm) were calculated from the first derivatives of the smoothed heating curves and the reported values are the result of at least two independent measurements.

3. In Vitro Reporter Assays

COS-7 cells were cultured at 37° C., 5% CO2 in Dulbecco's Modified Eagle Medium (DMEM) supplemented with 10% fetal bovine serum (FBS). Cells were co-transfected in 96-well plates (15,000 cells/well) with 10 ng luciferase reporter plasmid and 50 fM to 50 nM siRNA in 10-fold dilutions using 2 µg/mL Lipofectamine 2000 (Thermo Fisher Scientific) according to manufacturer's instructions. Cells were harvested at 48 h after transfection for the dual luciferase assay (Promega) according to manufacturer's instructions. The on-target reporter plasmid contained a single perfectly-complementary site to the antisense strand in the 3' untranslated (3' UTR) of *Renilla* luciferase. The off-target reporter plasmid contained four tandem seed-complementary sites separated by 21-28 nucleotides in the 3' UTR of *Renilla* luciferase. Both plasmids co-expressed Firefly luciferase as a transfection control.

4. Gene Expression Analysis

Cryopreserved mouse, rat, or human hepatocytes (Biorec-lamation) were cultured at 37° C., 5% CO2 in InVitroGRO CP Medium with Torpedo Antibiotic Mix. Cells were transfected in 96-well plates (20,000 cells/well) with 10 nM siRNA using 2 µg/mL Lipofectamine RNAiMAX (Thermo Fisher Scientific) according to manufacturer's instructions. Cells were harvested at 24 h after transfection for RNA extraction with the miRNeasy Kit (Qiagen) according to manufacturer's instructions and was used for cDNA library preparation with the TruSeq Stranded Total RNA Library Prep Kit (Illumina) and sequenced on the HiSeq or Next-Seq500 sequencers (Illumina), all according to manufacturers' instructions. Raw RNAseq reads were filtered with minimal mean quality scores of 25 and minimal remaining length of 36, using fastq-mcf. Filtered reads were aligned to the *Rattus norvegicus* genome (Rnor 6.0) using STAR (ultrafast universal RNA-seq aligner) version 2.4.2a. Uniquely aligned reads were counted by featureCounts version 1.5.0. Differential gene expression analysis was performed by the R package DESeq2 version 1.16.1.

5. Code Availability

The following open-source software packages were used for RNAseq data analysis. Code is available at the following locations:

fastq-mcf: https://github.com/ExpressionAnalysis/ea-utils

STAR Aligner: https://github.com/alexdobin/STAR featureCounts: http://subread.sourceforge.net DESeq2: https://github.com/mikelove/DESeq2

6. In Vivo Mouse and Rat Studies

All studies were conducted using protocols consistent with local, state and federal regulations as applicable and approved by the Institutional Animal Care and Use Committees (IACUCs) at Alnylam Pharmaceuticals.

In mouse pharmacodynamic studies, female C57BL/6 mice (Charles River Laboratories) were administered a single dose of a vehicle control (0.9% sodium chloride, saline) or 0.5 or 1 mg/kg siRNA subcutaneously in the upper back. On Day 7 or 8, livers were collected, rinsed in cold saline, immediately snap frozen in liquid nitrogen, and stored at −80° C. for mRNA and siRNA analysis.

In rat toxicity studies, male Sprague Dawley rats (Charles River Laboratories) were administered three repeat weekly doses (qw×3) of a vehicle control (0.9% sodium chloride, saline) or 30 mg/kg siRNA subcutaneously in the upper back. On Day 16, serum was collected for clinical pathology evaluation, and livers were collected for histopathology evaluation and for mRNA and siRNA analysis.

7. mRNA and siRNA Quantitation

RNA was extracted with the miRNeasy Kit (Qiagen) according to manufacturer's instructions, converted to cDNA with the High-Capacity cDNA Reverse Transcription Kit (Thermo Fisher Scientific) according to manufacturer's instructions, and mRNA levels were assessed by quantitative polymerase chain reaction (qPCR) using gene-specific Taqman probes (Thermo Fisher Scientific) on Roche Light Cycler 480 II using LightCycler 480 Probes Master (Roche).

To quantitate exposure to siRNAs, cell pellets were resuspended in phosphate-buffer saline (PBS) containing 0.25% Triton X-100, heated at 95° C. for 10 min, centrifuged at 14,000 rpm at 4° C. for 10 min, and reverse transcription was performed on the supernatants using TaqMan MicroRNA Reverse Transcription Kit (Thermo Fisher Scientific) according to the manufacturer's instructions. qPCR was performed on Roche Light Cycler 480 II using Light-Cycler 480 Probes Master (Roche) according to the manufacturer's instructions.

8. Evaluation of In Vivo Stability in Mice

Sample Preparation: To 50 mg of frozen lyophilized mouse liver that was allowed to thaw at room temperature, 0.43 mL of proteinase K digestion buffer was added. The proteinase K digestion buffer consisted of 105 mM Tris HCl, 17.5% Tween 20%, 1.26% Triton X-100, 50 mM $CaCl_2$, 3 mM disodium EDTA, pH 8.0. Then the samples were briefly vortexed (~20 seconds) and sonicated for 10 minutes at room temperature in a bath sonicator. To this solution, 20 µL of proteinase K solution (Qiagen, Cat. 19133) was added and the samples were vortexed for 5 seconds. The samples were incubated at 50° C. for 3 hours with shaking. Following this, the samples were centrifuged at 12,700 RPM for 10 minutes from which 300 µL of supernatant was collected. The supernatant was separated into three 100 µL fractions and transferred into separate wells of a 96-well plate. To these fractions, 0.9 mL of lysis-loading buffer (Phenomenex, Cat. ALO-8579) adjusted to pH 5.5 was added, followed by an internal standard oligonucleotide (12mer poly-2'-O-methyluridine) at 0.5 ng/mL final concentration.

Weak anion-exchange (WAX) solid-phased extraction (SPE): SPE was performed on Clarity OTX WAX 96 well plates (Phenomenex) with the aid of an automated positive pressure manifold (Biotage). SPE plate was conditioned with 1 mL of methanol per well and the plate was washed with 1.9 mL of equilibration buffer (50 mM ammonium acetate, 2 mM sodium azide, pH 5.5). Samples were loaded in to the SPE wells and the flow through was discarded. Following this, the sorbent was washed with 1.5 mL×5 of wash buffer (50 mM ammonium acetate, 50:50 Water:Acetonitrile, pH 5.5) and the siRNA was eluted in to a clean 2 mL, 96 deep well plate (Thermo scientific) with 0.6 mL of elution buffer (10 mM EDTA, 10 mM DTT, 100 mM ammonium bicarbonate, 50:40:10 Water:ACN:THF, pH 8.8). The samples were evaporated to dryness in a Turbovap nitrogen manifold (Biotage) at 40° C. and 65 psi of nitrogen pressure.

LC-MS and Data Analysis: Samples were reconstituted with 40 uL LC-MS grade water. The three replicate samples were recombined to a final volume of 120 uL and subjected to LC-MS analysis. The analysis of was performed on Thermo QExactive mass spectrometer coupled to Dionex Ultimate 3000 UPLC equipped with an auto-sampler, UV detector and thermostatic column compartment. Samples (30 μL) were chromatographed on Waters XBridge BEH XP C8, 130 Å, 2.5 μm, 2.1×30 mm column at 80° C. Sample elution was performed by a linear gradient of buffer A (16 mM triethylamine, 200 mM 1,1,1,3,3,3-hexafluoro-2-propanol in water) to 35% buffer B (Methanol) in 4.1 min at a flow rate 1 mL/min. Mass spectrometer was equipped with a HESI II source and was operated in negative ion mode. Data analysis and signal deconvolution were performed using XCalibur software (Thermo Scientific) interfaced to Pro-massHR software (Novatia LLC).

Results

1. In Vitro Studies

Results of in vitro reporter assay are summarized in Tables 1 and 2. As the data in Table 1 show, exemplary patterns of glycolic nucleic acid (GNA) modifications, for example at at position 6-7 of the antisense strand, preserve the on-target activity while mitigating the off-target activity in vitro.

TABLE 1

In vitro reporter assays data for GNA modification at position 7 of anti-sense strands

|  |  | On-target IC$_{50}$ (nM) | Off-target IC$_{50}$ (nM) |
|---|---|---|---|
| GO1 | Parent (AD-65644) | 10.7 | >500 |
|  | (S)-GNA @ AS6 (AD-72841) | 2.6 | >500 |
|  | (S)-GNA @ AS7 (AD-72842) | 2.5 | >500 |
| TTR | Parent (AD-65958) | 0.012 | >500 |
|  | (S)-GNA @ AS6 (AD-72787) | 0.006 | >500 |
|  | (S)-GNA @ AS7 (AD-72788) | 0.004 | >500 |
| AAT | Parent (AD-77407) | 0.013 | 0.97 |
|  | (S)-GNA @ AS7 (AD-77412) | 0.013 | >500 |

Luciferase reporter plasmids were co-transfected with siRNAs into COS-7 cells and the luciferase assay was performed at 48 h.

TABLE 2

In vitro reporter assays data for various destabilizing modifications at positions 5, 6, 7 and 8 of antisense strands

| Modification | TMP | | GO1 | | F12 | | TMP | | GO1 | | F12 | |
| | On-target | Off-target | On-target | Off-target | On-target | Off-target | On-target | Off-target | On-target | Off-target | On-target | Off-target |
|---|---|---|---|---|---|---|---|---|---|---|---|---|
| | Position 5 | | | | | | Position 6 | | | | | |
| Mod 1 (S) | −1.12 | 0.41 | −0.11 | 1.34 | 0.01 | 0.64 | −0.51 | 2.28 | −0.41 | 1.52 | 0.68 | 0.59 |
| Mod 1 (R) | −0.24 | 0.13 | −0.48 | 0.57 | 0.16 | −0.71 | −0.36 | 1.74 | −0.82 | 0.67 | 0.61 | 0.81 |
| Mod 2 | −0.51 | 1.76 | −0.61 | 1.33 | −0.29 | 0.74 | −0.38 | 2.38 | −0.79 | 1.32 | 0.51 | 0.98 |
| Mod 3 | 0.24 | 1.60 | −0.66 | 0.67 | 0.27 | 0.19 | 0.11 | 0.49 | −0.13 | 1.11 | 0.93 | 0.24 |
| Mod 4 (S) | 0.02 | 0.97 | −0.04 | 0.03 | −0.51 | 0.56 | −0.16 | 1.06 | n.d. | n.d. | 0.14 | 0.07 |
| Mod 4 (R) | 0.02 | 2.17 | −0.04 | 0.51 | 1.16 | 1.12 | 0.25 | 2.33 | n.d. | n.d. | 0.68 | 1.11 |
| Mod 5 | −0.39 | 4.84 | −0.32 | 0.50 | −0.32 | 1.01 | −0.12 | 4.81 | −0.18 | 0.39 | 0.29 | 0.85 |
| Mod 6 | −0.79 | 0.15 | 0.45 | 0.01 | 0.78 | −0.08 | −0.98 | 0.17 | 0.17 | 0.05 | 0.91 | 0.20 |
| Mod 7 | −1.03 | 0.25 | 0.84 | 0.33 | 0.13 | 0.19 | −0.85 | 0.69 | n.d. | n.d. | 0.22 | 0.08 |
| Mod 10 | n.d. | n.d. | 0.15 | 0.06 | 0.64 | 0.05 | 0.25 | 0.69 | n.d. | n.d. | 1.68 | 0.08 |
| Mod 11 | −1.03 | −0.36 | −0.91 | 1.21 | 0.17 | 0.70 | −0.63 | 2.01 | −0.50 | 0.97 | −0.55 | 0.76 |
| Mod 12 | −1.62 | 1.33 | −0.66 | 1.31 | −0.18 | 0.63 | −0.36 | 2.01 | −0.56 | 1.35 | 0.03 | 0.61 |
| | Position 7 | | | | | | Position 8 | | | | | |
| Mod 1 (S) | 0.30 | 2.21 | −0.16 | 1.42 | 0.82 | 0.85 | −0.25 | 2.01 | −0.83 | 1.50 | 2.77 | 0.87 |
| Mod 1 (R) | 0.06 | 2.51 | −0.55 | 0.85 | 1.56 | 0.71 | 0.40 | 2.45 | −0.35 | 0.76 | 2.59 | 0.65 |
| Mod 2 | 0.27 | 2.09 | −0.54 | 1.77 | 1.62 | 0.76 | −0.06 | 1.93 | −0.56 | 1.20 | 2.54 | 0.77 |
| Mod 3 | −0.03 | 0.26 | −0.95 | 0.77 | 0.29 | 0.61 | −0.15 | 1.61 | 0.10 | 1.01 | 1.10 | 0.18 |
| Mod 4 (S) | 0.50 | 3.85 | −0.05 | −0.03 | −0.23 | 1.09 | 0.27 | 1.53 | 0.22 | 0.17 | 0.23 | 0.71 |
| Mod 4 (R) | −0.32 | 0.45 | −0.07 | 0.44 | 0.28 | 0.57 | −0.02 | 0.82 | 0.05 | 0.38 | 0.38 | 0.77 |
| Mod 5 | 0.48 | 4.74 | −0.59 | 1.26 | 1.32 | 1.13 | −0.14 | 4.14 | 0.62 | 0.47 | 2.57 | 1.16 |
| Mod 6 | −0.66 | 0.76 | 0.68 | 0.03 | 0.23 | 0.17 | −0.79 | 0.75 | 0.62 | 0.14 | 1.66 | 0.13 |
| Mod 7 | −0.73 | 0.87 | 1.02 | 0.16 | 0.57 | 0.19 | −0.49 | 0.81 | 0.66 | 0.10 | 1.80 | 0.22 |
| Mod 10 | −0.37 | 0.66 | n.d. | n.d. | 0.71 | 0.07 | −0.21 | 0.54 | 0.06 | 0.08 | 0.98 | 0.21 |

TABLE 2-continued

In vitro reporter assays data for various destabilizing modifications at positions 5, 6, 7 and 8 of antisense strands

| | TMP | | GO1 | | F12 | | TMP | | GO1 | | F12 | |
|---|---|---|---|---|---|---|---|---|---|---|---|---|
| Modification | On-target | Off-target | On-target | Off-target | On-target | Off-target | On-target | Off-target | On-target | Off-target | On-target | Off-target |
| Mod 11 | −0.19 | 2.46 | 0.03 | 1.48 | 0.66 | 0.58 | 0.24 | 1.75 | −0.11 | 1.64 | 2.08 | 0.70 |
| Mod 12 | 0.18 | 2.02 | −0.32 | 2.07 | 0.80 | 0.82 | −0.41 | 1.82 | 0.11 | 1.33 | 2.74 | 0.49 |

All values are log2 transformed and relative to the parent. Modifications are as specified in FIG. 1; Mod 11 = UNA, Mod 12 = C3-spacer. Values for the parents are as follows (percent of target remaining): TMP (AD-76463), On-target 22.4 ± 3.3 %, Off-target 17.8 ± 11.7%; GO1 (AD-65644), On-target 41.6 ± 11.0 ±, Off-target 61.6 ± 32.0%; F12 (AD-71371), On-target 8.8 ± 1.4%, Off-target 42.7 ± 4.9%.

2. Temperature-Dependent UV Spectroscopy

Results of temperature-dependent UV spectroscopy are summarized in Table 3.

TABLE 3

Thermal melting temperatures (Tm) of some exemplary modified dsRNAs.

| | Position 5 | | | Position 6 | | | Position 7 | | | Position 8 | | |
|---|---|---|---|---|---|---|---|---|---|---|---|---|
| Modification | TMP | GO1 | F12 | TMP | GO1 | F12 | TMP | GO1 | F12 | TMP | GO1 | F12 |
| Mod 1 (S) | 67.0 | 62.2 | 55.3 | 63.3 | 63.1 | 55.3 | 62.3 | 66.1 | 56.3 | 63.3 | 65.2 | 51.3 |
| Mod 1 (R) | 66.1 | 60.4 | 53.4 | 63.1 | 62.3 | 53.4 | 62.3 | 64.2 | 56.4 | 62.3 | 63.2 | 51.4 |
| Mod 2 | 64.1 | 61.2 | 52.4 | 59.3 | 54.4 | 51.5 | 58.3 | 58.3 | 51.5 | 58.2 | 61.2 | 49.4 |
| Mod 3 | 68.0 | 65.2 | 56.5 | 68.0 | 64.2 | 57.3 | 67.1 | 65.3 | 57.3 | 67.2 | 63.3 | 57.3 |
| Mod 4 (S) | 72.2 | 69.6 | 61.2 | 72.6 | n.d. | 61.3 | 71.6 | 69.1 | 60.7 | 72.5 | 68.6 | 61.2 |
| Mod 4 (R) | 70.5 | 67.3 | 59.3 | 71.0 | n.d. | 60.3 | 70.1 | 67.6 | 59.8 | 71.0 | 68.2 | 59.3 |
| Mod 5 | 63.7 | 59.8 | 51.5 | 59.9 | 54.4 | 51.0 | 57.8 | 56.3 | 51.5 | 57.3 | 58.8 | 48.6 |
| Mod 6 | 66.6 | 61.7 | 54.3 | 64.6 | 63.6 | 55.2 | 65.1 | 64.1 | 55.2 | 65.5 | 61.7 | 53.8 |
| Mod 7 | 67.1 | 62.7 | 54.8 | 65.6 | n.d. | 55.8 | 65.1 | 64.1 | 55.2 | 66.1 | 60.7 | 55.3 |
| Mod 10 | n.d. | 65.2 | 57.2 | 69.0 | n.d. | 58.2 | 70.0 | n.d. | 58.2 | 69.0 | 65.7 | 57.3 |
| Mod 11 | 64.2 | 60.4 | 51.4 | 61.1 | 61.2 | 52.4 | 60.1 | 62.2 | 53.4 | 59.2 | 60.2 | 49.5 |
| Mod 12 | 64.1 | 61.2 | 52.4 | 61.3 | 55.4 | 51.4 | 58.3 | 57.3 | 51.5 | 58.3 | 59.3 | 48.5 |

Modifications are as specifed in FIG. 1; Mod 11 = UNA, Mod 12 = C3-spacer. Values for the parent duplexes are as follows: TMP (AD-76463) 72.0° C.; GO1 (AD-65644) 70.0° C., F12 (AD-71371) 60.3° C.

3. Gene Expression Analysis

Figure 52:
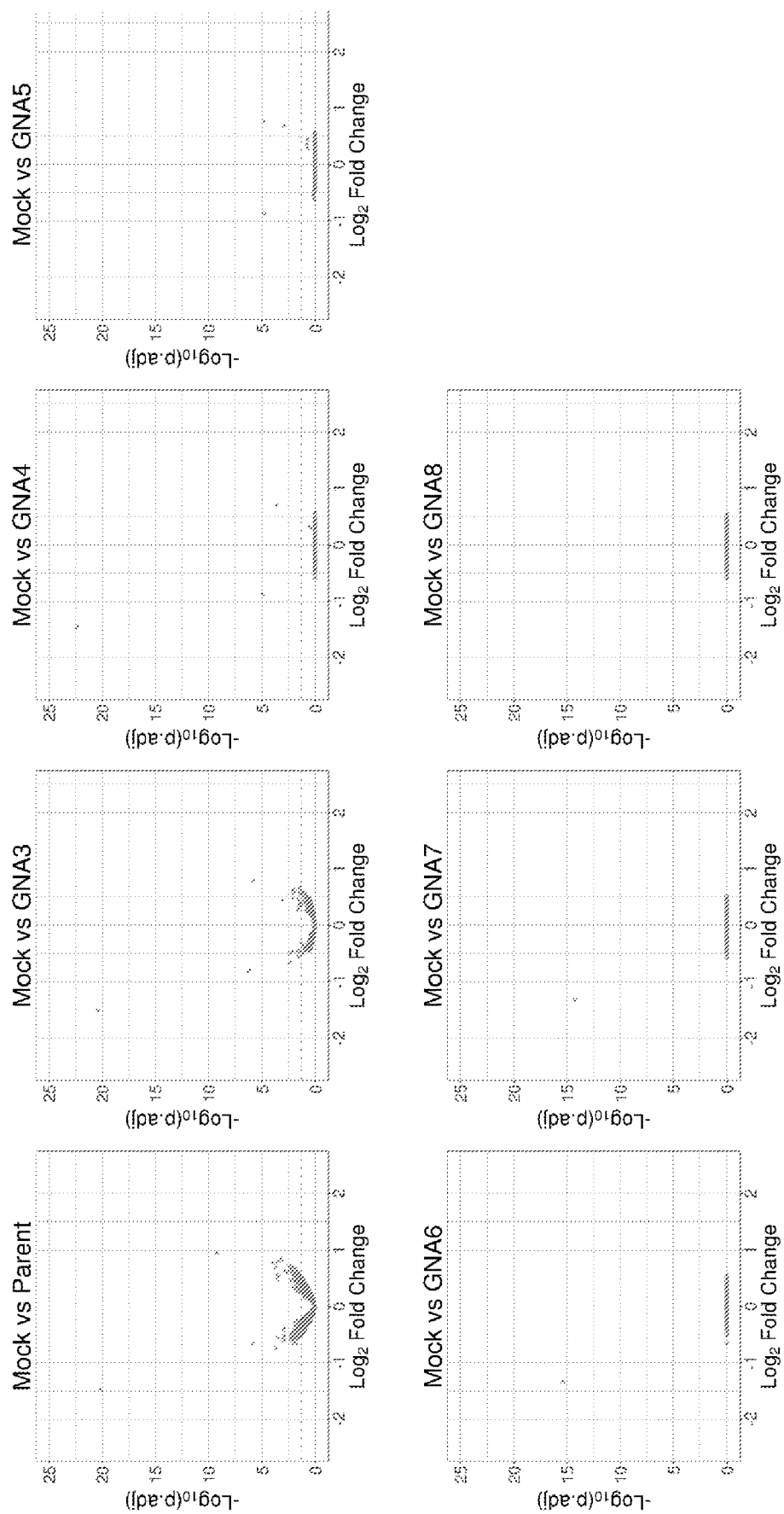
FIGS. 52 and 53 show that exemplary dsRNAs of the invention against TTR (FIG. 52) and F9 (FIG. 53) mitigate endogenous off-target effects.
Figure 53:
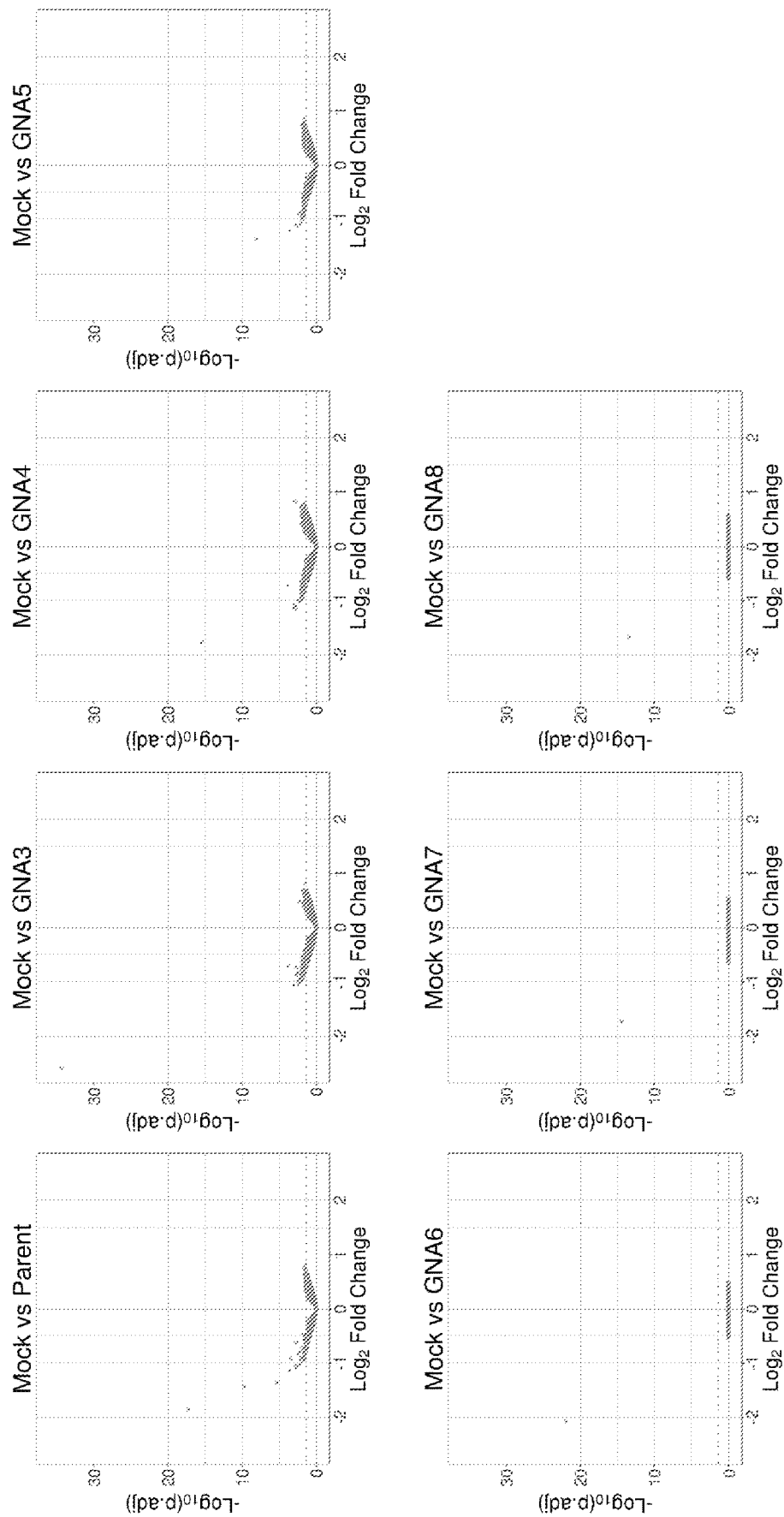

Results of in vitro gene expression analysis utilizing equipotent siRNAs are shown in FIGS. 52 and 53 and summarized in Table 4. As seen from Table 4, GNA modification at positions 6-8 (F9) or positions 5-8 (TTR) of the antisense strand mitigated off-target activity in vitro.

TABLE 4

Positional walk analysis

| | | Mouse | | Rat | | Human | |
|---|---|---|---|---|---|---|---|
| Target | Test Article | # downregulated genes (p < 0.05) | # upregulated genes (p < 0.05) | # downregulated genes (p < 0.05) | # upregulated genes (p < 0.05) | # downregulated genes (p < 0.05) | # upregulated genes (p < 0.05) |
| AAT | Parent (AD-61444) | | | | | 100 | 11 |
| | AS7-GNA (AD-77412) | | | | | 1 | 2 |
| GO1 | Parent (AD-65644) | | | 190 | 160 | | |
| | AS7-GNA (AD-72842) | | | 15 | 6 | | |
| TTR | Parent (AD-64958) | | | 235 | 144 | 151 | 36 |
| | AS3-GNA (AD-72784) | | | 12 | 18 | | |
| | AS4-GNA (AD-72785) | | | 2 | 1 | | |
| | AS5-GNA (AD-72786) | | | 1 | 2 | | |
| | AS6-GNA (AD-72787) | | | 1 | 0 | | |
| | AS7-GNA (AD-72788) | | | 1 | 0 | 1 | 5 |
| | AS8-GNA (AD-72789) | | | 1 | 0 | | |
| F9 | Parent (AD-66573) | 179 | 101 | | | | |
| | AS3-GNA (AD-72826) | 277 | 99 | | | | |
| | AS4-GNA (AD-72827) | 492 | 337 | | | | |
| | AS5-GNA (AD-72828) | 450 | 543 | | | | |
| | AS6-GNA (AD-72829) | 1 | 0 | | | | |
| | AS7-GNA (AD-72830) | 1 | 0 | | | | |
| | AS8-GNA (AD-72831) | 1 | 0 | | | | |

Mouse hepatocytes (F9), rat hepatocytes (GO1 and TTR), or human hepatocytes (AAT) were transfected with siRNAs (10 μM; AD-72786 was dosed @ 50 μM) and RNA was collected at 24 h for RNA sequencing.

4. In Vivo Mouse and Rat Studies

Results of in vivo studies are summarized in Tables 5-7. As seen, GNA modification at position 7 of the antisense strand preserves potency in vivo (Table 5) and mitigates toxicity in vivo (Tables 6 and 7). Table 8 shows in vitro reporter assays data for various destabilizing modifications at positions 5, 6, 7 and 8 of antisense strands.

TABLE 5

Mouse pharmacodynamics data

| | | % mRNA remaining at Day 8 |
|---|---|---|
| G01 | Parent | 41 |
| | (S)-GNA at AS pos. 7 | 24 |
| TTR | Parent | 40 |
| | (S)-GNA at AS pos. 7 | 47 |
| AAT | Parent | 30 |
| | (S)-GNA at AS pos. 7 | 29 |

Values represent the level of mRNA (G01) or protein (TTR, AAT) remaining with respect to PBS control at D7 in the liver or circulation, respectively. All values represent the results from a single experiment with an n = 3 animals Mice were administered a single dose of siRNAs at 1 mg/kg (G01 and AAT) or 0.5 mg/kg (TTR), and liver mRNA knockdown was assessed at Day 7 or 8.

Rat toxicity data

| | | ALT (% control) | AST (% control) | ALP (% control) | TBILI (% control) | TBA (% control) | GLDH (% control) |
|---|---|---|---|---|---|---|---|
| G01 | Parent (AD-65644) | 134 | 178 | 299 | 350 | 373 | 850 |
| | (S)-GNA @ AS7 (AD-72842) | 122 | 150 | 195 | 150 | 181 | 883 |
| TTR | Parent (AD-65958) | 190 | 258 | 225 | 331 | 460 | 1160 |
| | (S)-GNA @ AS6 (AD-72787) | 103 | 82 | 104 | 114 | 146 | 123 |

Rats were administered three doses of siRNAs at 30 mg/kg weekly, and liver function tests were evaluated 24 h after the last dose (Day 16).

TABLE 7

Rat toxicity data

| Group | 0.9% NaCl | G01 Parent (AD-65644) | G01 GNA7 (AD-72842) | TTR Parent (AD-64958) | TTR GNA7 (AD-72788) |
|---|---|---|---|---|---|
| LIVER Degeneration: hepatocellular | | | | | |
| Minimal | 0 | 0 | 3 | 0 | 0 |
| Mild | 0 | 3 | 1 | 2 | 0 |
| Moderate | 0 | 1 | 0 | 2 | 0 |
| TOTAL | 0 | 4 | 4 | 4 | 0 |
| Fibrosis | | | | | |
| Minimal | 0 | 1 | 0 | 0 | 0 |
| Mild | 0 | 2 | 0 | 0 | 0 |
| TOTAL | 0 | 3 | 0 | 0 | 0 |
| Hyperplasia: bile duct | | | | | |
| Minimal | 0 | 0 | 0 | 1 | 0 |
| TOTAL | 0 | 0 | 0 | 1 | 0 |
| Hypertrophy/Hyperplasia: kupffer cell | | | | | |
| Minimal | 0 | 3 | 0 | 0 | 0 |
| Mild | 0 | 1 | 0 | 0 | 0 |
| TOTAL | 0 | 4 | 0 | 0 | 0 |
| Increased mitotic figures: hepatocellular | | | | | |
| Minimal | 0 | 3 | 2 | 0 | 0 |
| Mild | 0 | 0 | 0 | 3 | 0 |
| Moderate | 0 | 0 | 0 | 1 | 0 |
| TOTAL | 0 | 3 | 2 | 4 | 0 |
| Necrosis, coagulative: hepatocellular | | | | | |
| Minimal | 0 | 0 | 0 | 1 | 0 |
| TOTAL | 0 | 0 | 0 | 1 | 0 |
| Necrosis, single cell: hepatocellular | | | | | |
| Minimal | 0 | 0 | 3 | 1 | 1 |
| Mild | 0 | 3 | 0 | 3 | 0 |
| Moderate | 0 | 1 | 0 | 0 | 0 |
| TOTAL | 0 | 4 | 3 | 4 | 1 |
| Vacuolation: hepatocellular | | | | | |
| Minimal | 1 | 0 | 3 | 0 | 3 |
| Mild | 0 | 3 | 1 | 4 | 0 |
| Moderate | 0 | 1 | 0 | 0 | 0 |
| TOTAL | 1 | 4 | 4 | 4 | 3 |

Rats were administered three doses of siRNAs at 30 mg/kg weekly, and liver microscopic findings were evaluated 24 h after the last dose (Day 16).

TABLE 8

In vitro reporter assays data for various destabilizing modifications at positions 5, 6, 7 and 8 of antisense strands.

| Modification | GO1 On-target | St.Dev. | TTR On-target | St.Dev. | GO1 On-target | St.Dev. | TTR On-target | St.Dev. |
|---|---|---|---|---|---|---|---|---|
| | Position 5 | | | | Position 6 | | | |
| Mod 1 (S) | 0.70[a] | 0.20 | 0.82[a] | 0.32 | 0.36 | 0.05 | 0.64[a] | 0.17 |
| Mod 2 | | | | | 0.36 | 0.09 | | |
| Mod 3 | 0.19[a] | 0.15 | 0.27 | 0.06 | 0.19 | 0.08 | | |
| Mod 5 | 0.28 | 0.05 | | | 0.19 | 0.09 | | |
| Mod 6 | 0.24[a] | 0.09 | 0.24 | 0.06 | 0.10 | 0.05 | 0.21 | 0.03 |
| Mod 7 | 0.28[a] | 0.11 | 0.62 | 0.05 | | | | |
| Mod 10 | 0.29[a] | 0.09 | 0.37 | 0.04 | 0.25 | 0.09 | 0.20 | 0.02 |
| Mod 11 | 0.59 | 0.15 | | | 0.24 | 0.09 | | |
| Mod 12 | | | | | 0.73 | 0.51 | | |
| | Position 7 | | | | Position 8 | | | |
| Mod 1 (S) | 0.25[b] | 0.21 | 0.34[a] | 0.14 | 0.43 | 0.08 | 0.44 | 0.28 |
| Mod 2 | 0.51 | 0.05 | | | | | | |
| Mod 3 | 0.12[a] | 0.05 | 0.20 | 0.02 | | | | |
| Mod 5 | 0.38 | 0.20 | | | | | | |
| Mod 6 | 0.18[a] | 0.13 | 0.13 | 0.04 | | | | |
| Mod 7 | 0.22[a] | 0.18 | 0.20 | 0.02 | | | | |
| Mod 10 | 0.18[a] | 0.11 | 0.17 | 0.05 | | | | |
| Mod 11 | 0.19 | 0.03 | | | 0.80 | 0.39 | | |
| Mod 12 | 0.65 | 0.30 | | | | | | |

Values represent the level of mRNA (GO1) or protein (TTR) remaining with respect to PBS control at D7 in the liver or circulation, respectively. Parent knockdown at the specified dose was as follows: 0.255[c] ± 0.167 for GO1; 0.362[a] ± 0.162 for TTR. All values represent the results from a single experiment with an n = 3 animals unless otherwise indicated by superscript: a = average of 2 individual experiments, each with n = 3 animals; b = average of 3 individual experiments, each with n = 3 animals; c = average of 4 individual experiments, each with n = animals. Modifications are as specified in FIG. 1; Mod 11 = UNA, Mod 12 = C3-spacer.

TABLE 9

Sequences of exemplary siRNAs

| siRNA duplex | Passenger (5'-3') | Guide (5'-3') | target |
|---|---|---|---|
| AD-65644 | g•a•auguGaaAGucaucgacaa(L) | u•U•gucGaUGacuuUcAcauuc•u•g | GO1 |
| AD-72840 | g•a•auguGaaAGucaucgacaa(L) | u•U•guCGaUGacuuUcAcauuc•u•g | GO1 |
| AD-72841 | g•a•auguGaaAGucaucgacaa(L) | u•U•gucGaUGacuuUcAcauuc•u•g | GO1 |
| AD-72842 | g•a•auguGaaAGucaucgacaa(L) | u•U•gucGAUGacuuUcAcauuc•u•g | GO1 |
| AD-72843 | g•a•auguGaaAGucaucgacaa(L) | u•U•gucGaTGacuuUcAcauuc•u•g | GO1 |
| AD-64958 | a•a•caguGuUCUugcucuauaa(L) | u•U•auaGagcaagaAcAcuguu•u•u | TTR |
| AD-72784 | a•a•caguGuUCUugcucuauaa(L) | u•U•AuaGagcaagaAcAcuguu•u•u | TTR |
| AD-72785 | a•a•caguGuUCUugcucuauaa(L) | u•U•aTaGagcaagaAcAcuguu•u•u | TTR |
| AD-72786 | a•a•caguGuUCUugcucuauaa(L) | u•U•auAGagcaagaAcAcuguu•u•u | TTR |
| AD-72787 | a•a•caguGuUCUugcucuauaa(L) | u•U•auaGagcaagaAcAcuguu•u•u | TTR |
| AD-72788 | a•a•caguGuUCUugcucuauaa(L) | u•U•auaGAgcaagaAcAcuguu•u•u | TTR |
| AD-72789 | a•a•caguGuUCUugcucuauaa(L) | u•U•auaGaGcaagaAcAcuguu•u•u | TTR |
| AD-66573 | u•g•gaagCaGUAuguugaugga(L) | u•C•cauCaacauacUgCuucca•a•a | F9 |
| AD-72826 | u•g•gaagCaGUAuguugaugga(L) | u•C•CauCaacauacUgCuucca•a•a | F9 |
| AD-72827 | u•g•gaagCaGUAuguugaugga(L) | u•C•cAuCaacauacUgCuucca•a•a | F9 |
| AD-72828 | u•g•gaagCaGUAuguugaugga(L) | u•C•caTCaacauacugcuucca•a•a | F9 |
| AD-72829 | u•g•gaagCaGUAuguugaugga(L) | u•C•cauCaacauacUgCuucca•a•a | F9 |
| AD-72830 | u•g•gaagCaGUAuguugaugga(L) | u•C•cauCAacauacUgCuucca•a•a | F9 |
| AD-72831 | u•g•gaagCaGUAuguugaugga(L) | u•C•cauCaAcauacUgCuucca•a•a | F9 |

TABLE 9-continued

Sequences of exemplary siRNAs

| siRNA duplex | Passenger (5'-3') | Guide (5'-3') | target |
|---|---|---|---|
| AD-76463 | c•u•gguaUuUCCuaggguacaa(L) | u•U•guaCccuaggaAaUaccag•a•g | TMP |
| AD-71371 | a•a•uaaaGuGCUuugaaaacgu(L) | a•C•guuUucaaagcAcUuuauu•g•a | F12 |
| AD-61444 | c•u•ucuuaauGAuugaacaaaa(L) | u•U•uUgUuCaAucaUuAaGaAg•a•c | AAT |
| AD-75994 | c•u•ucuuaauGAuugaacaaaa(L) | u•U•uUgTuCaAucaUuAaGaAg•a•c | AAT |
| AD-75995 | c•u•ucuuaauGAuugaacaaaa(L) | u•U•uUgUTCaAucaUuAaGaAg•a•c | AAT |
| AD-77407 | c•u•ucuuAaUGAuugaacaaaa(L) | u•U•uuguucaaucaUuAagaag•a•c | AAT |
| AD-77412 | c•u•ucuuAaUGAuugaacaaaa(L) | u•U•uuguTcaaucaUuAagaag•a•c | AAT |

Uppercase, lower-case, and uppercase bold underlined letters represent 2'-F, 2'-OMe, and (S)-GNA sugar modifications, respectively to Adenosine, Cytosine, Guanosine, and Uridine. (L) represents the tri-N-acetylgalactosamine ligand. Phosphorothioate linkages are indicated by the "•" symbol.

5. In Vivo Mouse Stability

Figure 32B:
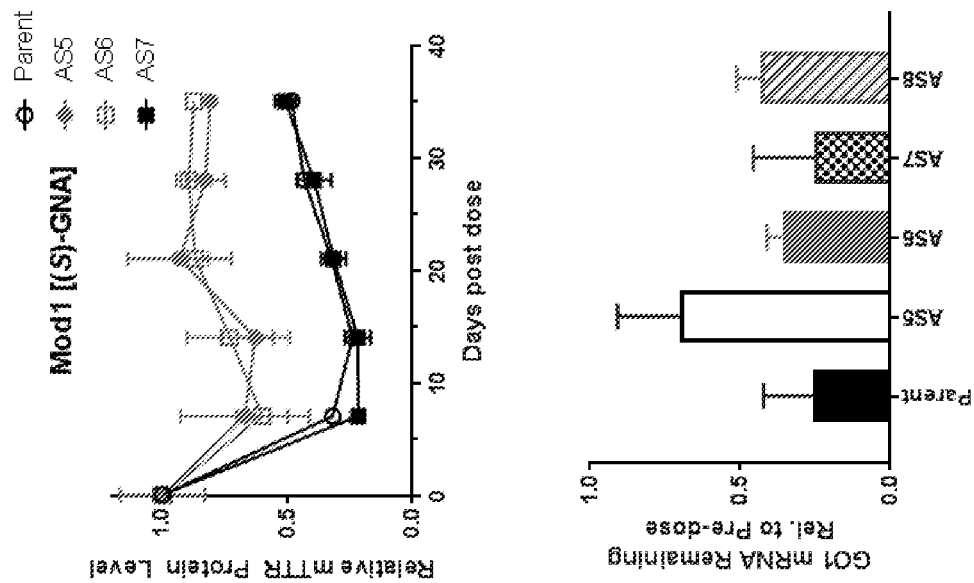
FIGS. 32A and 32B show position specific metabolic stability of exemplary dsRNAs in vivo and the influence of metabolic stability on the resulting pharmacodynamics.
Figure 32A:
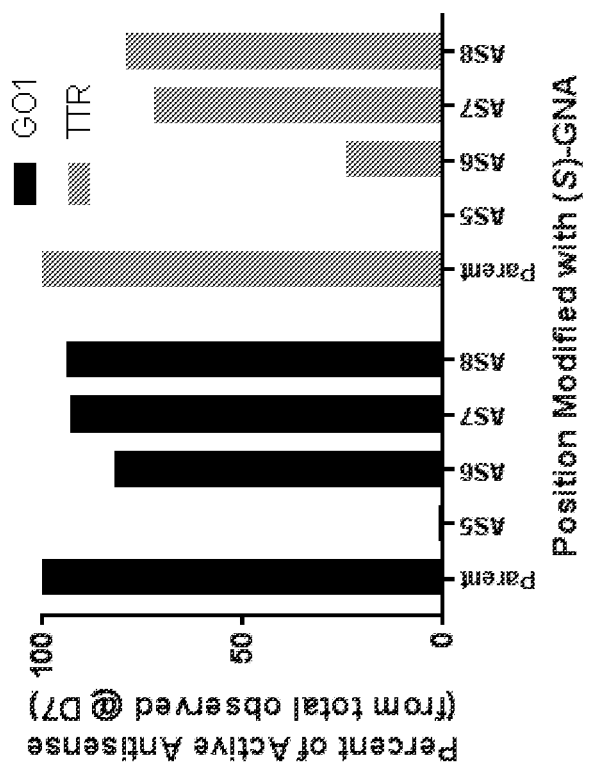
Figure 32C:
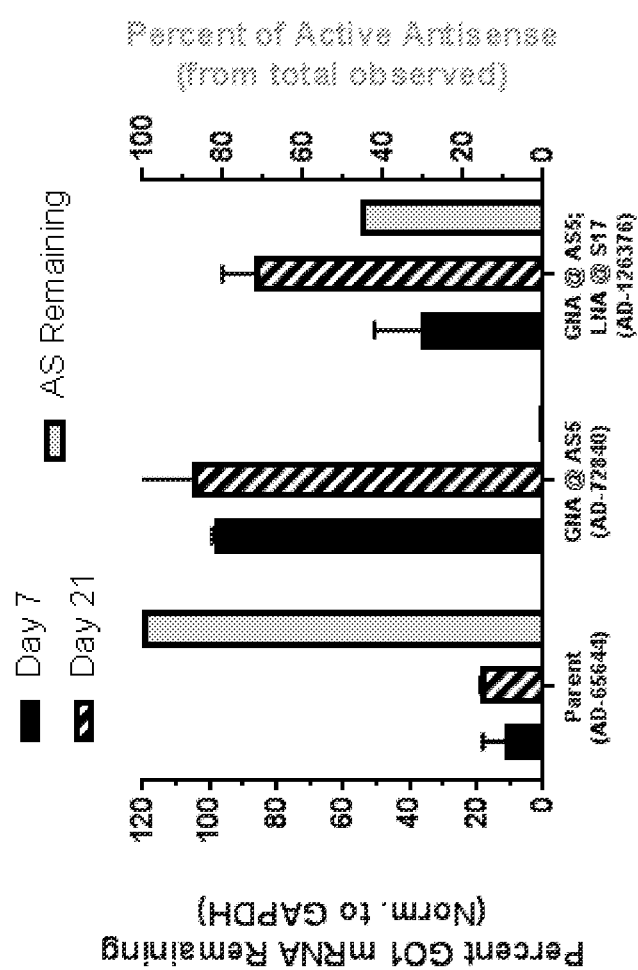
FIG. 32C shows thermal stabilization of the sense strand opposite GNA improves metabolic stability and potency of exemplary dsRNAs.

Results of the studies are summarized in FIGS. 32A-32C. As seen from FIGS. 32A and 32B, in vivo translation is impacted by metabolic stability of the antisense strand where there is a strong correlation between the amount of full length antisense strand remaining in the liver and target knockdown.

6. $IC_{50}$

Figure 50:
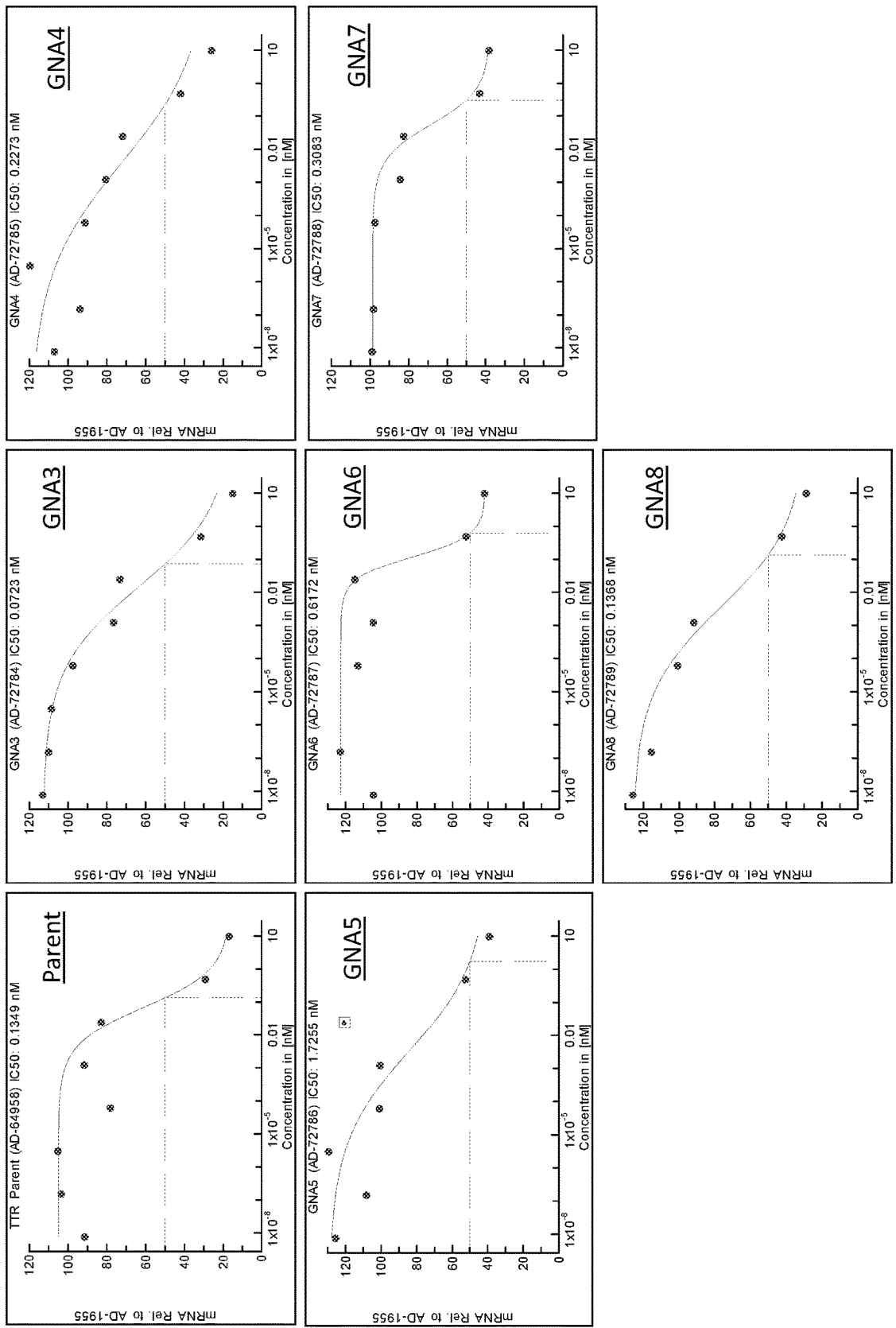
FIGS. 50 and 51 show $IC_{50}$ curves of exemplary dsRNAs targeting TTR (FIG. 50) and dsRNAs targeting Factor IX (F9) (FIG. 51) in rat hepatocytes (FIG. 50) and mouse hepatocytes (FIG. 51).
Figure 51:
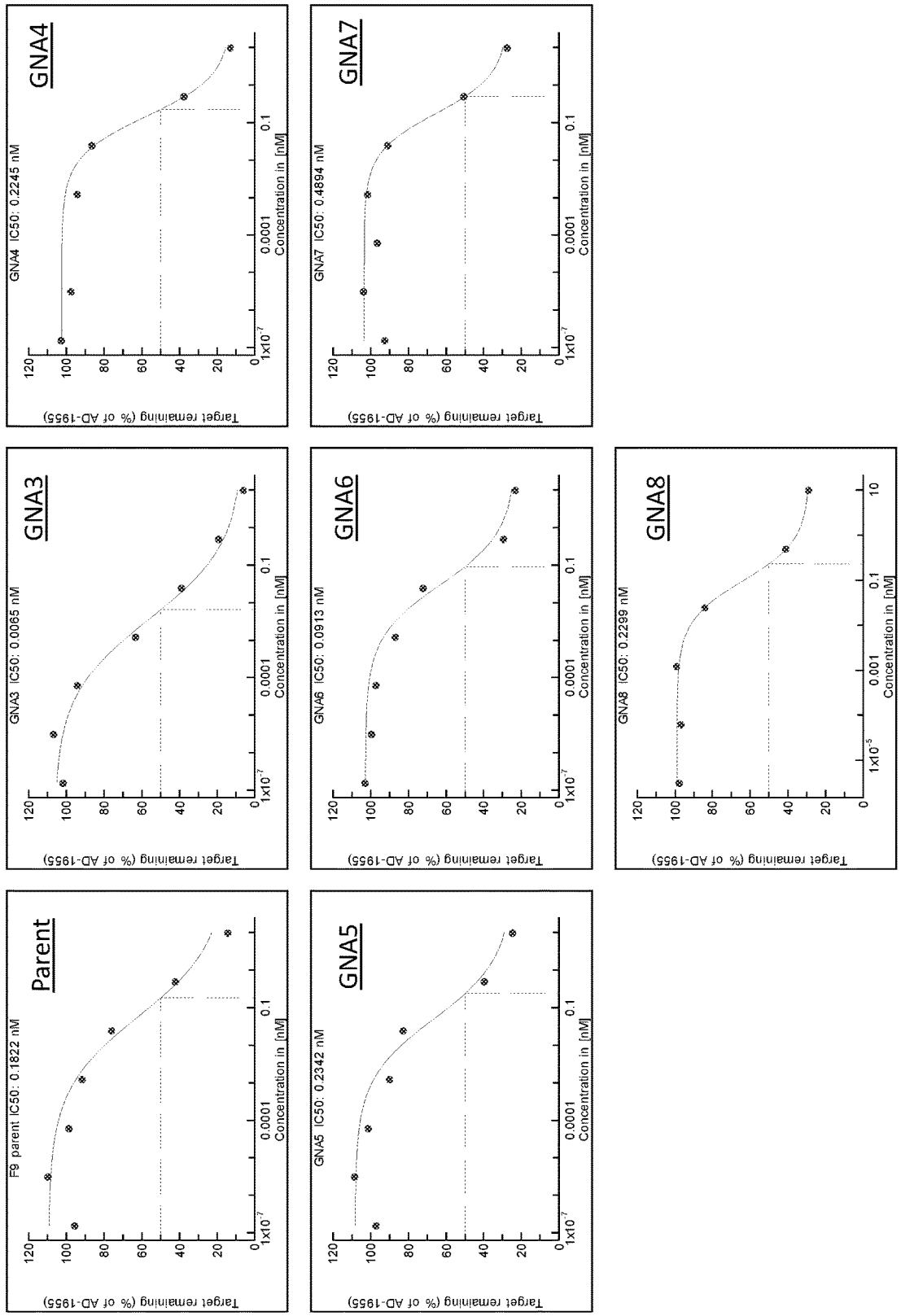

Results of the studies with exemplary dsRNAs targeting TTR or F9 are shown in FIG. 50 (TTR) and FIG. 51 (F9).

7. Other Modifications

Figure 54:
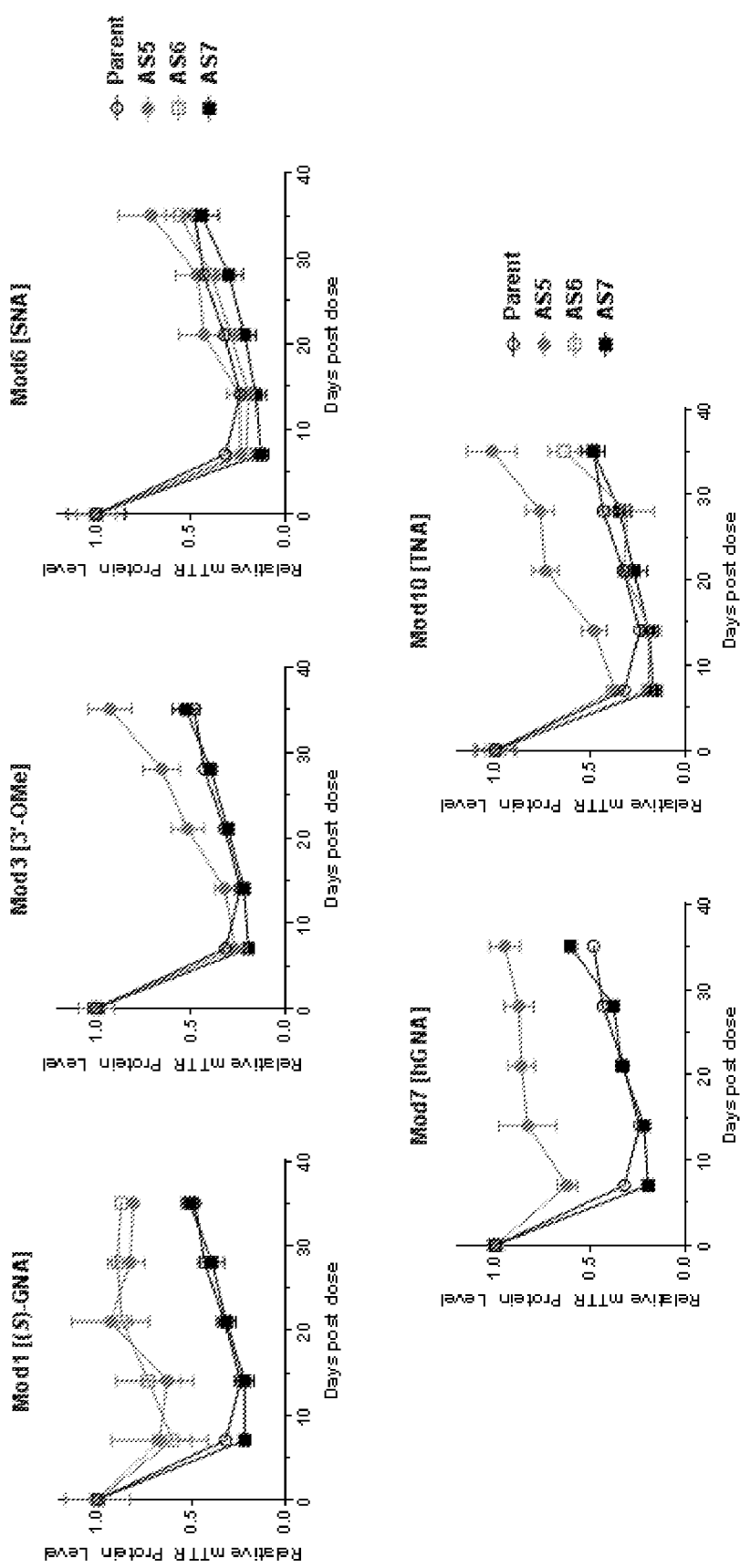
FIG. 54 are line graphs showing knockdown of the target TTR with exemplary dsRNAs containing thermally-destabilizing modifications Mods 3, 6, 7, and 10. As can be seen, all modifications are capable of maintaining activity similar to the parent.
Figure 55:
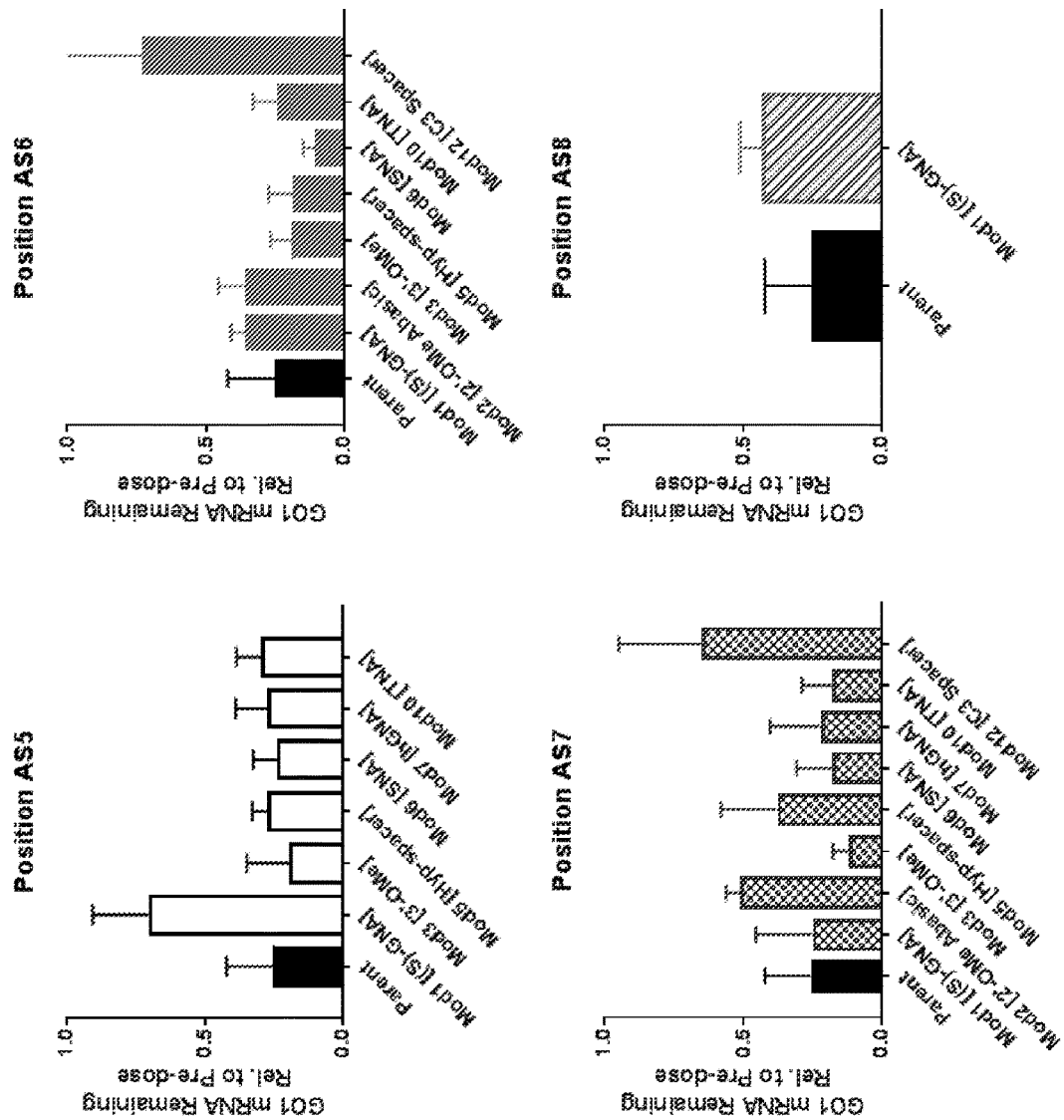
FIG. 55 are bar graphs showing knockdown of the target GO1 with exemplary dsRNAs containing thermally-destabilizing modifications Mods 3, 5, 6, 7, 10, and 12. As can be seen, all modifications are capable of maintaining activity similar to the parent.

Results of the studies with exemplary dsRNAs containing other thermally destabilizing modifications are shown in FIGS. 54 and 55. As seen, all tested modifications are capable of maintaining activity similar to the parent.

Example 4: Impact of Glycol Nucleic Acid (GNA) on siRNA Structure and Function

Chemical modifications of siRNA duplexes are necessary to stabilize these molecules against nuclease degradation, to facilitate their uptake into cells, and to affect formation of active RISC as well as RNAi-mediated target silencing. Thermally destabilizing modifications incorporated at certain positions of the siRNA duplex can lead to an increase in potency by improving strand bias and/or sense strand dissociation during RISC loading. In the present study, the inventors investigated the simple three-carbon, acyclic nucleic acid analog, Glycol Nucleic Acid (GNA) within the context of some exemplary siRNA duplexes.

1. Thermal Melting ($T_m$) Analysis of (S)-GNA-Containing siRNA Duplexes

Figure 33:
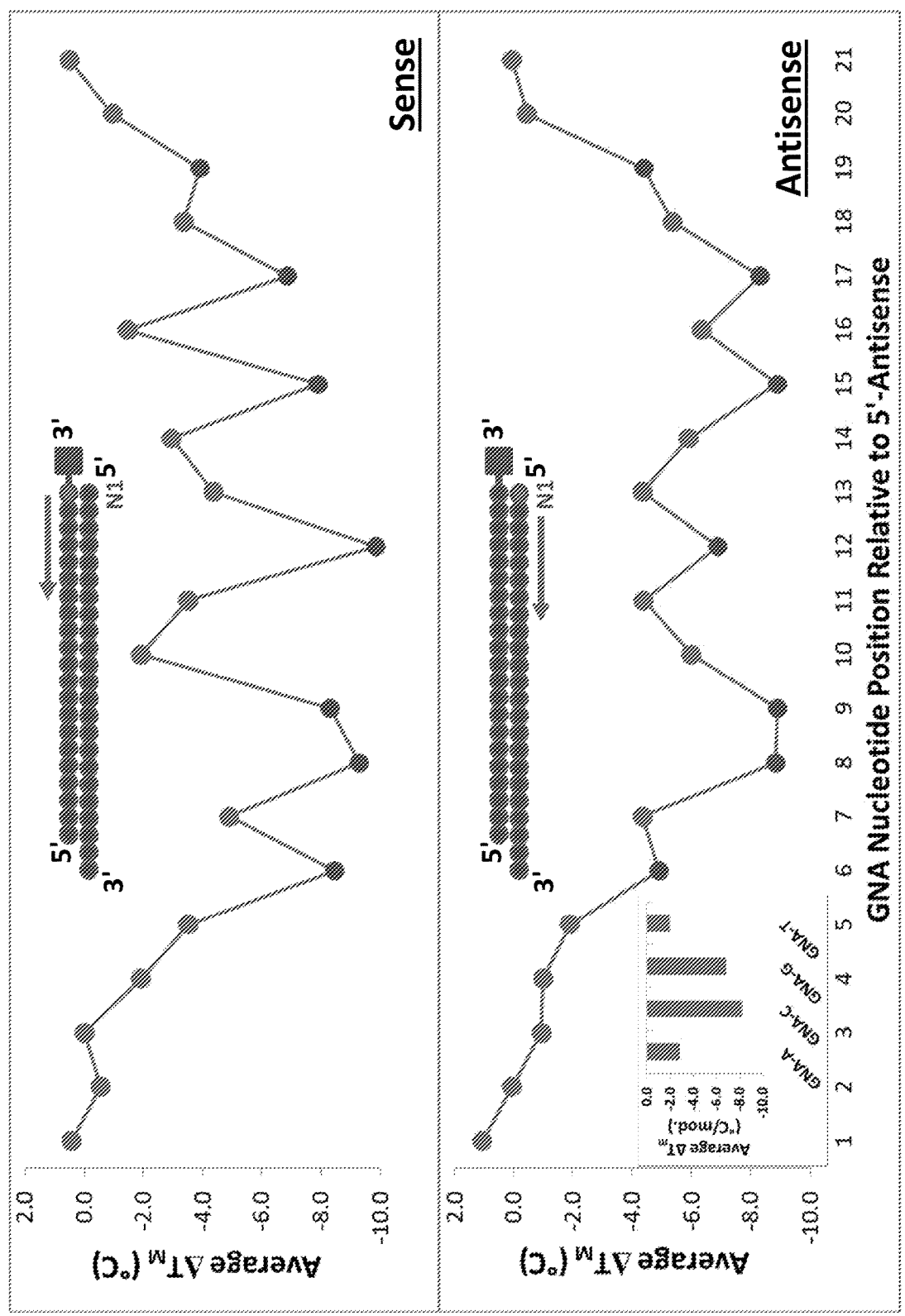
FIG. 33 is a line graph showing Thermal Melting (Tm) analysis of (5)-GNA-containing exemplary siRNA duplexes.

Results of single GNA nucleotide incorporation on siRNA duplex stability are shown in FIG. 33. GNA nucleotides were incorporated into either the sense or antisense strand at the indicated position. Blue and Red points indicate A:T and G:C base pairs, respectively. Measurements were performed in 0.25×PBS at a duplex concentration of 1 μM. Each data point is the average of two measurements. The bottom left inset shows the average change in melting temperature upon incorporation of a single (S)-GNA nucleotide at any position of the duplex (the overhangs were excluded from this analysis). As can be seen GNA incorporation resulted in a position-dependent thermal destabilization of the resulting duplex. The extent of destabilization was mostly nucleotide dependent; whereas substitution for an A or U nucleotide resulted in a significantly smaller $\Delta T_M$ compared to GNA substitution for G or C nucleotides.

2. Crystal Structure of RNA Duplexes Containing (S)- and (R)-GNA Nucleotides

Figure 34A:
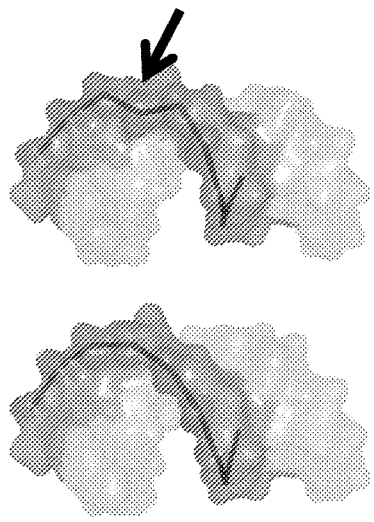
FIGS. 34A-34F show crystal structure analysis of RNA duplexes modified with both GNA-T stereoisomers.
Figure 34B:
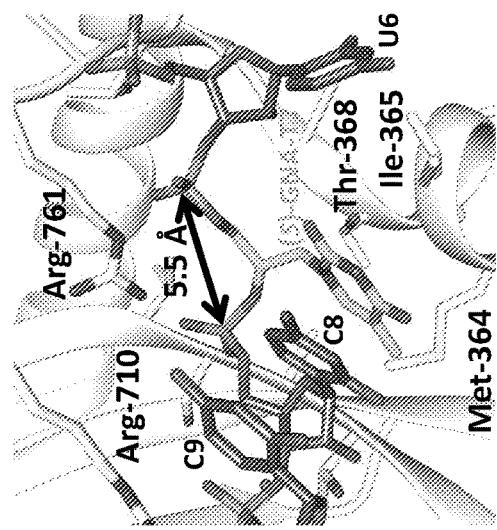
Figure 34C:
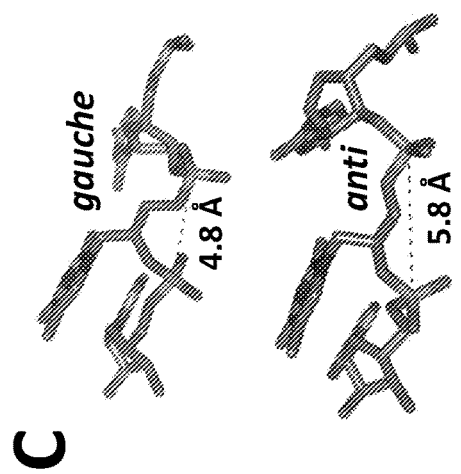
Figure 34D:
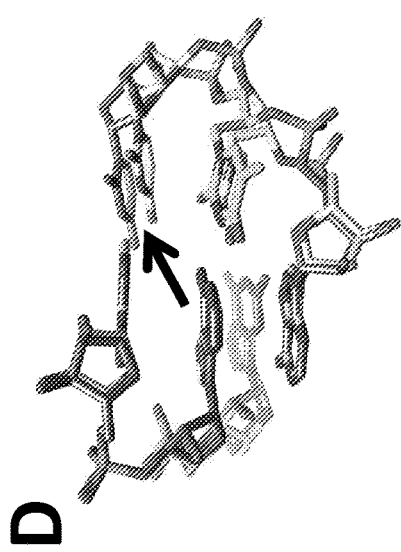
Figure 34E:
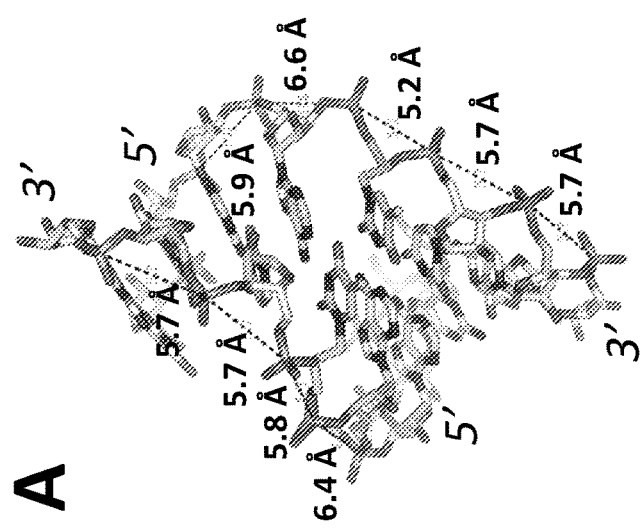
Figure 34F:
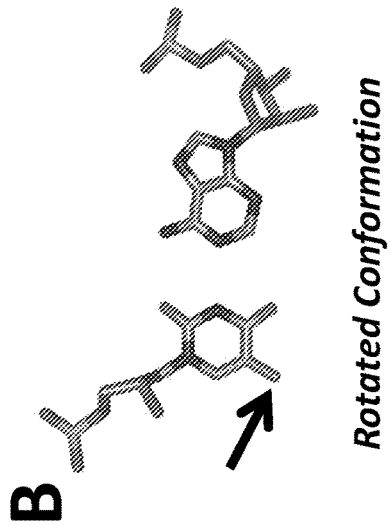

Results of crystal structure analysis of RNA duplexes modified with crystal structures of RNA duplexes modified with both GNA-T stereoisomers are shown in FIGS. 34A-34F. In the figures, FIG. 34A shows variations in intrastrand P . . . P distances as a consequence of the incorporated GNA-T residues (carbon atoms highlighted in green) in an 8-mer RNA duplex. FIG. 34B is an example of an (S)-GNA-T:RNA-A base pair showing a rotated nucleobase conformation for the GNA nucleotide (arrow). FIG. 34C shows that GNA nucleotides adopt both gauche and anti conformations within the structures. FIG. 34D shows that (R)-GNA-T residues distort RNA duplex and pairing geometry to a greater extent than (S)-GNA-T residues. Superimposition of A:U and G:A base pairs flanking (S)-GNA-T(green):RNA-A and (R)-GNA-T(yellow):RNA-A in two 12-mer duplexes reveals a disruption of the neighboring A:U pair in the (R)-GNA-T-modified 12-mer (arrow). FIG. 34E shows global structures of the RNA duplexes incorporating both (S)- and (R)-isomers of GNA which highlight the phosphate backbones. The two isomers are accommodated differently within the global RNA structure and result in a slight kink in the (R)-isomer-containing duplex (arrow). FIG. 34F shows that an (S)-GNA-T residue can seamlessly and with optimal geometry replace an RNA nucleotide at position 7 of the guide strand RNA bound to human Ago 2.14. The RNA strand assumes a kink at that site that is associated with Ile-365 and results in unstacking of the bases of nucleotides 6 and 7.

As can be seen, crystal structures of RNA duplexes containing either (S)- or (R)-GNA exhibit the flexibility of the glycol backbone within the duplex structure, allowing the nucleobases of GNA-T residues to adopt a non-canonical base pair with a rotated conformation. The latter result is further supported by crosspairing experiments with isoC and isoG nucleotides (discussed below). Furthermore, (R)-isomer incorporation, preferring a left-handed duplex, resulted in a stronger thermal destabilization and a larger perturbation of the overall duplex structure.

3. Crosspairing of (S)-GNA with isoC and isoG RNA Nucleotides

Figure 35:
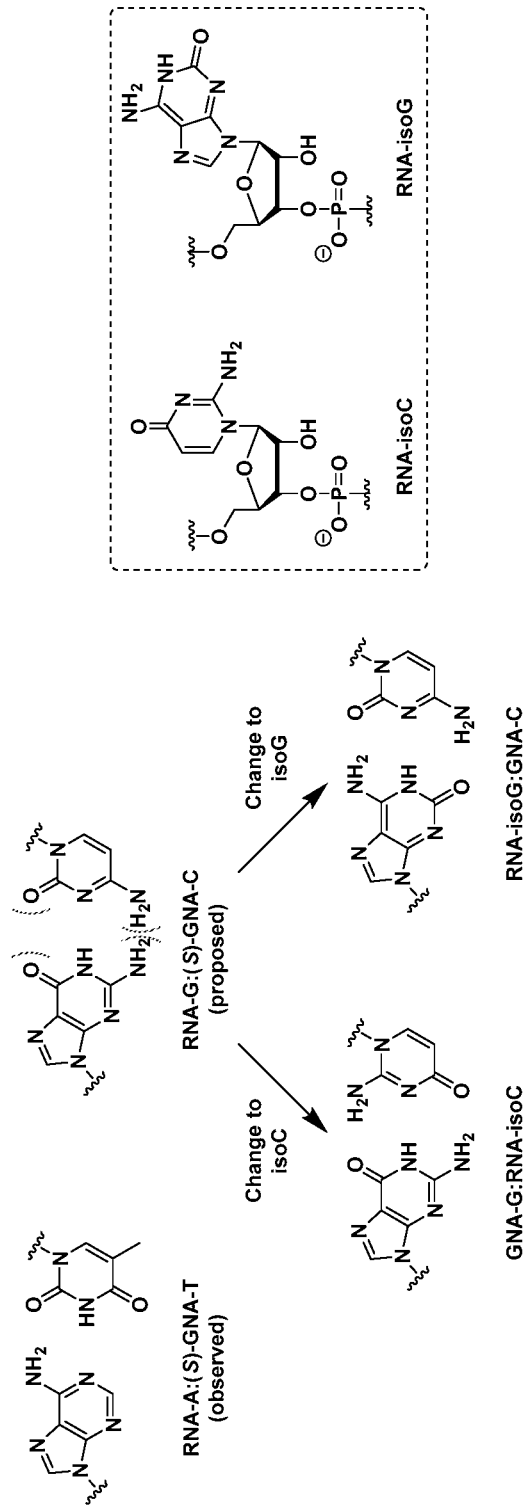
FIG. 35 shows structures of isocytidine and isoguanosine nucleotides and their potential to form fully complementary base pairs to "rotated" GNA-C or GNA-G.

Thermal stability of (S)-GNA with isoC and isoG RNA nucleotides in exemplary dsRNA was measured. Results are summarized in Table 10. Structures of isoC and isoG are shown in FIG. 35.

TABLE 10

Thermal melting data for isocytidine and isoguanosine nucleotides*
5'-UACAGUXUAUGU-3'
3'-AUGUCAYAUACA-5'

| X:Y | $T_m$ (° C.) | $\Delta T_m$ (° C.) | X:Y | $T_m$ (° C.) | $\Delta T_m$ (° C.) | $\Delta\Delta T_m$ (° C.) |
|---|---|---|---|---|---|---|
| C:G | 51.2 | 0.0 | isoC:isoG | 48.7 | −2.5 | — |
| C:isoG | 48.5 | −2.7 | isoC:G | 35.8 | −15.4 | — |
| C:G | 34.4 | −16.8 | C:isoG | 39.7 | −11.5 | +5.3 |
| C:G | 39.2 | −12.1 | isoC:G | 40.7 | −10.5 | +1.6 |

*Uppercase bold underlined letters represent (S)-GNA nucleotides. All values are the average of two independent measurements at a duplex concentration of 2 μM in 1x PBS buffer.

4. In Vitro siRNA Activity

Figure 36:
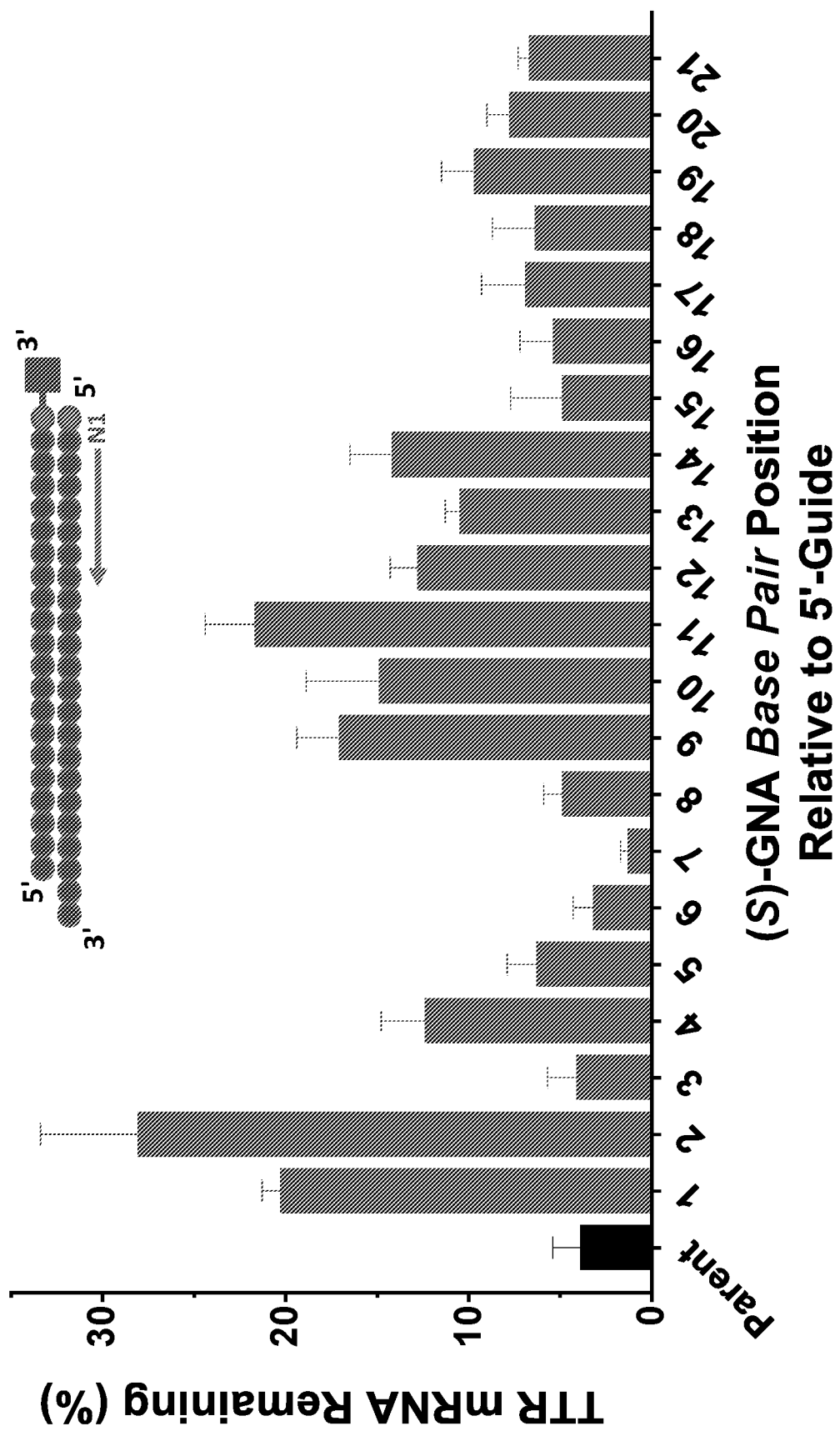
FIG. 36 shows positional effect of a single (S)-GNA base pair substitution on in vitro silencing. The base pair at the indicated position of the guide strand was substituted with the corresponding GNA base pair.

Results of positional impact of single (S)-GNA nucleotide substitution on in vitro silencing activity at a concentration of 10 nM siRNA is shown in FIG. 36. The nucleotide at the indicated position of the guide or passenger strand was substituted with the corresponding GNA nucleotide. As can be seen, incorporation of a single (S)-GNA nucleotide or base pair into the seed or supplemental regions of siRNA duplexes resulted in similar levels of TTR mRNA knockdown in vitro.

$IC_{50}$ curves of exemplary dsRNA targeting TTR are shown in FIG. 50 and $IC_{50}$ curves of exemplary dsRNA targeting Factor IX (also referred to as F9) are shown in FIG. 51.

5. In Vivo siRNA Activity

Figures 37A, 37B:
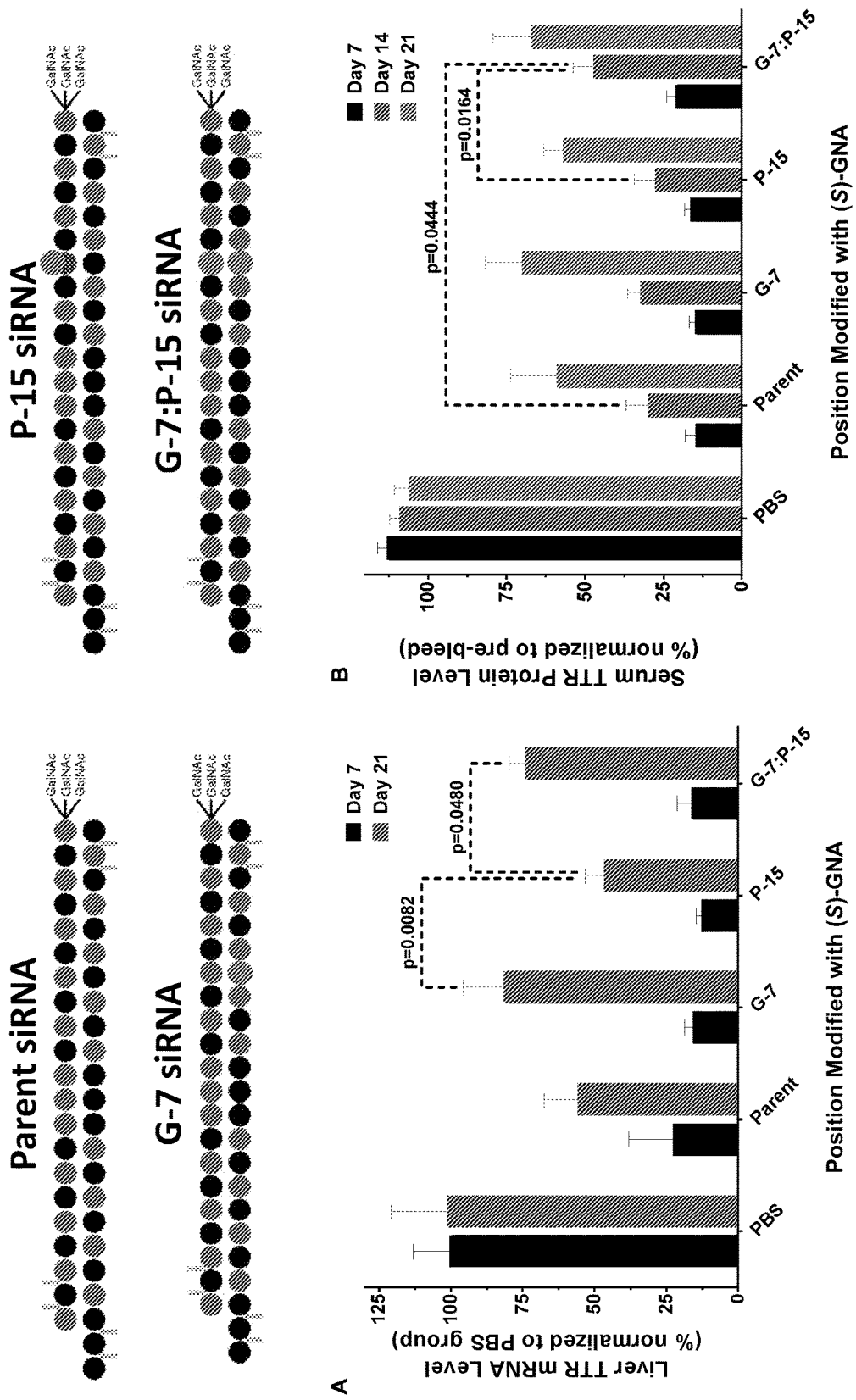
FIGS. 37A and 37B are bar graphs showing knockdown of TTR in mice with (S)-GNA modified siRNA duplexes dosed at 2.5 mg/kg.

Results of knockdown of TTR in mice with (S)-GNA modified siRNA duplexes dosed at 2.5 mg/kg are shown in FIGS. 37A and 37B. Levels of gene silencing were maintained in vivo with the exemplary siRNA modified using a single (S)-GNA nucleotide in the passenger or guide strand. Modification using a single base pair of (5)-GNA trended towards a lower potency and duration of effect.

Example 5: Selection of Well-Tolerated Exemplary GalNAc-Conjugated siRNAs by Screening for RNAi-Mediated Off-Target Effects in Rodent Toxicity Studies 1. Care and Use of Laboratory Animals All studies were conducted using protocols consistent with local, state and federal regulations, as applicable, and approved by the Institutional Animal Care and Use Committee (IACUC) at Alnylam Pharmaceuticals. The test articles were diluted with 0.9% NaCl to achieve appropriate dosing concentrations and dosed subcutaneously on the upper back to male Sprague Dawley rats (6-8 weeks old) or male CD-1 mice (6-8 weeks old) in a dose volume of 5 mL/kg with N=3 animals/group. Randomization was performed using the partitioning algorithm in the Pristima® Suite (Xybion) that avoids group mean body weight bias. Investigators were not blinded to the group allocation during the experiment or when assessing the outcome.

2. Clinical Pathology

Whole venous blood was collected into serum separator tubes (BD Microtainer) and allowed to clot at room temperature for 30 min prior to centrifugation at 3,000 RPM (1,489 g) for 10 minutes at 4° C. Serum was then aliquoted and stored at −80° C. until analyses. Serum chemistries were analyzed using the AU400 chemistry analyzer (Beckman Coulter-Brea, Calif., USA), with reagents provided by Beckman Coulter, Randox, and Sekisui Diagnostics. Differences between group means were evaluated for statistical significance using one-way ANOVA in GraphPad Prism 7.

3. Histopathology

All animals were euthanized as per Alnylam standard operating procedures and tissues of interest were collected. All tissues were fixed in 10% neutral buffered formalin (10% NBF) for 72 h prior to routine processing using TissueTek VIP 6A1 (Sakura). Tissues were trimmed, embedded into paraffin blocks, sectioned at four microns, stained with Hematoxylin and Eosin (H&E) using TissueTek Prisma A1D (Sakura), and coverslipped using TissueTek Glass g2 (Sakura). Two sections were examined microscopically from each liver in an un-blinded fashion, followed by blinded assessment to confirm subtle findings. The range of severity grade for each histologic finding was graded on a scale of 1-5 with 1 indicating minimal severity and 5 indicating severe severity.

4. Monomer and Oligonucleotide Synthesis

All oligonucleotides were synthesized and characterized as previously described (Nair, J. K. et al. J Am Chem Soc, 136, 16958-16961; Schlegel, M. K., et al. J Am Chem Soc, 139, 8537-8546). Phosphoramidite monomers of 2'F-, 2'OMe-, and LNA-modified adenosine (A), cytidine (C), guanosine (G), uridine (U), as well as inverted abasic (iB) phosphoramidite monomers were obtained from commercial sources. The synthesis of GNA phosphoramidites monomers has been previously reported (Schlegel, M. K., et al. J Am Chem Soc, 139, 8537-8546 and references therein). 5'-Deoxy-5'-(4-morpholinyl)-uridine, 5'-deoxy-5'-(4-morpholinyl)-cytidine and 5'-deoxyuridine phosphoramidites were synthesized in-house. The identities and purities of all oligonucleotides were confirmed using ESI-LC/MS and IEX HPLC, respectively. Sequences of siRNAs used in this example are shown in Table 11.

TABLE 11

Exemplary siRNAs used in this example.

| siRNA duplex | Passenger (5'-3') | Guide (5'-3') | Target |
|---|---|---|---|
| siRNA-1 (AD-58641) | U•g•AcAaAaUAAcUcAcUaUaA(L) | u•U•aUaGuGaGuuaUutJuGuCa•a•u | C5 |
| siRNA-2 (AD-65421) | G•u•gcacUuCGCuucaccucua(L) | u•A•gagGugaagcgAaGugcac•u•u | HBV |
| siRNA-3 (AD-61102) | G•g•UuAaCaCGUuUuAgAuCaA(L) | u•U•gAuCuAaAacgUgUuAaCc•a•g | Scrambled |
| siRNA-4 (AD-57727) | A•a•CaGuGuUCUuGcUcUaUaA(L) | u•U•aUaGaGcAagaAcAcUgUu•u•u | TTR |
| siRNA-5 (AD-65644) | g•a•auguGaaAGucaucgacaa(L) | u•U•gucGaUGacuuUcAcauuc•u•g | GO1 |

TABLE 11-continued

Exemplary siRNAs used in this example.

| siRNA duplex | Passenger (5'-3') | Guide (5'-3') | Target |
|---|---|---|---|
| siRNA-6 (AD-60940) | C•u•GgUaUuUCCuAgGgUaCaA(L) | u•U•gUaCcCuAggaAaUaCcAg•a•g | TMP |
| siRNA-7 (AD-77407) | c•u•ucuuAaUGAuugaacaaaa(L) | u•U•uuguucaaucaUuAagaag•a•c | AAT |
| siRNA-8 (AD-58643) | A•a•GcAaGaUAUuUuUaUaAuA(L) | u•A•uUaUaAaAauaUcUuGcUu•u•u | C5 |

Uppercase, lower-case, and uppercase bold underlined letters represent 2'-F, 2'-OMe, and (S)-GNA sugar modifications, respectively to Adenosine, Cytosine, Guanosine, and Uridine. (L) represents the tri-N-acetylgalactosamine ligand. Phosphorothioate linkages are indicated by the "•" symbol.

5. Quantification of Whole Liver and Ago2-Associated siRNA Levels

Liver and Ago2-associated (RISC-loaded) siRNA levels were quantified by stem-loop reverse transcription quantitative PCR (RT-qPCR) (Parmar, R. et al. Chembiochem, 17, 985-989).

6. RNAseq and Bioinformatics Analysis

Rat livers were collected 24 h post-50 mg/kg single dose of GalNAc-siRNAs and snap-frozen. Rat hepatocytes (BioreclamationIVT) were transfected with 10 nM GalNAc-siRNAs using Lipofectamine RNAiMAX (Thermo Fisher Scientific) according to manufacturer's instructions, and harvested 24 h post-transfection. Rat hepatocytes were not tested for mycoplasma contamination. RNA extracted with the miRNeasy kit (Qiagen) was used for cDNA library preparation with the TruSeq Stranded Total RNA Library Prep Kit (Illumina) and sequenced on the HiSeq or NextSeq500 sequencers (Illumina), all according to manufacturers' instructions. Raw RNAseq reads were filtered with minimal mean quality scores of 25 and minimal remaining length of 36, using fastq-mcf. Filtered reads were aligned to the *Rattus norvegicus* genome (Rnor_6.0) using STAR (ultrafast universal RNA-seq aligner) with default parameters. Uniquely aligned reads were counted by featureCounts. Differential gene expression analysis was performed by the R package DESeq2.

7. Code Availability

The open source DESeq2 R package was used for the RNAseq data analysis.

Results

1. Blocking RISC Loading of the Antisense Strand Mitigates Hepatotoxicity

Figures 38A, 38B, 38C:
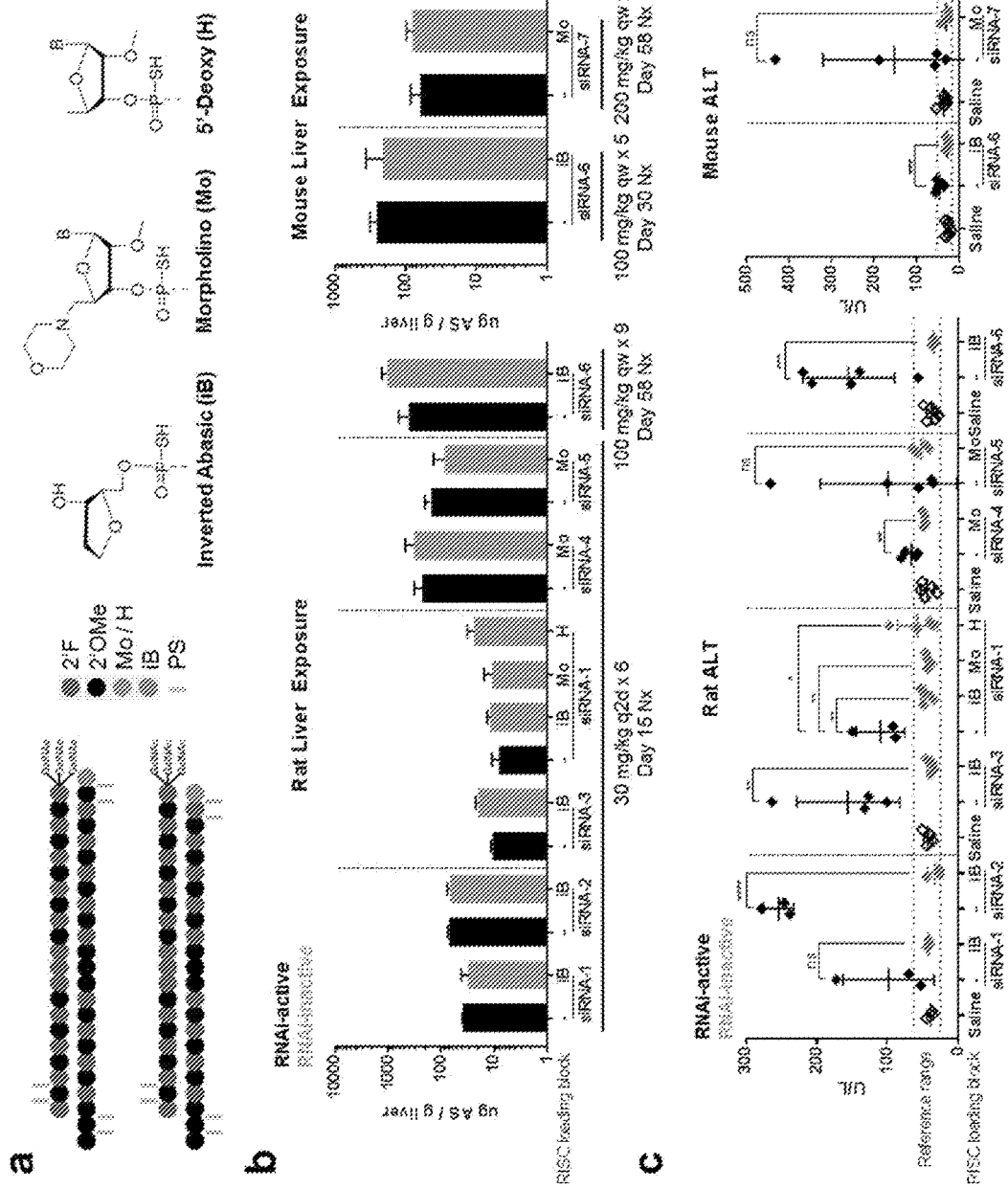
FIGS. 38A-38D show that blocking RISC loading mitigates hepatotoxicity.

Efficient RISC loading and activity of small RNAi triggers depends on the presence of a monophosphate moiety at the 5'-end. While endogenous miRNAs naturally contain a 5'-monophosphate as a result of their biogenesis, exogenous siRNAs are thought to be dependent on phosphorylation by kinases following intracellular uptake. To characterize the relationship of RISC loading to the hepatotoxicity observed with a subset of modified GalNAc-siRNAs in rodent toxicity studies (Table 11), 5'-ends of duplexes with previously-established hepatotoxicity were capped (FIG. 38A) with three types of nucleotide modifications designed to impede 5'-phosphorylation and thus RISC loading: 5'-inverted abasic (iB), 5'-deoxy-5'-(4-morpholinyl), or 5'-deoxy nucleotides. These capped siRNAs defective in RISC loading had the same PS, 2'OMe, and 2'F content as their RNAi-active counterparts that were identified in previous short-term repeat-dose rat toxicity screening studies as hepatotoxic and were designed against various target mRNAs with or without expected on-target activity in rodents.

Figure 38D:
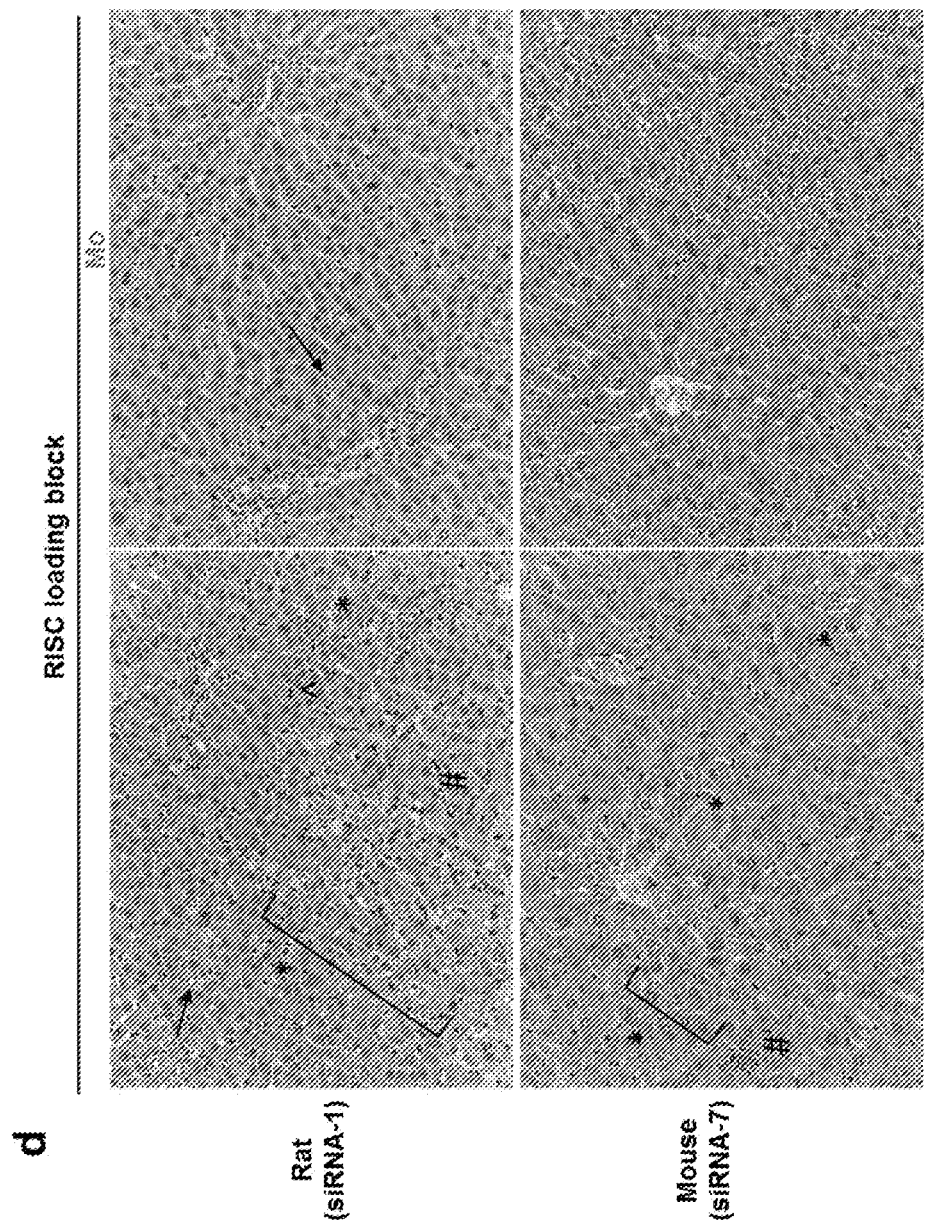
Figures 39A, 39B:
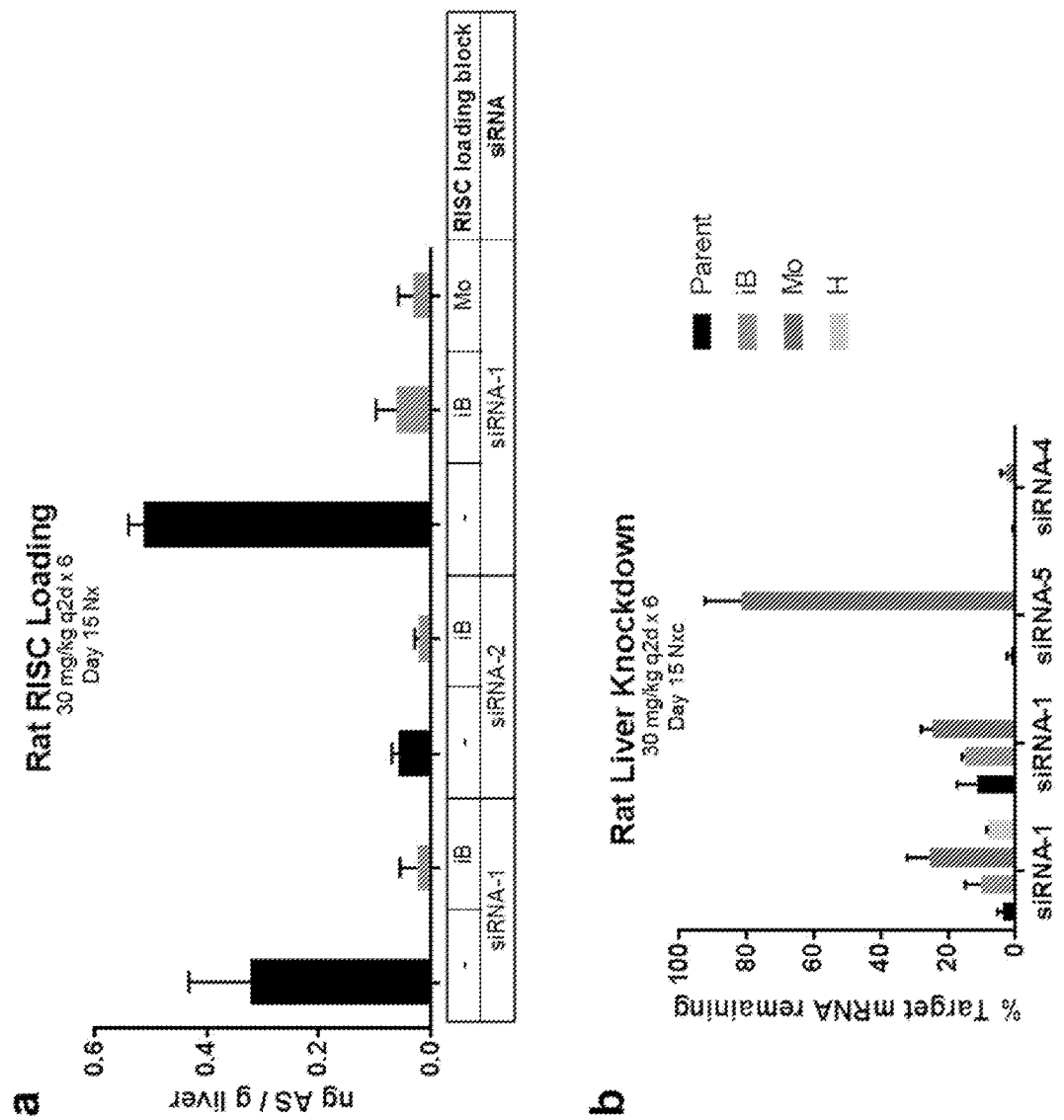
Figure 39C:
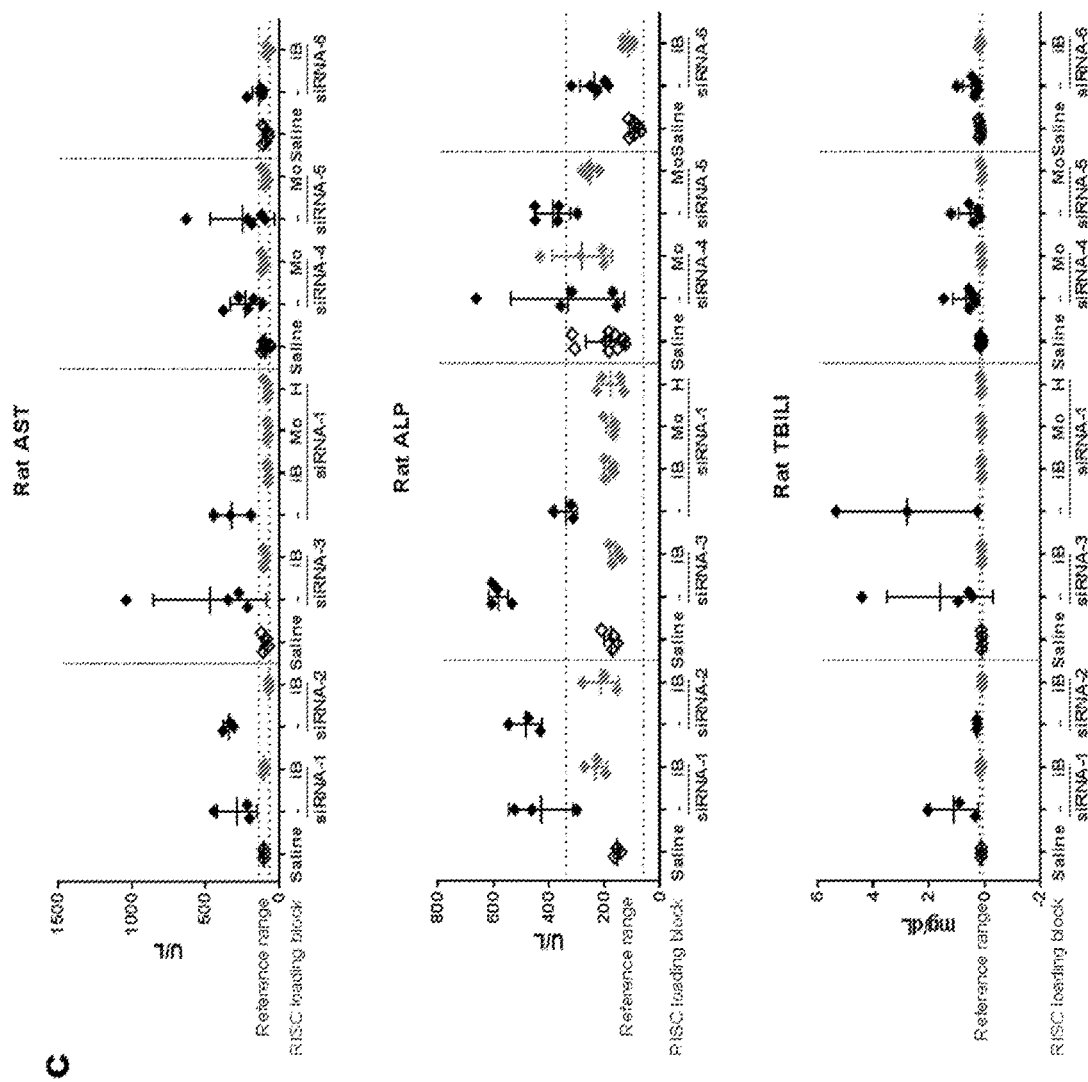
FIG. 39C shows serum aspartate aminotransferase (AST), alkaline phosphatase (ALP) and total bilirubin (TBILI) levels measured at necropsy for the RISC loading block studies. Q2d, every other day dosing; iB, inverted abasic; Mo, morpholino; H, 5'-deoxy.
Figures 40A, 40B, 40C:
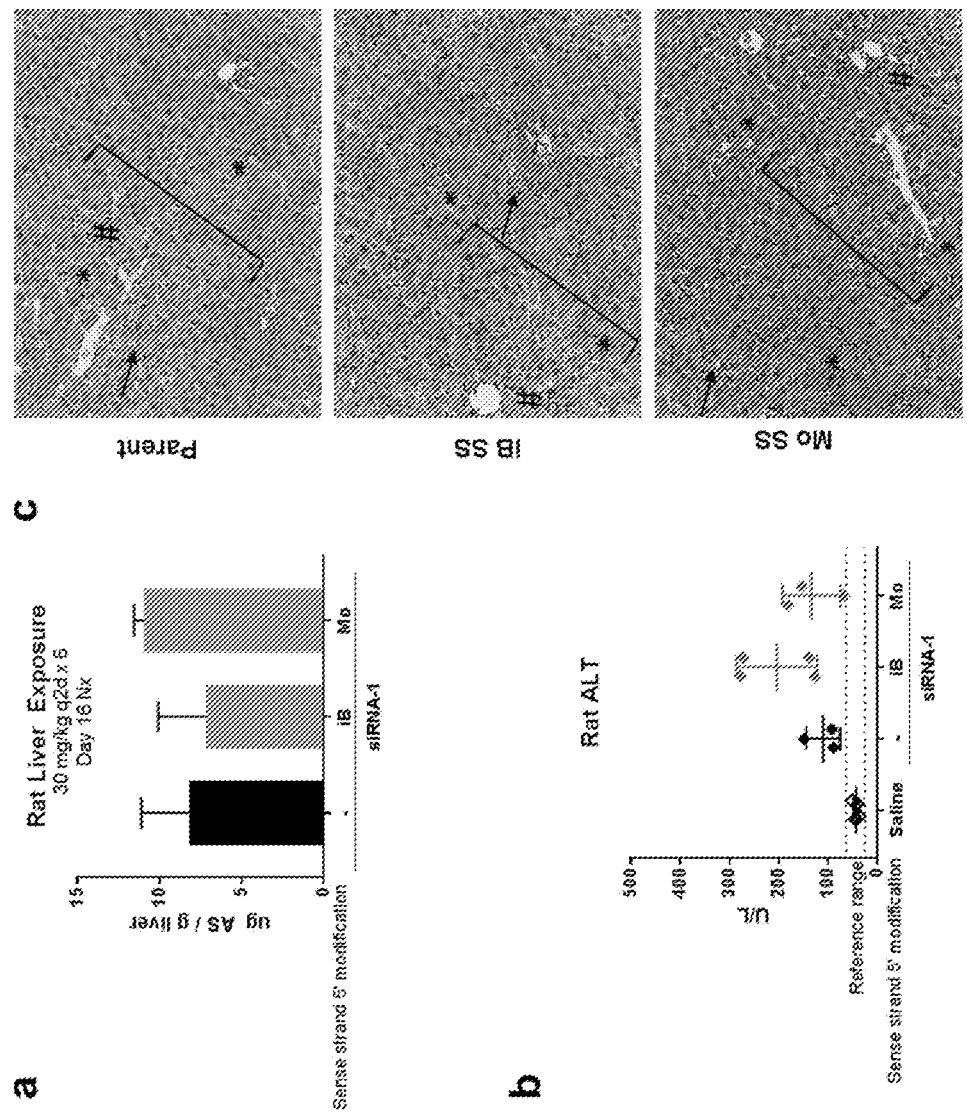
FIGS. 40A-40C show effects of sense strand 5'-modification on hepatotoxicity of an exemplary toxic GalNAc-siRNA in rat toxicity studies.
Figures 41A, 41B, 41C:
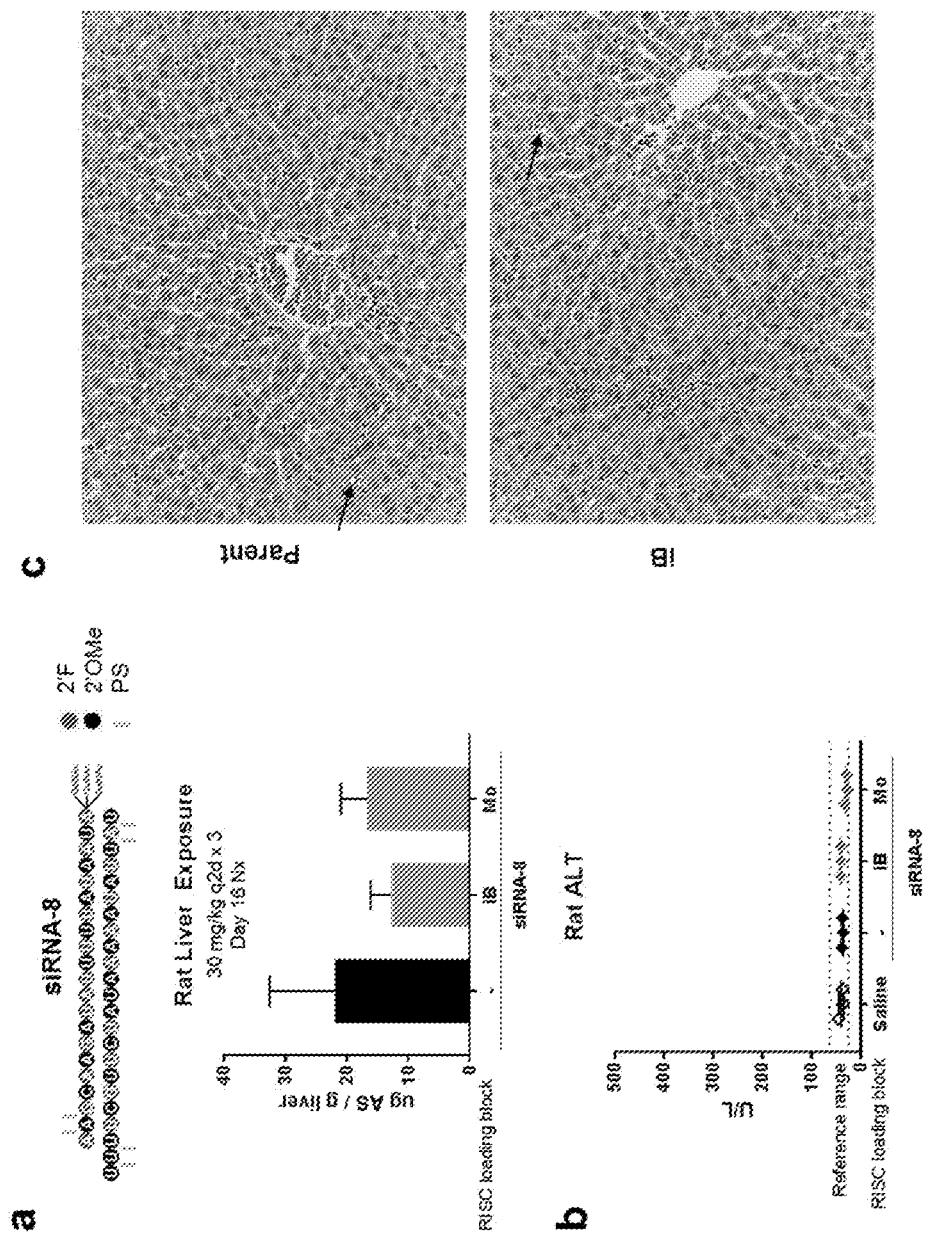
FIGS. 41A-41C show effects of 5'-modifications on hepatotoxicity of an exemplary non-toxic GalNAc-siRNA in rat toxicity studies.

The effects of blocking RISC loading on hepatotoxicity were tested at toxicological doses in rodents. Rats or mice received 5-9 weekly or every other day doses of 30-100 mg/kg, which represented 2-3 log exaggeration of the pharmacological dose range. Phosphorylation-blocking 5'-capping modifications of the antisense strand reduced RISC loading (FIG. 39A) and target mRNA knockdown (FIG. 39B) relative to parent siRNAs. Across all studies, there were no significant differences in liver concentrations between RNAi-active and RNAi-inactive siRNAs of the same sequence and backbone chemistry (FIG. 38B), confirming that the endo-lysosomal system and intracellular proteins were exposed to equivalent amounts of each siRNA regardless of its RISC loading capacity. Despite equivalent liver exposures, blocking RISC loading of known hepatotoxic siRNAs eliminated liver enzyme elevations (FIGS. 38C and 39C) and most to all microscopic liver findings, including fibrosis, single cell necrosis, and hepatocellular degeneration in both mice and rats (FIG. 38D and Table 12). Importantly, placing modifications which block RISC loading on the 5'-end of the sense strand alone (FIGS. 40A-40C) or on a non-toxic toolkit GalNAc-siRNA (FIGS. 41A-41C) had no effects on liver enzyme elevations or microscopic liver findings (Tables 13 and 14), indicating that these 5'-caps are unlikely to impact intracellular trafficking of siRNAs or introduce additional safety liabilities.

TABLE 12

Histological findings with RNAi-active and RNAi-inactive GalNAc-siRNAs

| | Rat | | | | | | | Mouse | |
|---|---|---|---|---|---|---|---|---|---|
| | siRNA-1 | siRNA-2 | siRNA-3 | siRNA-4 | siRNA-5 | siRNA-6 | siRNA-6 | siRNA-7 | |
| RISC loading block | — | iB | — | iB | — | iB | — | Mo | — | Mo | — | iB | — | iB | — | Mo |
| Degeneration, hepatocellular | 1-3 | | | | 3 | | 2-3 | | 2 | | 3-4 | | | | 1 | |
| Necrosis, single cell, hepatocellular | 1-3 | | 1-2 | | 3 | | | | 1 | | 2 | | 1-2 | | 1 | | 1-2 |
| Nerosis, coagulative, hepatocellular | | | | | | | | | | | | | | | | |

TABLE 12-continued

Histological findings with RNAi-active and RNAi-inactive GalNAc-siRNAs

| | Rat | | | | | | | | | | | | Mouse | | | |
|---|---|---|---|---|---|---|---|---|---|---|---|---|---|---|---|---|
| | siRNA-1 | | siRNA-2 | | siRNA-3 | | siRNA-4 | | siRNA-5 | | siRNA-6 | | siRNA-6 | | siRNA-7 | |
| RISC loading block | — | iB | — | iB | — | iB | — | Mo | — | Mo | — | iB | — | iB | — | Mo |
| Anisocytosis, hepatocellular | | | | | | | | | | | | 1-3 | | | | |
| Vacuolation, hepatocellular | 1-2 | 1 | 1 | | 1 | | 3 | 1-3 | 1-2 | 1 | | 1-2 | 1 | | | |
| Kupffer cell hyperplasia/Cellular infiltrates | 1 | | | 2 | | 2-3 | | | | 2 | | 1-3 | | | | 1 |
| Hyperplasia, bile duct | | | | | | 1 | | | | | | 1-3 | | | | |
| Fibrosis | | | | | | | | | | 3 | | | | | | |
| Increased mitoses | 1 | | | | | | | | | 1 | | 1 | | | | |
| Vacuolation, Kupffer cell | | | | | | | | | | | | | | | | |

Table 12 shows that blocking RISC loading mitigates hepatotoxicity. The range of severity grade for each histologic finding is indicated on a scale of 1-5 with 1 indicating minimal severity and 5 indicating severe severity.

TABLE 13

Histologic findings with a GalNAc-siRNA with 5'-RISC blocking modifications on the sense strand

| | Rat siRNA-1 RISC loading block | | |
|---|---|---|---|
| | — | iB | Mo |
| Degeneration, hepatocellular | 1-4 | 2-3 | 2-3 |
| Necrosis, single cell, hepatocellular | 2-3 | 2-3 | 2 |
| Nerosis, coagulative, hepatocellular | | | 1 |
| Anisocytosis, hepatocellular | | | |
| Vacuolation, hepatocellular | 1-2 | 2-3 | 1-2 |
| Kupffer cell hyperplasia/Cellular infiltrates | 1-3 | 1 | 1 |
| Hyperplasia, bile duct | 1 | | |
| Fibrosis | | | |
| Increased mitoses | 1-2 | 1-2 | 1 |
| Vacuolation, Kupffer cell | | | |

Table 13 shows the effects of sense strand 5'-modifications on hepatotoxicity of a toxic GalNAc-siRNA in rat toxicity studies. The range of severity grade for each histologic finding is indicated on a scale of 1-5 with 1 indicating minimal severity and 5 indicating severe severity. iB, inverted abasic; Mo, morpholino.

TABLE 14

Histologic findings with a non-toxic GalNAc-siRNA with 5'-RISC blocking modifications on both the sense and antisense strand

| | Rat siRNA-8 RISC loading block | | |
|---|---|---|---|
| | — | iB | Mo |
| Degeneration, hepatocellular | | | |
| Necrosis, single cell, hepatocellular | | | |
| Nerosis, coagulative, hepatocellular | | | |
| Anisocytosis, hepatocellular | | | |
| Vacuolation, hepatocellular | 1 | 1 | 1 |
| Kupffer cell hyperplasia/Cellular infiltrates | 1 | 1 | 1 |
| Hyperplasia, bile duct | | | |
| Fibrosis | | | |
| Increased mitoses | | | |
| Vacuolation, Kupffer cell | | | |

Table 14 shows the effects of sense strand 5'-modifications on hepatotoxicity of a non-toxic GalNAc-siRNA in rat toxicity studies. The range of severity grade for each histologic finding is indicated on a scale of 1-5 with 1 indicating minimal severity and 5 indicating severe severity. iB, inverted abasic; Mo, morpholino These studies show that rodent hepatotoxicity of a subset of GalNAc-siRNAs is dependent on RISC loading of the antisense strand but independent of siRNA chemistry-related mechanisms upstream of RISC loading, such as perturbation of the endo-lysosomal system or undesired intracellular protein binding to the relatively hydrophobic backbone modifications such as PS or 2'F.

2. Changing siRNA Chemical Modifications does not Mitigate Hepatotoxicity

Figures 42A, 42B, 42C, 42D:
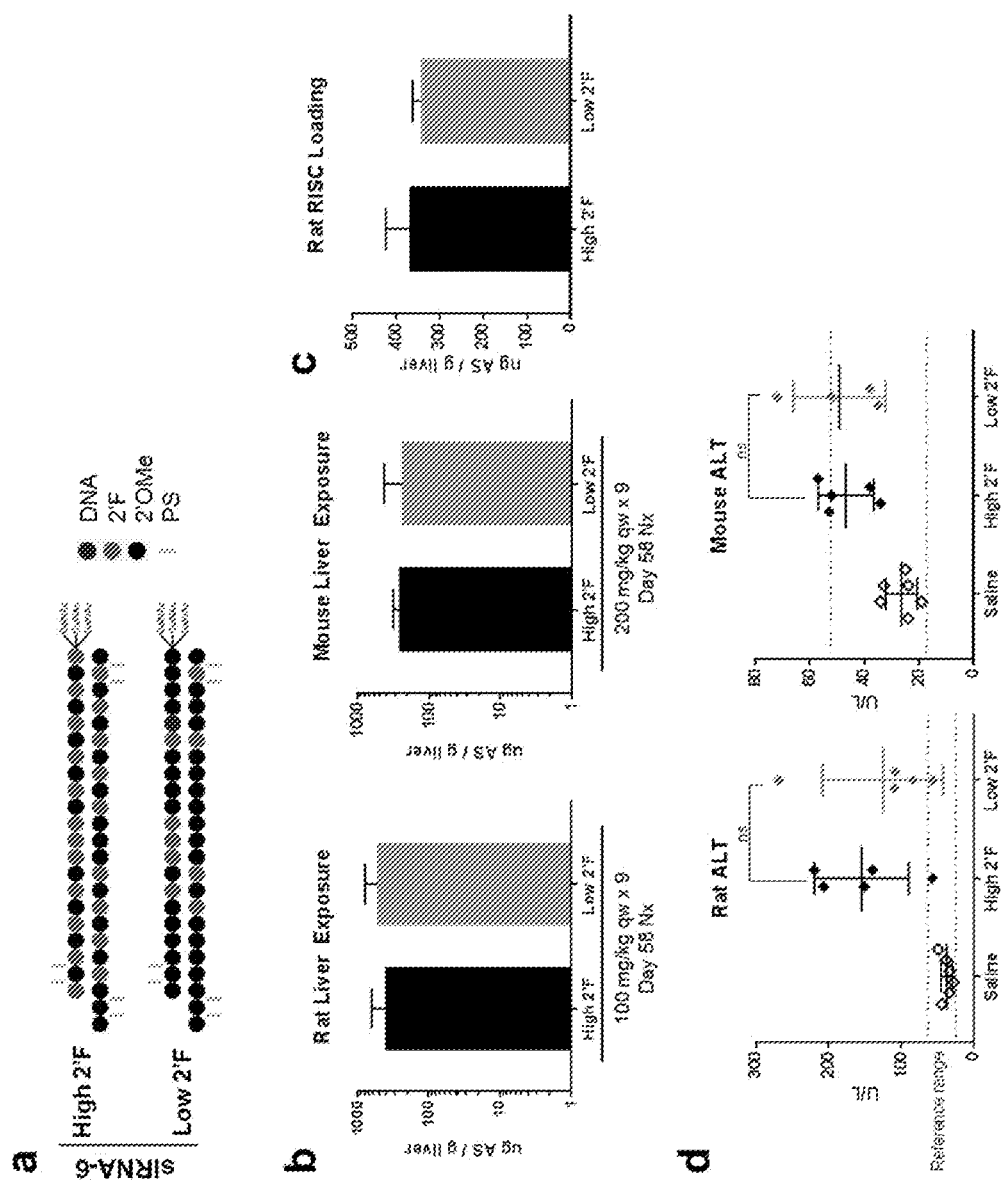
FIGS. 42A-42E show that changing siRNA chemical modifications does not mitigate hepatotoxicity.
Figure 42E:
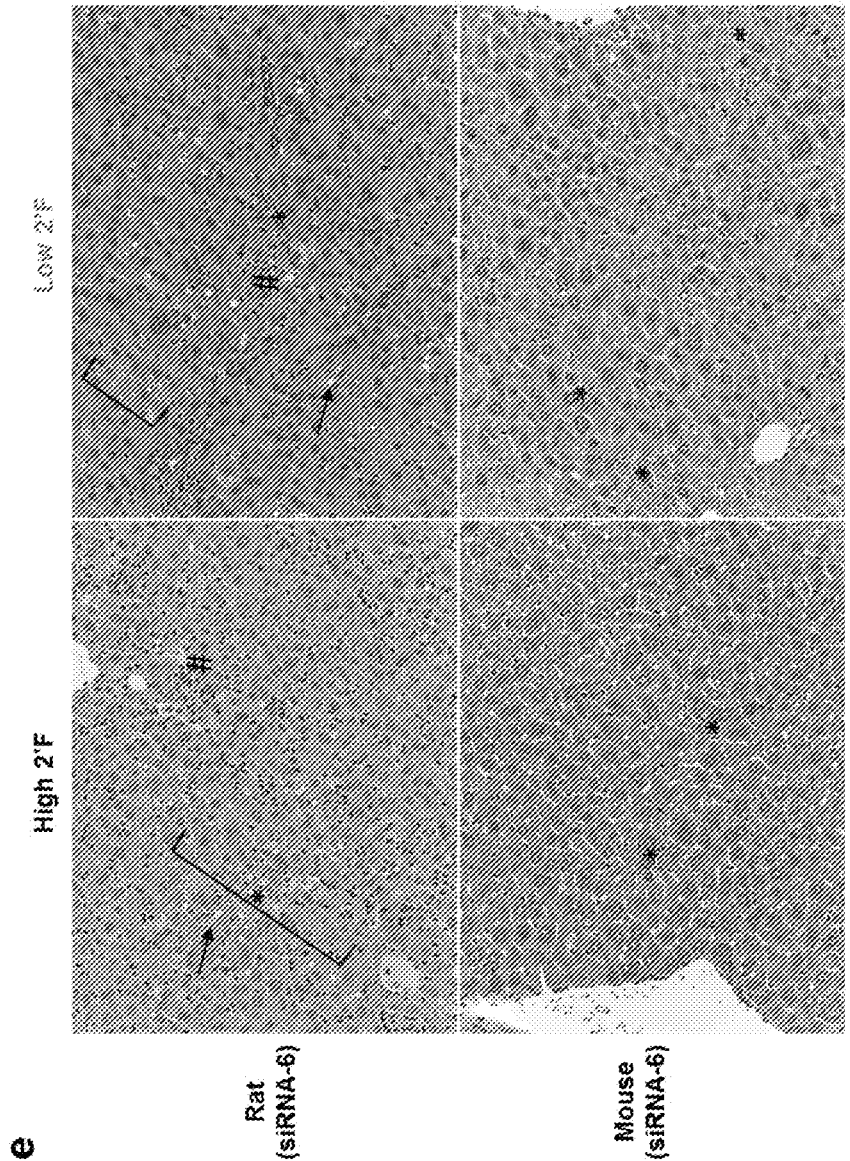
Figure 43:
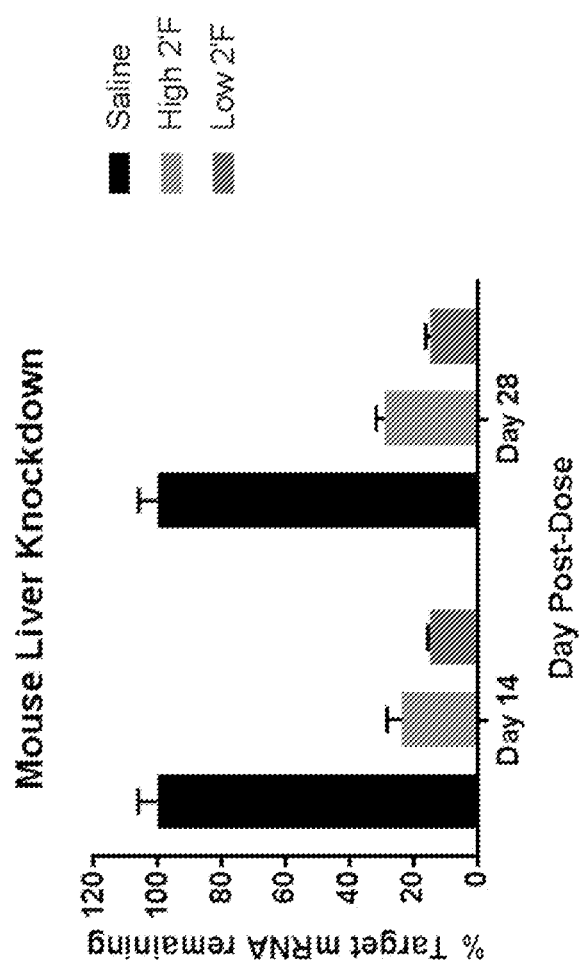
FIG. 43 is a bar graph showing in vivo potency of a high 2'F version (48% 2'F and 52% 2'OMe) and a low 2'F version (21% 2'F and 79% 2'OMe) of siRNA-6. After a single subcutaneous injection of 3 mg/kg to C57BL/6 female mice, liver on-target mRNA knockdown was assessed on Days 14 and 28 by RT-qPCR for target mRNA and normalized to a housekeeping mRNA (GAPDH), relative to the saline control group.

In order to further de-risk the potential contribution of 2'F and 2'OMe content to siRNA hepatotoxicity, two differentially-modified versions of a model hepatotoxic siRNA were tested in rodent toxicity studies: a high 2'-F version (48% 2'F and 52% 2'OMe) and a low 2'-F version (21% 2'F and 79% 2'OMe) (FIG. 42A). Both compounds had identical sequence and PS content and retained potent silencing activity (FIG. 43). These compounds were dosed weekly in rats at 100 mg/kg and in mice at 200 mg/kg over the course of nine weeks. With this frequent dosing paradigm, liver exposures (FIG. 42B) and RISC loading (FIG. 42C) were comparable for the low and high 2'-F siRNAs at the end of each study. Similarly, liver enzyme elevations (FIG. 42D) and microscopic liver findings (FIG. 42E and Table 15) were independent of the number of 2'-F or 2'-OMe modifications in this sequence in both rodent species. These data provide further evidence against siRNA chemical modifications as the driving force behind rodent hepatotoxicity of GalNAc-siRNAs.

TABLE 15

Histologic findings with GalNAc-siRNAs with high or low 2'F content

| | Rat | | Mouse | |
|---|---|---|---|---|
| | siRNA-6 | | | |
| | High 2'F | Low 2'F | High 2'F | Low 2'F |
| Degeneration, hepatocellular | 3-4 | 2-3 | | 1 |
| Necrosis, single cell, hepatocellular | 1-2 | 1-2 | 1 | 1 |
| Nerosis, coagulative, hepatocellular | | | | |
| Anisocytosis, hepatocellular | 1-3 | 2-3 | | |
| Vacuolation, hepatocellular | 1-2 | 2-3 | | |
| Kupffer cell hyperplasia/Cellular infiltrates | 1-3 | 1-2 | | |
| Hyperplasia, bile duct | 1-3 | 1 | | |
| Fibrosis | | 1 | | |
| Increased mitoses | 1 | 1 | | |
| Vacuolation, Kupffer cell | | 2-3 | | |

Table 15 shows that changing siRNA chemical modifications does not mitigate hepatotoxicity. The range of severity grade for each histologic finding is indicated on a scale of 1-5 with 1 indicating minimal severity and 5 indicating severe severity.

3. Reversing Antisense Strand-Loaded RISC Activity Mitigates Hepatotoxicity

Since siRNA chemistry-related mechanisms upstream of RISC loading did not appear to have a significant impact on hepatotoxicity in rodents, the focus was on distinguishing RNAi-mediated off-target effects from the perturbation of endogenous RNAi pathways. The strategy allowed for siRNA RISC loading by keeping the siRNA chemistry and sequence unchanged, but prevented binding of siRNA-loaded RISC to potential off-target mRNAs. To achieve this, RNAi activity downstream of RISC loading was blocked using GalNAc-conjugated short single-stranded oligonucleotides complementary to the siRNA antisense strand, known as REVERSIR™ compounds, in two types of rat toxicity studies: prevention and treatment (FIG. 44A).

In prevention studies, REVERSIR™ molecules complementary to the antisense strand of a hepatotoxic siRNA or a control scrambled REVERSIR™ sequence of the same length and chemistry composition were pre-dosed at high pharmacological doses (3 or 10 mg/kg) either 24 h before the first siRNA dose or 24 h before the first and second siRNA dose. In treatment studies, REVERSIR™ compounds were dosed at high pharmacological doses (3 or 10 mg/kg) 24 h after the last siRNA dose. Hepatotoxic GalNAc-siRNAs were dosed weekly (three times) or every other day (six times) at 30 mg/kg. Both the complementary and the scrambled REVERSIR™ molecules were confirmed bioinformatically to exhibit no full complementarity to any liver-expressed miRNAs that could potentially be blocked by REVERSIR™ compounds.

Figures 44A, 44B, 44C, 44D:
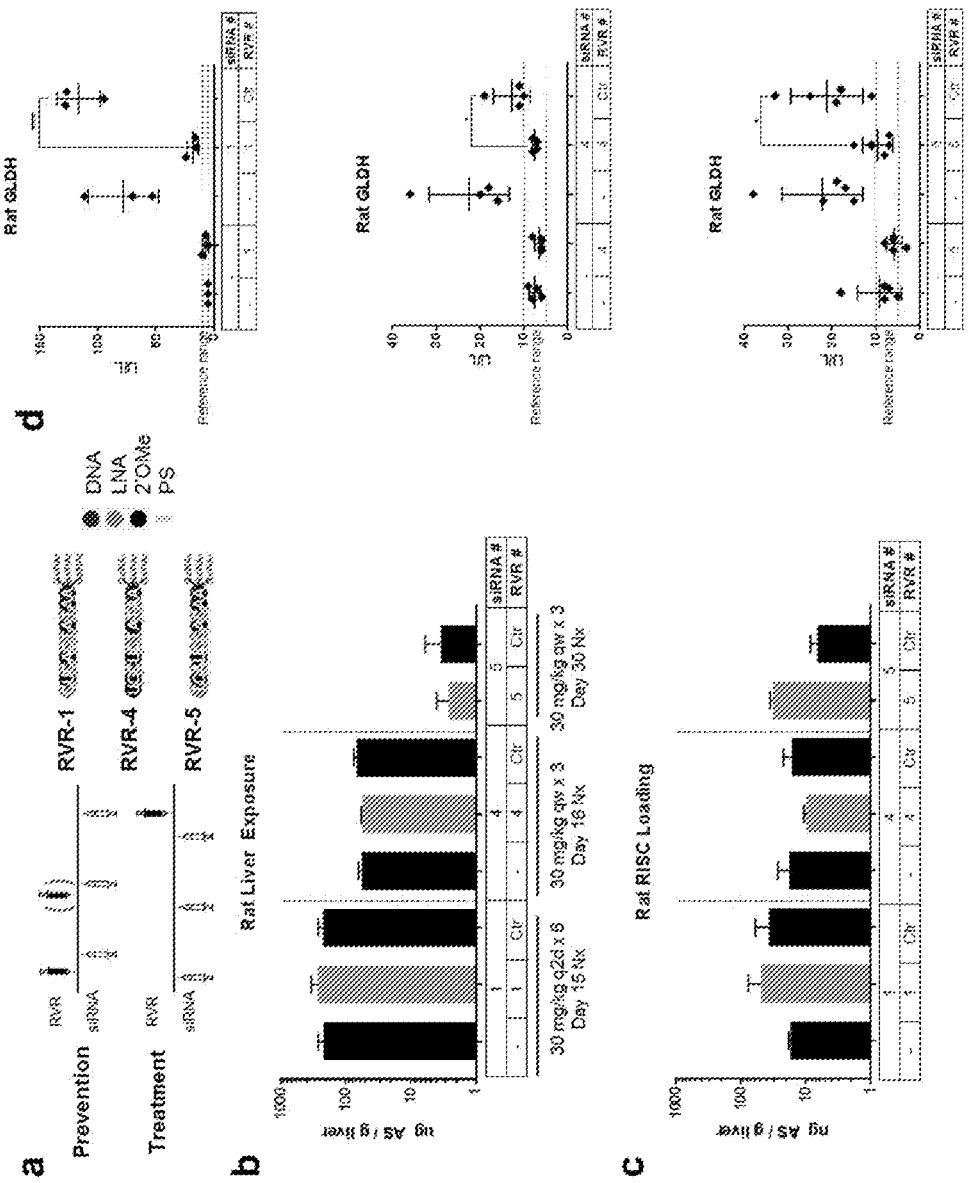
FIGS. 44A-44E show that reversing antisense strand-loaded RISC activity mitigates hepatotoxicity.
Figure 44E:
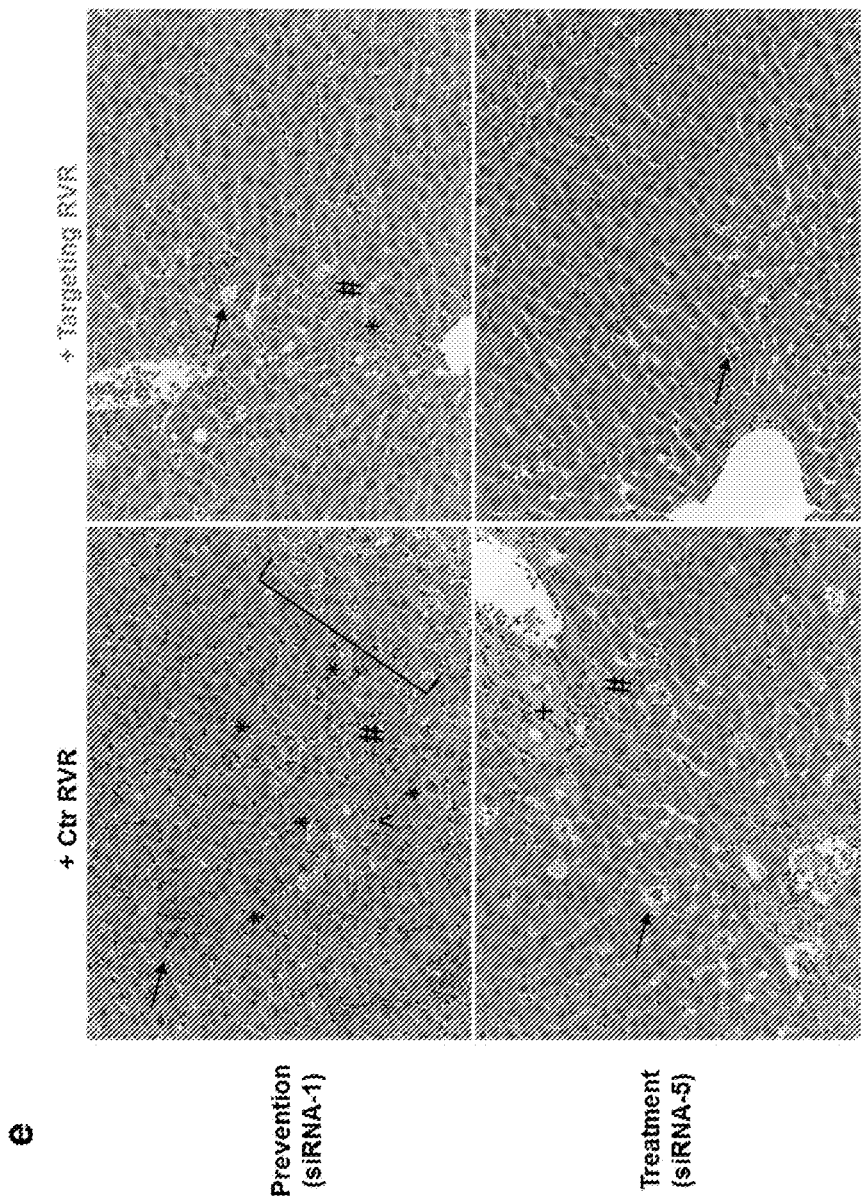
Figure 45:
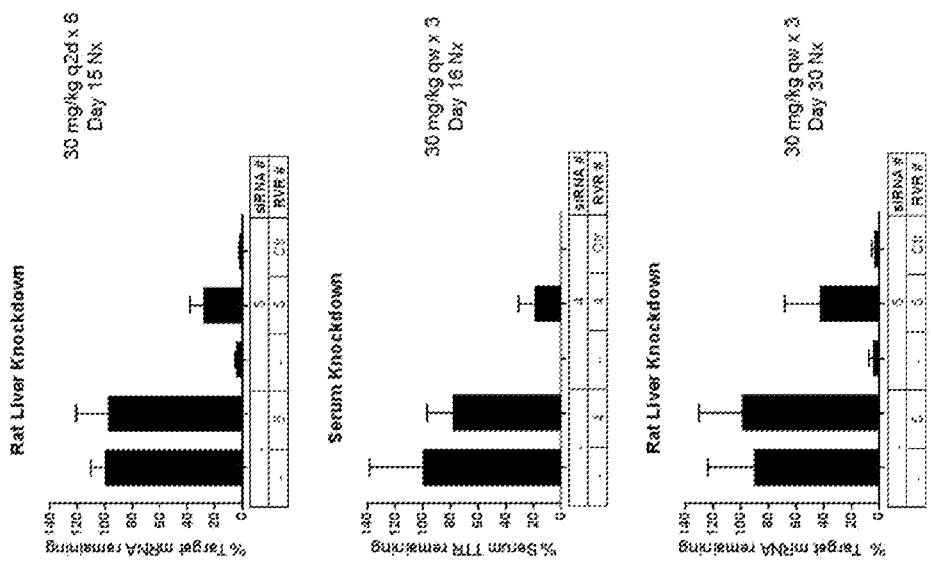
FIG. 45 are bar graphs showing effects of REVERSIR™ compounds on RNAi activity in rat toxicity studies. Liver on-target mRNA knockdown with siRNA-1 and siRNA-5 was assessed at necropsy (nx) by RT-qPCR for target mRNA and normalized to a housekeeping mRNA (18S rRNA), relative to the saline control group. On-target serum protein levels with siRNA-4 were assessed at necropsy by ELISA, relative to the saline control group. Q2d, every other day dosing; qw, weekly dosing.

REVERSIR™ treatment pre- or post-siRNA administration reduced on-target knockdown (FIG. 45) but did not affect liver siRNA levels (FIG. 44B) or RISC loading (FIG. 44C). However, the complementary REVERSIR™ compounds (RVR-1, RVR-4, or RVR-5) but not the control, scrambled REVERSIR™ (Ctr RVR) reduced the liver enzyme elevations observed with their respective targets, siRNA-1, siRNA-4, or siRNA-5 (FIG. 44D), and decreased the severity and incidence of microscopic liver findings (FIG. 44E and Table 16). REVERSIR™ compounds administered alone had no toxic effects (FIG. 44D). By deploying the REVERSIR™ approach, siRNA-induced hepatotoxicity was mitigated without affecting RISC loading and without changing siRNA chemistry. Thus, these data support the hypothesis that hepatotoxicity is driven by antisense strand-mediated RNAi off-target effects, and not by competition for RISC complexes with endogenous RNAi pathways or siRNA chemistry-mediated effects.

TABLE 16

Histologic findings with GalNAc-siRNAs with or without treatment with REVERSIR™ compounds targeting the antisense strand

| | Rat | | | | | |
|---|---|---|---|---|---|---|
| | siRNA-1 | | siRNA-4 | | siRNA-5 | |
| | Ctr RVR | RVR-1 | Ctr RVR | RVR-4 | Ctr RVR | RVR-5 |
| Degeneration, hepatocellular | 2-3 | 1-2 | | | | |
| Necrosis, single cell, hepatocellular | 2-3 | 1 | 1 | | 1 | 1 |
| Nerosis, coagulative, hepatocellular | 1 | | | | | |
| Anisocytosis, hepatocellular | | | | | | |
| Vacuolation, hepatocellular | 2-3 | 2-3 | | | 2-3 | 1-2 |
| Kupffer cell hyperplasia/Cellular infiltrates | 1-2 | 1-2 | 1 | | 1-2 | 1-2 |
| Hyperplasia, bile duct | | | | | 1 | |
| Fibrosis | | | | | 1-2 | |
| Increased mitoses | 1-2 | | 1 | | | |
| Vacuolation, Kupffer cell | | | 1 | 1 | | |

Table 16 shows that reversing antisense-loaded RISC activity mitigates hepatotoxicity. The range of severity grade for each histologic finding is indicated on a scale of 1-5 with 1 indicating minimal severity and 5 indicating severe severity.

4. Swapping Seed Regions Mitigates Hepatotoxicity

Figures 46A, 46B, 46C, 46D:
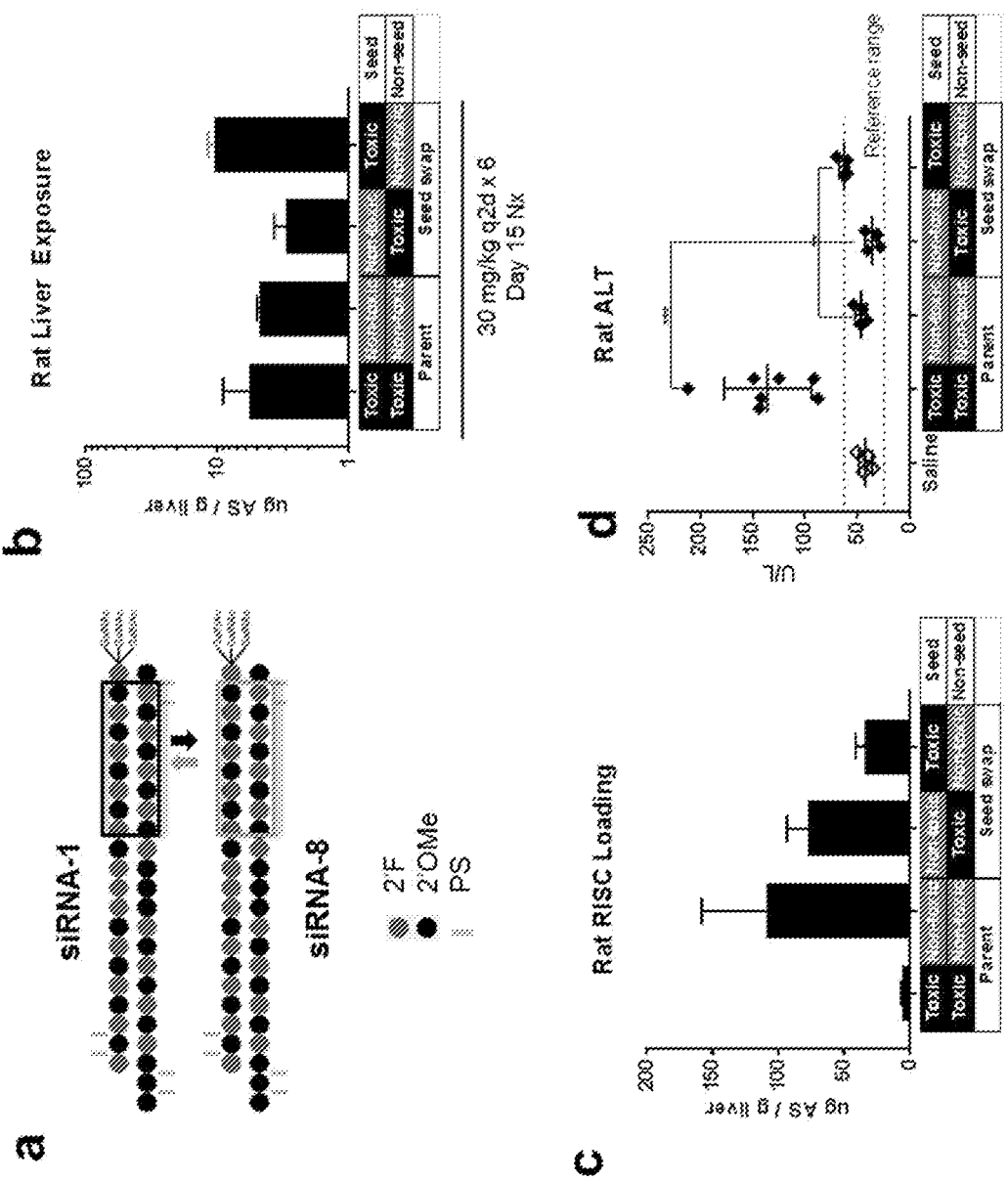
FIGS. 46A-46E show that swapping seed regions mitigates hepatotoxicity.

Analogous to miRNA mechanisms, RNAi-mediated off-target effects of siRNAs are typically driven by the seed region of the guide strand. If these effects elicit the observed rodent hepatotoxicity of GalNAc-siRNAs, the sequence of the seed region and not the flanking region outside nucleotides 2-8 should be a key determining factor of whether a specific sequence is associated with hepatotoxicity or not. To test this hypothesis, the seed region of a hepatotoxic siRNA was replaced with the seed region of a non-hepatotoxic siRNA without changing the chemical modification pattern, and vice versa where the seed region of a non-hepatotoxic siRNA was replaced with the seed region of a hepatotoxic siRNA, without changing the chemical modification pattern (FIG. 46A).

Figure 46E:
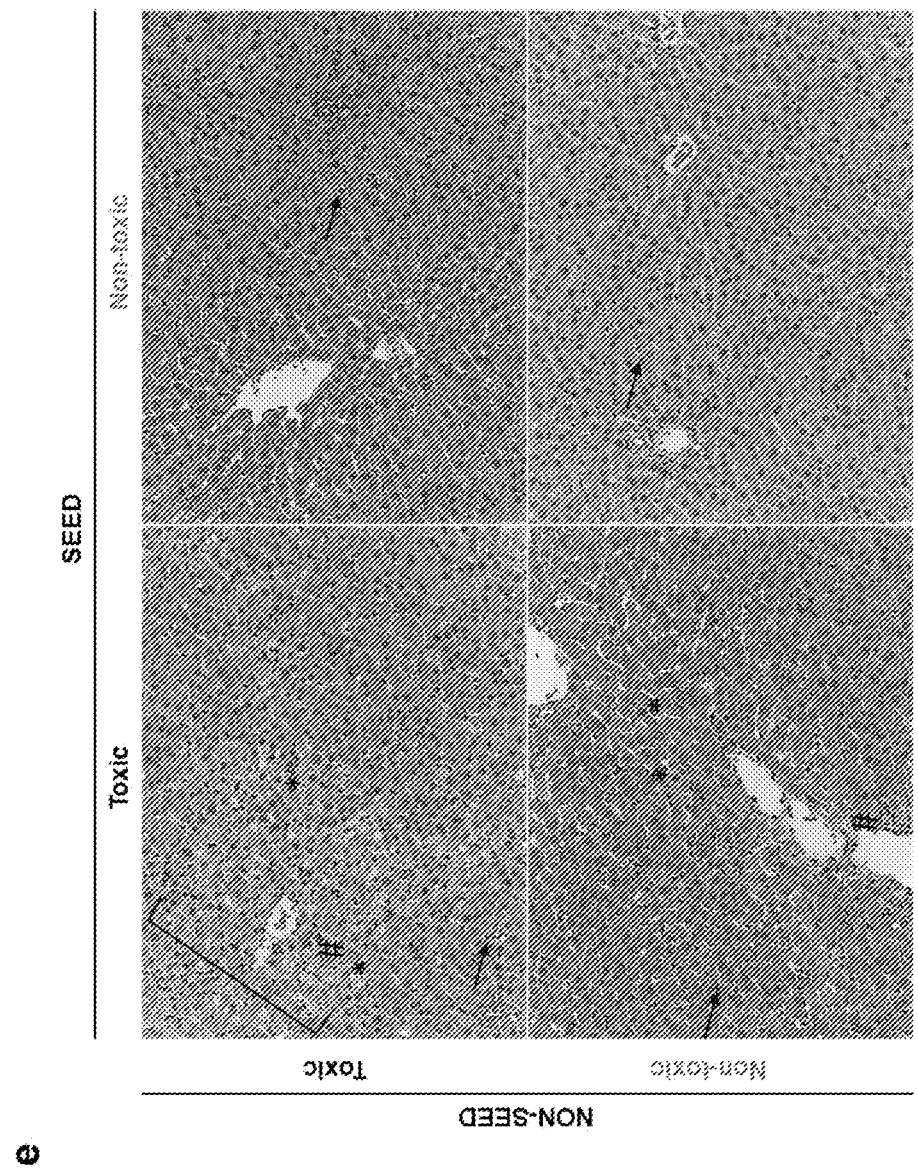

The two seed-swapped siRNAs along with the parent hepatotoxic and non-hepatotoxic siRNAs were administered to rats at a toxicological dose of 30 mg/kg six times every other day. Liver exposures were comparable for all four compounds (FIG. 46B). RISC loading was lower for the toxic parent siRNA as well as the siRNA containing the toxic seed region relative to the non-toxic parent siRNA or the siRNA containing the non-toxic seed region (FIG. 46C). Despite the lower levels of RISC loading, however, these two siRNAs were most hepatotoxic, arguing against competition for RISC loading as the major driver of hepatotoxicity. Replacing a toxic seed region with a non-toxic seed region mitigated liver enzyme elevations (FIG. 46D) and microscopic liver findings (FIG. 46E and Table 17), indicating that the seed region is necessary for hepatotoxicity with little to no contribution from siRNA chemistry. On the other hand, replacing a non-toxic seed region with a toxic seed region did not fully recapitulate hepatotoxicity of the toxic siRNA but did cause an increase in liver enzymes (FIG. 46D) and an increased severity of microscopic liver findings relative to the non-toxic parent siRNA (FIG. 46E and Table 17). This suggests that while complementarity to the antisense seed region is required for off-target activity, the siRNA 3' region may also contribute to off-target binding and repression. These data provide further support for RNAi-mediated, seed-based off-target effects and against chemistry-mediated or RNAi pathway competition class effects as the major driver of rat hepatotoxicity.

TABLE 17

Histologic findings with GalNAc-siRNAs with or without seed region swapping

| | Rat Seed | | | |
|---|---|---|---|---|
| | Toxic | Non-toxic | Non-toxic Non-seed | Toxic |
| | Toxic | Non-toxic | Toxic | Non-toxic |
| Degeneration, hepatocellular | 1-4 | | | |
| Necrosis, single cell, hepatocellular | 2-3 | | | 1-2 |
| Nerosis, coagulative, hepatocellular | | | | 1 |
| Anisocytosis, hepatocellular | | | | |
| Vacuolation, hepatocellular | 1-2 | 1 | 1 | 1-2 |
| Kupffer cell hyperplasia/ Cellular infiltrates | 1-3 | | | 1 |
| Hyperplasia, bile duct | 1 | | | |
| Fibrosis | | | | |
| Increased mitoses | | | 1-2 | 1 |
| Vacuolation, Kupffer cell | | | | |

Table 17 shows that swapping seed regions mitigates hepatotoxicity. The range of severity grade for each histologic finding is indicated on a scale of 1-5 with 1 indicating minimal severity and 5 indicating severe severity.

5. siRNA Off-Targets are Enriched for Seed Complementarity

Figure 47A:
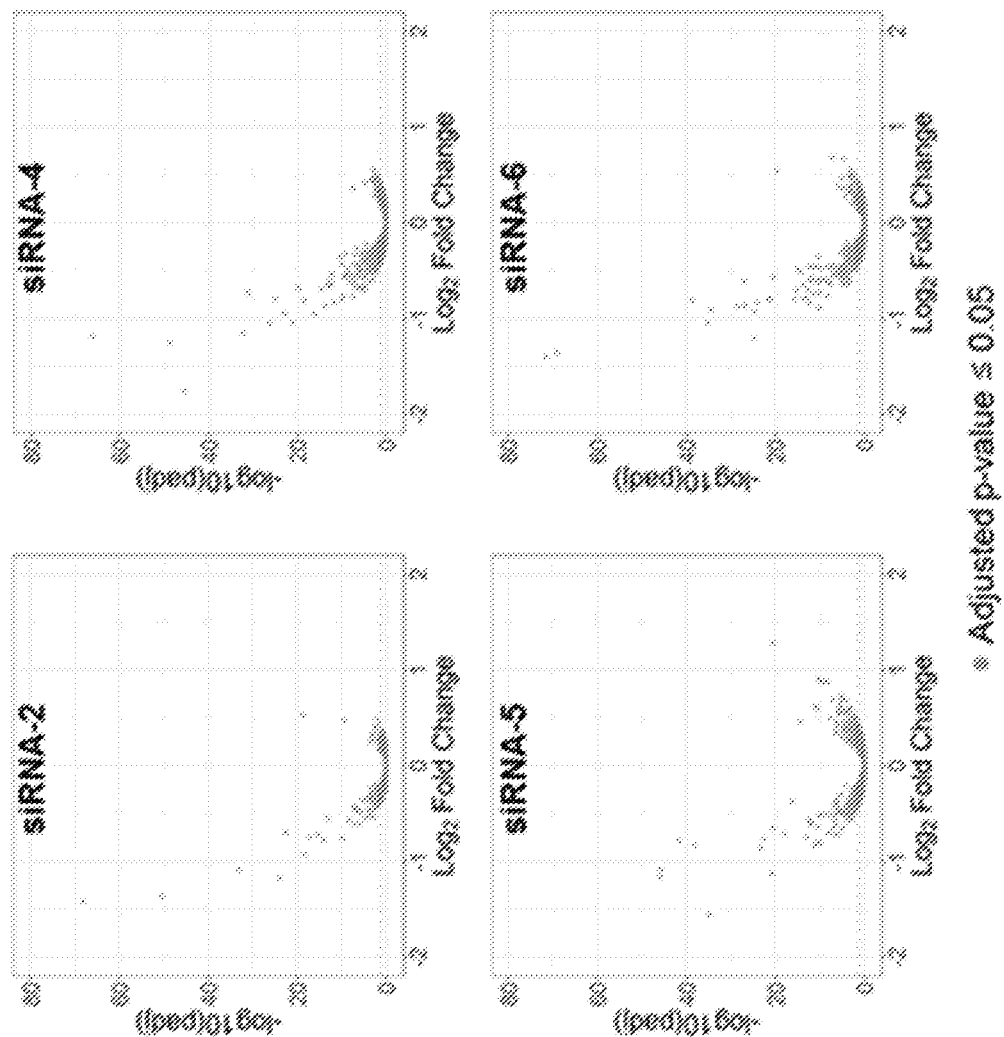
FIGS. 47A and 47B show that siRNA off-targets are enriched for seed complementarity in vitro and in vivo.
Figure 47B:
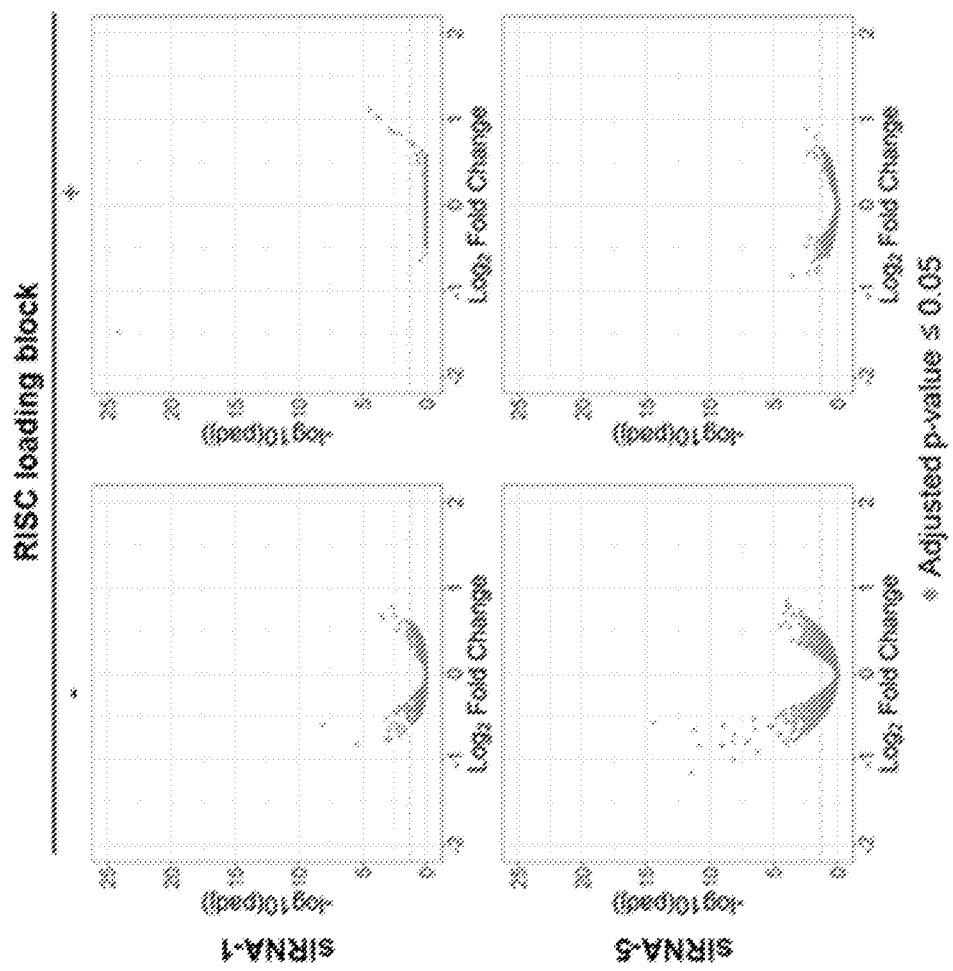

To confirm that GalNAc-siRNAs can cause gene dysregulation consistent with RNAi-mediated off-target effects, a series of siRNAs was transfected into rat hepatocytes for evaluation of global effects on the transcriptome by RNA sequencing (RNAseq) at 24 h at a "toxicological" dose of 10 nM that exceeded the $IC_{50}$ concentrations by 2-3 logs. Downregulated transcripts were enriched for perfect complementarity to the antisense seed region (nucleotides 2-8), and magnitude of change generally did not exceed two-fold (FIG. 47A and Table 18). No such pattern of enrichment was observed for upregulated transcripts, or against the seed region of the sense strand. Similar off-target profile characteristics were observed in vivo in rat livers at 24 h following a 50 mg/kg dose of GalNAc-siRNAs (FIG. 47B). The number of dysregulated genes was reduced with inactive siRNAs containing 5'-end caps, indicating that the 2'F, 2'OMe, or PS chemistry and/or other RISC-independent factors do not significantly contribute to gene dysregulation, consistent with the results from rodent toxicity studies (FIGS. 38A-38D). These data further support the conclusion that miRNA-like activity of the antisense strand, and not RNAi-independent effects based on siRNA chemistry, is the primary driver of off-target gene expression changes.

TABLE 18

Histologic findings with parent and seed GNA-modified GalNAc-siRNA

| | Rat Seed GNA modification | |
|---|---|---|
| | siRNA-5 | SiRNA-5-GNA |
| Degeneration, hepatocellular | 2-3 | 1-2 |
| Necrosis, single cell, hepatocellular | 2-3 | 1 |
| Nerosis, coagulative, hepatocellular | | |
| Anisocytosis, hepatocellular | | |
| Vacuolation, hepatocellular | 2-3 | 1-2 |
| Kupffer cell hyperplasia/Cellular infiltrates | 1-2 | |
| Hyperplasia, bile duct | | |
| Fibrosis | 1-2 | |
| Increased mitoses | 1 | 1 |
| Vacuolation, Kupffer cell | | |

Table 18 shows that destabilizing seed-mediated off-target binding mitigates hepatotoxicity. The range of severity grade for each histologic finding is indicated on a scale of 1-5 with 1 indicating minimal severity and 5 indicating severe severity.

6. Impact of Destabilizing Seed-Mediated Off-Target Binding

If seed-mediated recognition is necessary for off-target-driven hepatotoxicity of GalNAc-siRNAs, decreasing the binding affinity of the seed region to off-target mRNAs should have a mitigating effect. To test this hypothesis, a thermally-destabilizing GNA nucleotide was placed at position seven of the antisense strand in the hepatotoxic siRNA-5 sequence (FIG. 48A), analogous to previous approaches with other thermally-destabilizing modifications.

Figures 48A, 48B, 48C, 48D, 48E, 48F:
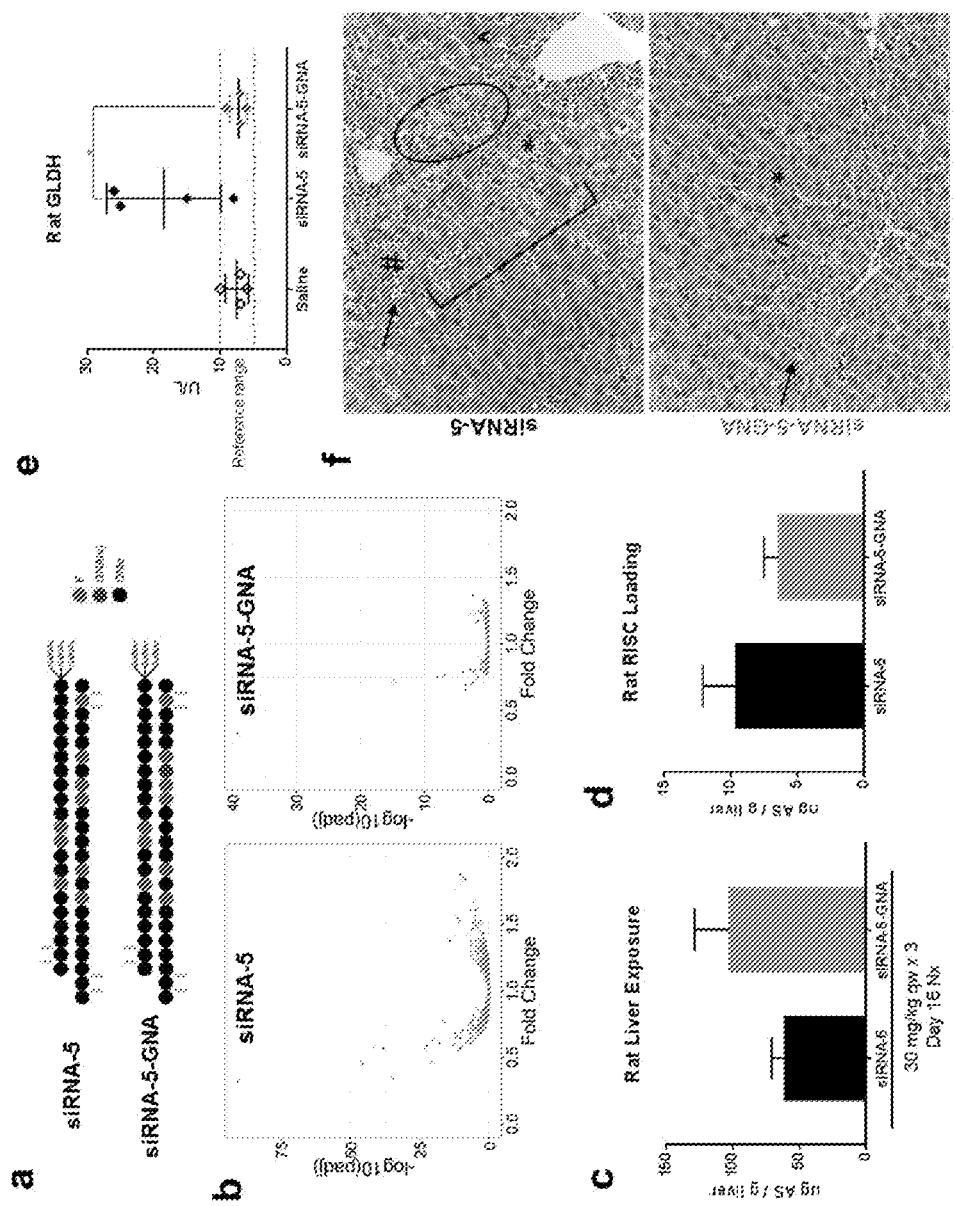
FIGS. 48A-48F show that destabilizing seed-mediated base-pairing minimizes off-target effects and mitigates hepatotoxicity.
Figures 49A, 49B:
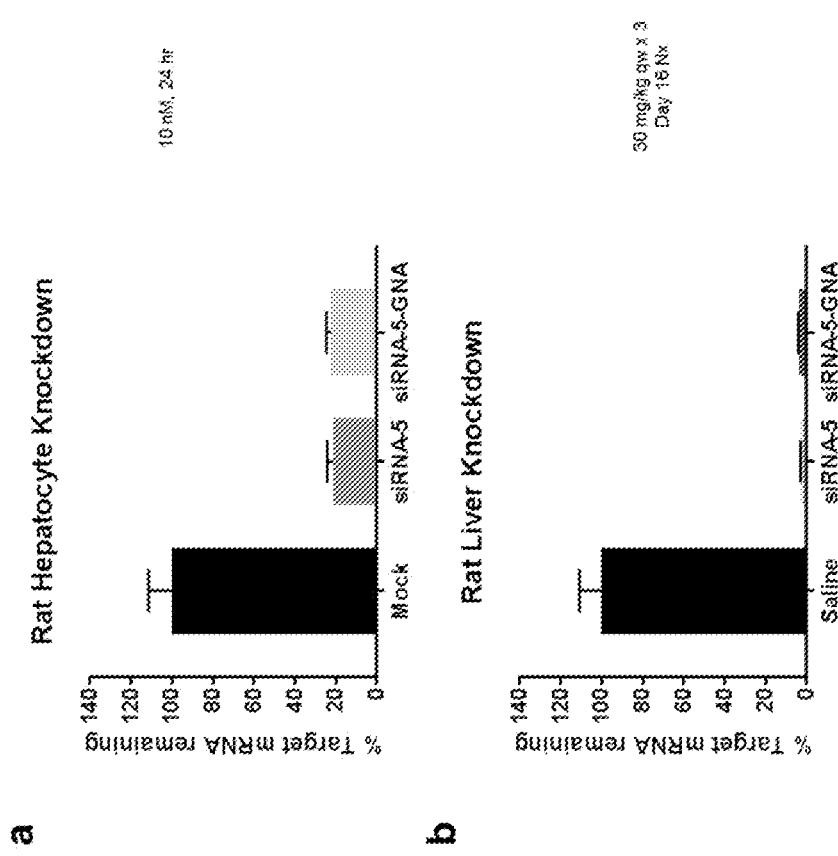
FIGS. 49A and 49B show effects of exemplary thermally-destabilizing GNA seed modifications on on-target activity.

Consistent with the hypothesis that seed-mediated off-target activity is driving gene expression changes, incorporating GNA in the antisense strand seed region reduced the off-target signature compared to the parent siRNA when transfected into rat hepatocytes at a high dose of 10 nM (FIG. 48B), while maintaining on-target activity (FIG. 49A). To further test whether reduction in the off-target signature translates into improved safety in vivo, these same two siRNAs were tested in a rat toxicity study dosed weekly three times at 30 mg/kg. Relative to the parent sequence, GNA nucleotide substitution in the seed region did not affect on-target mRNA knockdown (FIG. 49B), liver exposure (FIG. 48C), or RISC loading (FIG. 48D). However, seed modification mitigated liver enzyme elevations (FIG. 48E) and microscopic liver findings (FIG. 48F). In addition to providing additional evidence for off-target effects and against chemical toxicity or RNAi pathway perturbations as the major driver of hepatotoxicity, these data provide the first reported evidence that thermal destabilization of seed-mediated binding is a viable strategy for the selective reduction of off-target repression and hepatotoxicity of siRNAs in vivo.

All of the U.S. patents, U.S. patent application publications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A method for silencing a target gene in a cell, the method comprising a step of introducing a dsRNA molecule into the cell, wherein the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex within the first 9 nucleotide positions of the 5' region of the antisense strand or a precursor thereof, wherein the antisense strand further comprises one or both of the following characteristics:
   (i) 2, 3, 4, 5 or 6 2'-fluoro modifications; and
   (ii) 1, 2, 3, 4 or 5 phosphorothioate internucleotide linkages; and said sense strand comprises one, two or three of the following characteristics:
   (i) an asialoglycoprotein receptor (ASGPR) ligand;
   (ii) 2, 3, 4, or 5 2'-fluoro modifications; and
   (iii) 1, 2, 3, 4 or 5 phosphorothioate internucleotide linkages.

2. A method for suppressing off-target effects caused by the antisense strand of dsRNA molecules, the method comprising a step of introducing a dsRNA molecule into a cell, wherein the dsRNA molecule comprises a sense strand and an antisense strand, each strand having 14 to 40 nucleotides, wherein the antisense strand has sufficient complementarity to the target sequence to mediate RNA interference, wherein said antisense strand comprises at least one thermally destabilizing modification of the duplex within the first 9 nucleotide positions of the 5' region of the antisense strand or a precursor thereof, wherein the antisense strand further comprises one or both of the following characteristics:
   (i) 2, 3, 4, 5 or 6 2'-fluoro modifications; and
   (ii) 1, 2, 3, 4 or 5 phosphorothioate internucleotide linkages; and said sense strand comprises one, two or three of the following characteristics:
   (i) an asialoglycoprotein receptor (ASGPR) ligand;
   (ii) 2, 3, 4, or 5 2'-fluoro modifications; and
   (iii) 1, 2, 3, 4 or 5 phosphorothioate internucleotide linkages.

3. The method of claim 2, wherein the dsRNA comprises at least four 2'-fluoro.

4. The method of claim 3, wherein there are no 2'-fluoro modifications at nucleotide positions 3-9 of the antisense strand.

5. The method of claim 2, wherein:
   (i) the dsRNA molecule has the following characteristics:
      a) the thermally destabilizing modification of the duplex is located in position 4-8 of the 5' region of the antisense strand;
      b) and each of the sense and antisense strands comprise at least two 2'-fluoro modifications; and
      c) an ASGPR ligand attached to either end of the sense strand; or
   (ii) the dsRNA molecule has the following characteristics:
      a) the thermally destabilizing modification of the duplex modification is located in position 4 to 8 of the antisense strand;
      b) at least two 2'-fluoro modifications;

c) phosphorothioate internucleotide linkages between nucleotide positions 1 and 2 (counting from the 5' end); and
d) it has a length of 18 to 35 nucleotides; or (iii) the dsRNA molecule has the following characteristics:
a) the ASGPR ligand attached to either end of the sense strand;
b) at least two 2'-fluoro modifications; and
c) the sense strand and the antisense strand show sufficient complementarity to form a double stranded region spanning at least 19 nucleotide positions and wherein the thermally destabilizing modification of the duplex is located within said double-stranded region.

6. The method of claim 5, wherein there are no 2'-fluoro modifications at nucleotide positions 3-9 of the antisense strand.

7. The method of claim 2, wherein the thermally destabilizing modification of the duplex is selected from the group consisting of

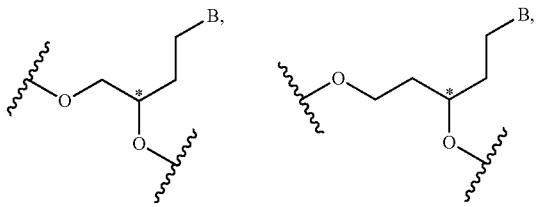

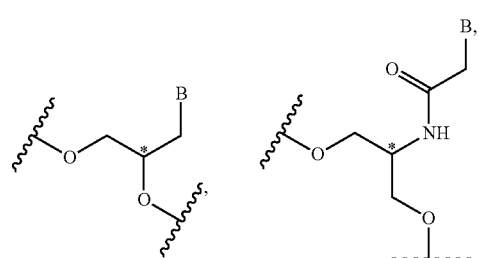

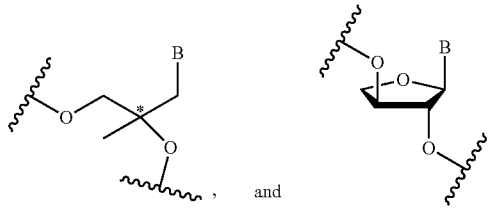

wherein B is nucleobase, and * is R, S or racemic.

8. The method of claim 2, wherein the thermally destabilizing modification is located in position 7 of the antisense strand.

9. The method of claim 2, wherein the ASGPR ligand is one or more GalNAc derivatives attached through a bivalent or trivalent branched linker.

10. The method of claim 2, wherein the ASGPR ligand is

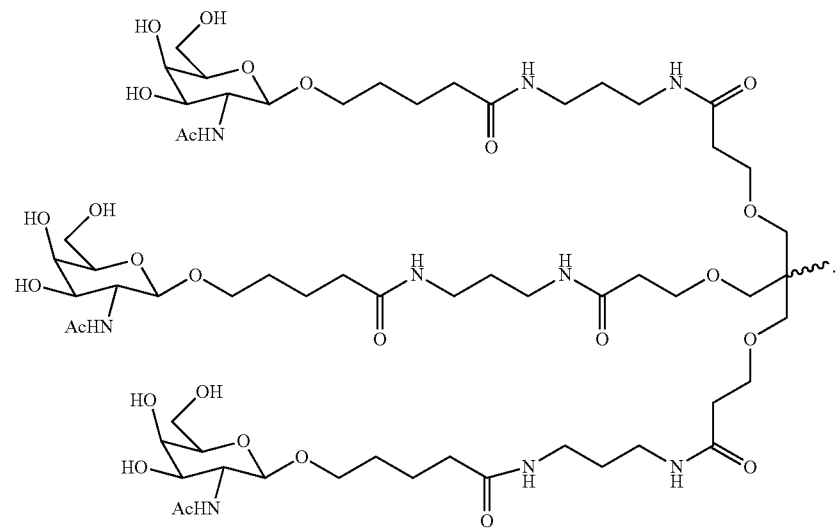 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

11. The method of claim 1, wherein the dsRNA comprises at least four 2'-fluoro.

12. The method of claim 11, wherein there are no 2'-fluoro modifications at nucleotide positions 3-9 of the antisense strand.

13. The method of claim 1, wherein:
(i) the dsRNA molecule has the following characteristics:
   a) the thermally destabilizing modification of the duplex is located in position 4-8 of the 5' region of the antisense strand;
   b) and each of the sense and antisense strands comprise at least two 2'-fluoro modifications; and
   c) an ASGPR ligand attached to either end of the sense strand; or
(ii) the dsRNA molecule has the following characteristics:
   a) the thermally destabilizing modification of the duplex modification is located in position 4 to 8 of the antisense strand;
   b) at least two 2'-fluoro modifications;
   c) phosphorothioate internucleotide linkages between nucleotide positions 1 and 2 (counting from the 5' end); and
   d) it has a length of 18 to 35 nucleotides; or
(iii) the dsRNA molecule has the following characteristics:
   a) the ASGPR ligand attached to either end of the sense strand;
   b) at least two 2'-fluoro modifications; and
   c) the sense strand and the antisense strand show sufficient complementarity to form a double stranded region spanning at least 19 nucleotide positions and wherein the thermally destabilizing modification of the duplex is located within said double-stranded region.

14. The method of claim 13, wherein there are no 2'-fluoro modifications at nucleotide positions 3-9 of the antisense strand.

15. The method of claim 1, wherein the thermally destabilizing modification of the duplex is selected from the group consisting of

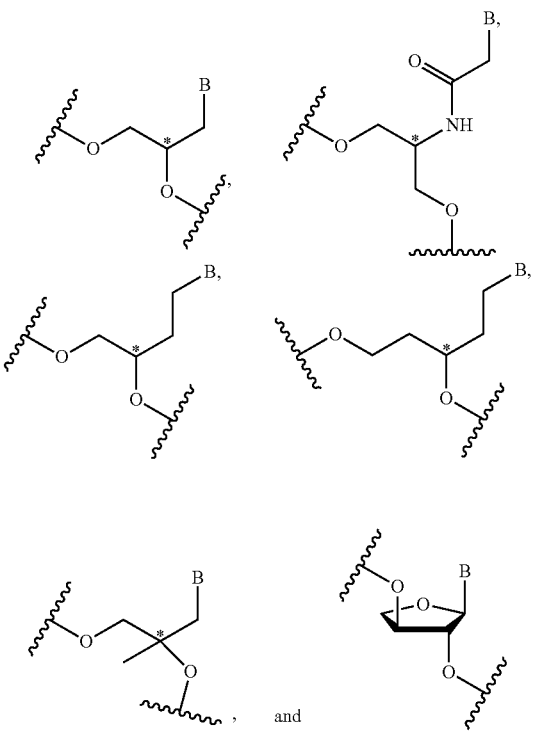

wherein B is nucleobase, and * is R, S or racemic.

16. The method of claim 1, wherein the thermally destabilizing modification is located in position 7 of the antisense strand.

17. The method of claim 1, wherein the ASGPR ligand is one or more GalNAc derivatives attached through a bivalent or trivalent branched linker.

18. The method of claim 1, wherein the ASGPR ligand is:

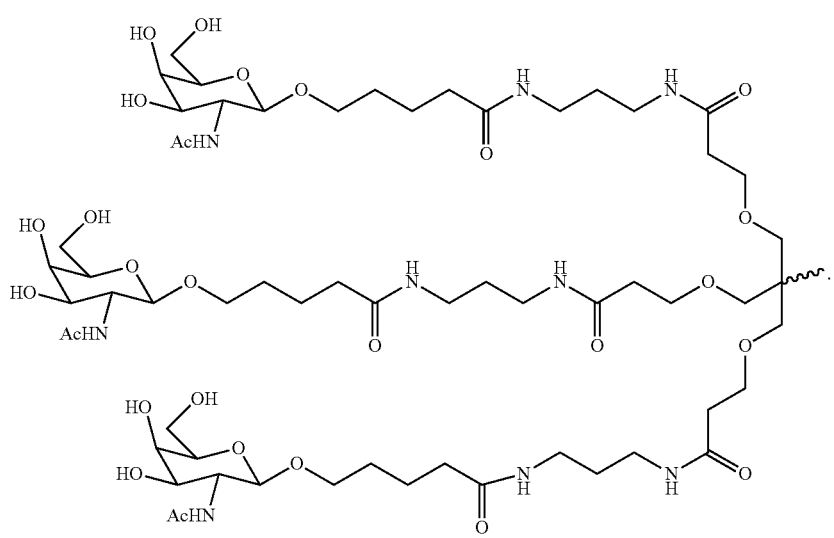 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

19. The method of claim 1, wherein the thermally destabilizing modification of the duplex is located at position 5, 6 or 7 of the antisense strand, counting from the 5'-end of the antisense strand.

20. The method of claim 19, wherein the thermally destabilizing modification is located in position 6 of the antisense strand, counting from the 5'-end of the antisense strand.

21. The method of claim 1, wherein the sense strand and the antisense strand show sufficient complementarity to form a double stranded region spanning at least 19 nucleotide positions and wherein the thermally destabilizing modification of the duplex is located within said double-stranded region.

22. The method of claim 19, wherein the thermally destabilizing modification of the duplex is selected from the group consisting of

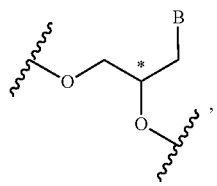

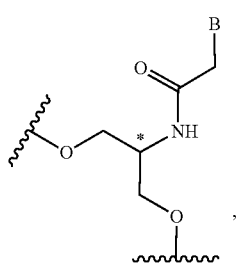

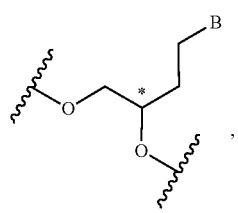

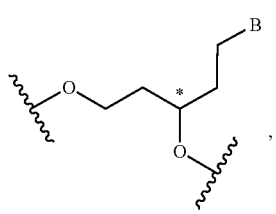

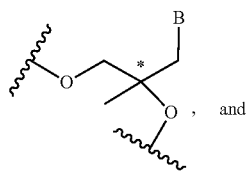, and

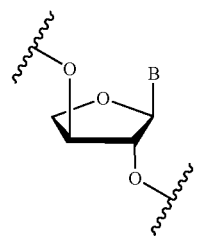

wherein B is a nucleobase and * is R, S or racemic.

23. The method of claim 22, wherein the thermally destabilizing modification of the duplex is

[structure] (GNA).

24. The method of claim 23, wherein the thermally destabilizing modification is an (S)-GNA modification.

25. The method of claim 1, wherein the antisense strand comprises:
 (i) 2'-fluoro modifications only at positions 2, 14 and 16, counting from the 5'-end of the antisense strand; or
 (ii) 2'-fluoro modifications only at positions 2, 6, 14 and 16, counting from the 5'-end of the antisense strand; or
 (iii) 2'-fluoro modifications only at positions 2, 6, 8, 9, 14 and 16, counting from the 5'-end of the antisense strand.

26. The method of claim 1, wherein the sense strand comprises a ligand.

27. The method of claim 26, wherein the ligand is attached at the 5'-end or 3'-end of the sense strand.

28. The method of claim 27, wherein the ligand is an asialoglycoprotein receptor (ASGPR) ligand.

29. The method of claim 28, wherein the ASGPR ligand is one or more GalNAc derivatives attached through a bivalent or trivalent branched linker.

30. The method of claim 29, wherein the ASGPR ligand is:

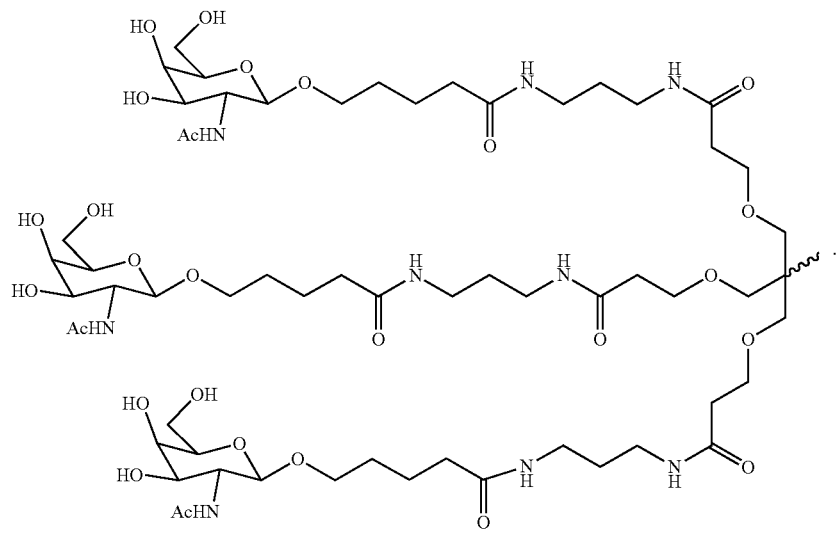

31. The method of claim 2, wherein the thermally destabilizing modification of the duplex is located at position 5, 6 or 7 of the antisense strand, counting from the 5'-end of the antisense strand.

32. The method of claim 31, wherein the thermally destabilizing modification is located in position 6 of the antisense strand, counting from the 5'-end of the antisense strand.

33. The method of claim 2, wherein the sense strand and the antisense strand show sufficient complementarity to form a double stranded region spanning at least 19 nucleotide positions and wherein the thermally destabilizing modification of the duplex is located within said double-stranded region.

34. The method of claim 31, wherein the thermally destabilizing modification of the duplex is selected from the group consisting of

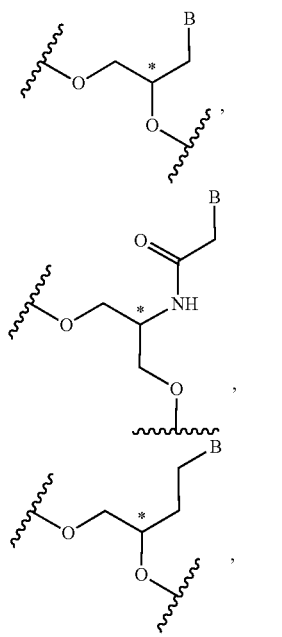

-continued

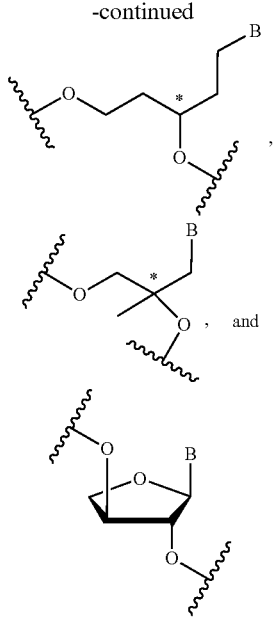

wherein B is a nucleobase and * is R, S or racemic.

35. The method of claim 34, wherein the thermally destabilizing modification of the duplex is

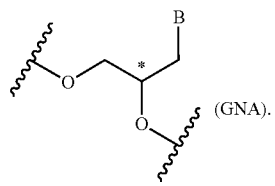

(GNA).

36. The method of claim 35, wherein the thermally destabilizing modification is an (S)-GNA modification.

37. The method of claim 2, wherein the antisense strand comprises:
(i) 2'-fluoro modifications only at positions 2, 14 and 16, counting from the 5'-end of the antisense strand; or (ii) 2'-fluoro modifications only at positions 2, 6, 14 and 16, counting from the 5'-end of the antisense strand; or
(iii) 2'-fluoro modifications only at positions 2, 6, 8, 9, 14 and 16, counting from the 5'-end of the antisense strand.

38. The method of claim 2, wherein the sense strand comprises a ligand.

39. The method of claim 38, wherein the ligand is attached at the 5'-end or 3'-end of the sense strand.

40. The method of claim 39, wherein the ligand is an asialoglycoprotein receptor (ASGPR) ligand.

41. The method of claim 40, wherein the ASGPR ligand is one or more GalNAc derivatives attached through a bivalent or trivalent branched linker.

42. The method of claim 41, wherein the ASGPR ligand is:

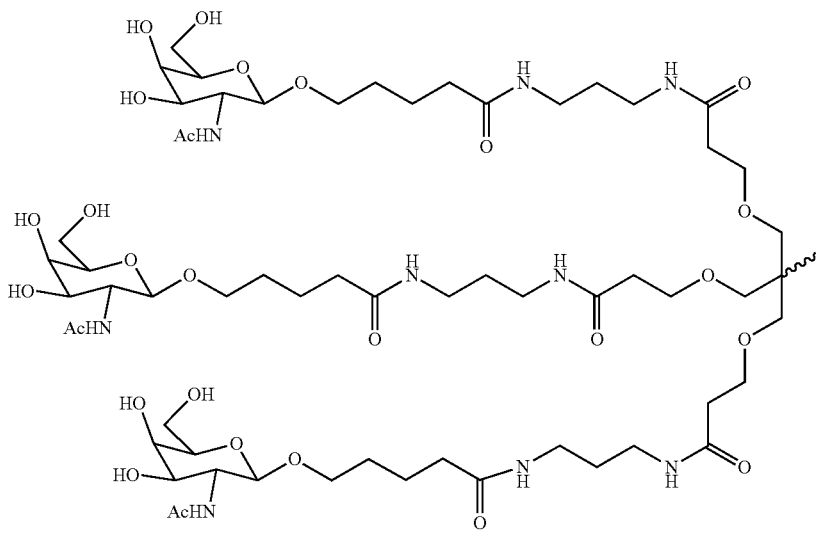

* * * * *

SEQUENCE LISTING

```
<160> NUMBER OF SEQ ID NOS: 79

<210> SEQ ID NO 1
<211> LENGTH: 16
<212> TYPE: PRT
<213> ORGANISM: Homo sapiens

<400> SEQUENCE: 1

Ala Ala Val Ala Leu Leu Pro Ala Val Leu Leu Ala Leu Leu Ala Pro
1               5                   10                  15

<210> SEQ ID NO 2
<211> LENGTH: 11
<212> TYPE: PRT
<213> ORGANISM: Homo sapiens

<400> SEQUENCE: 2

Ala Ala Leu Leu Pro Val Leu Leu Ala Ala Pro
1               5                   10

<210> SEQ ID NO 3
<211> LENGTH: 13
<212> TYPE: PRT
<213> ORGANISM: Human immunodeficiency virus

<400> SEQUENCE: 3

Gly Arg Lys Lys Arg Arg Gln Arg Arg Arg Pro Pro Gln
1               5                   10

<210> SEQ ID NO 4
<211> LENGTH: 16
<212> TYPE: PRT
<213> ORGANISM: Drosophila sp.

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gaaugugaaa gucaucgaca a                                            21

<210> SEQ ID NO 6
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 6
uugucgauga cuuucacauu cug                                             23

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gaaugugaaa gucaucgaca a                                               21

<210> SEQ ID NO 8
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uugucgauga cuuucacauu cug                                             23

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gaaugugaaa gucaucgaca a                                               21

<210> SEQ ID NO 10
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uugucgauga cuuucacauu cug                                             23

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
gaaugugaaa gucaucgaca a                                               21

<210> SEQ ID NO 12
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 12
uugucgauga cuuucacauu cug                                              23

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gaaugugaaa gucaucgaca a                                                21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
uugucgatga cuuucacauu cug                                              23

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aacaguguuc uugcucuaua a                                                21

<210> SEQ ID NO 16
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uuauagagca agaacacugu uuu                                              23

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aacaguguuc uugcucuaua a                                                21

<210> SEQ ID NO 18
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uuauagagca agaacacugu uuu                                            23

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
aacaguguuc uugcucuaua a                                              21

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
uuatagagca agaacacugu uuu                                            23

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
aacaguguuc uugcucuaua a                                              21

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uuauagagca agaacacugu uuu                                            23

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
aacaguguuc uugcucuaua a                                              21
```

```
<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uuauagagca agaacacugu uuu                                            23

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
aacaguguuc uugcucuaua a                                              21

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uuauagagca agaacacugu uuu                                            23

<210> SEQ ID NO 27
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
aacaguguuc uugcucuaua a                                              21

<210> SEQ ID NO 28
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
uuauagagca agaacacugu uuu                                            23

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uggaagcagu auguugaugg a                                              21

<210> SEQ ID NO 30
```

<210> SEQ ID NO 30
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 30
uccaucaaca uacugcuucc aaa                    23

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 31
uggaagcagu auguugaugg a                      21

<210> SEQ ID NO 32
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 32
uccaucaaca uacugcuucc aaa                    23

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 33
uggaagcagu auguugaugg a                      21

<210> SEQ ID NO 34
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 34
uccaucaaca uacugcuucc aaa                    23

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 35
uggaagcagu auguugaugg a                      21

<210> SEQ ID NO 36
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
uccatcaaca uacugcuucc aaa                                            23

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uggaagcagu auguugaugg a                                              21

<210> SEQ ID NO 38
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uccaucaaca uacugcuucc aaa                                            23

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
uggaagcagu auguugaugg a                                              21

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
uccaucaaca uacugcuucc aaa                                            23

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uggaagcagu auguugaugg a                                              21
```

```
<210> SEQ ID NO 42
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
uccaucaaca uacugcuucc aaa                                              23

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cugguauuuc cuaggguaca a                                                21

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uuguacccua ggaaauacca gag                                              23

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
aauaaagugc uuugaaaacg u                                                21

<210> SEQ ID NO 46
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
acguuuucaa agcacuuuau uga                                              23

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
cuucuuaaug auugaacaaa a                                                21

<210> SEQ ID NO 48
```

-continued

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
uuuuguucaa ucauuaagaa gac                                            23

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
cuucuuaaug auugaacaaa a                                              21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
uuuugtucaa ucauuaagaa gac                                            23

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
cuucuuaaug auugaacaaa a                                              21

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
uuuugutcaa ucauuaagaa gac                                            23

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
```
cuucuuaaug auugaacaaa a                                      21

<210> SEQ ID NO 54
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
uuuuguucaa ucauuaagaa gac                                    23

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
cuucuuaaug auugaacaaa a                                      21

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
uuuugutcaa ucauuaagaa gac                                    23

<210> SEQ ID NO 57
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uacagucuau gu                                                12

<210> SEQ ID NO 58
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
acauagacug ua                                                12

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 59
ugacaaaaua acucacuaua a                                              21

<210> SEQ ID NO 60
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uuauagugag uuauuuuguc aau                                            23

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
gugcacuucg cuucaccucu a                                              21

<210> SEQ ID NO 62
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
uagaggugaa gcgaagugca cuu                                            23

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
gguuaacacg uuuuagauca a                                              21

<210> SEQ ID NO 64
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
uugaucuaaa acguguuaac cag                                            23

<210> SEQ ID NO 65
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
aacaguguuc uugcucuaua a                                              21

<210> SEQ ID NO 66
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
uuauagagca agaacacugu uuu                                            23

<210> SEQ ID NO 67
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
gaaugugaaa gucaucgaca a                                              21

<210> SEQ ID NO 68
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
uugucgauga cuuucacauu cug                                            23

<210> SEQ ID NO 69
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
cugguauuuc cuaggguaca a                                              21

<210> SEQ ID NO 70
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uuguacccua ggaaauacca gag                                            23

<210> SEQ ID NO 71
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
cuucuuaaug auugaacaaa a                                     21

<210> SEQ ID NO 72
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uuuuguucaa ucauuaagaa gac                                   23

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aagcaagaua uuuuuauaau a                                     21

<210> SEQ ID NO 74
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uauuauaaaa auaucuugcu uuu                                   23

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
aagcaagaua uuuuuauaau a                                     21

<210> SEQ ID NO 76
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
uauuauaaaa auaucuugcu uuu                                   23

<210> SEQ ID NO 77
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 77
cucactataa                                                          10

<210> SEQ ID NO 78
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
ugcuctataa                                                          10

<210> SEQ ID NO 79
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
tcaucgacaa                                                          10
```